(12) United States Patent
Kelly et al.

(10) Patent No.: US 8,546,579 B2
(45) Date of Patent: Oct. 1, 2013

(54) BICYCLOHETEROARYL COMPOUNDS AS $P2X_7$ MODULATORS AND USES THEREOF

(75) Inventors: Michael G. Kelly, Thousand Oaks, CA (US); John Kincaid, San Mateo, CA (US); Yunfeng Fang, Foster City, CA (US); Jianhua He, legal representative, Foster City, CA (US); Yeyu Cao, Foster City, CA (US); Carl Kaub, San Mateo, CA (US); Sumithra Gowlugari, San Mateo, CA (US); Zhan Wang, Palo Alto, CA (US)

(73) Assignee: Evotec (US) Inc., So. San Francisco, CA (US)

( * ) Notice: Subject to any disclaimer, the term of this patent is extended or adjusted under 35 U.S.C. 154(b) by 536 days.

(21) Appl. No.: 12/225,274

(22) PCT Filed: Mar. 16, 2007

(86) PCT No.: PCT/US2007/006700
§ 371 (c)(1),
(2), (4) Date: Jul. 30, 2010

(87) PCT Pub. No.: WO2007/109172
PCT Pub. Date: Sep. 27, 2007

(65) Prior Publication Data
US 2010/0292235 A1 Nov. 18, 2010

Related U.S. Application Data

(60) Provisional application No. 60/782,923, filed on Mar. 16, 2006, provisional application No. 60/783,121, filed on Mar. 16, 2006, provisional application No. 60/783,590, filed on Mar. 16, 2006, provisional application No. 60/783,748, filed on Mar. 16, 2006, provisional application No. 60/831,416, filed on Jul. 17, 2006, provisional application No. 60/846,993, filed on Sep. 25, 2006, provisional application No. 60/918,261, filed on Mar. 15, 2007.

(51) Int. Cl.
*A61K 31/47* (2006.01)
*C07D 213/00* (2006.01)

(52) U.S. Cl.
USPC .......................................... 546/308; 514/307

(58) Field of Classification Search
None
See application file for complete search history.

(56) References Cited

FOREIGN PATENT DOCUMENTS

| | | |
|---|---|---|
| JP | 2005526723 | 9/2005 |
| WO | WO 99/21836 | 5/1999 |
| WO | WO 03/068749 | 8/2003 |
| WO | WO 03/080579 | 10/2003 |
| WO | WO 2004/035545 | 4/2004 |
| WO | WO 2004/106305 | 12/2004 |
| WO | WO 2004106324 A1 * | 12/2004 |
| WO | WO 2005/009968 | 2/2005 |
| WO | WO 2006/102588 | 9/2006 |
| WO | WO 2006/102610 | 9/2006 |
| WO | WO 2008/112205 | 9/2008 |

OTHER PUBLICATIONS

Baraldi, Pier Giovanni, et al., "Synthesis of Conformationally Constrained Analogues of KN62, a Potent Antagonist of the P2X7-Receptor," Bioorganic & Medicinal Chemistry Letters, 2000, vol. 10, pp. 681-684.

* cited by examiner

*Primary Examiner* — Janet Andres
*Assistant Examiner* — Heidi Reese
(74) *Attorney, Agent, or Firm* — Klauber & Jackson LLC

(57) ABSTRACT

Bicycloheteroaryl compounds are disclosed that have a formula represented by the following:

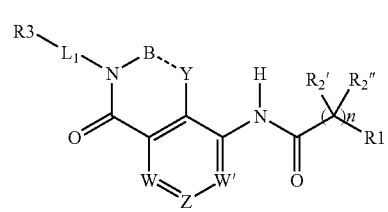

The compounds may be prepared as pharmaceutical compositions, and may be used for the prevention and treatment of a variety of conditions in mammals including humans, including by way of non-limiting example, pain, inflammation, traumatic injury, and others.

21 Claims, No Drawings

BICYCLOHETEROARYL COMPOUNDS AS P2X₇ MODULATORS AND USES THEREOF

CROSS REFERENCE TO RELATED APPLICATIONS

The present application is a National Stage Application claiming the priority of co-pending PCT Application No. PCT/US2007/006700 filed Mar. 16, 2007, which in turn, claims priority from U.S. Provisional application Ser. Nos.: 60/783,590; 60/783,748; 60/783,121; and 60/782,923, all filed Mar. 16, 2006; Ser. No. 60/831,416, filed Jul. 17, 2006; Ser. No. 60/846,993, filed Sep. 25, 2006; and Ser. No. 60/918,261, filed Mar. 15, 2007. Applicants claim the benefits of 35 U.S.C. §120 as to the PCT application and priority under 35 U.S.C. §119 as to the said U.S. Provisional applications, and the entire disclosures of all applications are incorporated herein by reference in their entireties.

FIELD OF THE INVENTION

This invention relates to novel compounds of the class bicycloheteroaryls that are capable of modulating $P2X_7$ receptor activity, and to pharmaceutical compositions containing such compounds. This invention also relates to methods for preventing and/or treating conditions that are causally related to aberrant $P2X_7$ activity, such as inflammation-related conditions in mammals, comprising (but not limited to) rheumatoid arthritis, osteoarthritis, Parkinson's disease, uveitis, asthma, cardiovascular conditions including myocardial infarction, the treatment and prophylaxis of pain syndromes (acute and chronic or neuropathic), traumatic brain injury, acute spinal cord injury, neurodegenerative disorders, inflammatory bowel disease and autoimmune disorders, using the compounds and pharmaceutical compositions of the invention.

BACKGROUND OF THE INVENTION

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members ($P2-X_1-P2X_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three primary ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, that has been interpreted to indicate that $ATP^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor ($rP2X_7$) thus corresponds to the P2Z receptor. $rP2X_7$ is structurally related to other members of the P2X family but it has a longer cytoplasmic C-terminus domain (there is 35-40% amino acid identity in the corresponding region of homology, but the C-terminus is 239 amino acids long in the $rP2X_7$ receptor compared with 27-20 amino acids in the others). The $rP2X_7$ receptor functions both as a channel permeable to small cations and as a cytolytic pore. Brief applications of ATP (1-2s) transiently open the channel, as is the case of other P2X receptors. Repeated or prolonged applications of agonist cause cell permeabilization reducing the extracellular magnesium concentration potentiates this effect. The unique C-terminal domain of $rP2X_7$ is required for cell permeabilization and the lytic actions of ATP (Suprenant et al, Science 272:735 (1996)).

The $P2Z/rP2X_7$ receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). Certain functional differences exist between rodent and man (Hickman et al, Blood 84:2452 (1994)). The human macrophage $P2X_7$ receptor ($P2X_7$) has now been cloned and its functional properties determined (Rassendren et al, J. Biol. Chem. 272:5482 (1997). When compared with the rat $P2X_7$ receptor, elicited cation-selective currents in the human $P2X_7$ receptor required higher concentrations of agonists, were more potentiated by removal of extracellular magnesium ions, and revised more rapidly on agonist removal. Expression of chimeric molecules indicated that some of the differences between rat and human $P2X_7$ receptors could be revised by exchanging the respective C-terminal domains of the receptor proteins.

It has been reported that certain compounds act as $P2X_7$ antagonists. For example, WO99/29660 and WO99/29661 disclose that certain adamantane derivatives exhibit $P2X_7$ antagonistic activity having therapeutic efficacy in the treatment of rheumatoid arthritis and psoriasis. Similarly, WO99/29686 discloses that certain heterocyclic derivatives are $P2X_7$ receptor antagonists and are useful as immunosuppressive agents and treating rheumatoid arthritis, asthma, septic shock and atherosclerosis. Finally, WO00/71529 discloses certain substituted phenyl compounds exhibiting immunosuppressing activity. All of the references described herein are incorporated herein by reference in their entirety.

A need therefore exists for therapeutic agents, and corresponding pharmaceutical compositions and related methods of treatment, that address the conditions causally related to aberrant $P2X_7$ activity, and it is toward the fulfillment and satisfaction of that need, that the present invention is directed.

SUMMARY OF THE INVENTION

Bicycloaryl derivatives of formulae I-XIIj, and their pharmaceutical compositions are disclosed as therapeutic agents useful for the treatment of conditions in mammals associated with abnormal or aberrant activity of the $P2X_7$ receptor, including inflammatory-mediated conditions such as (but not limited to) arthritis, myocardial infarction, the treatment and prophylaxis of pain syndromes (acute and chronic [neuropathic]), traumatic brain injury, acute spinal cord injury, neurodegenerative disorders, inflammatory bowel disease and immune dysfunctions such as autoimmune disorders.

It has now been found that the present bicycloheteroaryl compounds are capable of mediating the activity of the $P2X_7$ receptor. This finding leads to novel compounds having therapeutic value. It also leads to pharmaceutical compositions having the compounds of the present invention as active ingredients and to their use to treat, prevent or ameliorate a range of conditions in mammals such as but not limited to inflammation of various genesis or etiology, for example rheumatoid arthritis, cardiovascular disease, inflammatory bowel disease, acute, chronic, inflammatory and neuropathic pain, dental pain and headache (such as migraine, cluster headache and tension headache) and other conditions causally related to inflammation or immune dysfunction.

The compounds of the present invention are also useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, uveitis, asthma, myocardial infarction, traumatic brain injury, spinal cord injury, neurodegenerative disorders, inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides bicycloheteroaryl compounds which are capable of modulating the activity of the $P2X_7$ receptor, in vivo. In a further aspect, the compounds of the invention are capable of antagonizing (suppressing or inhibiting) the activity of the $P2X_7$ receptor, and thereby treating those conditions, representative ones of which are causally related to aberrant $P2X_7$ activity.

The compounds of the present invention may show low toxicity, good absorption, good half-life, good solubility, low protein binding affinity, low drug-drug interaction, low inhibitory activity at the HERG channel, low QT prolongation and good metabolic stability.

Accordingly, in a first aspect of the invention, bicycloheteroaryl compounds are disclosed that are capable of capable of modulating the activity of the $P2X_7$ receptor in vivo, having a formula (I):

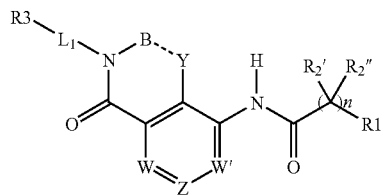

wherein
B and Y are independently selected from $CR^{2a}$ and $CR^{2a}R^{2b}$;
W, W' and Z are independently selected from $CR^4$ and N, provided that all three of W, W' and Z are not N at the same time;
$L^1$ is substituted or unsubstituted $C_1$-$C_5$ alkylene;
n is 0, 1, 2, 3 or 4;
$R^1$ is selected from a substituted or unsubstituted 3-13 membered cycloalkyl, heterocycloalkyl, aryl and heteroaryl ring;
each of $R^{2a}$, $R^{2b}$, $R^{2'}$ and $R^{2''}$ is independently selected from hydrogen, halo, and substituted or unsubstituted $C_1$-$C_6$ alkyl; or any of $R^{2'}$ and $R^{2''}$ join together to form a cycloalkyl or cycloheteroalkyl ring of 3-7 atoms;
$R^3$ is hydrogen or a functional group selected from acyl, substituted acyl, substituted or unsubstituted acylamino, substituted or unsubstituted alkylamino, substituted or unsubstituted dialkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted carbamoyl, cyano, substituted or unsubstituted cycloalkyl, substituted or unsubstituted cycloheteroalkyl, halo, heteroaryloxy, substituted or unsubstituted heteroaryl, substituted or unsubstituted heteroalkyl, nitro, and thio; provided that $R^3$ is other than hydrogen bond donor group;

$R^4$ is independently selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;

or a pharmaceutically acceptable salt, solvate or prodrug thereof;

and stereoisomers, isotopic variants and tautomers thereof.

In a further embodiment, with respect to compounds of formulae I, n is 0-4. In another embodiment, n is 0-2. In a particular embodiment, n is 1.

In a further embodiment, with respect to compounds of formula I, $L^1$ is a $C_1$-$C_5$ alkylene group unsubstituted or substituted by one or more substituents selected from alkyl, oxo, aryl, hydroxyl, or hydroxyalkyl.

In a further embodiment, with respect to compounds of formula I, B and Y are independently selected from $CR^{2a}$ and $CR^{2a}R^{2b}$.

In a further embodiment, with respect to compounds of formula I B and Y are independently selected from $CR^{2a}R^{2b}$ and the dotted bond is a single bond.

In a further embodiment, with respect to compounds of formula I, B and Y may all represent $CH_2$ and the dotted bond is a single bond.

In a further embodiment, with respect to compounds of formula I, B and Y are independently selected from $CR^{2a}$ and the dotted bond is a double bond.

In a further embodiment, with respect to compounds of formula I, B and Y may all represent CH and the dotted bond is a double bond.

In a further embodiment, with respect to compounds of formula I, n is 0, 1 or 2. In one particular embodiment, n is 1.

In another embodiment, with respect to compounds of formula I, each of $R^{2'}$ and $R^{2''}$ of the

group is H or Me. In one particular embodiment, each of $R^{2'}$ and $R^{2''}$ is H.

In a further embodiment, with respect to compounds of formula I, one of $R^{2'}$ and $R^{2''}$ of the

group may be selected from Me, Et, halo and Cl, and the other is H.

In a further embodiment, with respect to compounds of formula I, $R^1$ is substituted or unsubstituted aryl. In one particular embodiment, $R^1$ is substituted or unsubstituted phenyl.

In a further embodiment, with respect to compounds of formula I, $R^1$ is substituted or unsubstituted cycloalkyl. In another embodiment, $R^1$ is substituted or unsubstituted adamantyl. In yet another embodiment, $R^1$ is substituted or unsubstituted cyclohexyl or cycloheptyl.

In a further embodiment, with respect to compounds of formula I, each of W and W' is N.

In a further embodiment, with respect to compounds of formula I, each of W, Z and W' is $CR^4$. In one particular embodiment, each of W, Z and W' is CH.

In a further embodiment, with respect to compounds of formula I, each of W and Z is $CR^4$, W' is $CR^5$ and $R^5$ is H, alkyl, cycloalkyl or halo. In one embodiment. $R^5$ is halo or alkyl. In a particular embodiment, $R^5$ is H or halo. In a yet further particular embodiment, $R^5$ is H, Cl, F, Me or cyclopropyl.

In a further aspect, the present invention provides pharmaceutical compositions comprising a bicycloheteroaryl compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. inflammation, such as rheumatoid arthritis, osteoarthritis, uveitis, asthma, myocardial infarction, traumatic brain injury; septic shock, atherosclerosis, chronic pulmonary obstructive disease (COPD), acute spinal cord injury; inflammatory bowel disease and immune dysfunction, including autoimmune disorders, which method comprises administering an effective amount of one or more of the pharmaceutical compositions just described.

In yet another method of treatment aspect, this invention provides a method of treating a mammal susceptible to or afflicted with a condition that is causally related to aberrant $P2X_7$ receptor activity, and that for example, gives rise to pain responses or that relates to imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with conditions that are causally related to abnormal activity of the $P2X_7$ receptor, such as neurodegenerative diseases and disorders including, for example, Parkinson's disease, multiple sclerosis; diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and cardiovascular and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of the $P2X_7$ receptor and thus avert or treat any maladies that may be causally related thereto.

It is further an object of this invention to provide a series of compounds that can treat or alleviate maladies or symptoms of same, such as pain and inflammation, that may be causally related to the activation of the $P2X_7$ receptor.

A still further object of this invention is to provide pharmaceutical compositions that are effective in the treatment or prevention of a variety of disease states, including the diseases associated with the central nervous system, cardiovascular conditions, chronic pulmonary obstructive disease COPD), inflammatory bowel disease, rheumatoid arthritis, osteoarthritis, and other diseases where an inflammatory component is present.

Other objects and advantages will become apparent to those skilled in the art from a consideration of the ensuing detailed description.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, $C_2$-$C_6$ alkenyl, $C_3$-$C_6$ alkenyl, $C_1$-$C_6$ alkoxy, aryl and di-$C_1$-$C_6$ alkylamino. It should be further understood that the terms "groups" and "radicals" can be considered interchangeable when used herein.

"Acyl" refers to a radical —C(O)R$^{20}$, where R$^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR$^{21}$C(O)R$^{22}$, where R$^{21}$ is hydrogen, alkyl, cycloalkyl, cycloheteroalkyl, aryl, arylalkyl, heteroalkyl, heteroaryl, heteroarylalkyl and R$^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene; indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

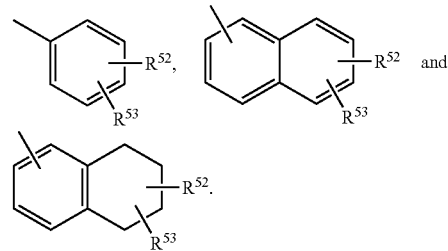

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

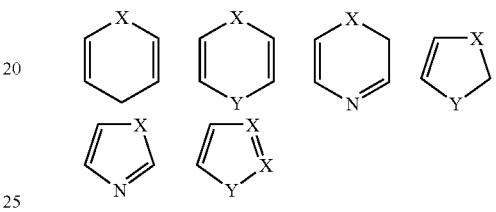

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

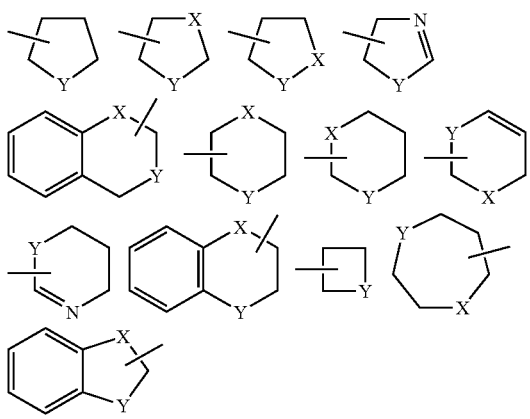

wherein each X is selected from CR$^{58}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

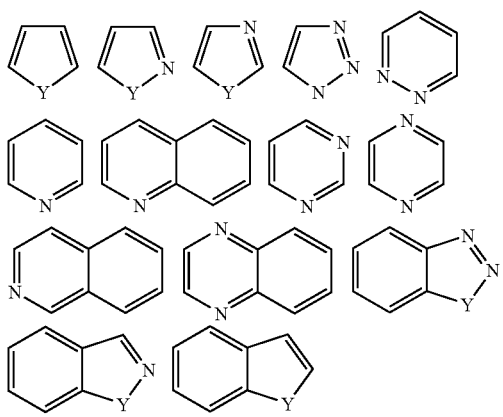

wherein each X is selected from CR$^{58}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

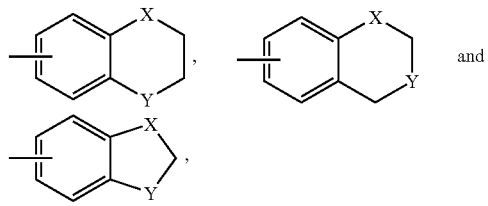

wherein each X is selected from C—R$^{58}_2$, Ne$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on A, B, W, Y or Z of the compounds of this invention' or may be present as a substituent in the "substituted" aryl and aliphatic groups present in the compounds.

Examples of hetero substituents include:
—halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$
wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, N—H functionality. Examples of "hydrogen bond donor" groups include —OH, —NH$_2$, and —NH—R$^{59a}$ and wherein R$^{59}$a is alkyl, cycloalkyl, aryl, or heteroaryl.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" or "substituted sulfonamide" refers to a radical such as R$^{62}$$_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides bicycloheteroaryl compounds useful for preventing and/or treating a broad range of conditions, associated with abnormalities in the activity of the P2X$_7$ receptor, among them, rheumatoid arthritis, Parkinson's disease, uveitis, asthma, cardiovascular conditions such as myocardial infarction, the treatment and prophylaxis of pain syndromes (acute and chronic or neuropathic), traumatic brain injury, acute spinal cord injury, neurodegenerative disorders, inflammatory bowel disease and immune dysfunctions such as autoimmune disorders or conditions, in mammals.

In a first aspect of the invention, bicycloheteroaryl compounds are disclosed that are capable of capable of modulating the activity of the P2X$_7$ receptor in vivo, having a formula (I):

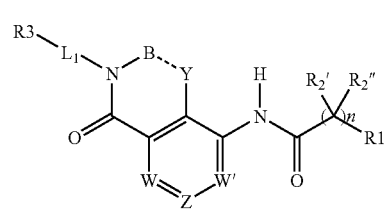

wherein
B and Y are independently selected from $CR^{2a}$ and $CR^{2a}R^2b$;
W, W' and Z are independently selected from $CR^4$ and N, provided that all three of W, W' and Z are not N at the same time;
$L^1$ is substituted or unsubstituted $C_1$-$C_5$ alkylene;
n is 0, 1, 2, 3 or 4;
$R^1$ is selected from a substituted or unsubstituted 3-13 membered cycloalkyl, heterocycloalkyl, aryl and heteroaryl ring;

each of $R^{2a}$, $R^{2b}$, $R^{2'}$ and $R^{2''}$ is independently selected from hydrogen, halo, and substituted or unsubstituted $C_1$-$C_6$ alkyl; or any of $R^{2'}$ and $R^{2''}$ join together to form a cycloalkyl or cyclohetereoalkyl ring of 3-7 atoms;

$R^3$ is hydrogen or a functional group selected from acyl, substituted acyl, substituted or unsubstituted acylamino, substituted or unsubstituted alkylamino, substituted or unsubstituted dialkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted carbamoyl, cyano, substituted or unsubstituted cycloalkyl, substituted or unsubstituted cycloheteroalkyl, halo, heteroaryloxy, substituted or unsubstituted heteroaryl, substituted or unsubstituted heteroalkyl, nitro, and thio; provided that $R^3$ is other than a hydrogen bond donor group;

$R^4$ is independently selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;
or a pharmaceutically acceptable salt, solvate or prodrug thereof;
and stereoisomers, isotopic variants and tautomers thereof.

In a further embodiment, with respect to compounds of formulae I, n is 0-4. In another embodiment, n is 0-2. In a particular embodiment, n is 1.

In a further embodiment, with respect to compounds of formula I, $L^1$ is a $C_1$-$C_5$ alkylene group unsubstituted or substituted by one or more substituents selected from alkyl, oxo, aryl, hydroxyl, or hydroxyalkyl.

In a further embodiment, with respect to compounds of formula I, B and Y are independently selected from $CR^{2a}$ and $CR^{2a}R^{2b}$.

In a further embodiment, with respect to compounds of formula I, B and Y are independently selected from $CR^{2a}R^{2b}$ and the dotted bond is a single bond.

In a further embodiment, with respect to compounds of formula I, B and Y may all represent $CH_2$ and the dotted bond is a single bond.

In a further embodiment, with respect to compounds of formula I, B and Y are independently selected from $CR^{2a}$ and the dotted bond is a double bond.

In a further embodiment, with respect to compounds of formula I, B and Y may all represent CH and the dotted bond is a double bond.

In a further embodiment, with respect to compounds of formula I, n is 0, 1 or 2. In one particular embodiment, n is 1.

In another embodiment, with respect to compounds of formula I, each of $R^{2'}$ and $R^{2''}$ of the

group is H or Me. In one particular embodiment, each of $R^{2'}$ and $R^{2''}$ is H.

In a further embodiment, with respect to compounds of formula I, one of $R^{2'}$ and $R^{2''}$ of the

group may be selected from Me, Et, halo and Cl, and the other is H.

In a further embodiment, with respect to compounds of formula I, $R^1$ is substituted or unsubstituted aryl. In one particular embodiment, $R^1$ is substituted or unsubstituted phenyl.

In a further embodiment, with respect to compounds of formula I, $R^1$ is substituted or unsubstituted cycloalkyl. In another embodiment, $R^1$ is substituted or unsubstituted adamantyl. In yet another embodiment, $R^1$ is substituted or unsubstituted cyclohexyl or cycloheptyl.

In a further embodiment, with respect to compounds of formula I, each of W and W' is N.

In a further embodiment, with respect to compounds of formula I, each of W, Z and W' is $CR^4$. In one particular embodiment, each of W, Z and W' is CH.

In a further embodiment, with respect to compounds of formula I, each of W and Z is $CR^4$, W' is $CR^5$ and $R^5$ is selected from alkyl, substituted alkyl, cycloalkyl, substituted cycloalkyl and halo. In one particular embodiment, $R^5$ is selected from Me, cyclopropyl, Cl, F and $CF_3$.

In another embodiment, with respect to compounds of formula I, the compound is according to formula II, III or IV:

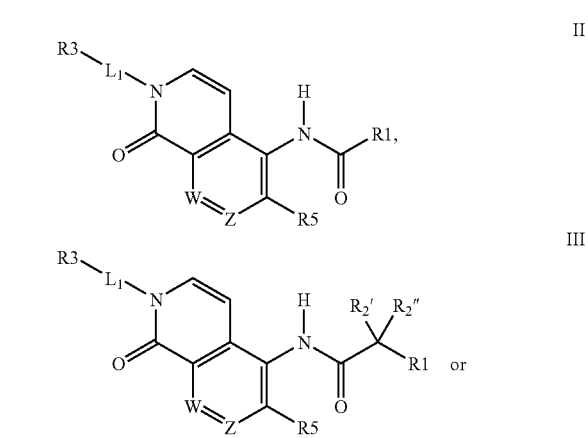

IV

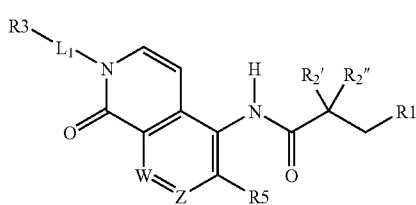

wherein
W is CR⁴; Z is CR⁴;
L¹, R¹ R²', R²", R³ and R⁴ are as described for formula I;
and R⁵ is selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
or a pharmaceutically acceptable salt, solvate or prodrug thereof;
and stereoisomers, isotopic variants and tautomers thereof.

In another embodiment, with respect to compounds of formulae III-IV each of $R^{2'}$ and $R^{2''}$ is H.

In another embodiment, with respect to compounds of formulae III-IV, $R^{2'}$ is halo; and $R^{2''}$ is H.

In another embodiment, with respect to compounds of formulae III-IV, $R^{2'}$ is Cl or F; and $R^{2''}$ is H.

In another embodiment, with respect to compounds of formulae III-IV, $R^{2'}$ is Me or Et; and $R^{2''}$ is H.

In another embodiment, with respect to compounds of formulae III-IV, each of $R^{2'}$ and $R^{2''}$ is Me.

In a more particular embodiment, with respect to compounds of formulae III-IV, $R^{2'}$ is Me; and $R^{2''}$ is H.

In another embodiment, with respect to compounds of formulae II-IV, each of $R^1$ is substituted or unsubstituted aryl.

In another embodiment, with respect to compounds of formulae II-IV, each of $R^1$ is substituted or unsubstituted phenyl or naphthalene.

In another embodiment, with respect to compounds of formulae II-IV, each of $R^1$ is substituted or unsubstituted naphthalene.

In another embodiment, with respect to compounds of formulae II-IV, each of $R^1$ is unsubstituted naphthalene.

In another embodiment, with respect to compounds of formulae II-IV, each of $R^1$ is substituted or unsubstituted phenyl.

In another embodiment, with respect to compounds of formulae II-IV, each of $R^1$ is substituted or unsubstituted heteroaryl.

In another embodiment, with respect to compounds of formulae II-IV, each of $R^1$ is substituted or unsubstituted pyridyl, quinoline, benzodioxole, benzodioxane, benzofuran, benzothiophene, and benzodioxepine.

In another embodiment, with respect to compounds of formula I, the compound is according to formula V, VI or VII:

V

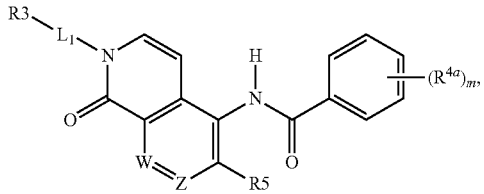

VI

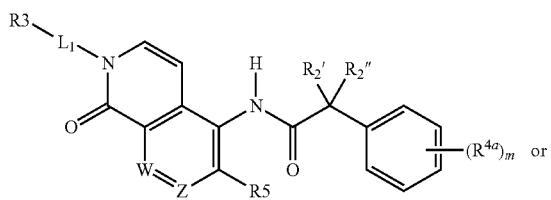

or

VII

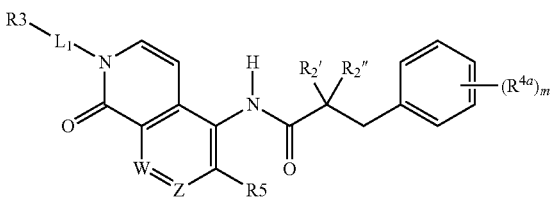

wherein
W is CR⁴; Z is CR⁴;
L¹, R¹ R²', R²", R³ and R⁴ are as described for formula I; R⁵ is as described for formulae II-IV;
R⁴ᵃ is selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5;
or a pharmaceutically acceptable salt, solvate or prodrug thereof;
and stereoisomers, isotopic variants and tautomers thereof.

With respect to the compounds of the invention wherein m is 0-5 as set forth above, and at any and all locations herein, it is to be understood that when m=0, the ring is unsubstituted.

In one embodiment, with respect to compounds of formulae VI-VII, each of $R^{2'}$ and $R^{2''}$ is H.

In another embodiment, with respect to compounds of formulae VI-VII, $R^{2'}$ is halo; and $R^{2''}$ is H.

In another embodiment, with respect to compounds of formulae VI-VII, $R^{2'}$ is Cl or F; and $R^{2''}$ is H.

In another embodiment, with respect to compounds of formulae VI-VII, $R^{2'}$ is Me or Et; and $R^{2''}$ is H.

In another embodiment, with respect to compounds of formulae VI-VII, each of $R^{2'}$ and $R^{2''}$ is Me.

In a more particular embodiment, with respect to compounds of formulae VI-VII, $R^{2'}$ is Me; and $R^{2''}$ is H.

In another embodiment, with respect to compounds of formula I, the compound is according to formula VIII, IX or X:

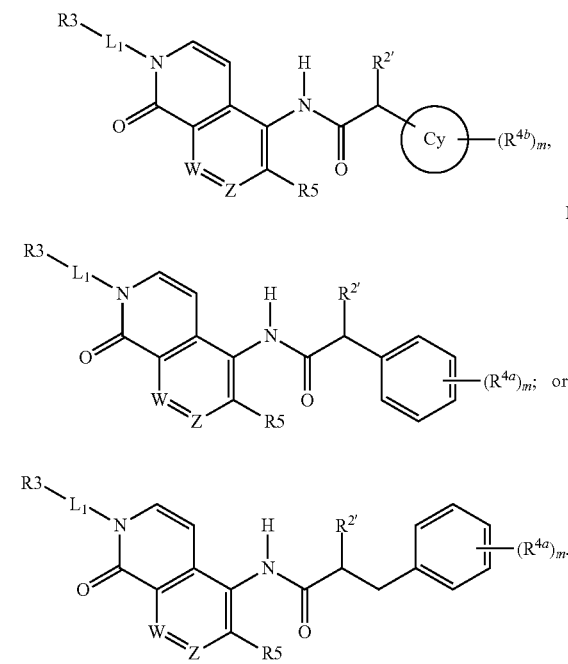

wherein
W is $CR^4$; Z is $CR^4$;
$L^1$, $R^3$ and $R^4$ are as described for formula I; $R^5$ is as described for formulae II-IV; m and $R^{4a}$ are as described for formulae V-VII; $R^{2'}$ is H or Me; Cy is adamantyl, cyclohexyl or cycloheptyl; and each $R^{4b}$ is independently selected from $C_1$-$C_4$ alkyl and hydroxy; or a pharmaceutically acceptable salt, solvate or prodrug thereof;
and stereoisomers, isotopic variants and tautomers thereof.

In one embodiment, with respect to compounds of formulae V-X, R is H or
Me. In another embodiment, $R^{2'}$ is Me. In one particular embodiment, $R^{2'}$ is H.

In another embodiment, with respect to compounds of formulae V-X, in is 1, 2 or 3.

In another embodiment, with respect to compounds of formulae V-X, m is 1 or 2. In a particular embodiment m is 1.

In another embodiment, with respect to compounds of formulae V-X, each of $R^{4a}$ is independently selected from Me, Et, Ph, Cl, F, Br, CN, OH, OMe, OEt, OPh, COPh, $CF_3$, $CHF_2$, $OCF_3$, i-Pr, t-Bu, SMe, $CH=CH-CO_2H$, SOMe, $SO_2Me$, $SO_3H$, $SO_3Me$, and pyridyl.

In another embodiment, with respect to compounds of formulae I-X, $L^1$ is a $C_1$-$C_5$ alkylene group.

In another embodiment, with respect to compounds of formulae I-X, $L^1$ is a $C_1$-$C_5$ alkylene group unsubstituted or substituted by one or more substituents selected from alkyl, hydroxyl, oxo and hydroxyalkyl.

In another embodiment, with respect to compounds of formulae I-X, $L^1$ is an ethylene group unsubstituted or substituted by one or more substituents selected from Me, Et, i-Pr, hydroxy, and hydroxymethyl.

In another embodiment, with respect to compounds of formulae I-X, $L^1$ is a methylene group unsubstituted or substituted by one or more substituents selected from Me, Et, i-Pr, and hydroxymethyl.

In another embodiment, with respect to compounds of formulae I-X, $R^3$ is selected from alkyl, dialkylamino, acyloxy, alkoxy, and —$SO_2$-alkyl.

In another embodiment, with respect to compounds of formulae I-X, $R^3$ is selected from t-Bu, NMe2, $SO_2Me$, OMe, and OCOMe.

In another embodiment, with respect to compounds of formulae I-X, $R^3$ is substituted or unsubstituted aryl, heteroaryl, cycloalkyl or cycloheteroalkyl.

In another embodiment, with respect to compounds of formulae I-X, $R^3$ is substituted or unsubstituted phenyl, pyridyl, pyran, tetrahydropyran, piperidine, morpholine, pyrrolidine, pyrrolidinone and benzodioxane In another embodiment, with respect to compounds of formulae I-X, the group -$L_1$-$R^3$ is selected from

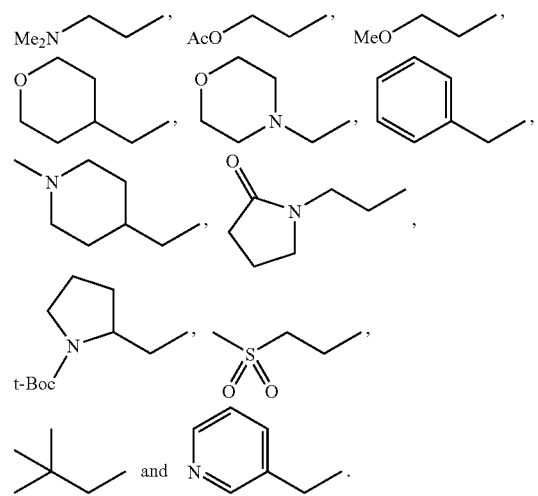

In another embodiment, with respect to compounds of formula I, the compound is according to formula XIa, XIb, XIc, XId, XIe, XIf, XIg, XIh or XIj:

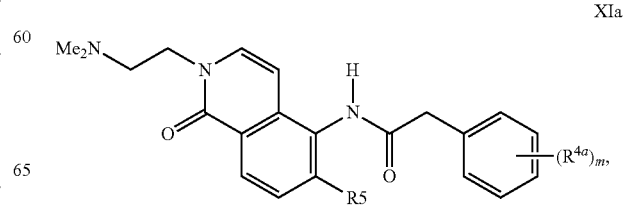

-continued

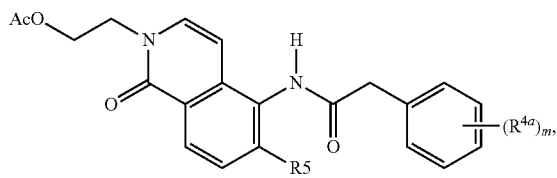
XIb

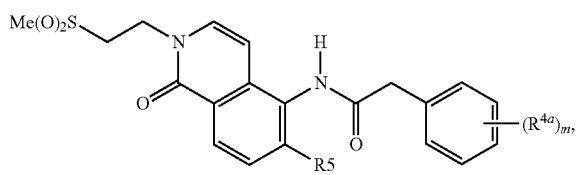
XIc

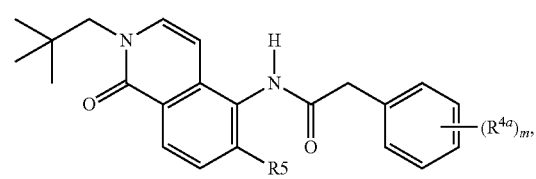
XId

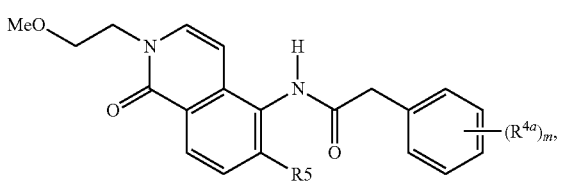
XIe

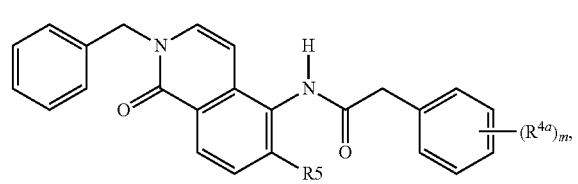
XIf

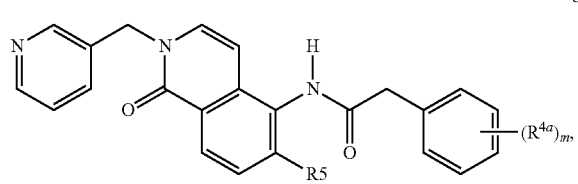
XIg

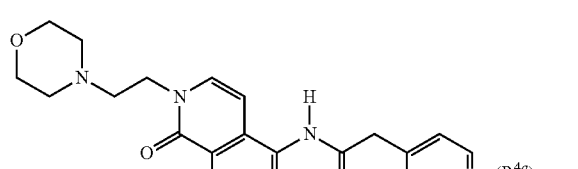
XIh

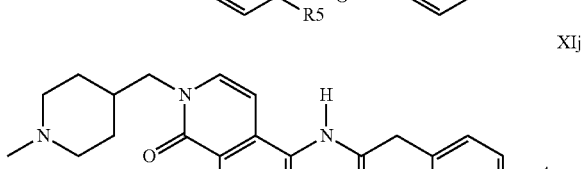
XIj wherein m and $R^{4a}$ are as described for formulae V-VII; and $R^5$ is selected from H, alkyl, or halo.

In one embodiment, with respect to compounds of formulae V-XIj, m is 1, 2 or 3.

In another embodiment, with respect to compounds of formulae V-XIj, m is 1 or 2. In a particular embodiment m is 2.

In another embodiment, with respect to compounds of V-XIj, each of $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2H$, SOMe, $SO_2Me$, $SO_3H$, $SO_3Me$, and pyridyl.

In another embodiment, with respect to compounds of V-XIj, m is 1 and $R^a$ is $CF_3$.

In another embodiment, with respect to compounds of V-XIj, m is 2 and $R^{4a}$ is F and $CF_3$.

In another embodiment, with respect to compounds of V-XIj, m is 2 and $R^{4a}$ is F and Cl.

In another embodiment, with respect to compounds of formula I, the compound is according to formula XIIa, XIIb, XIIc, XIId, XIIe, XIIf, XIIg, XIIh or XIIj:

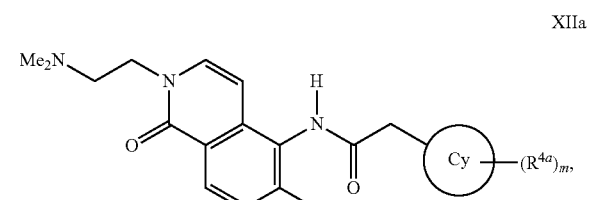
XIIa

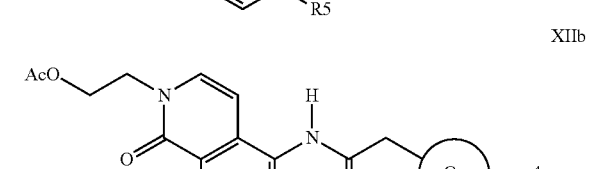
XIIb

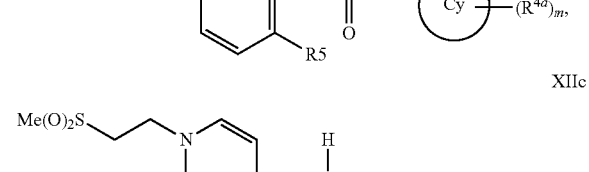
XIIc

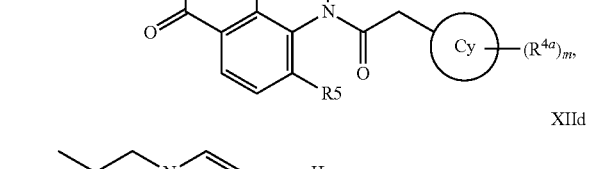
XIId

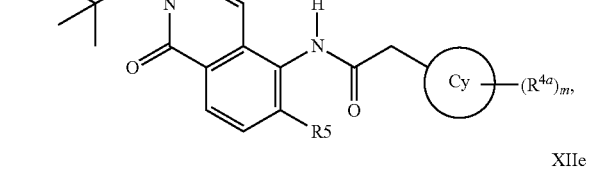
XIIe

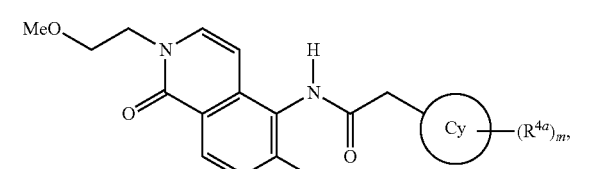

-continued

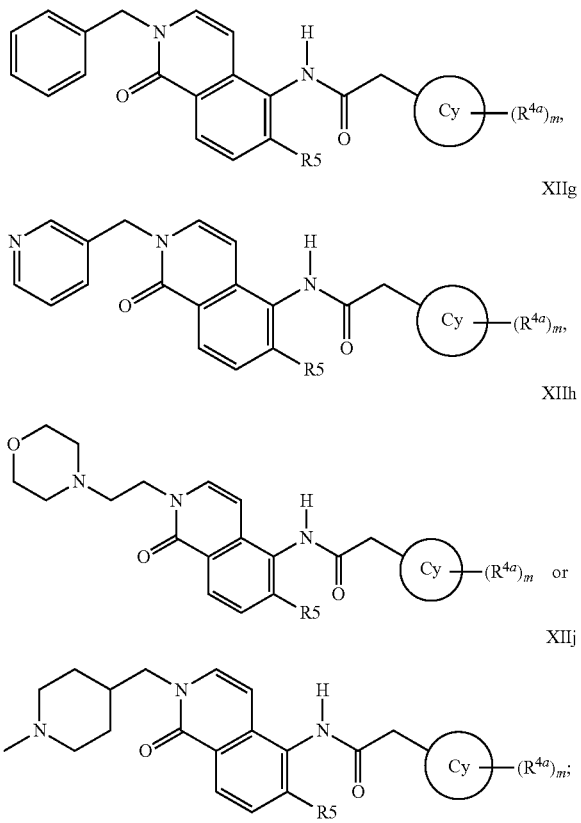

wherein Cy is cyclohexyl or cycloheptyl; $R^{4a}$ is independently selected from hydrogen, alkyl, substituted alkyl, or hydroxyl; m is selected from 0-5; and $R^5$ is selected from H, alkyl, or halo.

In another embodiment, with respect to compounds of formulae XIIa-XIIj, Cy is cyclohexyl; m is 1 and $R^{4a}$ is hydroxy.

In another embodiment, with respect to compounds of formulae XIIa-XIIj, m is 1 and $R^{4a}$ is hydroxy.

In another embodiment, with respect to compounds of formulae XIIa-XIIj, m is 1-4 and $R^{4a}$ is methyl.

In another embodiment, with respect to compounds of formulae XIIa-XIIj, m is 1-4 and $R^{4a}$ is methyl.

In one embodiment, with respect to compounds of formulae I-X, each of W and Z is independently $CR^4$.

In one embodiment, with respect to compounds of formulae I-X, each of W and Z is independently CH.

In one embodiment, with respect to compounds of formulae I-X, W is N.

In one embodiment, with respect to compounds of formulae I-X, W is N and Z is H.

In one embodiment, with respect to compounds of formulae II-XIIj, $R^5$ is H.

In one embodiment, with respect to compounds of formulae II-XXIIj, $R^5$ is selected from alkyl, cycloalkyl, substituted alkyl and halo. In one particular embodiment, $R^5$ is selected from Me, cyclopropyl, Cl, F and $CF_3$.

In one embodiment, with respect to compounds of formulae II-XIIj, $R^5$ is Me.

In one embodiment, with respect to compounds of formulae II-XIIj, $R^5$ is $CF_3$.

In one embodiment, with respect to compounds of formulae II-XIIj, $R^5$ is F.

In a further embodiment with respect to compounds of formulae II-XIIj, $R^5$ is Cl.

In a further embodiment with respect to compounds of formulae II-XIIId, $R^5$ is cyclopropyl.

In certain aspects, the present invention provides prodrugs and derivatives of the compounds according to the formulae above. Prodrugs are derivatives of the compounds of the invention, which have metabolically, cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound—administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the $P2X_7$ receptor. Accordingly, the compounds and pharmaceutical compositions of this invention find use as therapeutics for preventing and/or treating autoimmune, inflammatory and cardiovascular conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, multiple sclerosis; diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, N.Y., 1991, and references cited therein.

The following schemes are presented with details as to the preparation of representative bicycloheteroaryls that have been listed hereinabove. The compounds of the invention may be prepared from known or commercially available starting materials and reagents by one skilled in the art of organic synthesis.

Representative Scheme 1

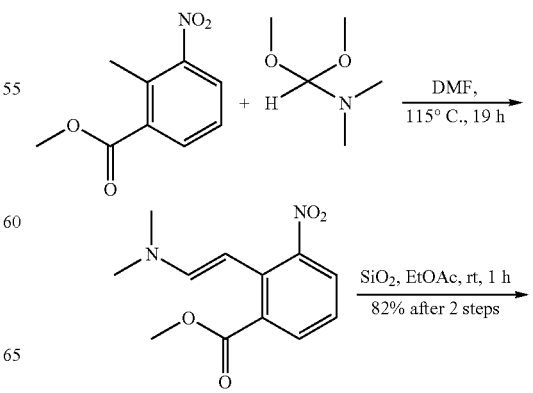

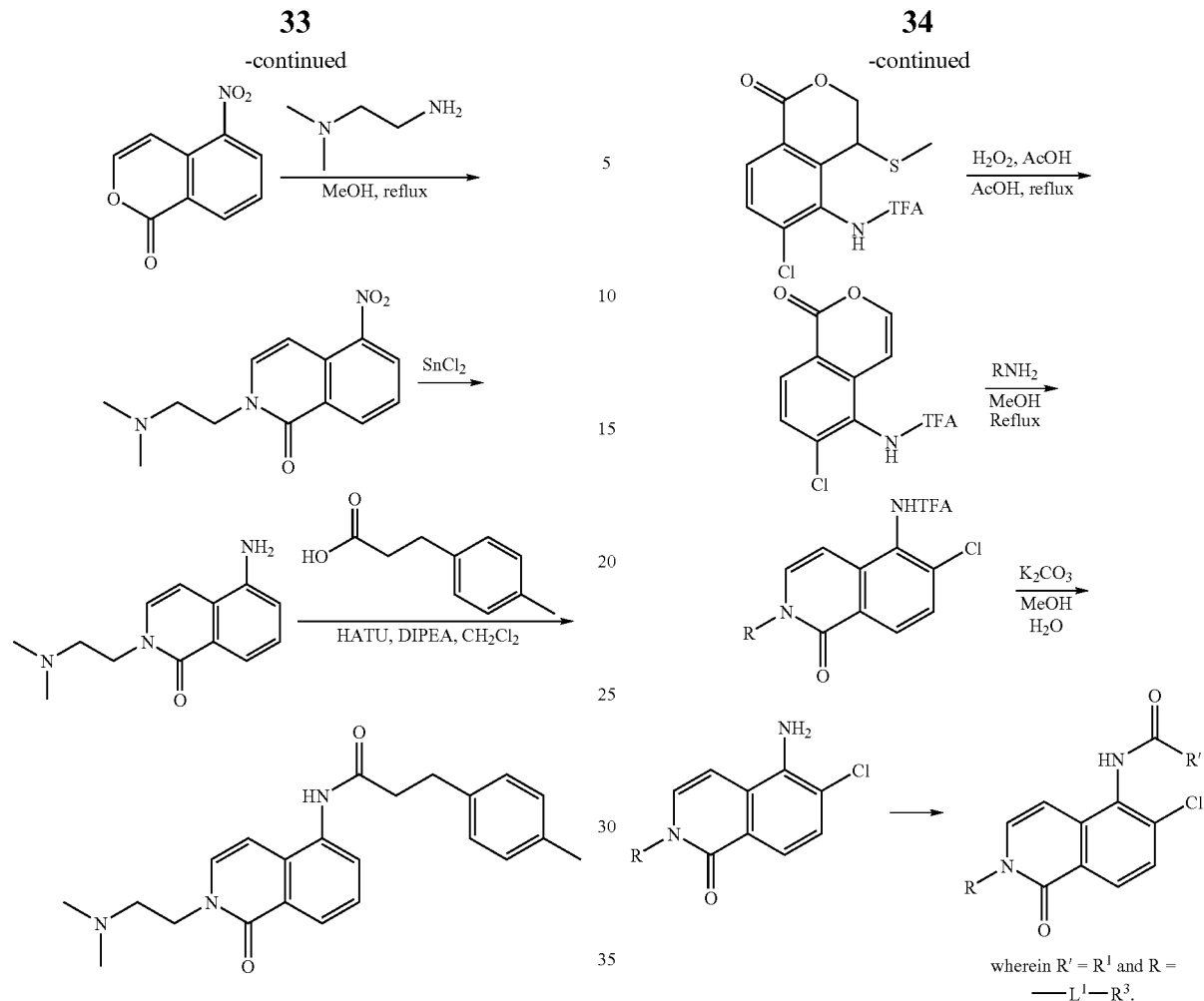

SYNTHESIS OF INTERMEDIATES

Intermediate 1

Preparation of (E)-methyl 2-(2-(dimethylamino)-vinyl)-3-nitrobenzoate

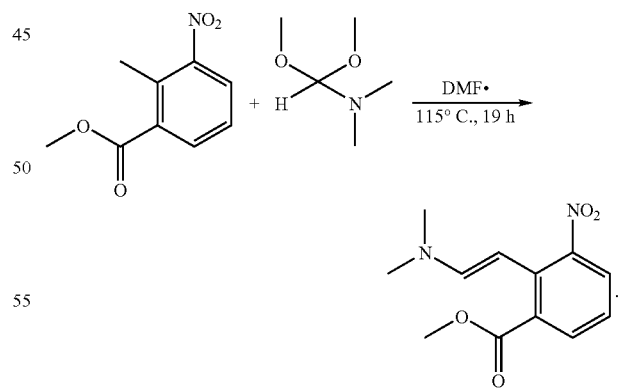

A mixture of methyl 2-methyl-3-nitrobenzoate (5.0 g, 25.6 mmol) and N,N-dimethylformamide dimethyl acetal (9.18 g, 77 mmol) in DMF (30 mL) was stirred at 115° C. for 17 h. The volatiles were removed under reduced pressure to give (E)-methyl 2-(2-(dimethylamino)-vinyl)-3-nitrobenzoate as brown oil.

$^1$H-NMR (300 MHz, CDCl$_3$) δ 7.68 (m, 2H), 7.07 (t, J=7.5 Hz 1H), 6.32 (d, J=13.5 Hz, 1H), 5.65 (d, J=13.5 Hz, 1H), 73.85 (s, 3H), 2.82 (s, 6H).

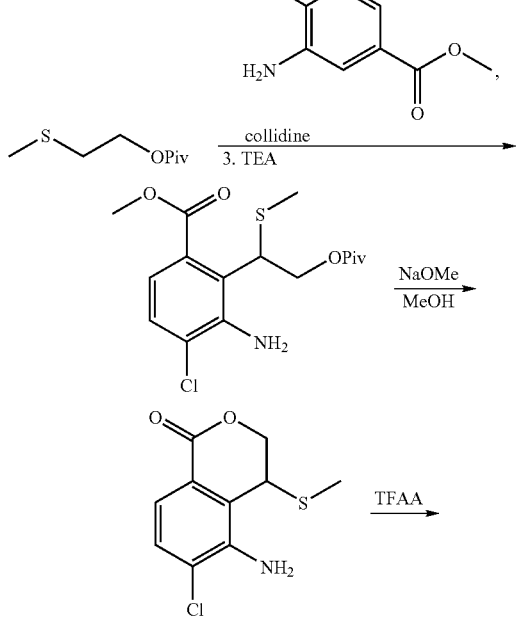

Intermediate 2

Preparation of 5-Nitro-1H-isochromen-1-one

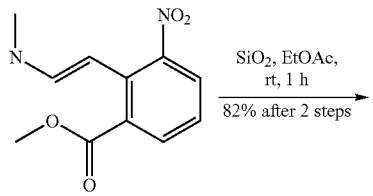

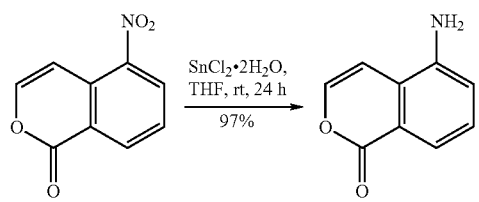 [SMILES: O=c1occc2c([N+](=O)[O-])cccc12 ; Nc1cccc2c(=O)occc12]

(E)-Methyl 2-(2-(dimethylamino)vinyl)-3-nitrobenzoate was re-dissolved in EtOAc (200 mL), and silica gel (200 g) was added. The resulting suspension was stirred at room temperature for 1 h. The EtOAc solution was filtered off. Silica gel was washed with EtOAc (2×150 mL) and the combined organics were evaporated and dried under reduced pressure to yield 5-nitro-1H-isochromen-1-one (4.0 g, 21.0 mmol, 82% after two steps) of as a brown solid.

$^1$H-NMR (300 MHz, CDCl$_3$) δ 8.62 (d, J=7.8 Hz, 1H), 8.47 (d, J=8.1 Hz, 1H), 7.65 (m, 1H), 7.42 (d, J=6.3 Hz, 1H), 7.36 (d, J=6.3 Hz, 1H). HPLC ret. time 1.72 min, 10-100% CH$_3$CN, 3.5 min gradient; ESI-MS m/z 192.1 (M+H)$^+$.

Additional information can be found in McDonald, M. C. et al. British J. Pharmacol. 2000, 130, 843, incorporated herein by reference.

Intermediate 3

Preparation of 5-Amino-1H-isochromen-1-one

Tin(II) chloride dihydrate (41.9 g, 185.7 mmol) was added to a stirred solution of 5-nitro-1H-isochromen-1-one (7.1 g, 37.1 mmol) in anhydrous THF (120 mL). The reaction mixture was stirred at room temperature for 18 h. The resulting mixture was diluted with EtOAc (400 mL) and treated with saturated aqueous sodium bicarbonate to pH=10. Water (100 mL) was added and the layers were separated. The aqueous phase was extracted with ethyl acetate (2×150 mL) and the combined organic fractions were dried over Na$_2$SO$_4$, filtered and evaporated to yield 5-amino-1H-isochromen-1-one (5.8 g, 36.0 mmol, 97%) as a yellow solid.

$^1$H-NMR (300 MHz, CD$_3$OD) δ 7.52 (d, J=7.8 Hz, 1H), 7.32 (d, J=5.7 Hz, 1H), 7.27 (t, J=7.8 Hz, 1H), 7.07 (d, J=7.8 Hz, 1H), 6.80 (d, J=5.7 Hz, 1H). HPLC ret. time 1.16 min, 10-100% CH$_3$CN, 3.5 min gradient; ESI-MS m/z 162.3 (M+H)$^+$. Additional information can be found in Lee, B. S.; et al. J. Org. Chem. 2004, 69, 3319 incorporated herein by reference.

Intermediate 4

Preparation of 2-(2-Dimethylamino-ethyl)-5-nitro-2H-isoquinolin-1-one

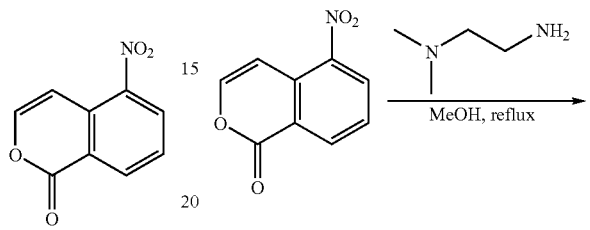

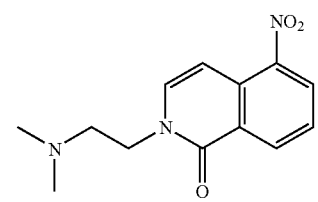

5-Nitro-isochromen-1-one (1.0 g, 5.2 mmol) and N,N-dimethyl-1,2-ethanediamine (4 g, 40 mmol) were refluxed in methanol (40 mL) for 1.5 hours. The volatiles were removed via rotovapor and the residue was purified via flash chromatography (12 of silica gel, 0-70% EtOAc/CH$_2$Cl$_2$ gradient) gave 2-(2-Dimethylamino-ethyl)-5-nitro-2H-isoquinolin-1-one as a yellow solid (1.4 g, 2.4 mmol, 46%).

LC/MS (0.1% formic acid modifier) calcd. (M+1)$^+$ 261.28, observed 262.2.

$^1$H NMR (CDCCl$_3$) δ 8.77 (d, J=7.4 Hz, 1H), 8.40 (d, J=8.0 Hz, 1H), 7.55 (t, J=8.0 Hz, 1H), 7.34-7.28 (m, 2H), 4.12 (t, J=6.4 Hz, 2H), 2.68 (t, J=6.4 Hz, 2H), 2.30 (s, 6H).

Intermediate 5

Preparation of 5-Amino-2-(2-dimethylamino-ethyl)-2H-isoquinolin-1-one

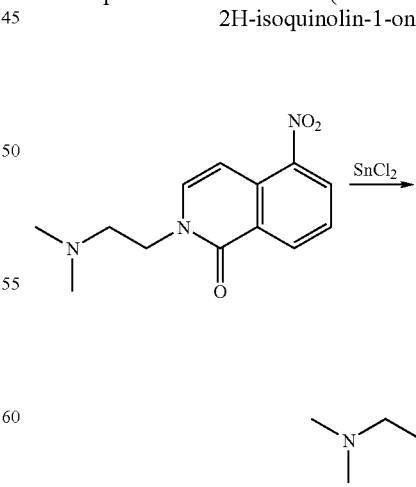

2-(2-Dimethylamino-ethyl)-5-nitro-2H-isoquinolin-1-one (0.67 g, 2.6 mmol) and dehydrate tin dichloride (2 g, 10 mml) were stirred in THF (10 mL) at room temperature for 24 hours. The volatiles were removed via rotovapor, and the residue was dissolved in $CH_2Cl_2$ (1 L), washed with aqueous saturated $NaHCO_3$ solution (30 mL×3). The organic layer was dried over $Na_2SO_4$, filtered and concentrated to dryness gave 5-Amino-2-(2-dimethylamino-ethyl)-2H-isoquinolin-1-one as a yellow solid. The compound was used for next steps without further purification.

$^1$H NMR ($CDCCl_3$) δ 7.88 (d, J=8.0 Hz, 1H), 7.27 (t, J=7.9 Hz, 1H), 7.08 (d, J=7.6 Hz, 1H), 6.93 (d, J=7.7 Hz, 1H), 6.41 (d, J=7.2 Hz, 1H), 4.08 (t, J=6.7 Hz, 2H), 2.66 (t, J=6.7 Hz, 2H), 2.29 (s, 6H).

Intermediate 6

Preparation of 2-Adamantan-1-yl-N-(1-oxo-1H-isochromen-5-yl)-acetamide

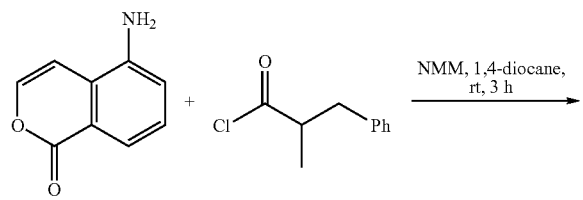

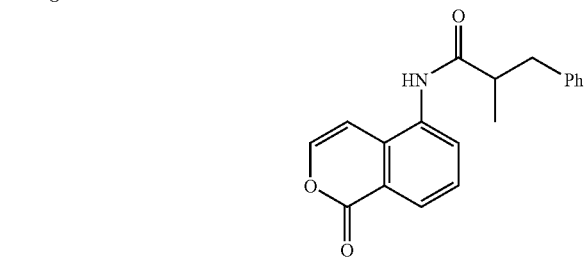

To a solution of 5-amino-1H-isochromen-1-one (2.95 g, 18.3 mmol) and NMM (2.02 mL, 18.3 mmol) in 1,4-dioxane (55 mL) is added dropwise at room temperature a solution of 1-methylphenethyl acid chloride (18.3 mmol) in 1,4-dioxane (40 mL). The reaction mixture is stirred at room temperature for 3 h and then is partitioned between DCM (400 mL) and water (200 mL). The layers are separated. The aqueous phase is washed with DCM (100 mL). The combined organic layers are dried over sodium sulfate, filtered and evaporated to yield the crude N-(1-oxo-1H-isochromen-5-yl)-acetamide derivative.

Preparation of N-[2-(2-Dimethylamino-ethyl)-1-oxo-1,2-dihydro-isoquinolin-5-yl]-3-p-tolyl-propionamide)

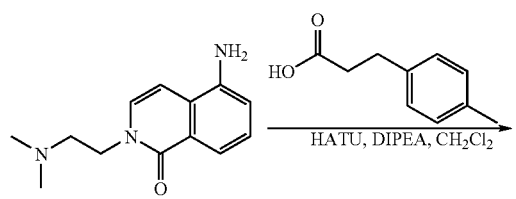

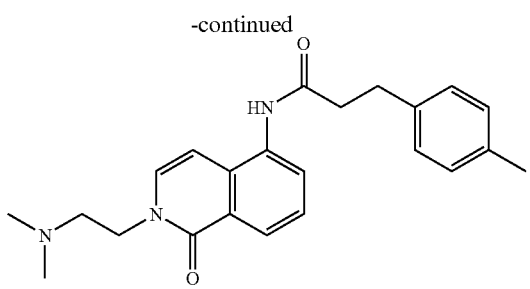

5-Amino-2-(2-dimethylamino-ethyl)-2H-isoquinolin-1-one (50 mg, 0.2 mmol), HATU (99 mg, 0.26 mmol), 3-(4-methylphenyl)propionic acid (42 mg, 0.26 mmol) and DIPEA (110 mg, 0.86 mmol) were stirred in methylene chloride (3 mL) at room temperature for 16 hours. The mixture was purified via flash chromatography (12 g of silica gel, 0-10% MeOH/$CH_2Cl_2$ gradient) gave N-[2-(2-Dimethylamino-ethyl)-1-oxo-1,2-dihydro-isoquinolin-5-yl]-3-p-tolyl-propionamide as a white solid (31 mg, 0.08 mmol, 40%).

LC/MS (0.1% formic acid modifier) calcd. $(M+1)^+$ 377.48, observed 378.2.

$^1$H NMR ($CDCCl_3$) δ 8.27 (d, J=8.0 Hz, 1H), 7.84 (d, J=7.6 Hz, 1H), 7.43 (t, J=7.9 Hz, 1H), 7.20-7.13 (m, 4H), 7.02 (d, J=7.6 Hz, 1H), 5.97 (d, J=7.6 Hz, 1H), 4.07 (t, J=6.5 Hz, 2H), 3.07 (t, J=7.3 Hz, 2H), 2.77 (t, J=7.3 Hz, 2H), 2.64 (t, J=6.5 Hz, 2H), 2.35 (s, 3H), 2.30 (s, 6H)

Preparation of N-[2-(2-Dimethylamino-ethyl)-1-oxo-1,2-dihydro-isoquinolin-5-yl]-2-p-tolyl-acetamide

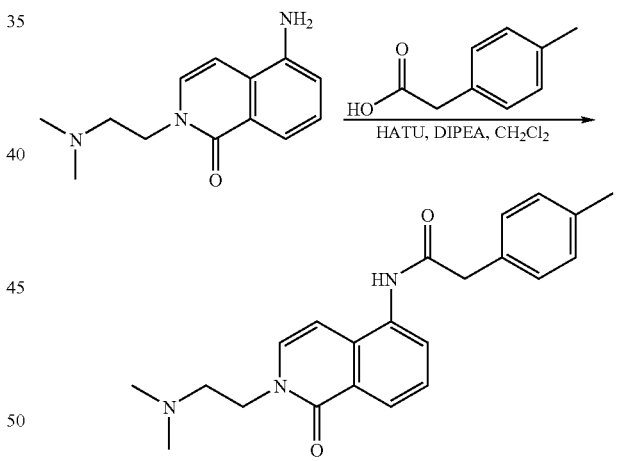

5-Amino-2-(2-dimethylamino-ethyl)-2H-isoquinolin-1-one (50 mg, 0.2 mmol), HATU (99 mg, 0.26 mmol), p-tolylacetic acid (39 mg, 0.26 mmol) and DIPEA (110 mg, 0.86 mmol) were stirred in methylene chloride (3 mL) at room temperature for 18 hours. The mixture was purified via flash chromatography (12 g of silica gel, 0-10% MeOH/$CH_2Cl_2$ gradient) gave N-[2-(2-Dimethylamino-ethyl)-1-oxo-1,2-dihydro-isoquinolin-5-yl]-2-p-tolyl-acetamide as a white solid (20 mg, 0.055 mmol, 27%).

LC/MS (0.1% formic acid modifier) calcd. $(M+1)^+$ 363.45, observed 364.5.

$^1$H NMR ($CDCl_3$) δ 8.24 (d, J=8.0 Hz, 1H), 8.01 (d, J=7.4 Hz, 1H), 7.46 (t, J=7.9 Hz, 1H), 7.31-7.26 (m, 4H), 7.04 (d, J=7.6 Hz, 1H), 5.93 (d, J=7.6 Hz, 1H), 4.05 (t, J=6.5 Hz, 2H), 3.81 (s, 2H), 2.63 (t, J=6.5 Hz, 2H), 2.40 (s, 3H), 2.28 (s, 6H).

Alternate Representative Method for Preparation of N-substituted-1-oxo-1,2-dihydro-isoquinolin-5-yl derivatives

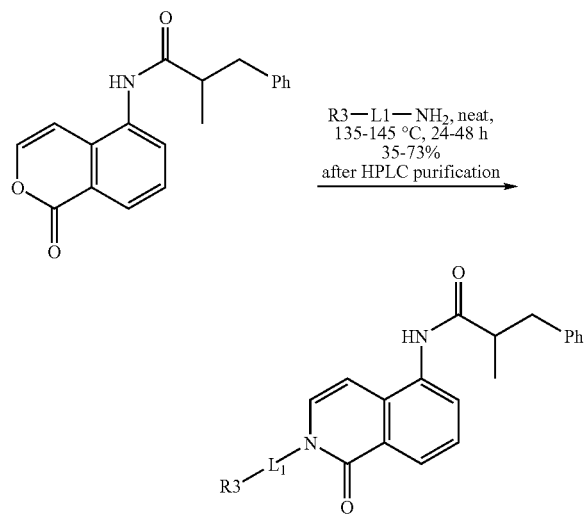

The reactions were performed using 0.089 mmoles of the pyrone and a 6-fold excess of the amine. All reactions were monitored by LC/MS for completion and upon completion were purified by preparative HPLC using 0.1% formic acid buffer. The N-$L^1$-$R^3$ substituted compounds of this invention, wherein $L^1$-$R^3$ is as described for formula I, are or can be prepared in a manner analogous to that described in Method B1, or some modification thereof, unless otherwise described.

Representative Synthetic Methods

Method A (Compound 1006)

N-[2-(2-Dimethylamino-ethyl)-1-oxo-1,2-dihydro-isoquinolin-5-yl]-benzamide a. 2-(2-Dimethylamino-ethyl)-5-nitro-2H-isoquinolin-1-one 5-Nitro-isochromen-1-one (1.83 g, 0.00957 mol) and N,N-dimethyl-1,2-ethanediamine (3 g, 0.03 mol) were refluxed in methanol (20 mL, 0.5 mol) for 1 hour. The volatiles were removed via rotovapor. The residue was purified via flash chromatography (40 g of silica gel, 50% EtOAc/$CH_2Cl_2$) and gave a light yellow solid.

MS m/z (M+H) 262.3.

b. 5-Amino-2-(2-dimethylamino-ethyl)-2H-isoquinolin-1-one 2-(2-Dimethylamino-ethyl)-5-nitro-2H-isoquinolin-1-one (1.10 g, 0.00358 mol) was dissolved in MeOH (30 mL), Pd/C (10%) was added and the mixture was stirred under an atmosphere of hydrogen at room temperature for 1 h. The mixture was filtered through Celite, and the solvent was removed in vacuo to give the titled product as a light yellow solid (0.82 g). MS m/z (M+H) 232.4.

c. N-[2-(2-Dimethylamino-ethyl)-1-oxo-1,2-dihydro-isoquinolin-5-yl]-benzamide

5-Amino-2-(2-dimethylamino-ethyl)-2H-isoquinolin-1-one (50 mg, 0.0002 mol), benzoyl chloride (36 mg, 0.00026 mol) and N,N-diisopropylethylamine (110 mg, 0.00086 mol) were stirred in methylene chloride (3 mL, 0.05 mol) at room temperature for 2 hours. The mixture was diluted with $CH_2Cl_2$ (20 mL) and the organic layer was separated and washed with $NaHCO_3$ (10 mL), dried over $Na_2SO_4$, and purified via flash column chromatography (12 g of silica gel, 10% MeOH/$CH_2Cl2$) to give the product as a light yellow solid.

$^1$H NMR δ (CDCl$_3$) δ: 8.34 (d, J=8.0 Hz, 1H), 8.08 (d, J=7.5 Hz, 1H), 7.96-7.92 (m, 3H), 7.66-7.52 (m, 5H), 6.53 (d, J=7.6 Hz, 1H), 4.26-4.17 (m, 2H), 3.09-3.07 (m, 2H), 2.46 (s, 6H). MS m/z (M+H) 336.4.

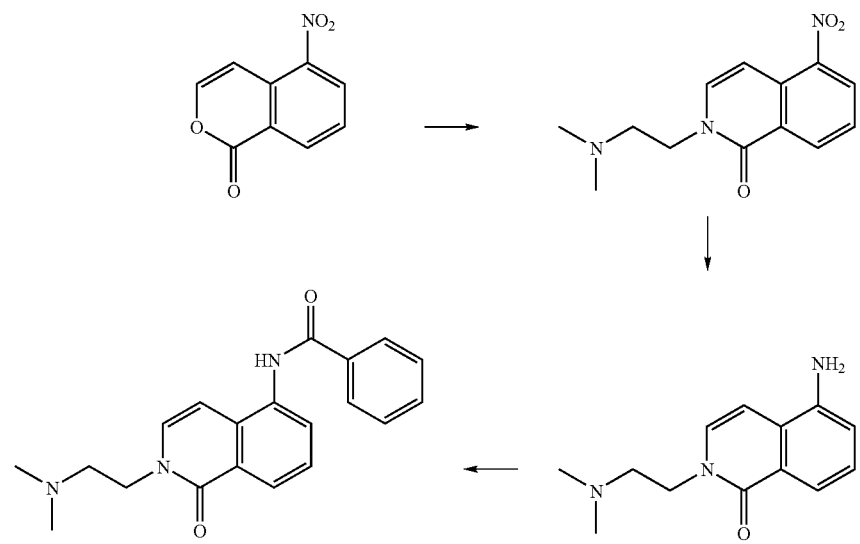

Method B (Compound 1013)

2-Cycloheptyl-N-[2-(2,3-dihydro-benzo[1,4]dioxin-6-ylmethyl)-1-oxo-1,2-dihydro-isoquinolin-5-yl]-acetamide

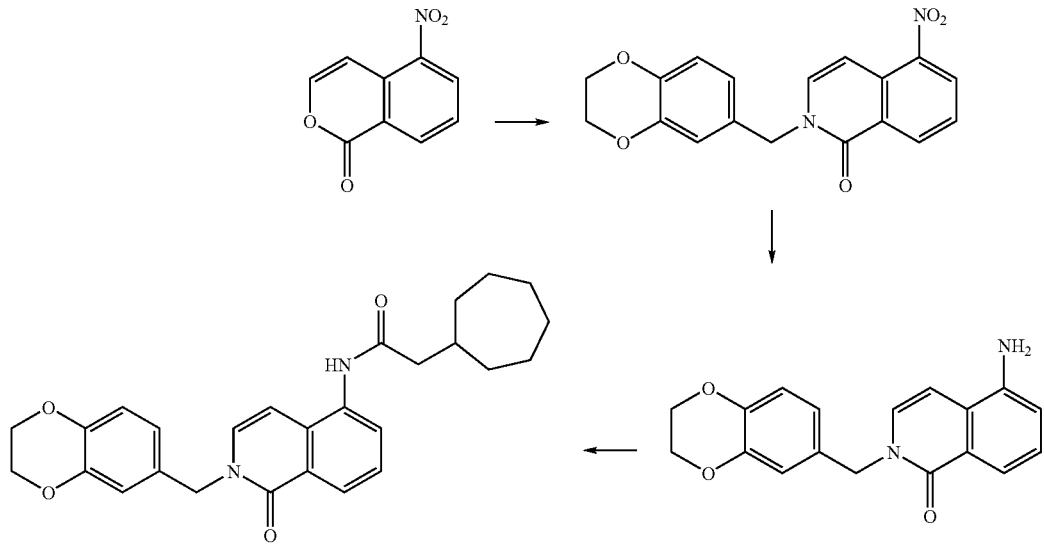 [SMILES: O=c1occc2c([N+](=O)[O-])cccc12 ; O=c1c2cccc([N+](=O)[O-])c2ccn1Cc1ccc2c(c1)OCCO2 ; O=C(CC1CCCCCC1)Nc1cccc2c(=O)n(Cc3ccc4c(c3)OCCO4)ccc12 ; Nc1cccc2c(=O)n(Cc3ccc4c(c3)OCCO4)ccc12]

a. 2-(2,3-Dihydro-benzo[1,4]dioxin-6-ylmethyl)-5-nitro-2H-isoquinolin-1-one

5-Nitro-isochromen-1-one (1.0 g, 0.0052 mol) and C-(2,3-dihydro-benzo[1,4]dioxin-6-yl)-methylamine (1.0 g, 0.0060 mol) were refluxed in methanol (40 mL, 1 mol) for 2 hours. The solvent was removed and the residue was purified via flash chromatography (40 g of silica gel, 0-30% EtOAc/Hexanes) to give a yellow solid.
MS m/z (M+H) 339.5 b. 5-Amino-2-(2,3-dihydro-benzo[1,4]dioxin-6-ylmethyl)-2H-isoquinolin-1-one 2-(2,3-Dihydro-benzo[1,4]dioxin-6-ylmethyl)-5-nitro-2H-isoquinolin-1-one (0.9 g, 0.002 mol), tin dichloride dihydrate (2 g, 0.009 mol) were stirred in tetrahydrofuran (10 mL, 0.1 mol) at room temperature for 20 hours. The volatiles were removed and the residue was purified via flash column chromatography (40 g of silica gel, 50% EtOAc/Hexanes) to give a red oil. MS m/z (M+H) 309.4.

c. 2-Cycloheptyl-N-[2-(2,3-dihydro-benzo[1,4]dioxin-6-ylmethyl)-1-oxo-1,2-dihydro-isoquinolin-5-yl]-acetamide 5-Amino-2-(2,3-dihydro-benzo[1,4]dioxin-6-ylmethyl)-2H-isoquinolin-1-one (50 mg, 0.0002 mol), 2-cycloheptylacetic acid (63 mg, 0.00041 mol), fluoro-N,N,N',N'-tetramethylformamidinium hexafluorophosphate (110 mg, 0.00041 mol) and N,N-diisopropylethylamine (100 mg, 0.0008 mol) were stirred in methylene chloride (3 mL, 0.05 mol) at room temperature for 72 hours. The mixture was purified via flash chromatography (12 g of silica gel, 50% EtOAc/Hexane) to give a light yellow solid.

$^1$H NMR δ (CDCl$_3$) δ: 8.33 (d, J=8.0 Hz, 1H), 7.94 (d, J=7.6 Hz, 1H), 7.47 (t, J=7.9 Hz, 1H), 7.19 (br, 1H), 7.10 (d, J=7.6 Hz, 1H), 6.82-6.78 (m, 3H), 6.42 (d, J=11.2 Hz, 1H), 5.09 (S, 2H), 4.14 (s, 4H), 2.35 (d, J=7.2 Hz, 2H), 2.20-2.13 (m, 1H), 1.85-1.26 (m, 12H).

Method C (Compound 1024)

2-Cycloheptyl-N-(2-methyl-1-oxo-1,2-dihydro-isoquinolin-5-yl)-acetamide

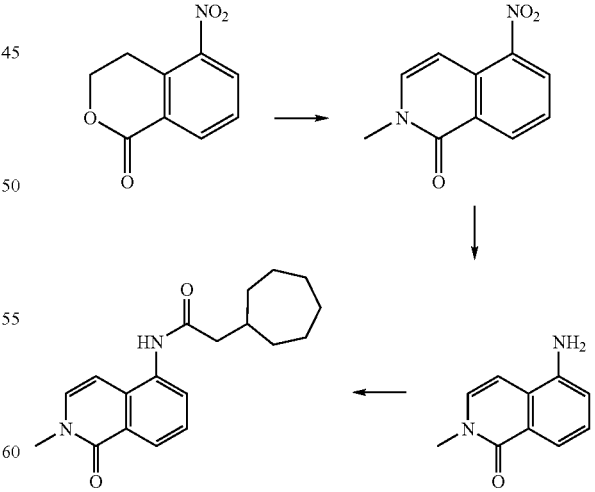

a. 2-Methyl-5-nitro-2H-isoquinolin-1-one

5-Nitro-isochromen-1-one (1.2 g, 0.0063 mol) and 40% aqueous methylamine (10 mL, 0.09 mol) were refluxed in methanol (40 mL, 1 mol) for 1 hour. The solvents were removed and the residue was diluted with CH$_2$Cl$_2$/MeOH (95:5 v/v, 100 mL), washed with brine (20 mL×2). The CH$_2$Cl$_2$ layer was dried over Na$_2$SO$_4$, purified via flash chromatography (40 g of silica gel, 0-50% EtOAc/Hexanes) to give a yellow solid. MS m/z (M+H) 204.8.

b. 5-Amino-2-methyl-2H-isoquinolin-1-one

2-Methyl-5-nitro-2H-isoquinolin-1-one (0.69 g, 0.0032 mol) and tin dichloride dihydrate (2 g, 0.01 mol) were stirred in tetrahydrofuran (10 mL, 0.1 mol) at room temperature overnight. The mixture was purified via flash chromatography (40 g of silica gel, 50% EtOAc/Hexanes) to give a brown solid. MS m/z (M+H) 174.9.

c. 2-Cycloheptyl-N-(2-methyl-1-oxo-1,2-dihydroisoquinolin-5-yl)acetamide

5-Amino-2-methyl-2H-isoquinolin-1-one (50 mg, 0.0003 mol), 2-cycloheptylacetic acid (90 mg, 0.0006 mol), fluoro-N,N,N',N'-tetramethylformamidinium hexafluorophosphate (200 mg, 0.0006 mol), N,N-diisopropylethylamine (100 mg, 0.0009 mol) were stirred in methylene chloride (2 mL, 0.03 mol) at room temperature over 72 hours. The mixture was purified via flash chromatography (12 g of silica gel, 0-50% EtOAc/Hexane) to give a yellow solid. $^1$H NMR δ (CDCl$_3$) δ: 8.31 (d, J=7.9 Hz, 1H), 7.95-7.92 (m, 1H), 7.47 (t, J=7.9 Hz, 1H), 7.20 (br, 1H), 7.11 (d, J=7.6 Hz, 1H), 6.41 (d, J=7.5 Hz, 1H), 3.60 (s, 3H), 2.37 (d, J=7.3 Hz, 2H), 2.17 (br, 1H), 1.86-1.25 (12H).

Method D (Compound 1373)

2-Cycloheptyl-N-[1-oxo-2-(tetrahydro-pyran-4-ylmethyl)-1,2-dihydro-isoquinolin-5-yl]-acetamide a. 5-Nitro-2-(tetrahydro-pyran-4-ylmethyl)-2H-isoquinolin-1-one

5-Nitro-isochromen-1-one (1.0 g, 0.0052 mol) and C-(tetrahydro-pyran-4-yl)-methylamine (0.72 g, 0.0063 mol) were stirred in 1,4-dioxane (3 mL, 0.04 mol) at 120° C. for 18 hours. The mixture was diluted with EtOAc (200 mL), washed with 1 N HCl (30 mL×2), brine (30 mL) and dried over Na$_2$SO$_4$. After the filtration the solvent was removed and the residue was purified via flash chromatography (40 g of silica gel, 40% EtOAc/Hexanes) to give a yellow oil. MS m/z (M+H) 289.1.

b. 5-Amino-2-(tetrahydro-pyran-4-ylmethyl)-2H-isoquinolin-1-one

5-Nitro-2-(tetrahydro-pyran-4-ylmethyl)-2H-isoquinolin-1-one (0.78 g, 0.0027 mol) and tin dichloride dihydrate (2 g, 0.01 mol) were stirred in tetrahydrofuran (10 mL, 0.1 mol) at room temperature for 24 hours. The mixture was partitioned between EtOAc (100 mL) and saturated aqueous NaHCO$_3$ solution, separated. The aqueous layer was extracted with EtOAc (50 mL×3). The combined organic layers were dried over Na$_2$SO$_4$, and purified via flash chromatography (40 g of silica gel, 0-100% EtOAc/Hexanes) to give a yellow solid. MS m/z (M+H) 259.2.

c. 2-Cycloheptyl-N-[1-oxo-2-(tetrahydro-pyran-4-ylmethyl)-1,2-dihydro-iso quinolin-5-yl]-acetamide 5-Amino-2-(tetrahydro-pyran-4-ylmethyl)-2H-isoquinolin-1-one (40 mg, 0.0002 mot), 2-cycloheptylacetic acid (63 mg, 0.00041 mol), fluoro-N,N,N',N'-tetramethylformamidinium hexafluorophosphate (110 mg, 0.00041 mol), N,N-diisopropylethylamine (100 mg, 0.0008 mol) were stirred in methylene chloride (3 mL, 0.05 mol) at room temperature over 72 hours. The mixture was purified via flash chromatography (12 g of silica gel, 0-50% EtOAc/Hexane) to give a light yellow solid.

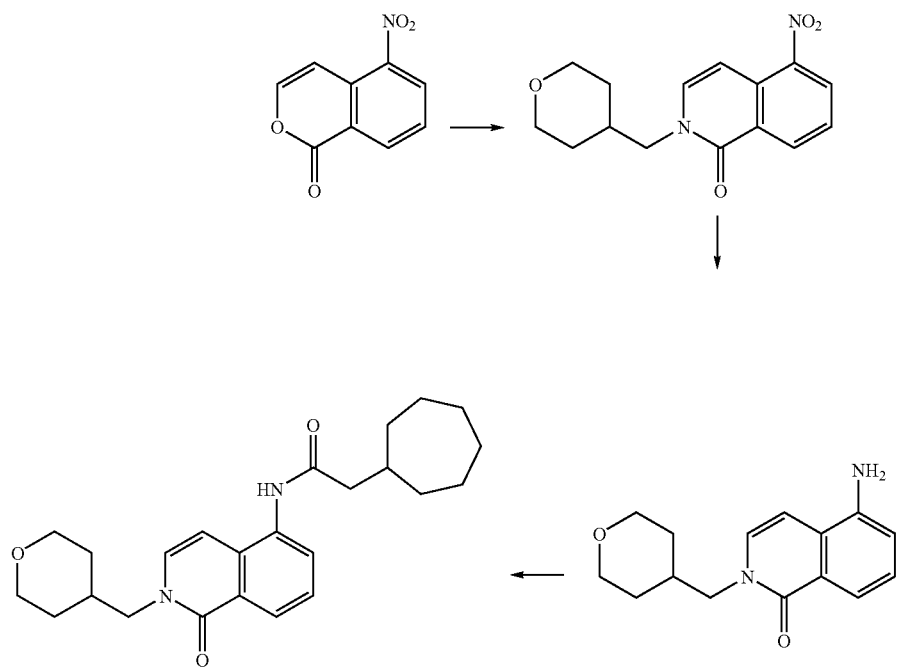

¹H NMR δ (CDCl₃) δ: 8.31 (d, J=6.9 Hz, 1H), 7.94 (d, J=8.2, 1H), 7.49 (t, J=8.1 Hz, 1H), 7.14 (br, 1H), 7.06 (d, J=7.5 Hz, 1H), 6.41 (d, J=7.1 Hz, 1H), 3.99-3.95 (m, 2H), 3.87 (d, J=7.3 Hz, 2H), 3.37-3.32 (m, 2H), 2.98-2.92 (m, 2H), 2.39-2.37 (m, 2H), 1.98-1.15 (m, 16H).

Method E (Compound 1380)

Acetic acid 2-{5-[2-(4-chloro-3-trifluoromethyl-phenyl)-acetylamino]-1-oxo-1H-isoquinolin-2-yl}-ethyl ester

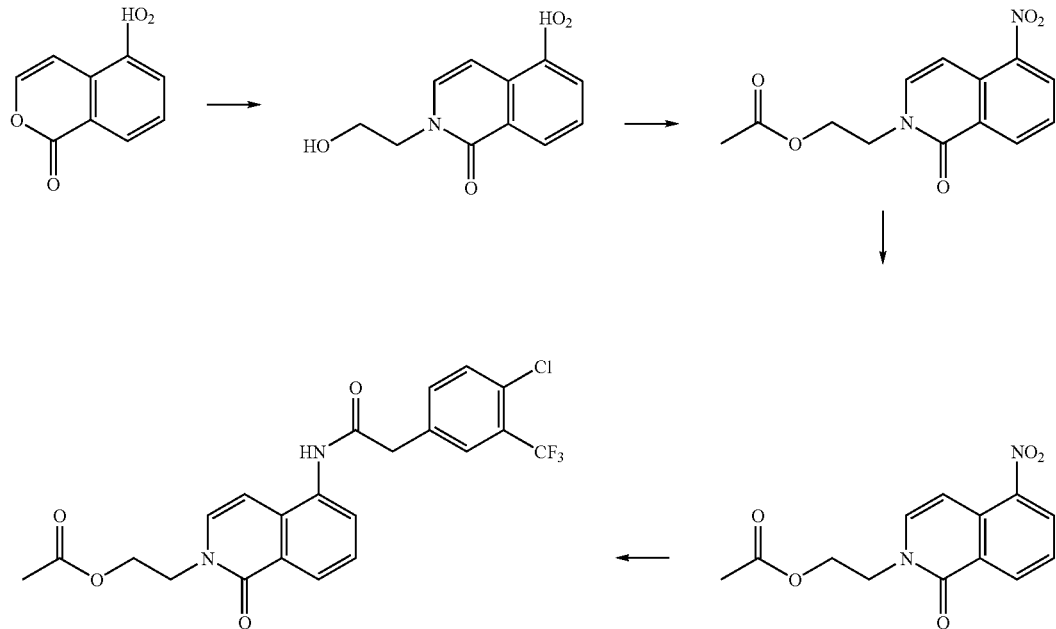

a. 2-(2-hydroxyethyl)-5-nitrosoquinolin-1(2H)-one

5-Nitro-isochromen-1-one (3.60 g, 0.0170 mol) was suspended in methanol (40 mL), ethanolamine (3.11 g, 0.0508 mol) was added and the reaction mixture was stirred at 70° C. for 2 h under an atmosphere of nitrogen. The mixture was cooled to room temperature and triethylamine (5 mL) was added. The reaction mixture was stirred at room temperature over weekend (2 days). Solid thus formed was filtered out (yellow solid was obtained as the desired product, 0.9 g). Filtrate was concentrated and the residue was dissolved in ethyl acetate, washed with water and brine, dried over sodium sulfate, solvent was removed to give the product as a yellow solid (1.3 g).

b. 2-(5-Nitro-1-oxoisoquinolin-2(1H)-yl)ethyl acetate 2-(2-Hydroxyethyl)-5-nitroisoquinolin-1(2H)-one (2.2 g, 0.0089 mol) was dissolved in the mixture of dichloromethane (20 mL) and dimethylformamide (10 mL), N,N-diisopropylethylamine (2.33 mL, 0.0134 mol) and acetyl chloride (1.06 g, 0.0134 mol) were added and the reaction mixture was stirred at room temperature for 30 min. The volatiles were removed, the residue was washed with water and then with diethyl ether to obtain a light yellow solid (2.45 g). MS m/z=276.5 (M+H).

c. 2-(5-Amino-1-oxoisoquinolin-2(1H)-yl)ethyl acetate

A mixture of 2-(5-Nitro-1-oxoisoquinolin-2(1H)-yl)ethyl acetate (2.45 g, 0.00842 mol) was dissolved in methanol (100 mL), palladium on charcoal (10%) was stirred under an atmosphere of hydrogen for 1 hour. The mixture was filtered through celite, solvent was removed to obtain the product as a light orange solid (1.98 g). MS m/z=248.0 (M+H).

d. Acetic acid 2-5-[2-(4-chloro-3-trifluoromethyl-phenyl)-acetylamino]-1-oxo-1#H!-isoquinolin-2-yl-ethyl ester A solution of 2-(4-chloro-3-(trifluoromethyl)phenyl)acetic acid (131 mg, 0.000548 mol) in thionyl chloride (5 mL) was stirred at 60° C. for 1 hour. Thionyl chloride was removed and the residue was dissolved in tetrahydrofuran (5 mL). 245-Amino-1-oxoisoquinolin-2(1H)-yl)ethyl acetate (100.0 mg, 0.0003655 mol) and N,N-diisopropylethylamine (95.5 uL, 0.000548 mol) were added to the THF solution and the reaction mixture was stirred at room temperature for 1 h. The volatiles were removed, residue was dissolved in ethylacetate, washed with water, 2N HCl and brine. The combined organic layers were dried over sodium sulfate and the solvent removed. The residue purified by column to obtain the product as a beige solid (65 mg). MS m/z=467.0 (M+H).

¹H NMR (400 MHz, DMSO-d₆) δ: 10.11 (s, 1H), 8.07 (d, J=7.71 Hz, 1H), 7.89 (s, 1H), 7.84 (d, J=7.71 Hz, 1H), 7.73-7.68 (m, 2H), 7.51-7.45 (m, 2H), 6.68 (d, J=7.71 Hz, 1H), 4.33 (t, J=5.46, 2H), 4.20 (t, J=5.46 Hz, 2H), 3.92 (s, 2H), 1.95 (s, 3H).

Method F (Compound 1623)

2-(4-Chloro-3-trifluoromethyl-phenyl)-N-[2-(2-methoxy-ethyl)-1-oxo-1,2-dihydro-isoquinolin-5-yl]-acetamide

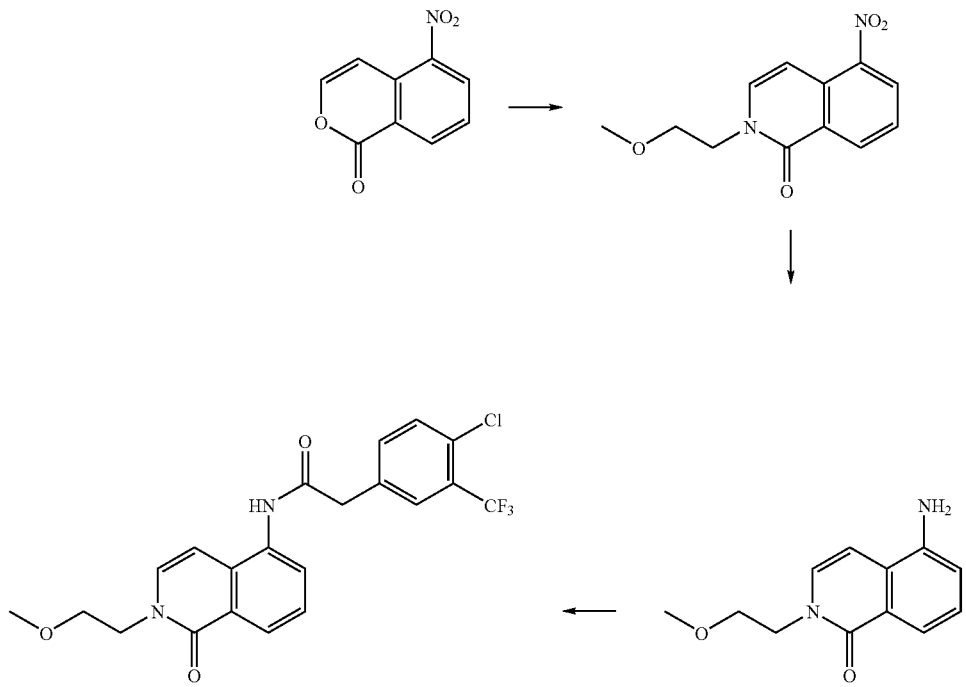

a. 2-2-methoxyethyl)-5-nitroisoquinolin-1(2H)-one

Into a round bottom flask was combined 5-nitro-isochromen-1-one (5.00 g, 0.0235 mol), 2-Methoxyethylamine (6.14 mL, 0.0706 mol) and methanol (150 mL, 3.7 mol). The mixture was heated at reflux for 1.5 hours. The mixture was cooled to room temperature and triethylamine (6.56 mL, 0.0471 mol) was added. The mixture was stirred at room temperature overnight. LC-MS showed the starting material was completely consumed. Excess triethylamine and ethyl acetate was added and the mixture was stirred at room temperature for 30 mins. A yellow precipitate was formed which was filtered and the filtrate was concentrated to yield a yellow solid. The combined solids were taken onto the next step without further purification.

b. 5-Amino-2-(2-methoxyethyl)isoquinolin-1(2H)-one

Into a 250 ml round bottom flask was combined 2-(2-methoxyethyl)-5-nitroisoquinolin-1(2H)-one (1.23 g, 0.00495 mol) palladium/C (0.05 g, 0.0005 mol) and methanol (50 mL, 1 mol). The flask was purged and evacuated with hydrogen twice and the mixture was allowed to stir under an atmosphere of hydrogen (1 atm) for two hours. The mixture was filtered over Celite and the filtrate reduced in vacuo to yield the title compound as a light brown solid.

c. 2-(4-Chloro-3-(trifluoromethyl)phenyl)-N-(1,2-dihydro-2-(2-methoxyethyl)-1-oxoisoquinolin-5-yl)acetamide Into a 20 ml reaction vial was combined 5-amino-2-(2-methoxyethyl)isoquinolin-1(2H)-one (0.020 g, 0.000087 mol) 2-(4-chloro-3-(trifluoromethyl)phenyl)acetic acid (31 mg, 0.00013 mol) N,N,N',N'-tetramethyl-O-(7-azabenzotriazol-1-yl)uronium hexafluorophosphate (81.66 mg, 0.0002148 mol) N,N-diisopropylethylamine (69.2 uL, 0.000397 mol) and N,N-dimethylformamide (1 mL, 0.02 mol). The mixture was heated at 40 degrees for 12 hours. The reaction was allowed to cool and was poured into sat sodium bicarbonate (200 ml). The mixture was extracted with ethyl acetate (3×100 ml). The combined extracts were dried over sodium sulfate and reduced in vacuo. The remaining residue was purified by reversed phase prep HPLC using acetonitrile:water gradient at pH 10. The combined pure fractions were reduced in vacuo to yield the compound as an off white solid. LC_MS (M+H)=439.2.

Method G (Compound 1624)

2-(4-Chloro-3-trifluoromethyl-phenyl)-N-[1-oxo-2-(6-trifluoromethyl-pyridin-3-ylmethyl)-1,2-dihydro-isoquinolin-5-yl]-acetamide

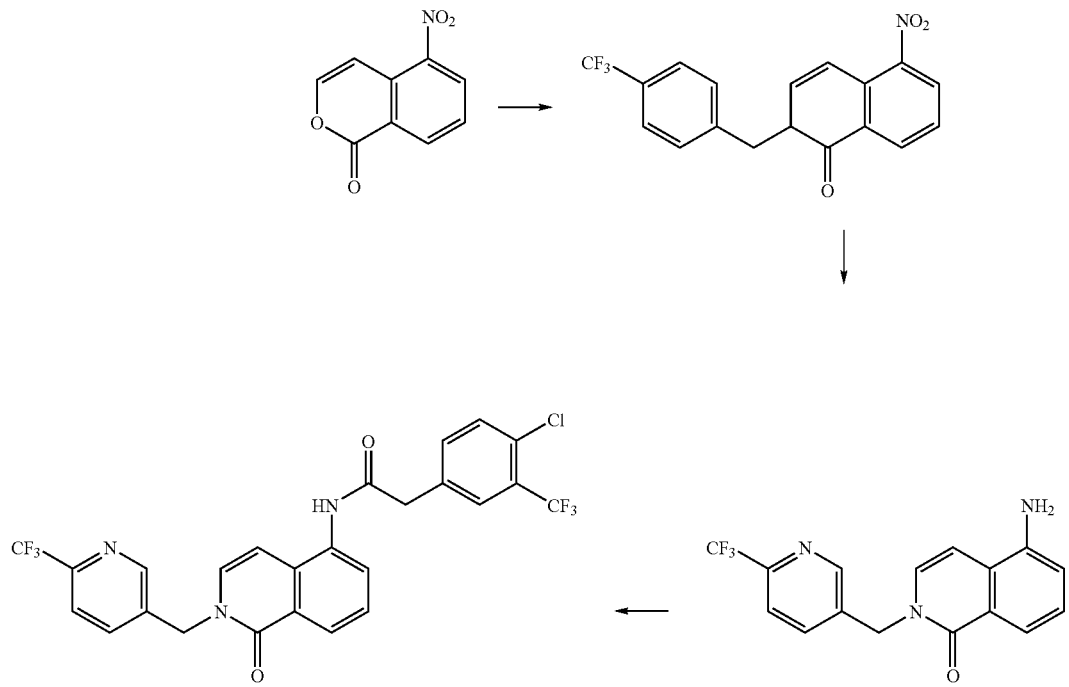

a. 2((6(Trifluoromethyl)pyridin-3-yl)methyl)-5-nitroisoquinolin-1(2H)-one

C-(6-Trifluoromethyl-pyridin-3-yl)-methylamine (1.00 g, 0.00568 mol) and 5-nitro-isochromen-1-one (1.14 g, 0.00568 mol) were suspended in methanol (10 mL) and the suspension was stirred at 60° C. for 3 hours, then the reaction was microwaved at 100 watts at 100° C. for 60 minutes, and then at 120° C. for 30 min. Solid thus formed was filtered out to yield the product as a yellow solid (1.2 g). MS m/z=350.4 (M+H).

b. 5-Amino-2-((6-(trifluoromethyl)pyridin-3-yl)methyl)isoquinolin-1(2H)-one

Palladium on charcoal (10%) was added to the solution of 2-((6-(trifluoromethyl)pyridin-3-yl)methyl)-5-nitroisoquinolin-1(2H)-one (1.16 g, 0.00315 mol) in methanol (30 mL) and the mixture was stirred under an atmosphere of hydrogen for 40 min. The mixture was filtered through celite. The filterate was concentrated and the residue was purified by column to obtain the product as a beige solid (0.83 g). MS m/z=320.3 (M+H).

c. 2-(4-Chloro-3-(trifluoromethyl)phenyl)-N-(2-((6-(trifluoromethyl)pyridin-3-yl)methyl)-1,2-dihydro-1-oxoisoquinolin-5-yl)acetamide 2-(4-Chloro-3-(trifluoromethyl)phenyl)acetic acid (142 mg, 0.000595 mol) was dissolved in thionyl chloride (10 mL) and the mixture was stirred at 60° C. for 3 hours. The volatiles were removed and the residue was dissolved in tetrahydrofuran. 5-Amino-2-((6-(trifluoromethyl)pyridin-3-yl)methyl)isoquinolin-1(2H)-one (100.0 mg, 0.0002975 mol) and N,N-diisopropylethylamine (0.104 mL, 0.000595 mol) were added and the mixture was stirred for 1 hour at room temperature. Methanol was added to quench the reaction and the volatiles were removed. The residue was dissolved in ethylacetate, washed with water, sodium carbonate solution and brine and purified by column to obtain the product as a beige solid (120 mg). MS m/z=540.4(M+H).

1H NMR (400 MHz, DMSO-d6): 10.14 (s, 1H), 8.81 (s, 1H), 8.08 (d, J=7.89 Hz, 1H), 7.96 (d, J=8.11 Hz, 1H), 7.89-7.85 (m, 2H), 7.76 (d, J=7.57 Hz, 1H), 7.71 (s, 2H), 7.49 (t, J=8.03 Hz, 1H), 6.77 (d, J=7.83 Hz, 1H), 5.32 (s, 2H), 3.93 (s, 2H).

Method H (Compound 1628)

2-(4-Chloro-3-trifluoromethyl-phenyl)-N-(1-oxo-2-pyridin-2-ylmethyl-1,2-dihydro-isoquinolin-5-yl)-acetamide

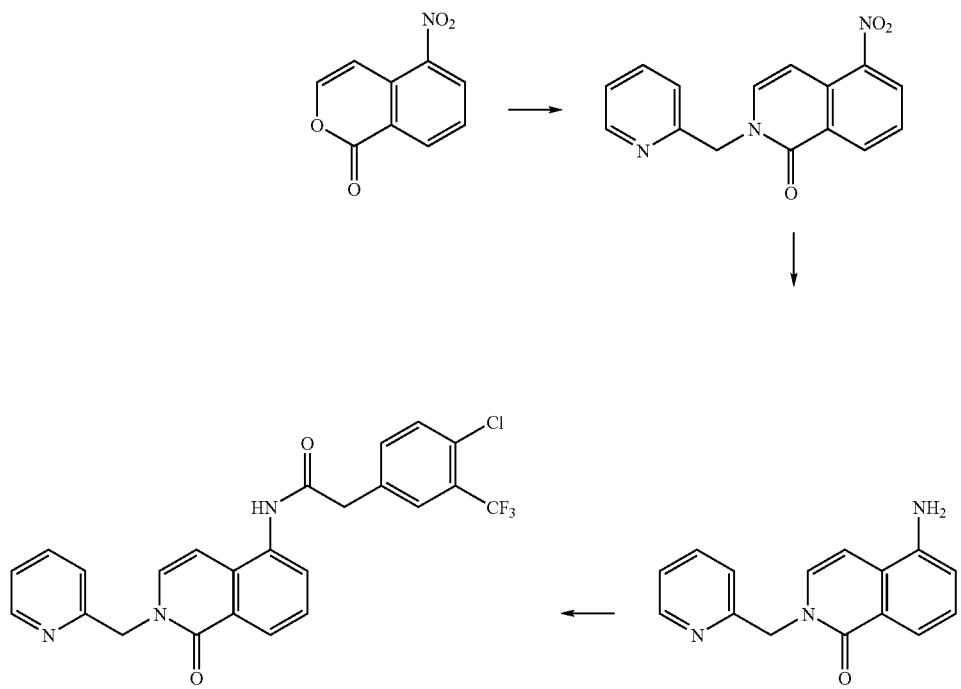

a. 5-nitro-2-(pyridin-2-ylmethyl)isoquinolin-1(2H)-one

Into a microwave vial was combined 5-nitro-isochromen-1-one (1 g, 0.005 mol), 2-pyridinemethanamine (1 g, 0.009 mol), and methanol (20 mL, 0.5 mol). The mixture was heated at 150° C. for 2 hours. The mixture was cooled to room temperature. The usual work up of the reaction mixture gave a crude product which was then purified using a flash chromatography over silica gel to give the pure product as a yellow solid (0.7 g). MS m/z=282.4 (M+1).

b. 5-Amino-2-(pyridin-2-ylmethyl)isoquinolin-1(2H)-one

Into a round bottom flask was combined 5-nitro-2-(pyridin-2-ylmethyl)isoquinolin-1(2H)-one (0.7 g, 0.002 mol), palladium/C (0.05 g, 0.0005 mol) and methanol (200 mL, 5 mol). The reaction mixture was stirred under hydrogen balloon at room temperature for 40 mins. The mixture was filtered over celite, MeOH was removed and the solid was yield (0.46 mg). MS m/z=252.4 (M+1). 1H NMR (DMSO) δ 8.49 (d, J=4.3 Hz, 1H), 7.74 (td, J=7.7, 1.6 Hz, 1H), 7.42 (t, J=7.3 Hz, 2H), 7.27 (dd, J=6.9, 5.0 Hz, 1H), 7.22-7.12 (m, 2H), 6.88 (d, J=7.2 Hz, 1H), 6.80 (d, J=7.6 Hz, 1H), 5.69 (s, 2H), 5.23 (s, 2H).

c. 2-(4-Chloro-3-(trifluoromethyl)phenyl)-N-(1-oxo-2-(pyridin-2-ylmethyl)-1,2-dihydroisoquinolin-5-yl)acetamide To a solution of 5-amino-2-(pyridin-2-ylmethyl)isoquinolin-1(2H)-one (100.00 mg, 0.4 mmol) in N,N-dimethylformamide (0.7 mL, 0.009 mol) was added 2-(4-chloro-3-(trifluoromethyl)phenyl)acetic acid (190 mg, 0.000796 mol), N,N,N',N'-tetramethyl-O-(7-azabenzotriazol-1-yl)uronium hexafluorophosphate (303 mg, 0.000796 mol) and N,N-diisopropylethylamine (277 uL, 0.00159 mol). The reaction mixture was stirred for 16 hours at 50° C. Checked LC/MS, the reaction was completed. The DMF reaction solution was directly applied to prep. HPLC to obtain the pure product (134.2 mg). MS m/z=472.3 (M+1). $^1$H NMR (DMSO) δ 10.13 (s, 1H), 8.48 (d, J=4.8 Hz, 1H), 8.06 (d, J=7/9 Hz, 1H), 7.90 (s, 1H), 7.84 (d, J=7.1 Hz, 1H), 7.76 (td, J=7.7, 1.8 Hz, 1H), 7.75-7.68 (m, 2H), 7.63 (d, J=7.7 Hz, 1H), 7.47 (t, J=7.9 Hz, 1H), 7.32-7.22 (m, 2H), 6.73 (d, J=7.6 Hz, 1H), 5.28 (s, 2H), 3.93 (s, 2H).

Method J (Compound 1630)

2-(4-Chloro-3-trifluoromethyl-phenyl)-N-[2-(2-methanesulfonyl-ethyl)-1-oxo-1,2-dihydro-isoquinolin-5-yl]acetamide

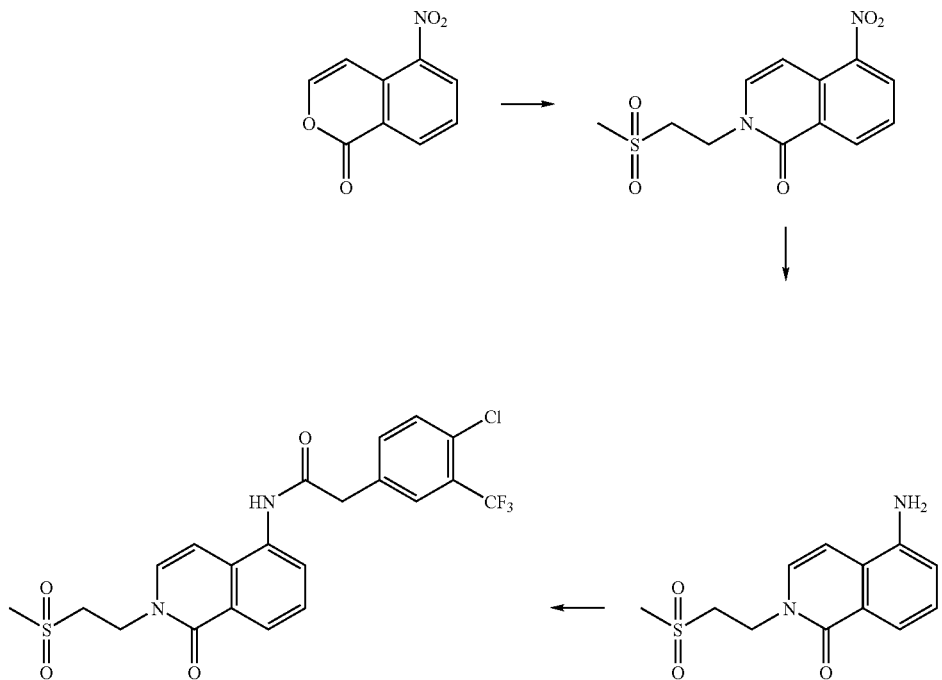 [SMILES: O=c1occc2c([N+](=O)[O-])cccc12 ; CS(=O)(=O)CCn1ccc2c([N+](=O)[O-])cccc2c1=O ; CS(=O)(=O)CCn1ccc2c(NC(=O)Cc3ccc(Cl)c(C(F)(F)F)c3)cccc2c1=O ; CS(=O)(=O)CCn1ccc2c(N)cccc2c1=O]

a. 2-(2-(Methylsulfonyl)ethyl)-5-nitroisoquinolin-1(2H)-one

Into a round bottom flask was combined 5-nitro-isochromen-1-one (1.5 g, 0.0071 mol), 2-(methylsulfonyl)ethanamine hydrochloride (2.2 g, 0.014 mol) and methanol (45 mL, 1.1 mol). The mixture was heated at reflux for 1.5 hours. The mixture was cooled to room temperature and was concentrated to yield a yellow solid. The solid was taken onto the next step without further purification.

b. 5-Amino-2-(2-(methylsulfonyl)ethyl)isoquinolin-1(2H)-one

Into a 250 ml round bottom flask was combined 2-(2-(methylsulfonyl)ethyl)-5-nitroisoquinolin-1(2H)-one (1.20 g, 0.00405 mol) Palladium/C (0.04 g, 0.0004 mol) and methanol (40 mL, 1 mol). The flask was evacuated and purged with hydrogen 3 times. The mixture was stirred at room temperature under hydrogen (1 atm) for three hours. The mixture was filtered over celite and the filtrate was reduced in vacuo. The mixture was purified by column chromatography using a Methanol:methylene chloride (0-10%) gradient. The combined pure fractions were reduced in vacuo to yield the title compound as an off white solid.

c. 2-(4-chloro-3-(trifluoromethyl)phenyl)-N-(2-(2-(methylsulfonyl)ethyl)-1-oxo-1,2-dihydroisoquinolin-5-yl)acetamide To a solution of 5-amino-2-(2-(methylsulfonyl)ethyl)isoquinolin-1(2H)-one (30 mg, 0.0001 mol) in N,N-dimethylformamide (700 µL, 0.009 mol) was added 2-(4-chloro-3-(trifluoromethyl)phenyl)acetic acid (51 mg, 0.00021 mol), N,N,N',N'-tetramethyl-O-(7-azabenzotriazol-1-yl)uronium hexafluorophosphate (102 mg, 0.000268 mol) and N,N-diisopropylethylamine (93 µL, 0.00054 mol). The reaction mixture was stirred for 16 hours at 50° C. LC-MS analysis showed the formation of the desired product. The mixture was taken up in saturated NaHCO$_3$ solution and washed twice with ethyl acetate. The organic layer was dried with sodium sulfate, reduced in vacuo and purified via HPLC to afford the title compound as a white solid.

$^1$H-NMR (400 MHz, DMSO-d) δ 10.10 (s, 1H), 8.08 (d, 1H, J=7.96 Hz), 7.86 (m, 2H), 7.71 (m, 2H), 7.55 (d, 1H, J=7.73 Hz), 7.47 (t, 1H, J=7.85 Hz), 6.70 (d, 1H, J=7.73 Hz), 4.36 (t, 2H, J=6.90 Hz), 3.92 (s, 2H), 3.60 (m, 2H), 3.06 (s, 3H).

Method K (Compound 1633)

2-(2-Fluoro-3-trifluoromethyl-phenyl)-N-[1-oxo-2-(1-pyridin-2-yl-ethyl)-1,2-dihydro-isoquinolin-5-yl]-acetamide

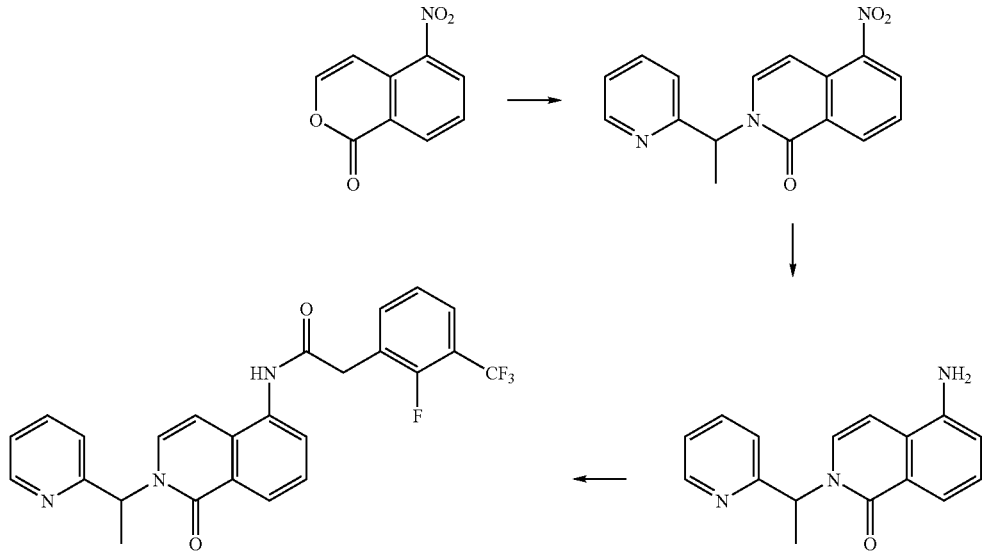

a. 5-nitro-2(1-(pyridin-2-yl))ethyl)isoquinolin-1(2H)-one

Into a microwave vial was combined 5-nitro-isochromen-1-one (1 g, 0.005 mol), 1-pyridin-2-yl-ethylamine (1 g, 0.009 mol), and methanol (20 mL, 0.5 mol). The mixture was heated at 150° C. for 2 hours. The mixture was cooled to room temperature. LC-MS showed the starting material was completely consumed. After silica gel column, a yellow solid was obtained (0.85 g). MS m/z=295.9 (M+1).

b. 5-amino-2-(1-(pyridin-2-yl)ethyl)isoquinolin-1(2H)-one

Into a round bottom flask was combined 5-nitro-2-(1-(pyridin-2-yl)ethyl)isoquinolin-1(2H)-one (0.85 g, 0.0029 mol), Palladium/C (0.05 g, 0.0005 mol) and methanol (200 mL, 5 mol). The reaction mixture was stirred under hydrogen balloon at room temperature for 40 mins. The mixture was filtered over celite, MeOH was removed and the solid was yield (0.54 mg). MS m/z=266.0 (M+1). $^1$H NMR (DMSO) δ 8.55 (d, J=4.8 Hz, 1 H), 7.77 (td, J=7.7, 1.8 Hz, 1 H); 7.44 (d, J=7.8 Hz, 1 H), 7.35-7.25 (m, 3 H), 7.17 (t, J=7.8 Hz, 1 H), 6.95-6.85 (m, 1 H), 6.78 (d, J=7.8 Hz, 1 H), 6.28 (q, J=7.2 Hz, 1 H), 5.66 (s, 2 H), 1.75 (d, J=7.2 Hz, 3 H).

c. 2-(2-Fluoro-3-(trifluoromethyl)phenyl)-N-(1-oxo-2-(1-(pyridin-2-yl)ethyl)-1,2-dihydroisoquinolin-5-yl)acetamide To a solution of 5-amino-2-(1-(pyridin-2-yl)ethyl)isoquinolin-1(2H)-one (100 mg, 0.0004 mol) in N,N-Dimethylformamide (1 mL, 0.01 mol) was added 2-(2-fluoro-3-(trifluoromethyl)phenyl)acetic acid (178 mg, 0.000801 mol), N,N,N',N'-tetramethyl-O-(7-azabenzotriazol-1-yl)uronium hexafluorophosphate (468.3 mg, 0.001232 mol) and N,N-diisopropylethylamine (300 uL, 0.002 mol). The reaction mixture was stirred for 16 hours at 50° C. LC/MS indicated that the reaction was completed. The DMF reaction solution was directly applied to prep. HPLC. The final product was obtained as a solid (102.4 mg). MS m/z=470.3 (M+1). $^1$H NMR (DMSO) δ 10.17 (s, 1 H), 8.54 (d, J=6.4 Hz, 1 H), 8.10 (d, J=8.0 Hz, 1 H), 7.82 (dd, J=7.8, 0.7 Hz, 1 H), 7.78 (td, J=9.5, 1.8 Hz, 2 H), 7.70 (t, J=7.1 Hz, 1 H), 7.55 (d, J=7.8 Hz, 1 H), 7.48 (t, J=7.9 Hz, 1 H), 7.40 (t, J=7.7 Hz, 1 H), 7.35 (d, J=8.0 Hz, 1 H), 7.31 (qd, J=4.8, 0.9 Hz, 1 H), 6.74 (d, J=7.8 Hz, 1 H), 6.28 (q, J=7.2 Hz, 1 H), 3.98 (s, 2 H), 1.78 (d, J=7.2 Hz, 3 H).

EXAMPLE 1

The P2X$_7$ receptor is strongly expressed in macrophage-derived cell lines, including, but not limited to, J774 (mouse macrophage line, American Type Culture Collection (ATCC), Rockville, Md., ATCC TIB-67), P388 (mouse cell line, ATCC CCL-46), P815 (mouse mast cell mastocytoma-derived line, ATCC TIB-64), THP-1 (Human monocyte-derived cell line, ATCC TIB202) and U937 (human cell line derived from histiocytic lymphoma, induceable to monocyte differentiation, ATCC CRL-1593.2) and in isolated macrophage cultures. Human or non-human animal macrophages are isolated using the procedure noted below.

The P2Z/P2X$_7$ receptor can be characterized by measuring channel opening, for instance ion flux, and/or by assessing pore formation, including by monitoring dye uptake or cell lysis in cells naturally expressing this receptor. Compounds such as ATP, 2' and 3'-(O)-(4-benzoyl benzoyl) ATP (BzATP) effect the formation of pores in the plasma membrane of these cells, particularly at low extracellular divalent ion concentrations (Buisman et al, Proc. Natl. Acad. Sci. USA 85:7988 (1988); Zambon et al, Cell. Immunol 156:458 (1994); Hickman et al Blood 84:2452 (1994)). Large molecular size dyes, including propidium dye YO-PRO-1, can be seen entering macrophage-derived cell lines during cell recordings (Hickman et al, Blood 84:2452 (1994); Wiley et al, Br J Pharmacol 112:946 (1994); Steinberg et al, J Biol Chem 262:8884

(1987)). Ethidium bromide (a fluorescent DNA probe) can also be monitored, where an increase in the fluorescence of intracellular DNA-bound ethidium bromide is observed. Expression of recombinant rat or human rP2X$_7$ in cells, including HEK293 cells, and in Xenopus oocytes demonstrates influx and pore formation by whole cell recordings and YO-PRO-1 fluorescence (Suprenant et al, Science 272:735 (1996); Rassendren et al, J Biol Chem 272:5482 (1997)).

The compounds of the invention may be tested for antagonist activity at the P2X$_7$ receptor. Tests to be performed include and are selected from: (i) electrophysiological experiments; (ii) YO-PRO1 fluorescence; (iii) ethidium bromide fluorescence; and (iv) IL-1β release from stimulated macrophages, including as described below. Compounds can be tested in vivo in animal models including for inflammation models (e.g. paw edema model, collagen-induced arthritis, EAE model of MS).

Isolation of Human Macrophages

Monocyte-derived human or non-human animal macrophage cultures are prepared as described by Blanchard et al (Blanchard et al, J Cell Biochem 57:452 (1995); Blanchard et al, J Immunol 147:2579 (1991)). Briefly, monocytes are isolated from leukocyte concentrates obtained from a healthy volunteer. Leukocytes are suspended in RPMI 1460 medium (Life Techologies, Inc.) with 20% serum (human for human cells), 2 mM glutamine, 5 mM HEPES, and 100 μg/ml streptomycin. Cells are allowed to adhere to culture flasks for 1-2 h, after which nonadherent cells are washed away. Adherent cells are cultured for 7-14d in this medium plus interferon-γ (human for human cells) (1000 units/ml). Macrophages are recovered from the culture flask by pipetting with cold phosphate-buffered saline and plated onto glass coverslips for electrophysiological or other experiments carried out 12-24 h later.

EXAMPLE 2

Electrophysiological Experiments

Whole cell recordings are made using the EPC9 patch-clamp amplifier and Pulse acquisition programs (HEKA, Lambrecht, Germany). Whole-cell recordings are obtained from cells, e.g. J774A.1 cells (American Type Culture Collection, Rockville, Md., ATCC TIB-67)); agonists are applied for periods of 1 to 3 s by a fast-flow U-tube delivery system [E. M. Fenwick, A. Marty, E. Neher, J. Physiol, (London) 331, 577 (1982)]. The internal pipette solution is 140 mM cesium-aspartate or potassium-aspartate, 20 mM NaCl, 10 mM EGTA, and 5 mM Hepes; normal external solution is 145 mM NaCl, 2 mM KCl, 2 mM CaCl$_2$, 1 mM MgCl$_2$, 10 mM Hepes, and 12 mM glucose. Low divalent external solution is nominally magnesium-free with 0.3 mM CaCl$_2$. Concentration-response curves are constructed in low divalent solution by recording currents in response to 1 s applications of agonist at 8 min intervals with normal external solution present for 6 min before each application. This protocol is necessary to prevent the development of sustained inward currents.

Reversal potentials ($E_{rev}$) are obtained by application of ATP (300 μM) or BzATP (30 μM)(controls), or the compound being tested, while the membrane is held at various potentials or by application of voltage ramps from −120 to 30 or 50 mV. Permeability ratios are calculated from $E_{rev}$, by first computing $\alpha(=P_{Na}/P_{K})$ where P is permeability) for internal (i) and external (o) concentrations $[Na]_i=20$ mM, $[Na]_o=145$ mM, $[K]_o=0$ mM, and $[K]_i=140$ mM from $\alpha=([145/\exp(E_{rev}F/RT)]-20)/140$ (where F is the Faraday, R is the gas constant, and T is the absolute temperature). Other $P_x/P_{Na}$ values, when $[X]_o=145$ mM, $[Na]_i=20$ mM, $[K]_i=140$ mM, and $[Na]_o=[K]_o=[X]_i=0$ mM, are computed from $P_x/P_{Na}=[(\exp E_{rev}F/RT)] (20+140\alpha))/145$. In order of size, X is cesium, methylamine, tris(hydroxymethyl)-aminomethane, tetraethylammonium, and N-methyl-D-glucamine. The internal solution also contains 10 mM EGTA and 5 mM Hepes. External solutions also contain 10 mM glucose and normal or low concentrations of divalent cations; pH is maintained at 7.3 with HCl, histidine, or Hepes as required, and the osmolarity of all solutions is 295 to 315.

EXAMPLE 3

YO-PRO1 Fluorescence

The Photonics Imaging (IDEA) system for microscopic fluorescence measurements (Photonics, Planegg, Germany) is used. Coverslips are placed at the stage of a Zeiss Axiovert 100 or equivalent inverted microscope and viewed under oil immersion with a 40× Fluor objective. YO-PRO-1 (10 μM; Molecular Probes, Eugene, Oreg.) is added to the superfusion fluid during electrophysiological recordings 3 to 6 min before switching to low divalent solution and washed out upon switching back to normal divalent solution, after which the fluorescent lamp is turned on and cells are examined with a fluorescein isothiocyanate filter. YO-PRO1 fluorescence is measured using 491/509 nm excitation/emission wavelengths. Images are obtained at 5-20s intervals during continuous superfusion (2 ml/min) with YO-PRO1 and varying concentrations of control ATP, BzATP or compound to be tested. For each experiment, the time course of YO-PRO1 fluorescence obtained for 10-20 individual cells and then averaged to obtain the mean fluorescence signal. Results were expressed as mean signal at 3 min for rP2X$_7$, and the signal at 10 min is used for P2X$_7$ and human macrophage cells. All experiments are carried out at room temperature.

EXAMPLE 4

Ethidium Bromide

Compounds of the invention are tested for antagonist activity at the P2X$_7$ receptor by monitoring Ethidium Bromide entering P2X$_7$ receptor-expressing cells on pore formation. The test is performed in 96-well flat bottomed microtitre plates, the wells being filled with 250 μl of test solution comprising 200 μl of a suspension of P2X$_7$-expressing cells (e.g. THP-1 cells, J774 cells, etc.)($2.5\times10^6$ cells/ml) containing $10^{-4}$M ethidium bromide, 25 μl of a high potassium buffer solution containing $10^{-5}$M BzATP, and 25 μl of a high potassium buffer solution containing test compound. The plate is covered with a plastic sheet and incubated at 37° C. for one hour. The plate is then read in a Perkin-Elmer fluorescent plate reader, excitation 520 nm, emission 595 nm, slit widths: Ex 15 nm, EM 20 nm. For the purposes of comparison, BzATP (a P2X$_7$ receptor agonist) and pyridoxal 5-phosphate (a P2X$_7$ receptor agonist) are used separately in the test as controls. From the readings obtained, a pIC$_{50}$ figure is calculated for each test compound. This figure is the negative logarithm of the concentration of test compound necessary to reduce the BzATP agonist activity by 50%.

EXAMPLE 5

IL-1β Release

This Example demonstrates the testing of the compounds of this invention for efficacy as inhibitors of P2X$_7$-mediated release of IL-1β from human macrophages activated by the Alzheimer's beta amyloid peptide 1-42.
Cell Isolation Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (generally, 5 to 6 washes). Monocytes are then purified from the PBMCs by negative selection using a monocyte isolation kit (Miltenyi Biotec, Inc.) that contains antibodies to non-monocytic cells, running the cells over a magnetic column to remove antibody-bound cells, and collecting the flow through volume of monocytes. Monocytes are washed once with wash buffer and seeded at 100,000 cells per well in 100 p. 1 serum-free RPMI 1640 in 96-well plates and incubated for 1 hour at 37° C. in a 5% $CO_2$/95% humidified tissue culture incubator. After 1 hour, the medium is replaced with 100 μl complete culture medium (RPMI 1640, 10% human serum-type AB (heat inactivated), 25 mM HEPES, 2 mM glutamine, 50 U/ml each of penicillin and streptomycin) and incubated overnight (16 hours).
Dosing Regimen The next day, the culture medium is replaced with 100 μl fresh complete culture medium in the absence or presence of human beta amyloid 1-42 peptide (5 μM) and incubated at 37° C. in a 5% $CO_2$/95% humidified tissue culture incubator for 5 hours. Medium is then removed and discarded. Each well is washed once with Hanks buffered saline (HBSS) containing 1 mM $CaCl_2$ followed by the addition of 80 μl of HBSS/$CaCl_2$-inhibiting compound of the present invention (10× stock in HBSS/$CaCl_2$ for a final concentration of 23 nM and 206 nM) and incubated 15 minutes in the tissue culture incubator followed by the addition of either 10 μl of HBSS/$CaCl_2$ or 10 μl of benzoyl ATP (BzATP; 3 mM stock in HBSS/$CaCl_2$ for a 300 μM final concentration) and incubated for a further 30 minutes in the tissue culture incubator. Medium is then removed to new 96-well plates for storage at –70° C. until the IL-1β content was quantitated by ELISA (from R&D Systems). The cells are washed once with HBSS/$CaCl_2$ followed by lysing the cells with 100 μl ice cold lysis buffer (100 mM Tris, pH 7.6, 1% Triton X-100, and 1 tablet per 30 ml Complete TM protease inhibitor from Roche Biochemicals, Inc). Cell lysates are stored at –70° C. until the IL-1β is quantitated by ELISA.

EXAMPLE 6

In Vivo Animal Models

A. This Example Illustrates the Efficacy of the Compounds of this Invention in the Treatment of Multiple Sclerosis.

As described herein, experimental autoimmune encephalomyelitis (EAE) model is used to show such an efficacy. The following procedures are employed in this model.
Animals SJL/J female mice, 8 wks. old, are obtained from Jackson Laboratories.
Antigens Myelin Proteolipid Protein (PLP 139-151) (HSLGK-WLGHPDKF) (Cat # H-2478) is obtained from BACHEM, Bioscience, Inc., 3700 Horizon Dr., King of Prussia, Pa. 19406, 1-610-239-0300 (phone), 1-610-239-0800 (fax).

Complete Freund's Adjuvant H37 Ra [1 mg/ml *Mycobacterium tuberculosis* H37 Ra] is obtained from Difco 1-800-521-0851 (Cat # 3114-60-5, 6×10 ml).

*Mycobacterium tuberculosis* is also obtained from Difco, 1-800-521-0851 (Cat # 3114-33-8, 6.times.100 mg).
Pertussis Toxin

*Bordetella pertussis*, (Lyophilized powder containing PBS and lactose) is obtained from List Biological Laboratories, 1-408-866-6363 (Product #180, 50 ug).
Induction of EAE in Mice PLP139-151 peptide is dissolved in $H_2O$:PBS (1:1) solution to a concentration 7.5 mg/10 ml (for 75 μg PLP per group) and emulsified with an equal volume of CFA supplemented with 40 mg/10 ml heated-killed *Mycobacterium tuberculosis* H37Ra. Mice are injected s.c. with 0.2 ml of peptide emulsion in the abdominal flank (0.1 ml on each side). On the same day and 72 hours later, mice are injected i.v. with 100% of 35 ng and 50 ng of *Bordetella pertussis* toxin in saline respectively.

Clinical Assessment
STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE
Clinical Courses of EAE
Acute phase: First clinical episode (Day 10-18)
Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

B. This Example Illustrates a Protocol for Determining the Efficacy of the Compounds of the Present Invention for the Treatment of Stroke Using an Animal Model.

Male Sprague Dawley rats (Charles River) weighing 280-320 g are given free access to food and water and acclimatized for a minimum of 4 days before use in experiments. All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.
Surgical Procedure A temporalis muscle probe is placed into the right temporalis muscle and "brain" temperature" is monitored. A midline neck incision is made in the upper thorax of the rat. Careful dissection, isolation and retraction of the sternomastoideus, digastricus, and sternohyoideus muscles is made to expose the right common, internal and external carotid arteries. The right common carotid artery is isolated with a 5-0 silk suture. During surgery the suture is released allowing reperfusion every 2-4 minutes. The right external carotid and superior thyroid arteries are also isolated and the superior thyroid is cauterized, while the external carotid is ligated distally with a 5-0 silk suture. Another 5-0 silk suture is loosely tied around the external carotid artery. The occipital artery is isolated, ligated and incised. The internal carotid is isolated.

With the common and external carotid arteries immobilized, an aneurysm clip is placed onto the internal carotid artery. A small incision is made at the distal end of the external carotid. A 3-0 nylon suture coated with poly-L-lysine is then inserted into the external carotid and up into the common carotid artery. The loosely tied 5-0 silk suture around the external carotid is now gently tightened around the filament. The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing <300 gm, 19 mm for rats weighing 0.300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture. The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%. The neck incision is reopened to expose the external carotid artery. The restoration of blood flow is accomplished by completely withdrawing the intraluminal suture from the carotid arteries. The incision is then closed with 3-0 silk in an interrupted stitch.

Compound Administration

Five groups of 15 animals are subjected to the above methodology. Compounds are infused (I.V.) at various doses (dose response) over different time periods post MCAo. A predetermined concentration is infused over a pre-selected time period beginning at various intervals post MCAo. Vehicle-treated controls receive an infusion of normally 0.9 ml/hr. A positive control compound is run at the same time.

Neurological Tests

Prior to surgery, 2 hours following the onset of ischaemia and 24 hours after ischaemia a battery of neurological tests are performed. The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation. The rats respond to a gentle lateral push with a finger behind the shoulders. A normal rat would resist such a push, whereas a rat with an infarction will not. The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

C. This Example Illustrates the Anti-Inflammatory Activity of the Compounds of this Invention Using a Model of 2,4-dinitrobenzenesulfonic Acid (DNBS) Induced Distal Colitis (a Model of Inflammatory Bowel Disease).

Test Substance and Dosing Pattern

A compound of this invention is dissolved in vehicle of 2% Tween 80 in distilled water for oral administration at a dose of 50 mg/kg or dissolved in vehicle of 2% Tween 80 and 0.9% NaCl for intraperitoneal injection at 30 mg/kg. The dose is given once daily for 7 consecutive days. Dosing volume is 10 ml/kg. DNBS was challenged 2 hours after dosing on the second day.

Animals

In these studies, male Wistar, Long Evans rats provided by animal breeding center of MDS Panlabs Taiwan, Ltd. and Balb/cByJ derived male mice (weighing 20±2 gms), provided by National Laboratory Animals Breeding Research center (NALBRC, Taiwan), may be used. Space allocation of 6 animals may be 45×23×15 cm. Animals are housed in APEC® cages (Allentown Caging, Allentown, N.J. 08501, USA) in a positive pressure isolator (NuAire®, Mode: Nu-605, airflow velocity 50±15 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water is granted. All aspects of this work including housing, experimentation and disposal of animals would be performed in general accordance with the International Guiding Principles for Biomedical Research Involving Animals (CIOMS Publication No. ISBN 92 90360194, 1985).

Chemicals

DNBS is obtained from TCI, Tokyo, Japan, ethanol is from Merck, Germany and Sulfasalazine is purchased from Sigma, USA.

Equipment

Electriconic scale (Tanita, model 1140, Japan), Electriconic scale (Sartorius, R160P, Germany), Glass syringe (2 ml, Mitsuba, Japan), Rat oral needle, Hypodermic needle (25G.times.1 "TOP Corporation, Japan), Stainless Scissors (Klappenclear, Germany), Stainless Forceps (Klappenclear, Germany).

Method

Groups of 3 Wistar derived male rats weighing 180-120 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instilled into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon is removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW×100%. The "Net"

increase in ratio of Vehicle-control +DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

D. This Example Illustrates the Anti-Inflammatory Activity of the Present Compounds Using a Model of Carrageenan Induced Paw Edema (a Model of Inflammation, Carrageenan).

Test Substance and Dosing Pattern

A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.

Animals

Animals are conditioned in accordance with the procedures set forth in the previous Example.

Chemicals

Carrageenan is obtained from TCI, Japan; Pyrogen free saline is from Astar, Taiwan; and Aspirin is purchased from ICN BioMedicals, USA.

Equipment

Glass syringe (1 ml and 2 ml Mitsuba, Japan), Hypodermic needle 24Gx1" (Top Corporation, Japan), Plethysmometer #7150 (UGO Basile, Italy), and Water cell 25 mm Diameter, #7157 (UGO Basile, Italy).

Method

Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. #7150) with water cell (25 mm diameter, Cat. #7157). Reduction of hind paw edema by 30 percent or more (30%) indicated significant acute anti-inflammatory activity.

E. This Example Illustrates the Anti-Inflammatory Activity of the Present Compounds Using a Model of Balb/c Mice Subjected to Monoclonal Antibody (mAb) Type II Collagen Induced Arthritis.

Test Substance and Dosing Pattern

A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen was injected. Dosing volume is 20 ml/kg.

Animals

Animals are conditioned in accordance with the procedures set forth in the previous Example.

Chemicals

Lipopolysaccharide is obtained from Sigma, USA; Indomethacin is from Sigma, USA; Arthrogen-CIA.TM. Monoclonal Antibodies D8, F10, DI-2G and A2 are obtained from IBL, Japan; Phosphated-Buffer Saline is purchased from Sigma, USA; and Tween 80 is from Wako, Japan.

Equipment

Plethysmometer (Ugo Basile, Italy) and Water Cell (Ugo Basile, Italy).

Method

Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mabs in a total of 4 mg/mouse at day 0, and followed by intravenous 25 µg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administered once daily for 3 consecutive days. A plethysmometer (Ugo Basile Cat #7150) with water cell (12 mm diameter) is used for the measurement of increase in volume of the two hind paws at day 0, 5, 7, 10, 14, and 17. The percent inhibition of increase in volume is calculated by the following formula:

$$\text{Inhibition (\%)}: [1-(T_n-T_0)/(C_n-C_0)] \times 100$$

Where:

$C_0$ ($C_n$): volume of day 0 (day n) in vehicle control $T_0$ ($T_n$): volume of day 0 (day n) in test compound-treated group The reduction of both of two hind paws edema by more than 30% is considered significant.

EXAMPLE 7

Neuropathic Pain Model

This example illustrates the analgesic activity of the compounds of this invention using a Sciatic Nerve ligation model of mononeuropathic pain Test System Adult male Sprague Dawley (SD) rats weighing 250-300 gm (Charles River Laboratories, San Diego, Calif.) are used. The animal room is lighted artificially at a 12-hr light-dark cycle (from 7:00 A.M. to 7:00 P.M) with water and food supply ad libitum. Animals are allocated randomly into groups.

Model Induction

Sciatic nerve ligation (SNL, Seltzer's model):

Under anesthesia with pentobarbital (50 mg/kg, i.p.) and aseptic techniques, the selective nerve injury is created by tightly ligating the selective portion of the common sciatic nerve according to the method of Seltzer (1990). Briefly, the high-thigh level of the left sciatic nerve is exposed after skin incision and blunt separation of muscles at a site near the trochanter just distal to the point at which the posterior biceps semitendious nerve nerve branches from the common sciatic nerve. The nerve is then fixed in this position with fine forceps by pinching the epineurium on its dorsal aspect, taking care not to press the nerve against underlying structures. An 8-0 silicon-treated silk suture is inserted into the nerve with a ⅜ curved, reversed-cutting mini-needle, and tightly ligated so that the dorsal ⅓-½ of the nerve is trapped in the ligature. The muscles are sutured in layers, and the skin closed with wound clips. Animals are then returned to their home cages. Rats exhibiting postoperative neurological deficits or poor grooming are excluded from the experiments.

Equipment

The following equipment is used in the current studies: von Frey filament set (Touch-test Sensory Evaluator, North Coast Medical Inc., Morgan Hill, Calif.).

Statistical Methods:

Within each experiment mean, standard error of the mean (SEM) and statistical significance are calculated using the average, standard error of the mean and unpaired, two-tailed t-Test functions, respectively, using Microsoft Excel®. Statistical significance of effects observed between individual experiments is determined, using Prism (GraphPad Software Inc., San Diego, Calif.) for the one-way or two-way analysis of variance (ANOVA) function. Statistical analyses are performed with a confidence limit of 0.95 and a significance level of 0.05.

EXAMPLE 8

Pore Formation

THP-1 cells (ATCC Cat # 2854F-100) are plated in 96 well plates at a concentration of 200,000 cells per well and allowed to differentiate in RPMI-1640 media (ATCC Cat # 30-2001) containing 10% FBS, 100 IU/mL penicillin, 100 ug/mL streptomycin, 100 ng/mL LPS and 100 ng/mL IFN-γ for 16 hours. Following differentiation, the cells are pretreated with the compound of interest at the appropriate concentration for 30 minutes in RPMI-1640 media containing 100 IU/mL penicillin, 100 ug/mL streptomycin. The pretreatment media is then replaced with assay buffer (20 mM HEPES, 10 mM d-glucose, 118 mM NMDG, 5 mM KCl, 0.4 mM $CaCl_2$) containing 5 uM Yo-Pro 1. (Molecular Probes Cat # Y3603) and the compound of interest at the appropriate concentration and the cells are incubated for an additional 10 minutes. 2',3'-O-(4-benzoylbenzoyl)-adenosine 5'-triphosphate (Sigma Aldrich Cat# B6396) is then added to a final concentration of 40 uM and fluorescence readings measured at 491/509 excitation/emission every minute for 50 minutes using a Tecan Safire plate reader. During this time temperature is maintained at of 37° C. Background adjusted fluorescence levels between drug treated and non-treated cells are used to calculate the percent inhibition.

EXAMPLE 9

IL-1β Release Assay

THP-1 cells (ATCC Cat # 285-IF-100) are plated in 96 well plates at a concentration of 200,000 cells per well and allowed to differentiate in RPMI-1640 media (ATCC Cat # 30-2001) containing 10% FBS, 100 IU/mL penicillin, 100 ug/mL streptomycin, 100 ng/mL LPS and 100 ng/mL IFN-γ for 16 hours. Following differentiation, the cells are treated for an additional 2 hours in RPMI-1640 media containing 100 IU/mL penicillin, 100 ug/mL streptomycin and fresh LPS at 100 ng/mL. The cells are then pretreated for 30 minutes with the compound of interest at the appropriate concentration in RPMI media containing 100 IU/mL penicillin, 100 ug/mL streptomycin. Following the pretreatment 2',3'-O-(4-benzoylbenzoyl)-adenosine 5'-triphosphate (Sigma Aldrich Cat # B6396) is added to a final concentration of 250 uM and the cells are incubated for an additional 45 minutes. 30 uL of cell supernatant is then collected and IL-1β levels determined via ELISA (R&D systems Cat. # HSLB50) according to manufacturer's recommendations using the Tecan Safire plate reader. Background adjusted IL-1β levels of drug treated and non-treated cells are used to calculate the percent inhibition.

The synthetic and biological examples described in this application are offered to illustrate this invention and are not to be construed in any way as limiting the scope of this invention. In the examples, all temperatures are in degrees Celsius (unless otherwise indicated). The compounds that have been prepared in accordance with the invention along with their biological activity data are presented in following Table. The syntheses of these representative compounds are carried out in accordance with the methods set forth above.

Exemplary Compounds of the Invention

The following compounds have been or can be prepared according to the synthetic methods described herein for example, method A-K. For the purpose of Table 1 below, activity of each compound, which can be determined using the IL-1β assay method described in Example 9, is expressed as follows:

"+" compound exhibited 0-25% inhibition at 0.3 μM concentration

"++" compound exhibited 26-50% inhibition at 0.3 μM concentration

"+++" compound exhibited 51-75% inhibition at 0.3 μM concentration

"++++" compound exhibited 76% or greater inhibition at 0.3 μM concentration

"*" compound exhibited 0-25% inhibition at 0.1 μM concentration

"**" compound exhibited 26-50% inhibition at 0.1 μM concentration

"***" compound exhibited 51-75% inhibition at 0.1 μM concentration

"****" compound exhibited 76% or greater inhibition at 0.1 μM concentration

Compounds with a percent inhibition represented by "++++" or "****" are of particular interest.

TABLE 1

IL-1β % Inhibition of Exemplary Compounds

| ID | Structure | MW | MS (obs) | IL-1β % Inhib. @ 0.3 μM |
|---|---|---|---|---|
| 1001 | 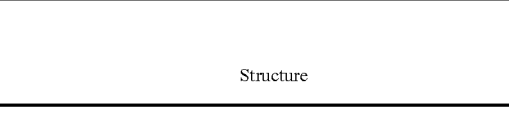 | 379.46 | 380.00 | +++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1002 | 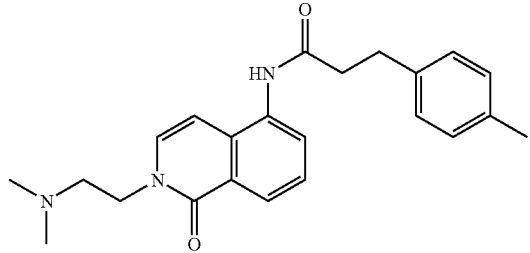 | 377.49 | 378.20 | ++++ |
| 1003 | 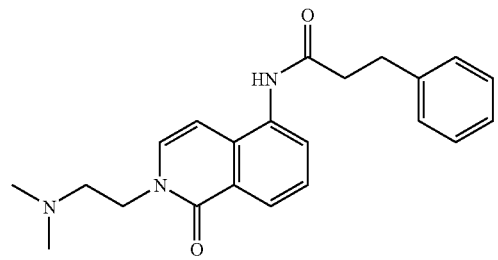 [SMILES: CN(C)CCn1ccc2c(NC(=O)CCc3ccccc3)cccc2c1=O] | 363.46 | 364.20 | + |
| 1004 | 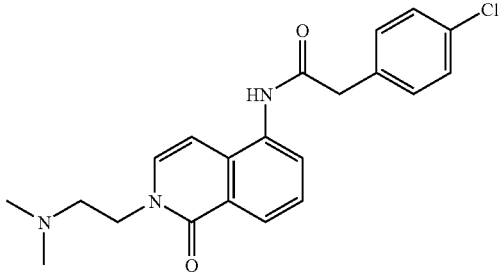 | 383.88 | 384.10 | ++++ |
| 1005 | 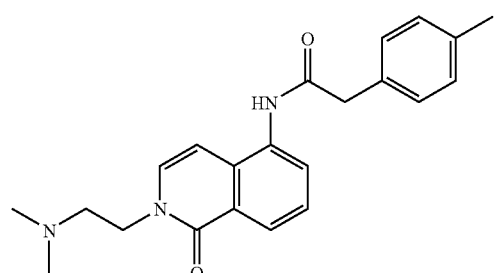 | 363.46 | 364.40 | ++++ |
| 1006 | 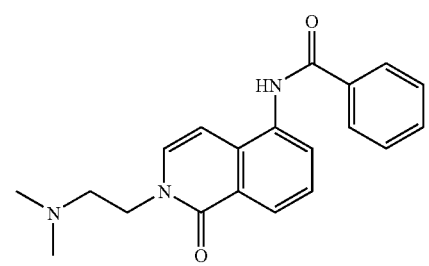 [SMILES: CN(C)CCn1ccc2c(NC(=O)c3ccccc3)cccc2c1=O] | 335.40 | 336.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1007 | 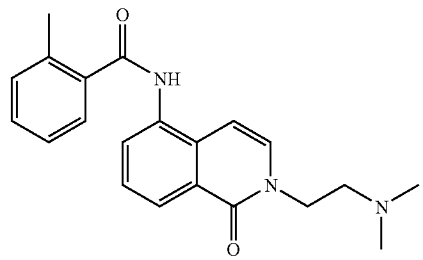 [SMILES: Cc1ccccc1C(=O)Nc1cccc2c(=O)n(CCN(C)C)ccc12] | 349.43 | 350.90 | + |
| 1008 | 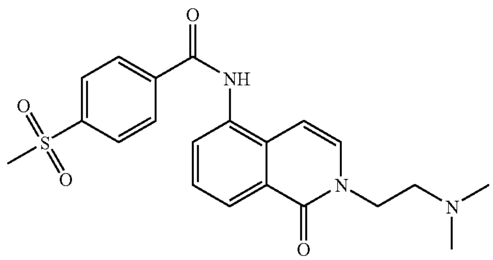 | 413.50 | 414.20 | |
| 1009 | 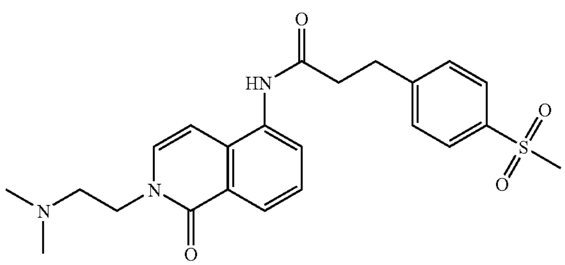 | 441.55 | 442.20 | + |
| 1010 | 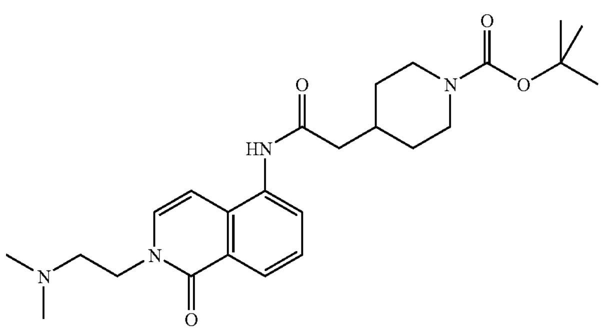 [SMILES: CN(C)CCn1ccc2c(NC(=O)CC3CCN(C(=O)OC(C)(C)C)CC3)cccc2c1=O] | 456.58 | 457.80 | + |
| 1011 | 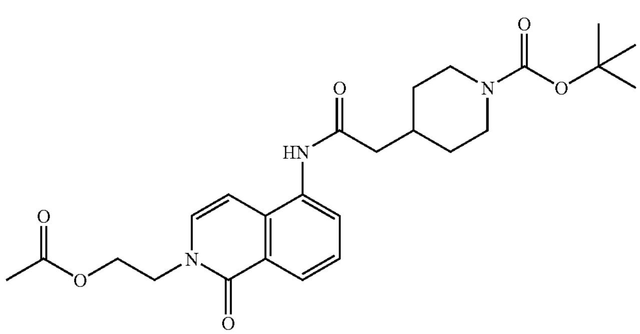 [SMILES: CC(=O)OCCn1ccc2c(NC(=O)CC3CCN(C(=O)OC(C)(C)C)CC3)cccc2c1=O] | 471.55 | 472.20 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1012 | 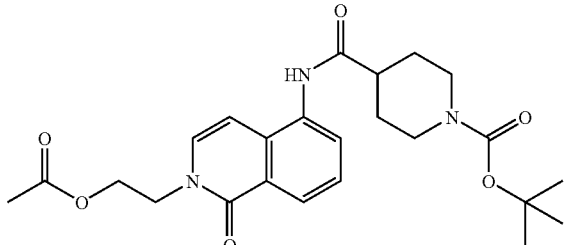 | 457.52 | 457.70 | ++ |
| 1013 | 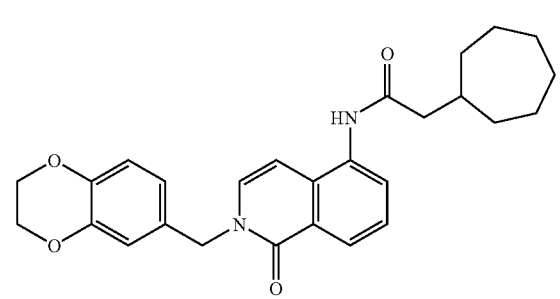 [SMILES: O=C(CC1CCCCCC1)Nc1cccc2c(=O)n(Cc3ccc4c(c3)OCCO4)ccc12] | 446.54 | 447.50 | ++++ |
| 1014 | 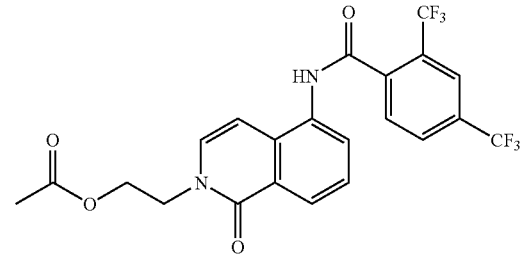 [SMILES: CC(=O)OCCn1ccc2c(NC(=O)c3ccc(C(F)(F)F)cc3C(F)(F)F)cccc2c1=O] | 486.37 | 487.00 | ++ |
| 1015 | 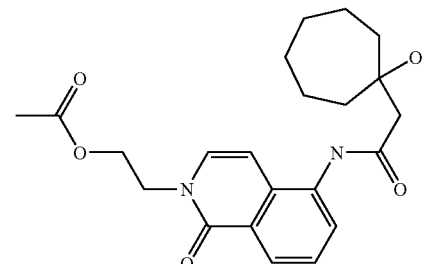 | 400.47 | 401.00 | ++++ |
| 1016 | 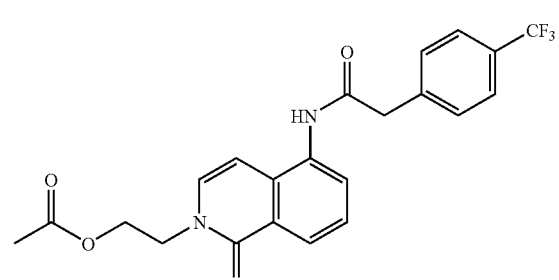 | 432.40 | 433.10 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1017 | 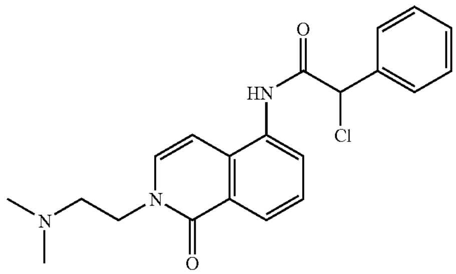 [SMILES: CN(C)CCn1ccc2c(NC(=O)C(Cl)c3ccccc3)cccc2c1=O] | 383.88 | 384.00 | ++ |
| 1018 | 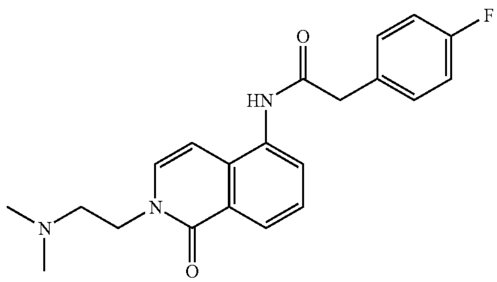 [SMILES: CN(C)CCn1ccc2c(NC(=O)Cc3ccc(F)cc3)cccc2c1=O] | 367.42 | 367.60 | + |
| 1019 | 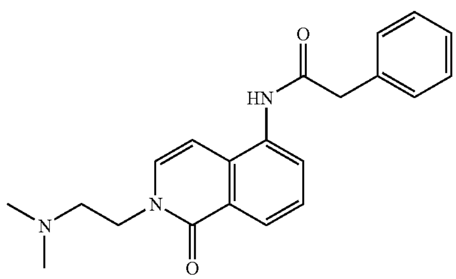 [SMILES: CN(C)CCn1ccc2c(NC(=O)Cc3ccccc3)cccc2c1=O] | 349.43 | 350.20 | + |
| 1020 | 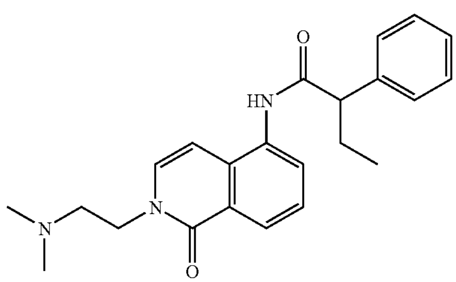 [SMILES: CCC(C(=O)Nc1cccc2c(=O)n(CCN(C)C)ccc12)c1ccccc1] | 377.49 | 377.80 | + |
| 1021 | 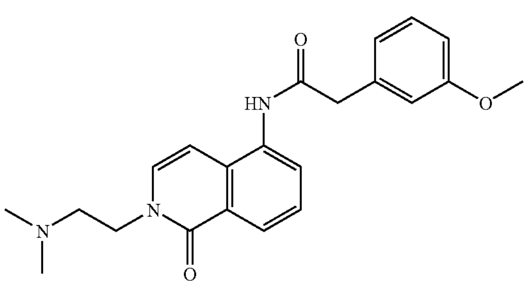 | 379.46 | 380.56 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1022 | 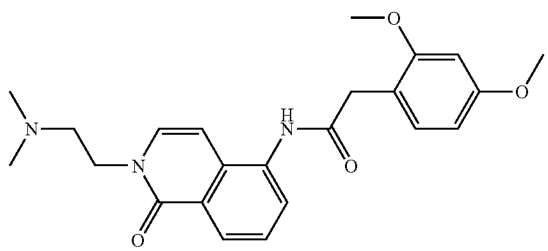 | 409.48 | 410.20 | + |
| 1023 | 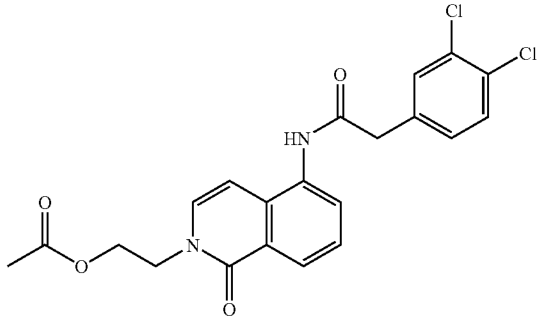 [SMILES: CC(=O)OCCn1ccc2c(NC(=O)Cc3ccc(Cl)c(Cl)c3)cccc2c1=O] | 433.29 | 434.50 | ++++ |
| 1024 | 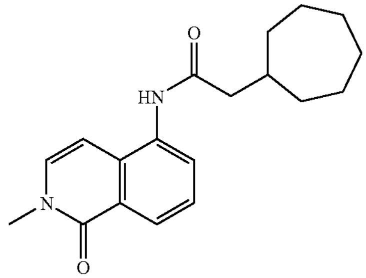 [SMILES: Cn1ccc2c(NC(=O)CC3CCCCCC3)cccc2c1=O] | 312.41 | 313.20 | ++++ |
| 1025 | 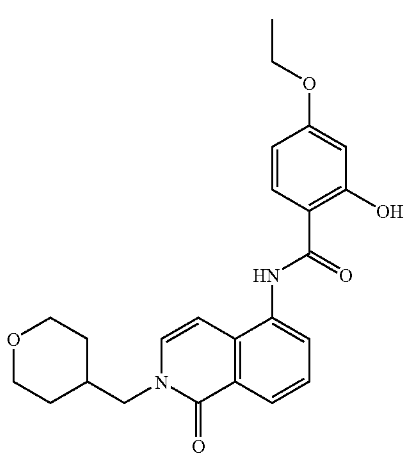 [SMILES: CCOc1ccc(C(=O)Nc2cccc3c(=O)n(CC4CCOCC4)ccc23)c(O)c1] | 422.48 | 423.31 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1026 | 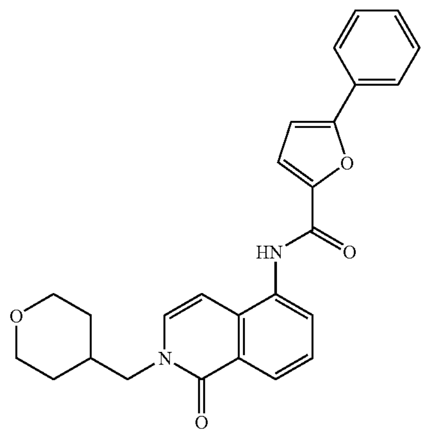 [SMILES: O=C(Nc1cccc2c(=O)n(CC3CCOCC3)ccc12)c1ccc(-c2ccccc2)o1] | 428.49 | 429.32 | ** |
| 1027 | 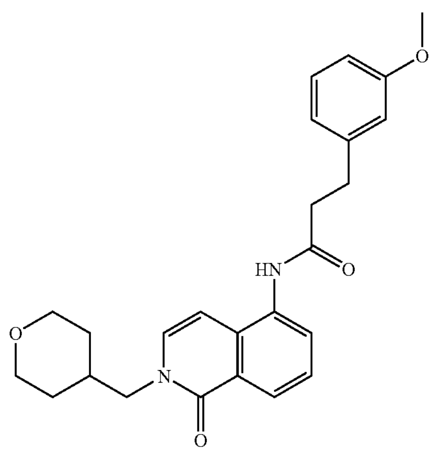 [SMILES: COc1cccc(CCC(=O)Nc2cccc3c(=O)n(CC4CCOCC4)ccc23)c1] | 420.51 | 421.18 | + |
| 1028 | 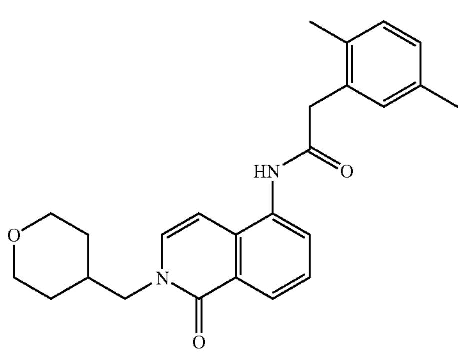 [SMILES: Cc1ccc(C)c(CC(=O)Nc2cccc3c(=O)n(CC4CCOCC4)ccc23)c1] | 404.51 | 405.50 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1029 | 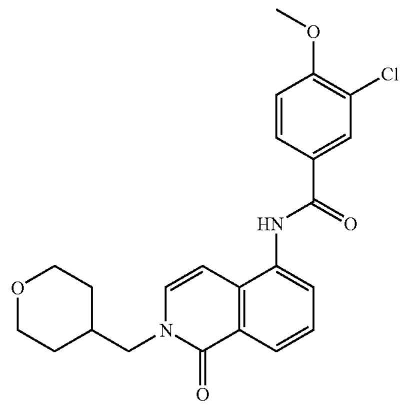 [SMILES: COc1ccc(C(=O)Nc2cccc3c(=O)n(CC4CCOCC4)ccc23)cc1Cl] | 426.90 | 427.03 | + |
| 1030 | 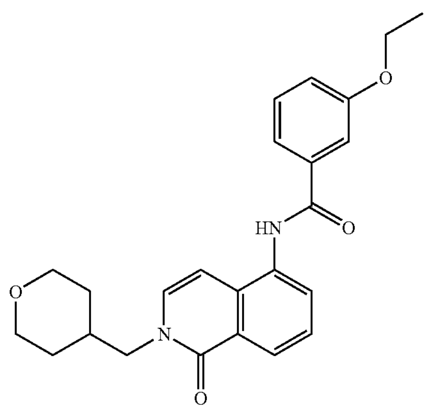 [SMILES: CCOc1cccc(C(=O)Nc2cccc3c(=O)n(CC4CCOCC4)ccc23)c1] | 406.48 | 407.40 | + |
| 1031 | 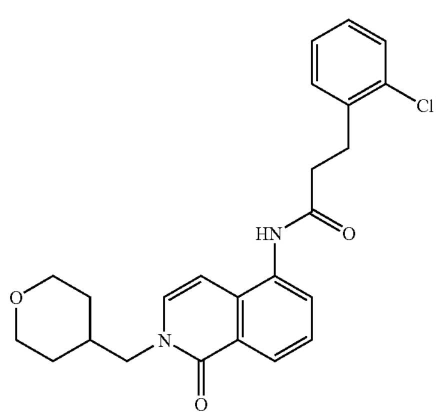 [SMILES: O=C(CCc1ccccc1Cl)Nc1cccc2c(=O)n(CC3CCOCC3)ccc12] | 424.93 | 425.11 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1032 | 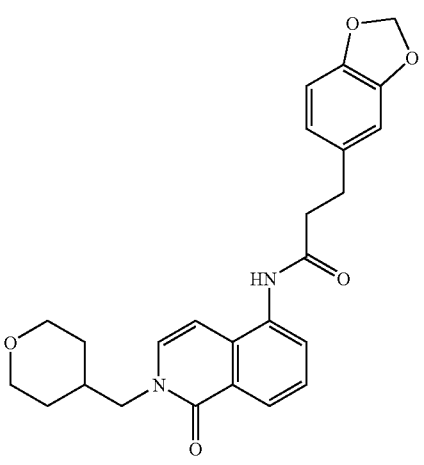 [SMILES: O=C(CCc1ccc2c(c1)OCO2)Nc1cccc2c(=O)n(CC3CCOCC3)ccc12] | 434.49 | 435.28 | + |
| 1033 | 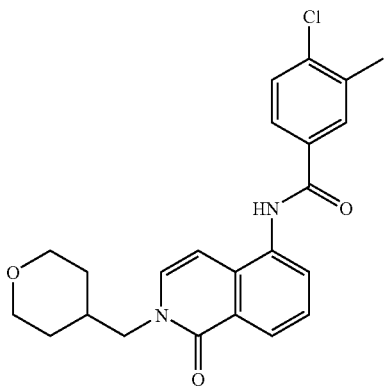 [SMILES: Cc1cc(C(=O)Nc2cccc3c(=O)n(CC4CCOCC4)ccc23)ccc1Cl] | 410.90 | 411.09 | + |
| 1034 | 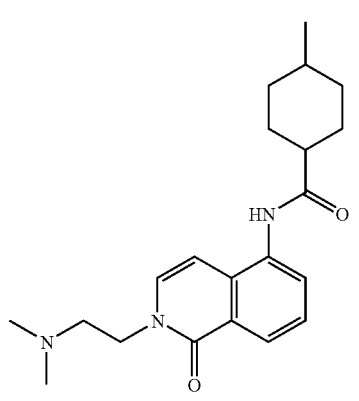 | 355.48 | 356.55 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1035 | 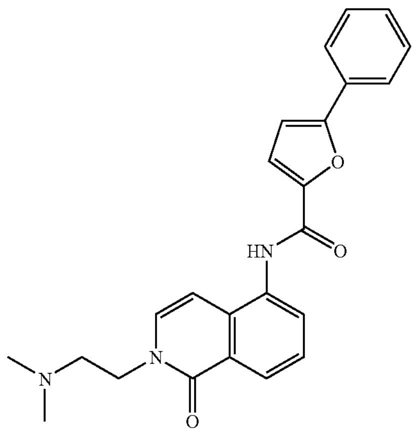 [SMILES: CN(C)CCn1ccc2c(NC(=O)c3ccc(-c4ccccc4)o3)cccc2c1=O] | 401.46 | 402.30 | * |
| 1036 | 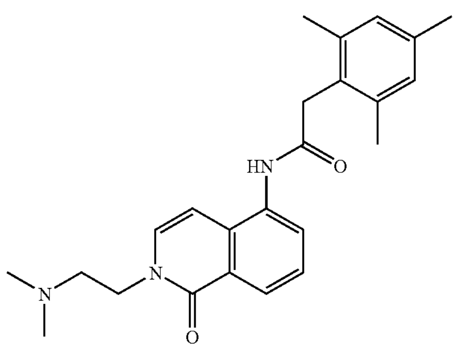 | 391.51 | 392.40 | + |
| 1037 | 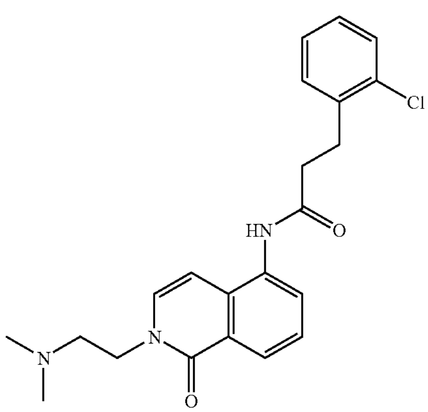 [SMILES: CN(C)CCn1ccc2c(NC(=O)CCc3ccccc3Cl)cccc2c1=O] | 397.90 | 398.24 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1038 | 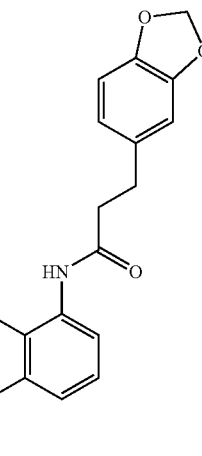 | 407.47 | 408.32 | + |
| 1039 | 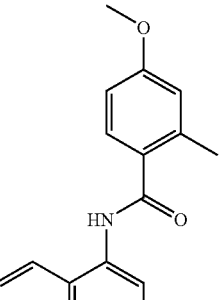 | 421.49 | 422.30 | * |
| 1040 | 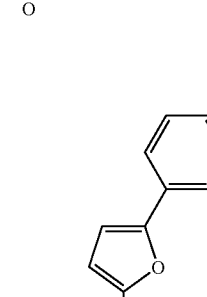 | 443.50 | 444.45 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1041 | 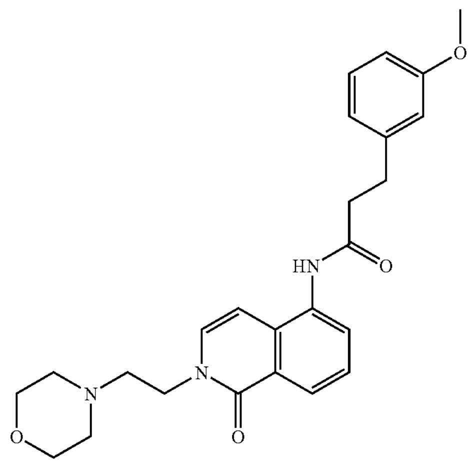 [SMILES: COc1cccc(CCC(=O)Nc2cccc3c(=O)n(CCN4CCOCC4)ccc23)c1] | 435.52 | 436.53 | * |
| 1042 | 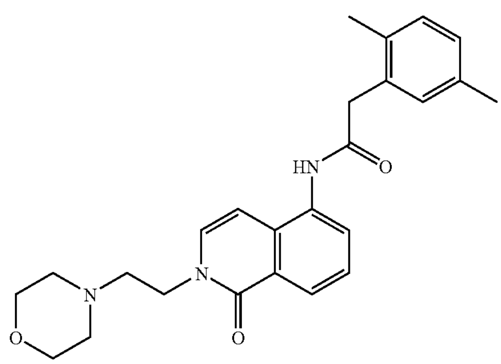 [SMILES: Cc1ccc(C)c(CC(=O)Nc2cccc3c(=O)n(CCN4CCOCC4)ccc23)c1] | 419.52 | 420.24 | + |
| 1043 | 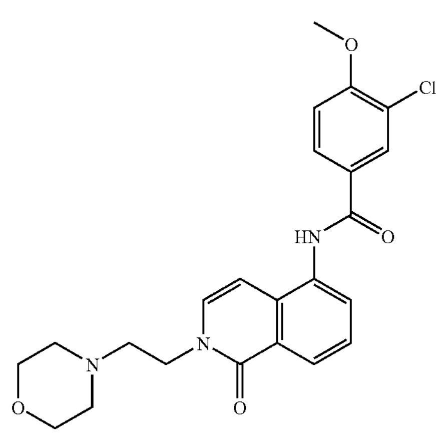 [SMILES: COc1ccc(C(=O)Nc2cccc3c(=O)n(CCN4CCOCC4)ccc23)cc1Cl] | 441.91 | 442.20 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1044 | 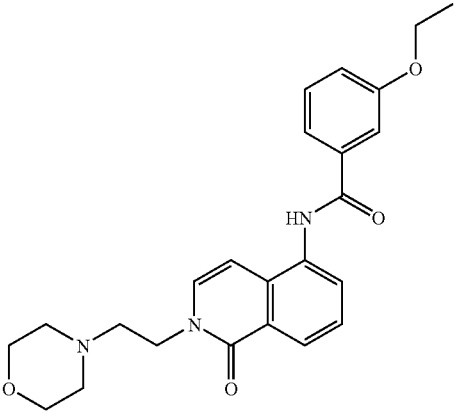 [SMILES: CCOc1cccc(C(=O)Nc2cccc3c(=O)n(CCN4CCOCC4)ccc23)c1] | 421.49 | 422.25 | + |
| 1045 | 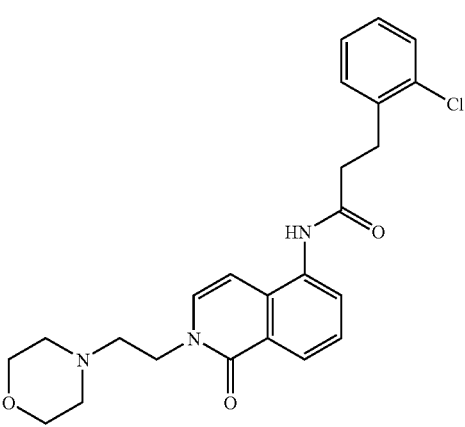 [SMILES: O=C(CCc1ccccc1Cl)Nc1cccc2c(=O)n(CCN3CCOCC3)ccc12] | 439.94 | 440.40 | + |
| 1046 | 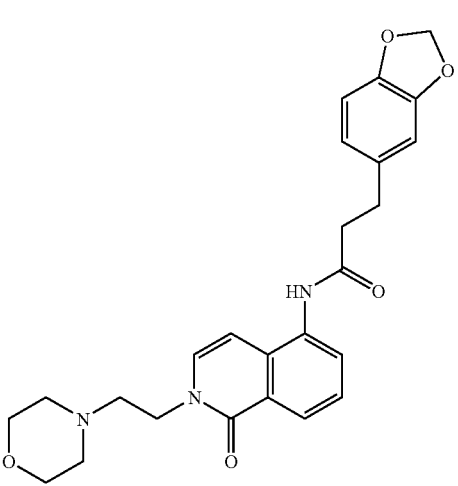 [SMILES: O=C(CCc1ccc2c(c1)OCO2)Nc1cccc2c(=O)n(CCN3CCOCC3)ccc12] | 449.50 | 450.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1047 | 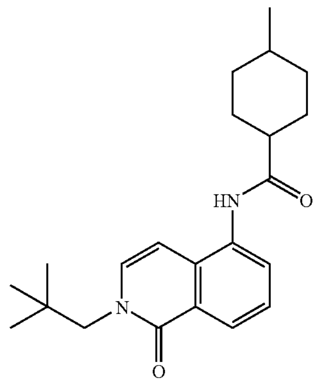 [SMILES: CC1CCC(C(=O)Nc2cccc3c(=O)n(CC(C)(C)C)ccc23)CC1] | 354.49 | 355.57 | * |
| 1048 | 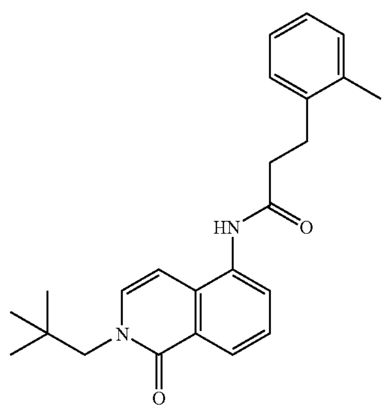 [SMILES: Cc1ccccc1CCC(=O)Nc1cccc2c(=O)n(CC(C)(C)C)ccc12] | 376.50 | 377.44 | * |
| 1049 | 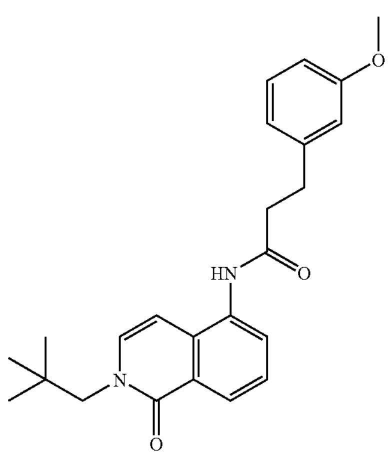 [SMILES: COc1cccc(CCC(=O)Nc2cccc3c(=O)n(CC(C)(C)C)ccc23)c1] | 392.50 | 393.35 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1050 | 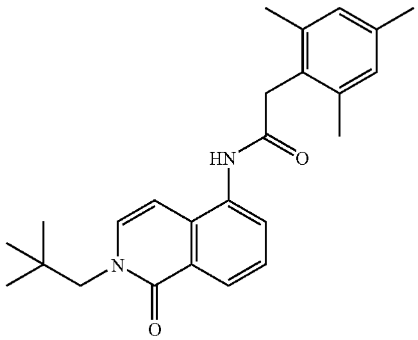 [SMILES: Cc1cc(C)c(CC(=O)Nc2cccc3c(=O)n(CC(C)(C)C)ccc23)c(C)c1] | 390.52 | 391.40 | + |
| 1051 | 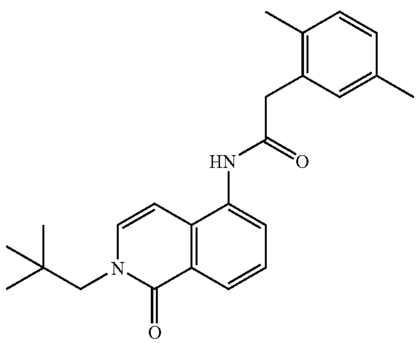 [SMILES: Cc1ccc(C)c(CC(=O)Nc2cccc3c(=O)n(CC(C)(C)C)ccc23)c1] | 376.50 | 377.47 | + |
| 1052 | 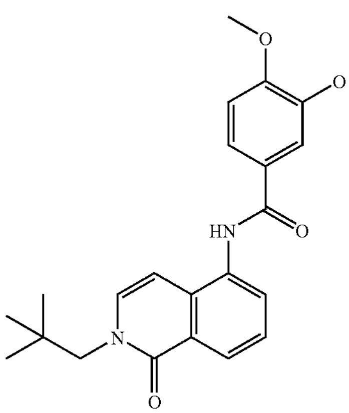 [SMILES: COc1ccc(C(=O)Nc2cccc3c(=O)n(CC(C)(C)C)ccc23)cc1O] | 398.89 | 399.14 | + |
| 1053 | 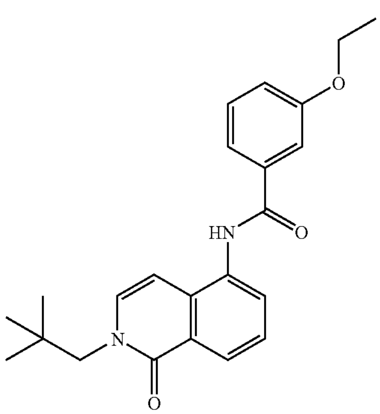 [SMILES: CCOc1cccc(C(=O)Nc2cccc3c(=O)n(CC(C)(C)C)ccc23)c1] | 378.47 | 379.45 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1054 | 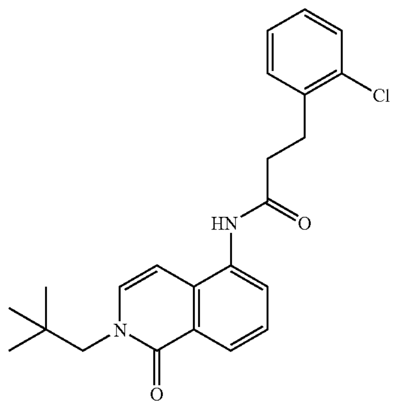 [SMILES: CC(C)(C)Cn1ccc2c(NC(=O)CCc3ccccc3Cl)cccc2c1=O] | 396.92 | 397.27 | + |
| 1055 | 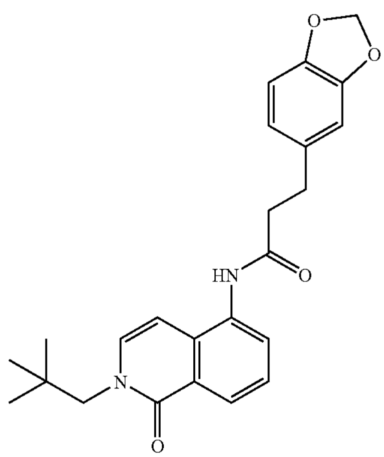 [SMILES: CC(C)(C)Cn1ccc2c(NC(=O)CCc3ccc4c(c3)OCO4)cccc2c1=O] | 406.48 | 407.58 | + |
| 1056 | 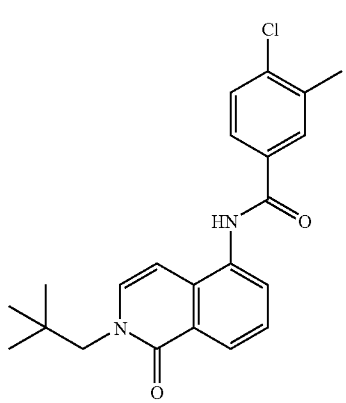 | 382.89 | 383.41 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1057 | 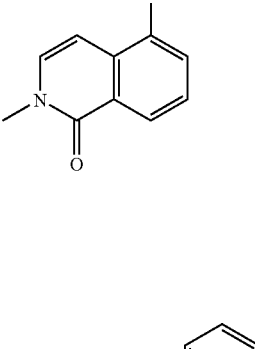 | 320.39 | 321.25 | * |
| 1058 | 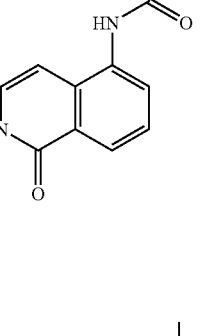 | 336.39 | 337.37 | + |
| 1059 | 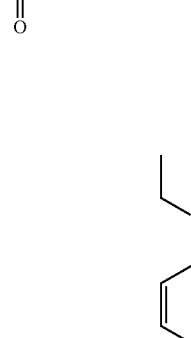 | 382.41 | 383.39 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1060 | 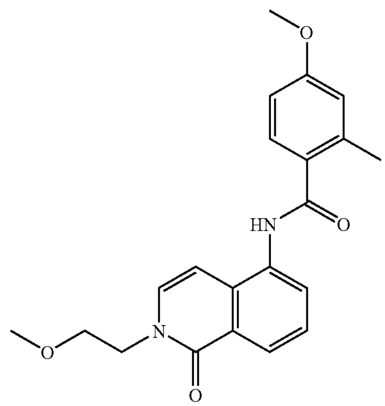 | 366.41 | 367.34 | + |
| 1061 | 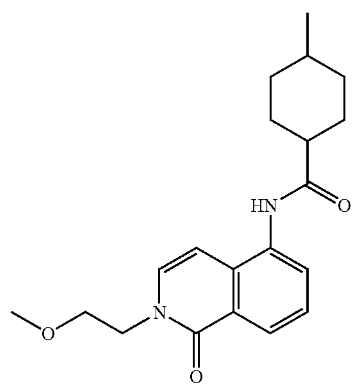 [SMILES: COCCn1ccc2c(NC(=O)C3CCC(C)CC3)cccc2c1=O] | 342.44 | 343.34 | + |
| 1062 | 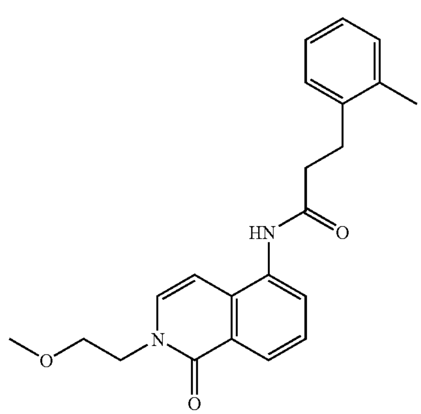 | 364.44 | 365.38 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1063 | 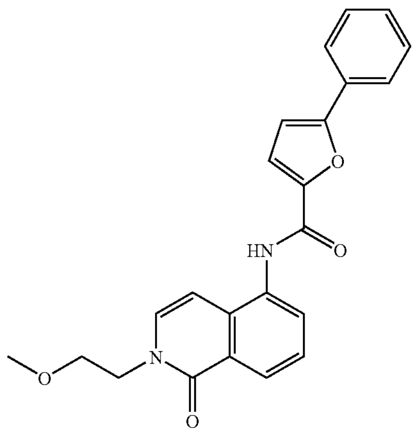 [SMILES: COCCn1ccc2c(NC(=O)c3ccc(-c4ccccc4)o3)cccc2c1=O] | 388.42 | 389.28 | * |
| 1064 | 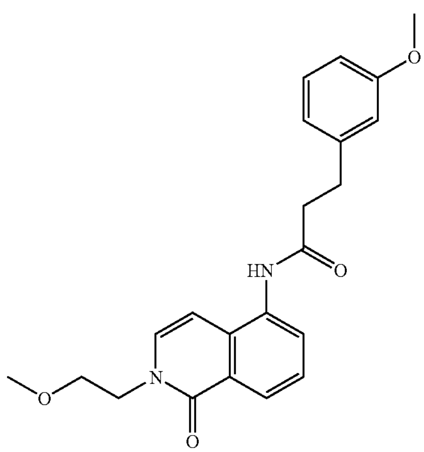 | 380.44 | 381.46 | * |
| 1065 | 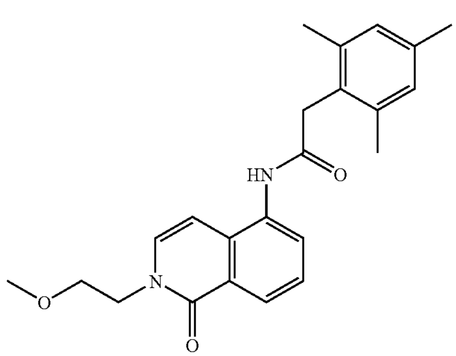 | 378.47 | 379.44 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1066 | 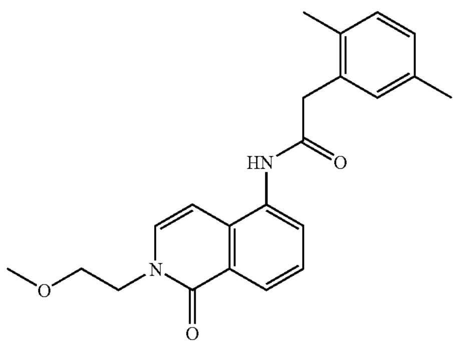 | 364.44 | 365.36 | + |
| 1067 | 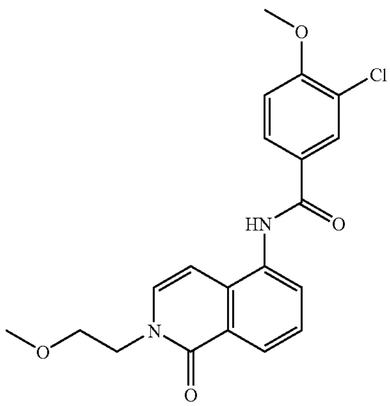 [SMILES: COCCn1ccc2c(NC(=O)c3ccc(OC)c(Cl)c3)cccc2c1=O] | 386.83 | 387.19 | ++ |
| 1068 | 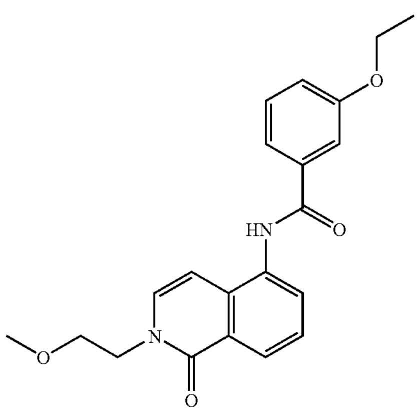 [SMILES: CCOc1cccc(C(=O)Nc2cccc3c(=O)n(CCOC)ccc23)c1] | 366.41 | 367.34 | + |
| 1069 | 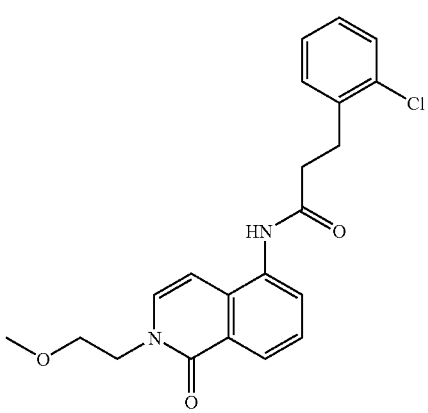 [SMILES: COCCn1ccc2c(NC(=O)CCc3ccccc3Cl)cccc2c1=O] | 384.86 | 385.44 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1070 | 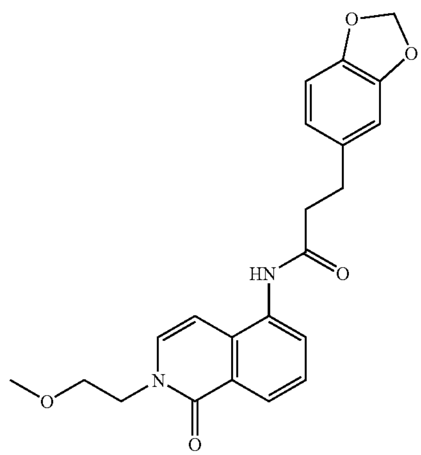 [SMILES: COCCn1ccc2c(NC(=O)CCc3ccc4c(c3)OCO4)cccc2c1=O] | 394.42 | 395.27 | + |
| 1071 | 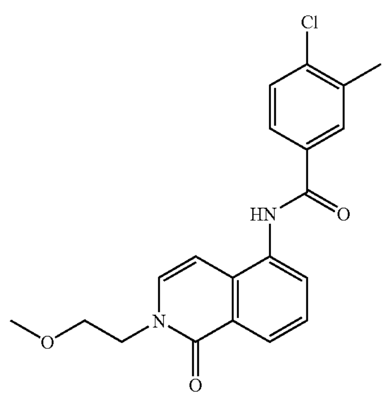 | 370.83 | 371.08 | + |
| 1072 | 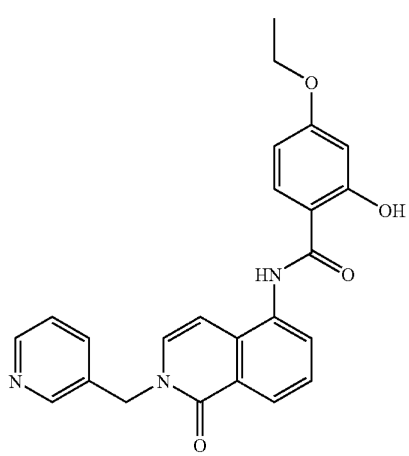 [SMILES: CCOc1ccc(C(=O)Nc2cccc3c(=O)n(Cc4cccnc4)ccc23)c(O)c1] | 415.45 | 416.31 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1073 | 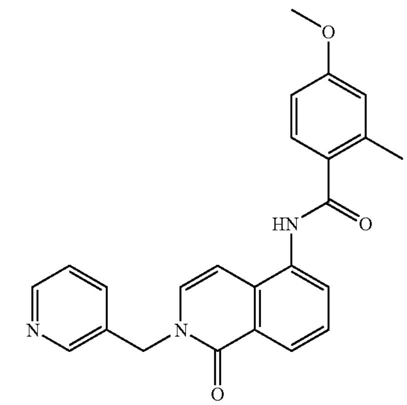 [SMILES: COc1ccc(C(=O)Nc2cccc3c(=O)n(Cc4cccnc4)ccc23)c(C)c1] | 399.45 | 400.39 | + |
| 1074 | 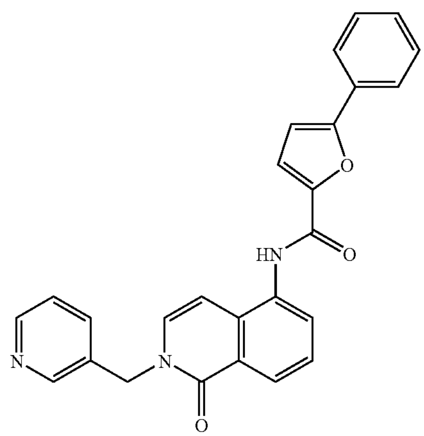 [SMILES: O=C(Nc1cccc2c(=O)n(Cc3cccnc3)ccc12)c1ccc(-c2ccccc2)o1] | 421.45 | 422.15 | + |
| 1075 | 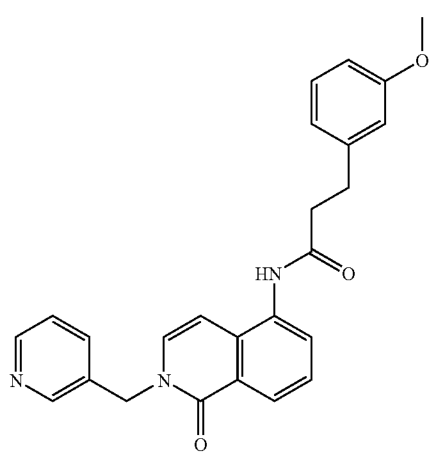 [SMILES: COc1cccc(CCC(=O)Nc2cccc3c(=O)n(Cc4cccnc4)ccc23)c1] | 413.47 | 414.30 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1076 | 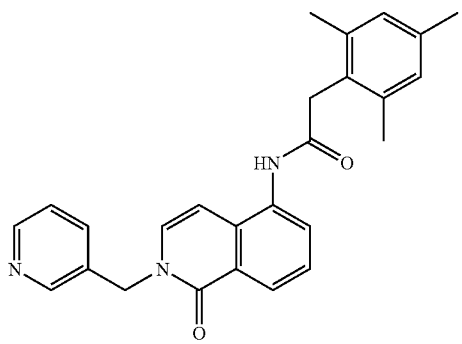 [SMILES: Cc1cc(C)c(CC(=O)Nc2cccc3c(=O)n(Cc4cccnc4)ccc23)c(C)c1] | 411.50 | 412.54 | + |
| 1077 | 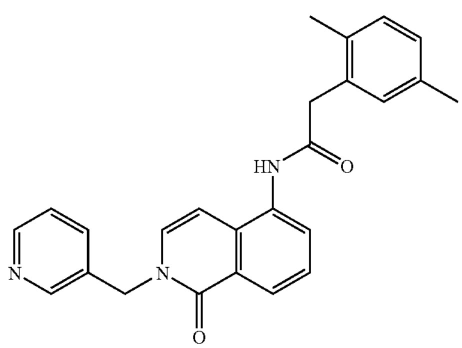 [SMILES: Cc1ccc(C)c(CC(=O)Nc2cccc3c(=O)n(Cc4cccnc4)ccc23)c1] | 397.48 | 398.16 | + |
| 1078 | 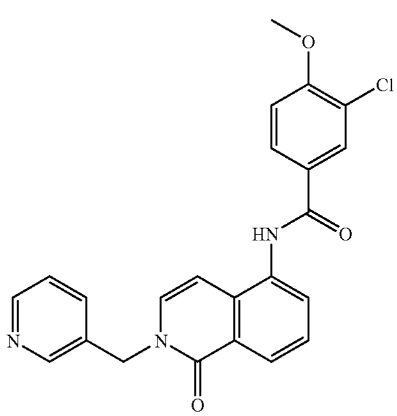 [SMILES: COc1ccc(C(=O)Nc2cccc3c(=O)n(Cc4cccnc4)ccc23)cc1Cl] | 419.87 | 420.17 | + |
| 1079 | 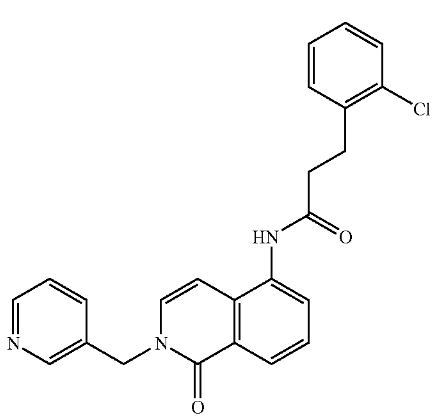 [SMILES: O=C(CCc1ccccc1Cl)Nc1cccc2c(=O)n(Cc3cccnc3)ccc12] | 417.89 | 418.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1080 | 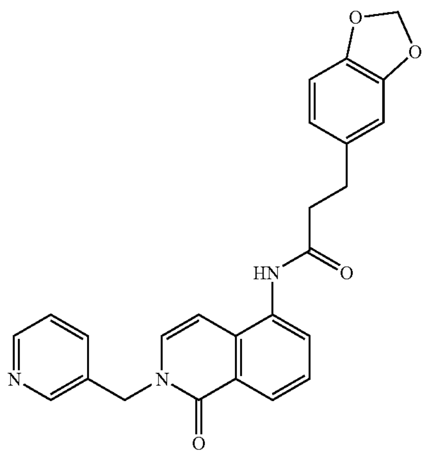 [SMILES: O=C(CCc1ccc2c(c1)OCO2)Nc1cccc2c(=O)n(Cc3cccnc3)ccc12] | 427.46 | 428.15 | + |
| 1081 | 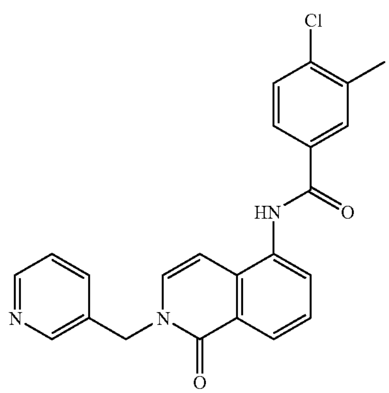 | 403.87 | 404.34 | + |
| 1082 | 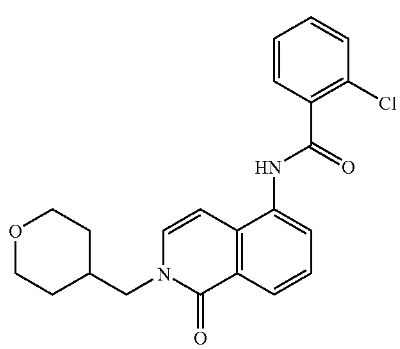 [SMILES: O=C(Nc1cccc2c(=O)n(CC3CCOCC3)ccc12)c1ccccc1Cl] | 396.87 | 397.20 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1083 | 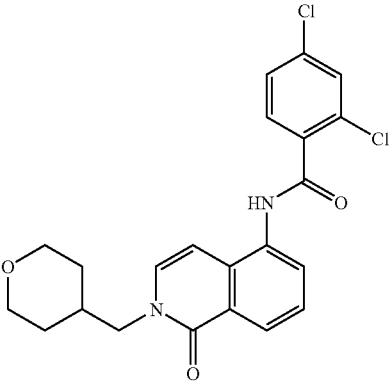 [SMILES: O=C(Nc1cccc2c(=O)n(CC3CCOCC3)ccc12)c1ccc(Cl)cc1Cl] | 431.32 | 431.10 | + |
| 1084 | 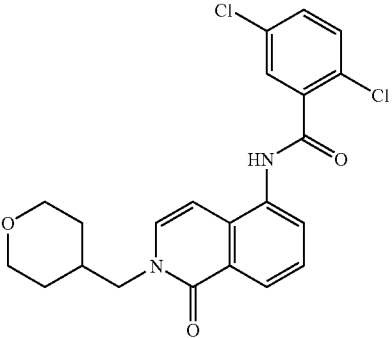 [SMILES: O=C(Nc1cccc2c(=O)n(CC3CCOCC3)ccc12)c1cc(Cl)ccc1Cl] | 431.32 | 431.10 | + |
| 1085 | 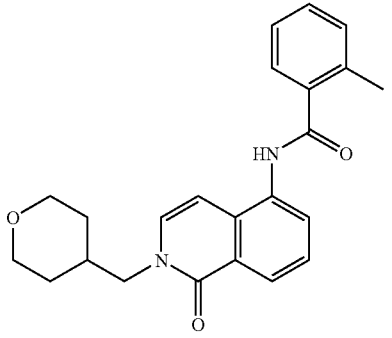 [SMILES: Cc1ccccc1C(=O)Nc1cccc2c(=O)n(CC3CCOCC3)ccc12] | 376.45 | 377.33 | + |
| 1086 | 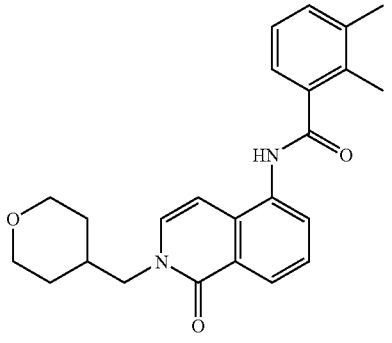 [SMILES: Cc1cccc(C(=O)Nc2cccc3c(=O)n(CC4CCOCC4)ccc23)c1C] | 390.48 | 391.50 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1087 | 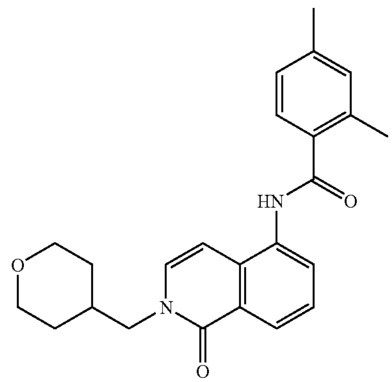 [SMILES: Cc1ccc(C(=O)Nc2cccc3c(=O)n(CC4CCOCC4)ccc23)c(C)c1] | 390.48 | 391.50 | + |
| 1088 | 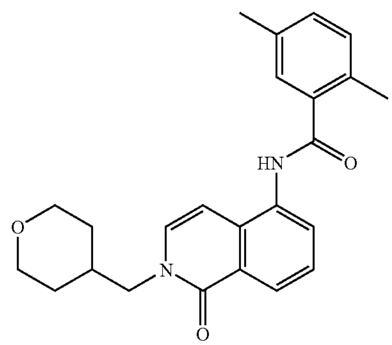 [SMILES: Cc1ccc(C)c(C(=O)Nc2cccc3c(=O)n(CC4CCOCC4)ccc23)c1] | 390.48 | 391.50 | + |
| 1089 | 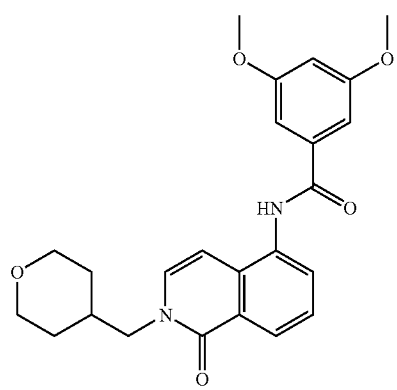 [SMILES: COc1cc(OC)cc(C(=O)Nc2cccc3c(=O)n(CC4CCOCC4)ccc23)c1] | 422.48 | 423.20 | + |
| 1090 | 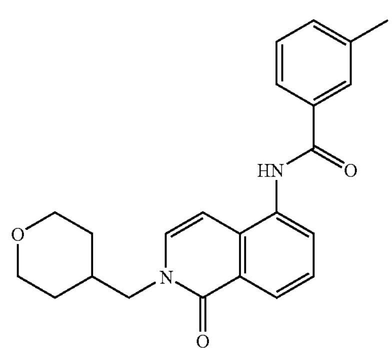 [SMILES: Cc1cccc(C(=O)Nc2cccc3c(=O)n(CC4CCOCC4)ccc23)c1] | 376.45 | 377.33 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1091 | 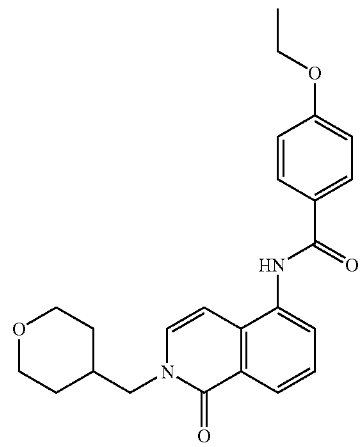 [SMILES: CCOc1ccc(C(=O)Nc2cccc3c(=O)n(CC4CCOCC4)ccc23)cc1] | 406.48 | 407.40 | + |
| 1092 | 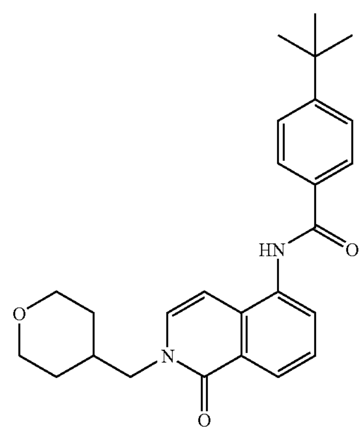 [SMILES: CC(C)(C)c1ccc(C(=O)Nc2cccc3c(=O)n(CC4CCOCC4)ccc23)cc1] | 418.53 | 419.38 | + |
| 1093 | 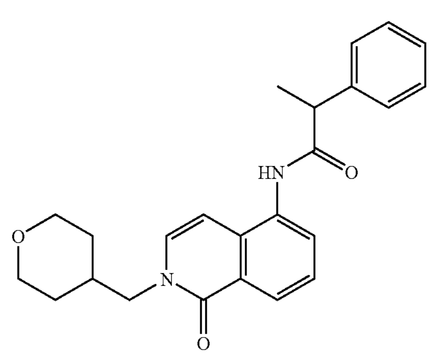 [SMILES: CC(C(=O)Nc1cccc2c(=O)n(CC3CCOCC3)ccc12)c1ccccc1] | 390.48 | 391.50 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1094 | 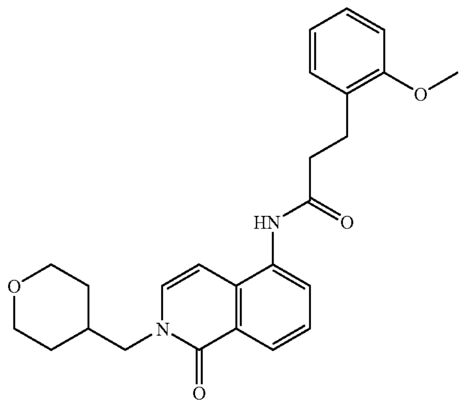 [SMILES: COc1ccccc1CCC(=O)Nc1cccc2c(=O)n(CC3CCOCC3)ccc12] | 420.51 | 421.17 | + |
| 1095 | 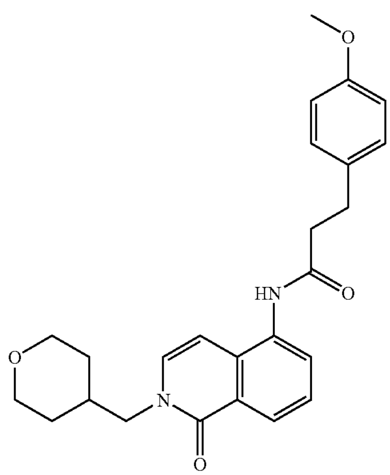 [SMILES: COc1ccc(CCC(=O)Nc2cccc3c(=O)n(CC4CCOCC4)ccc23)cc1] | 420.51 | 421.39 | + |
| 1096 | 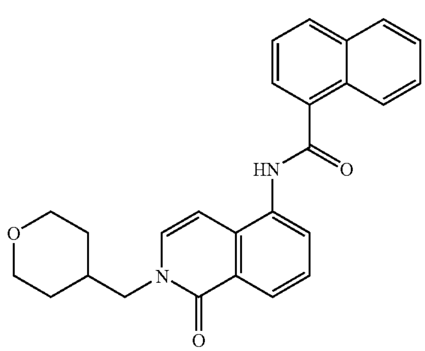 [SMILES: O=C(Nc1cccc2c(=O)n(CC3CCOCC3)ccc12)c1cccc2ccccc12] | 412.49 | 413.40 | + |

//
TABLE 1-continued
IL-1β % Inhibition of Exemplary Compounds
| ID | Structure | MW | MS (obs) | IL-1β % Inhib. @ 0.3 μM |
|---|---|---|---|---|
| 1097 | 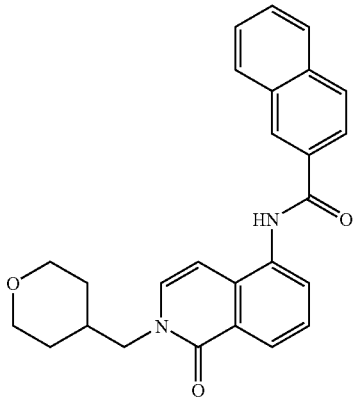 [SMILES: O=C(Nc1cccc2c(=O)n(CC3CCOCC3)ccc12)c1ccc2ccccc2c1] | 426.51 | 427.44 | + |
| 1098 | 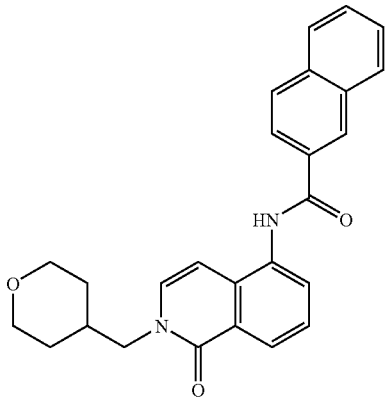 [SMILES: O=C(Nc1cccc2c(=O)n(CC3CCOCC3)ccc12)c1ccc2ccccc2c1] | 412.49 | 413.40 | + |
| 1099 | 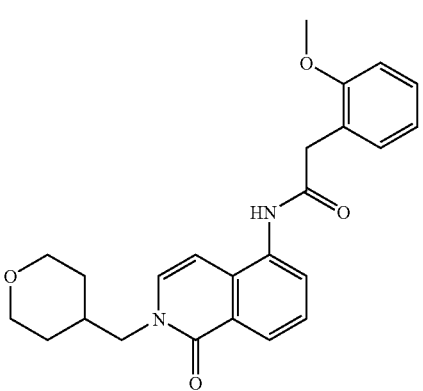 [SMILES: COc1ccccc1CC(=O)Nc1cccc2c(=O)n(CC3CCOCC3)ccc12] | 406.48 | 407.60 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1100 | 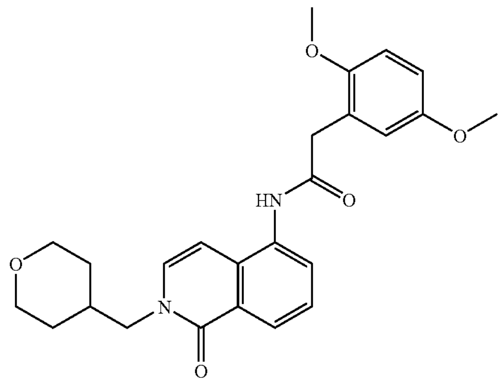 [SMILES: COc1ccc(OC)c(CC(=O)Nc2cccc3c(=O)n(CC4CCOCC4)ccc23)c1] | 436.51 | 437.58 | + |
| 1101 | 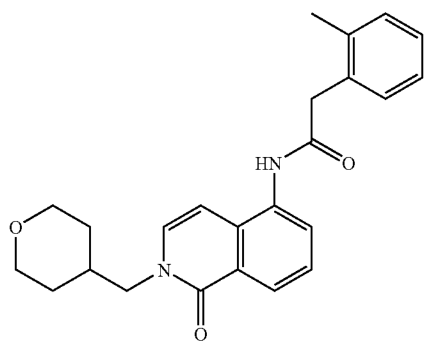 [SMILES: Cc1ccccc1CC(=O)Nc1cccc2c(=O)n(CC3CCOCC3)ccc12] | 390.48 | 391.39 | + |
| 1102 | 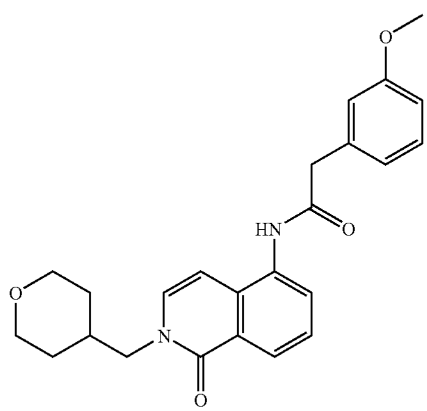 [SMILES: COc1cccc(CC(=O)Nc2cccc3c(=O)n(CC4CCOCC4)ccc23)c1] | 406.48 | 407.61 | + |
| 1103 | 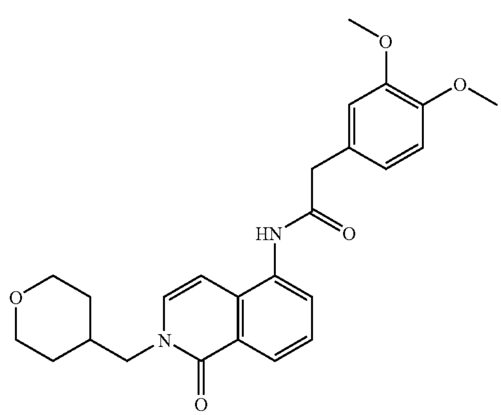 [SMILES: COc1ccc(CC(=O)Nc2cccc3c(=O)n(CC4CCOCC4)ccc23)cc1OC] | 436.51 | 437.56 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1104 | 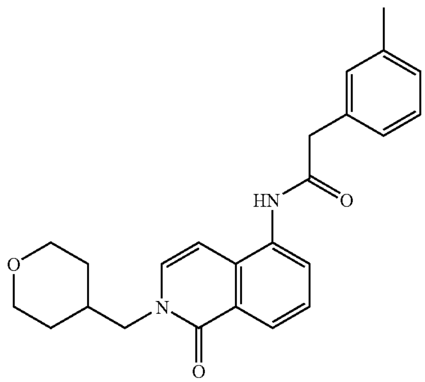 [SMILES: Cc1cccc(CC(=O)Nc2cccc3c(=O)n(CC4CCOCC4)ccc23)c1] | 390.48 | 391.38 | + |
| 1105 | 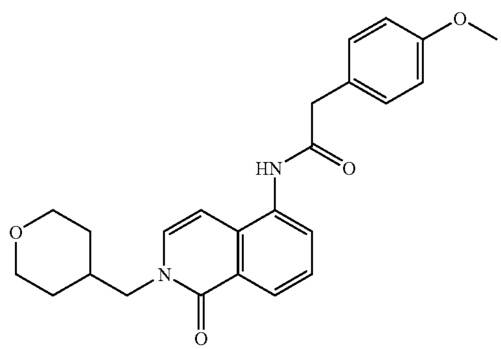 [SMILES: COc1ccc(CC(=O)Nc2cccc3c(=O)n(CC4CCOCC4)ccc23)cc1] | 406.48 | 407.58 | + |
| 1106 | 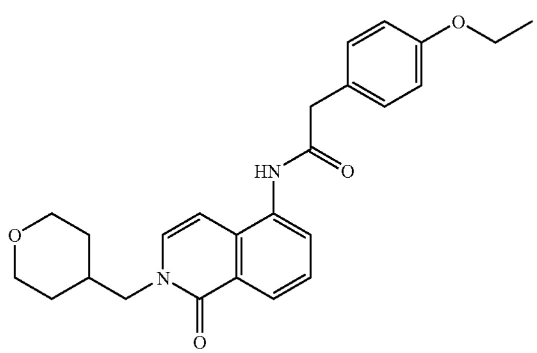 [SMILES: CCOc1ccc(CC(=O)Nc2cccc3c(=O)n(CC4CCOCC4)ccc23)cc1] | 420.51 | 421.39 | + |
| 1107 | 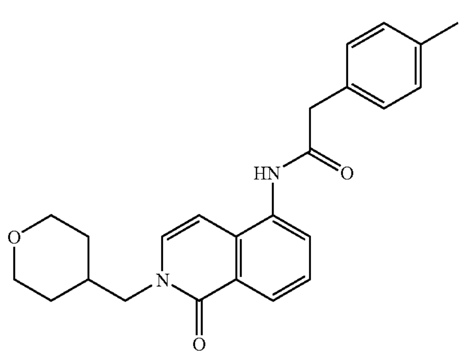 [SMILES: Cc1ccc(CC(=O)Nc2cccc3c(=O)n(CC4CCOCC4)ccc23)cc1] | 390.48 | 391.39 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1108 | 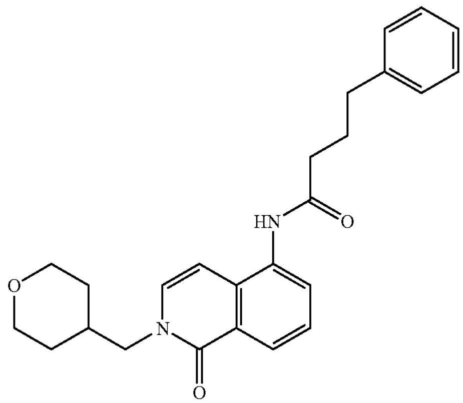 [SMILES: O=C(CCCc1ccccc1)Nc1cccc2c(=O)n(CC3CCOCC3)ccc12] | 404.51 | 405.53 | + |
| 1109 | 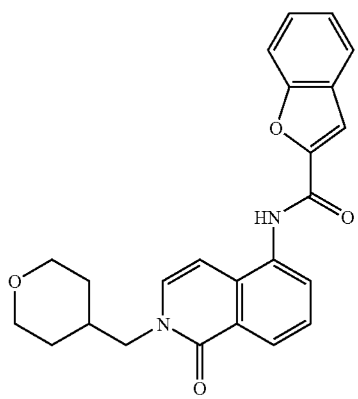 [SMILES: O=C(Nc1cccc2c(=O)n(CC3CCOCC3)ccc12)c1cc2ccccc2o1] | 402.45 | 403.30 | + |
| 1110 | 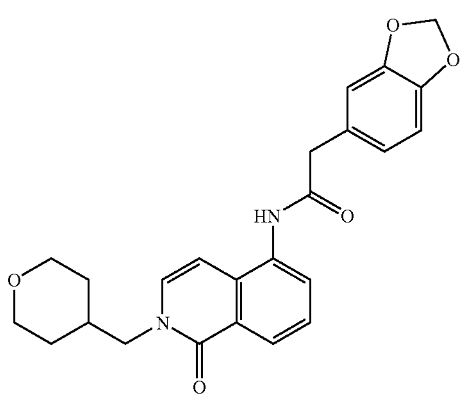 [SMILES: O=C(Cc1ccc2c(c1)OCO2)Nc1cccc2c(=O)n(CC3CCOCC3)ccc12] | 420.46 | 421.37 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1111 | 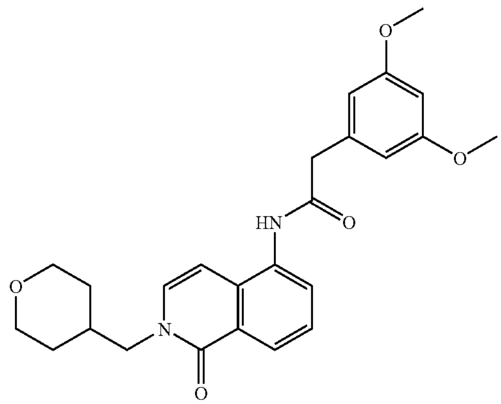 [SMILES: COc1cc(CC(=O)Nc2cccc3c(=O)n(CC4CCOCC4)ccc23)cc(OC)c1] | 436.51 | 437.58 | + |
| 1112 | 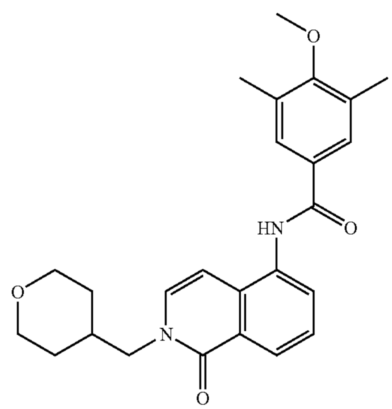 [SMILES: COc1c(C)cc(C(=O)Nc2cccc3c(=O)n(CC4CCOCC4)ccc23)cc1C] | 420.51 | 421.38 | + |
| 1113 | 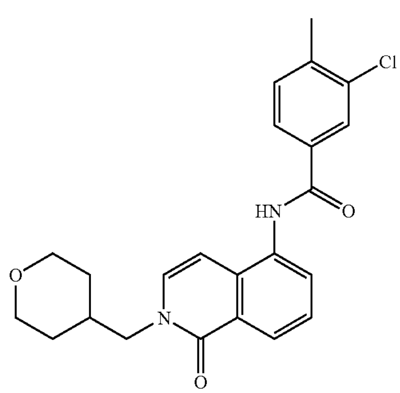 [SMILES: Cc1ccc(C(=O)Nc2cccc3c(=O)n(CC4CCOCC4)ccc23)cc1Cl] | 410.90 | 411.52 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1114 | 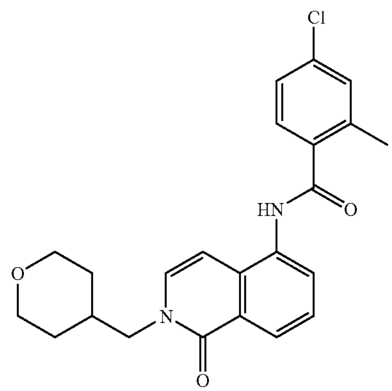 [SMILES: Cc1cc(Cl)ccc1C(=O)Nc1cccc2c(=O)n(CC3CCOCC3)ccc12] | 410.90 | 411.49 | + |
| 1115 | 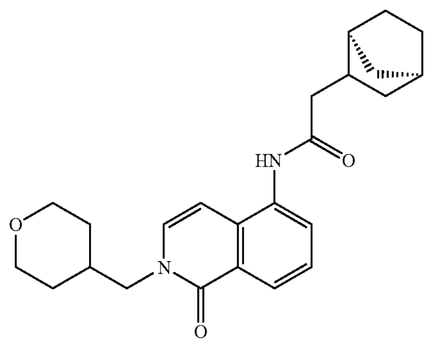 [SMILES: O=C(CC1C[C@@H]2CC[C@H]1C2)Nc1cccc2c(=O)n(CC3CCOCC3)ccc12] | 394.51 | 395.33 | ++ |
| 1116 | 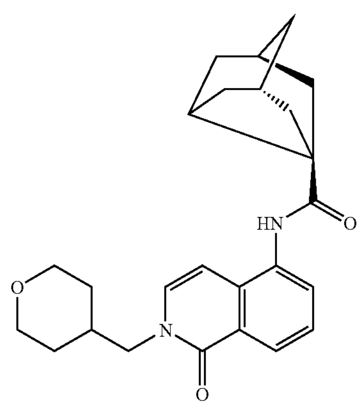 [SMILES: O=C(Nc1cccc2c(=O)n(CC3CCOCC3)ccc12)[C@]12C[C@@H]3CC1C[C@@H](C3)C2] | 406.52 | 407.60 | + |
| 1117 | 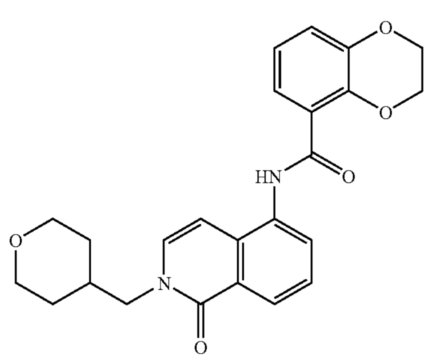 [SMILES: O=C(Nc1cccc2c(=O)n(CC3CCOCC3)ccc12)c1cccc2c1OCCO2] | 420.46 | 421.38 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1118 | 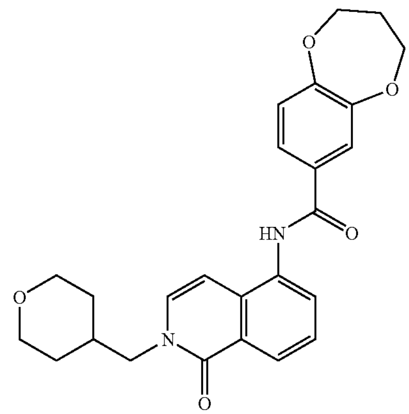 [SMILES: O=C(Nc1cccc2c(=O)n(CC3CCOCC3)ccc12)c1ccc2c(c1)OCCCO2] | 434.49 | 435.55 | + |
| 1119 | 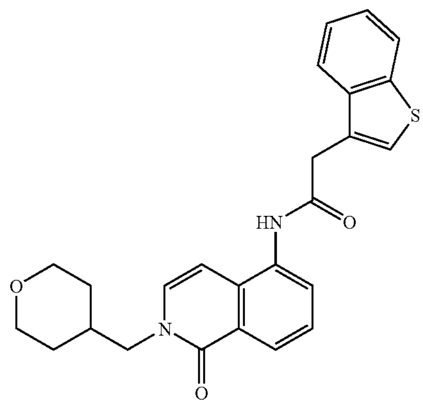 [SMILES: O=C(Cc1csc2ccccc12)Nc1cccc2c(=O)n(CC3CCOCC3)ccc12] | 432.54 | 433.44 | + |
| 1120 | 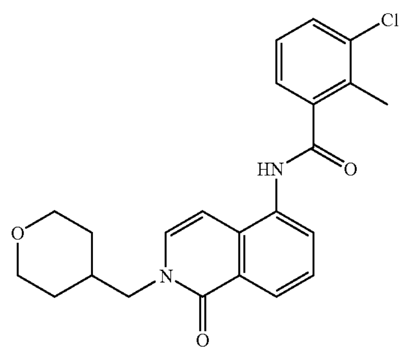 [SMILES: Cc1c(Cl)cccc1C(=O)Nc1cccc2c(=O)n(CC3CCOCC3)ccc12] | 410.90 | 411.52 | + |
| 1121 | 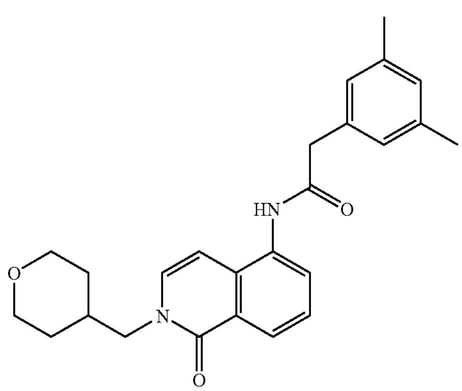 [SMILES: Cc1cc(C)cc(CC(=O)Nc2cccc3c(=O)n(CC4CCOCC4)ccc23)c1] | 404.51 | 405.52 | + |

TABLE 1-continued

IL-1β % Inhibition of Exemplary Compounds

| ID | Structure | MW | MS (obs) | IL-1β % Inhib. @ 0.3 μM |
|----|-----------|-----|----------|-------------------------|
| 1122 | 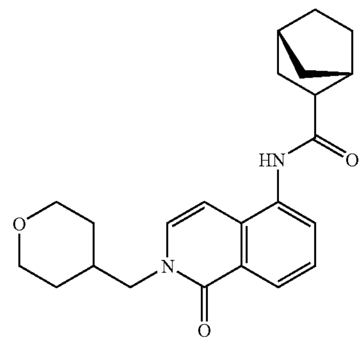 [SMILES: O=C(Nc1cccc2c(=O)n(CC3CCOCC3)ccc12)C1C[C@@H]2CC[C@H]1C2] | 380.49 | 381.48 | + |
| 1123 | 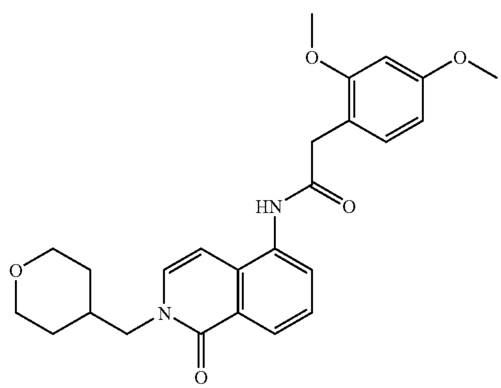 [SMILES: COc1ccc(CC(=O)Nc2cccc3c(=O)n(CC4CCOCC4)ccc23)c(OC)c1] | 436.51 | 437.57 | + |
| 1124 | 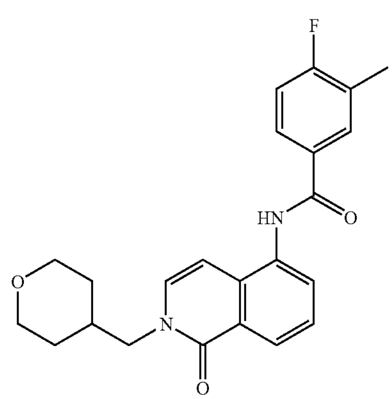 | 394.44 | 395.28 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1125 | 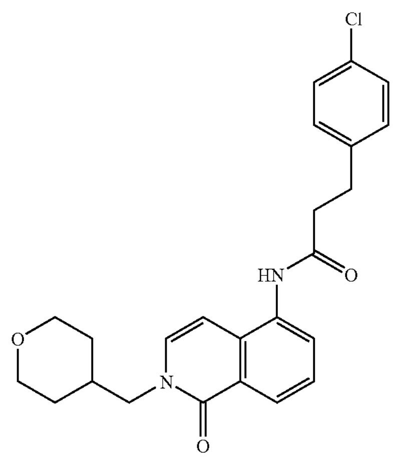 [SMILES: O=C(CCc1ccc(Cl)cc1)Nc1cccc2c(=O)n(CC3CCOCC3)ccc12] | 424.93 | 425.10 | + |
| 1126 | 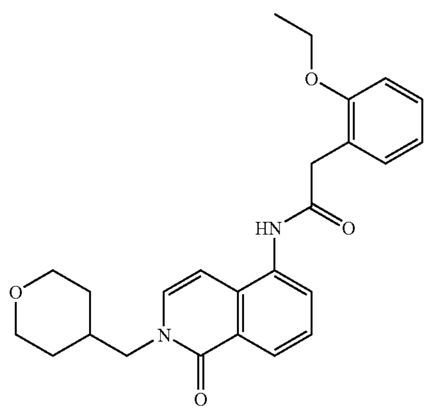 [SMILES: CCOc1ccccc1CC(=O)Nc1cccc2c(=O)n(CC3CCOCC3)ccc12] | 420.51 | 421.39 | + |
| 1127 | 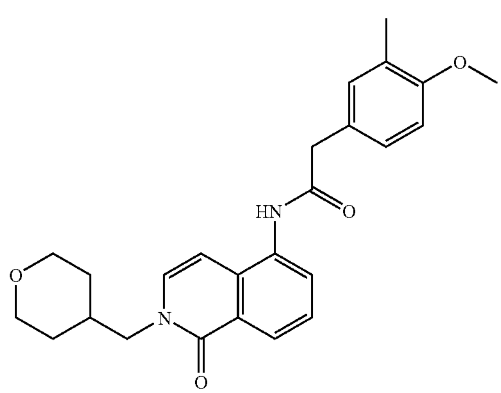 [SMILES: COc1ccc(CC(=O)Nc2cccc3c(=O)n(CC4CCOCC4)ccc23)cc1C] | 420.51 | 421.39 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1128 | 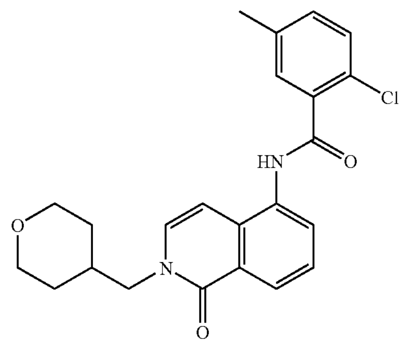 [SMILES: Cc1ccc(Cl)c(C(=O)Nc2cccc3c(=O)n(CC4CCOCC4)ccc23)c1] | 410.90 | 411.51 | + |
| 1129 | 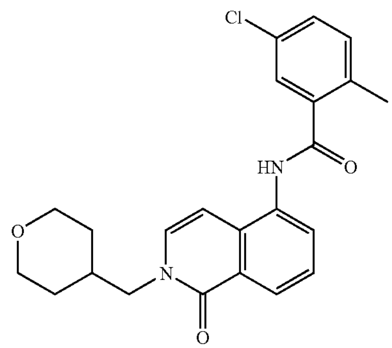 [SMILES: Cc1ccc(Cl)cc1C(=O)Nc1cccc2c(=O)n(CC3CCOCC3)ccc12] | 410.90 | 411.50 | + |
| 1130 | 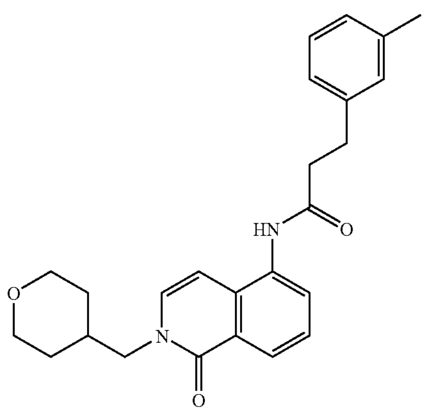 [SMILES: Cc1cccc(CCC(=O)Nc2cccc3c(=O)n(CC4CCOCC4)ccc23)c1] | 404.51 | 405.51 | + |
| 1131 | 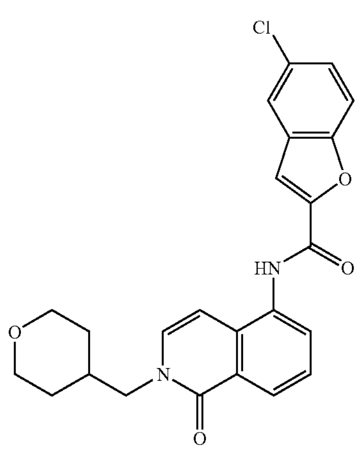 [SMILES: O=C(Nc1cccc2c(=O)n(CC3CCOCC3)ccc12)c1cc2cc(Cl)ccc2o1] | 436.89 | 437.41 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1132 | 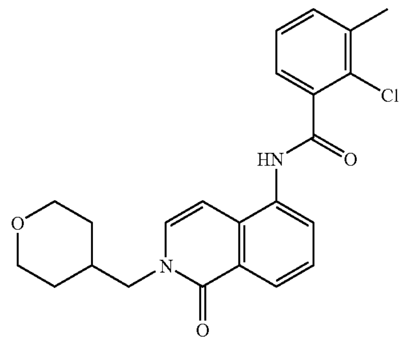 [SMILES: Cc1cccc(C(=O)Nc2cccc3c(=O)n(CC4CCOCC4)ccc23)c1Cl] | 410.90 | 411.50 | + |
| 1133 | 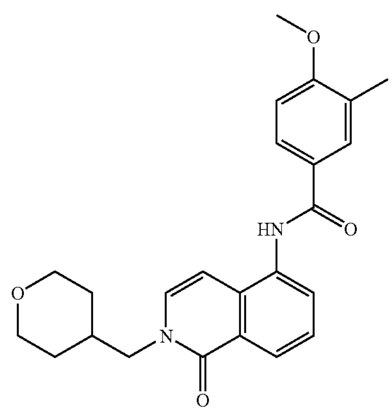 [SMILES: COc1ccc(C(=O)Nc2cccc3c(=O)n(CC4CCOCC4)ccc23)cc1C] | 406.48 | 407.59 | + |
| 1134 | 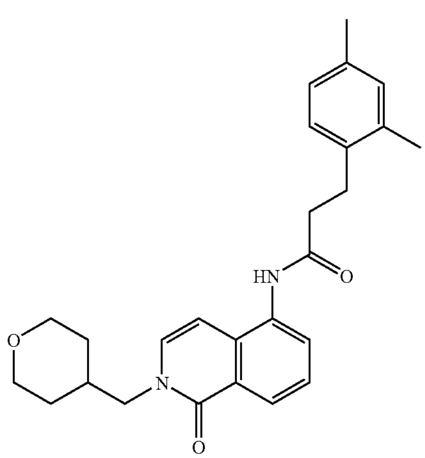 [SMILES: Cc1ccc(CCC(=O)Nc2cccc3c(=O)n(CC4CCOCC4)ccc23)c(C)c1] | 418.53 | 419.49 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1135 | 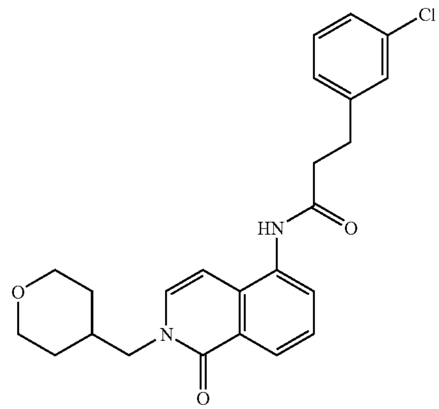 [SMILES: O=C(CCc1cccc(Cl)c1)Nc1cccc2c(=O)n(CC3CCOCC3)ccc12] | 424.93 | 425.11 | + |
| 1136 | 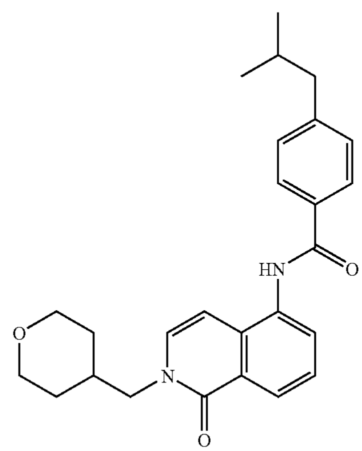 [SMILES: CC(C)Cc1ccc(C(=O)Nc2cccc3c(=O)n(CC4CCOCC4)ccc23)cc1] | 418.53 | 419.40 | + |
| 1137 | 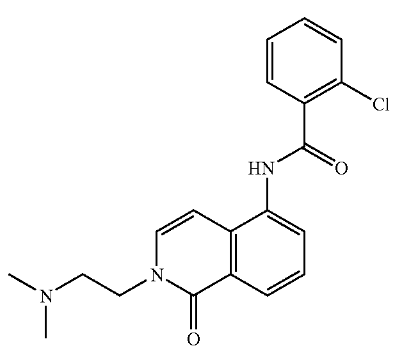 [SMILES: CN(C)CCn1ccc2c(NC(=O)c3ccccc3Cl)cccc2c1=O] | 369.85 | 370.14 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1138 | 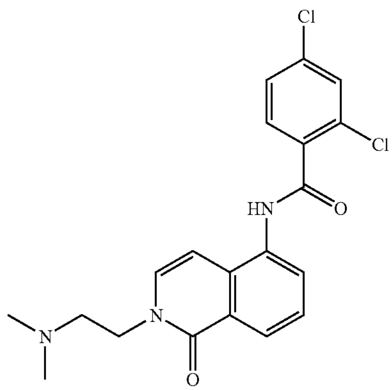 [SMILES: CN(C)CCn1ccc2c(NC(=O)c3ccc(Cl)cc3Cl)cccc2c1=O] | 404.30 | 404.37 | + |
| 1139 | 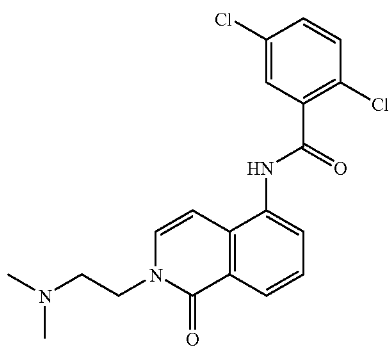 [SMILES: CN(C)CCn1ccc2c(NC(=O)c3cc(Cl)ccc3Cl)cccc2c1=O] | 404.30 | 404.38 | + |
| 1140 | 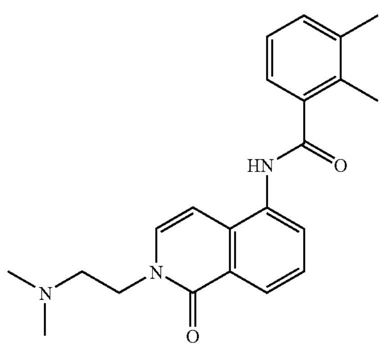 | 363.46 | 364.41 | + |
| 1141 | 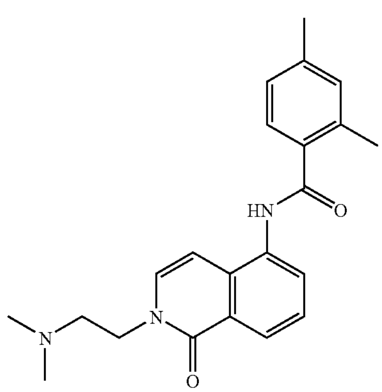 | 363.46 | 364.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1142 | 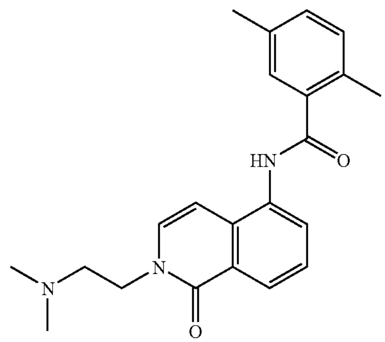 | 363.46 | 364.40 | + |
| 1143 | 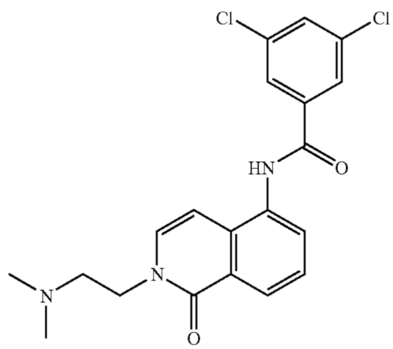 [SMILES: CN(C)CCn1ccc2c(NC(=O)c3cc(Cl)cc(Cl)c3)cccc2c1=O] | 404.30 | 404.37 | + |
| 1144 | 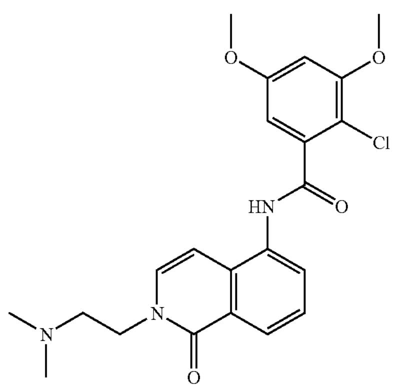 | 395.46 | 396.18 | + |
| 1145 | 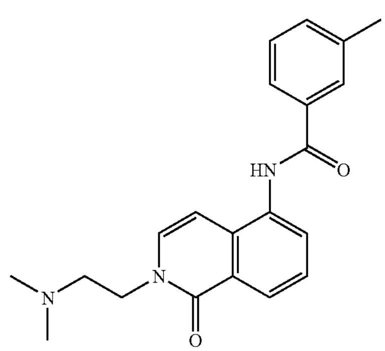 | 349.43 | 350.32 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1146 | 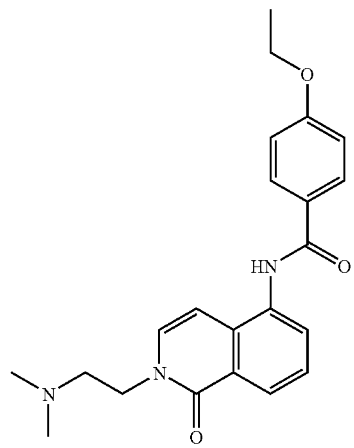 [SMILES: CCOc1ccc(C(=O)Nc2cccc3c(=O)n(CCN(C)C)ccc23)cc1] | 379.46 | 380.56 | * |
| 1147 | 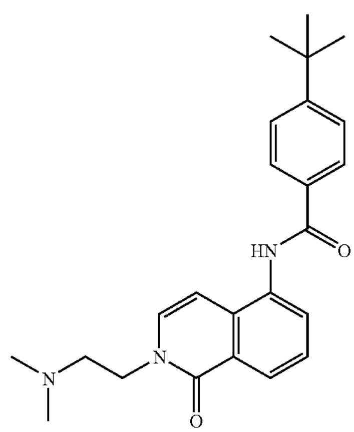 [SMILES: CN(C)CCn1ccc2c(NC(=O)c3ccc(C(C)(C)C)cc3)cccc2c1=O] | 391.51 | 392.43 | + |
| 1148 | 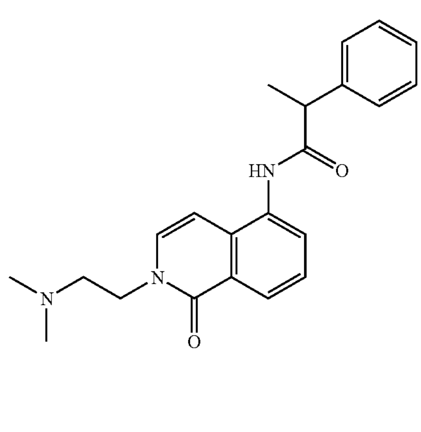 [SMILES: CC(C(=O)Nc1cccc2c(=O)n(CCN(C)C)ccc12)c1ccccc1] | 363.46 | 364.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1149 | 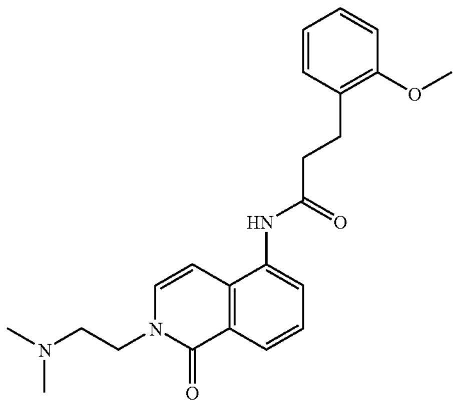 | 393.48 | 394.35 | * |
| 1150 | 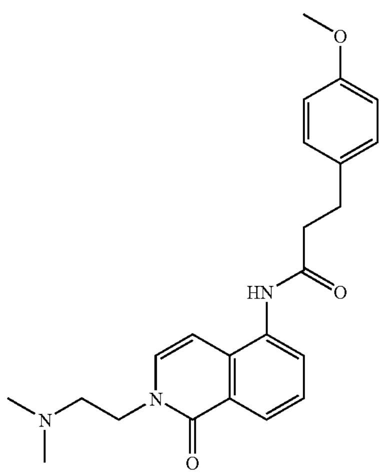 [SMILES: COc1ccc(CCC(=O)Nc2cccc3c(=O)n(CCN(C)C)ccc23)cc1] | 393.48 | 394.37 | + |
| 1151 | 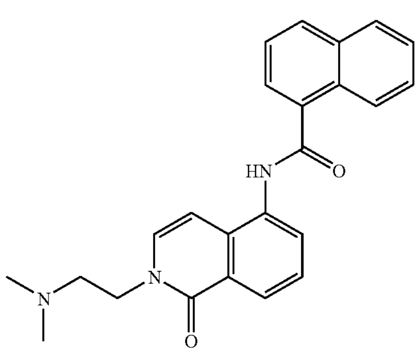 [SMILES: CN(C)CCn1ccc2c(NC(=O)c3cccc4ccccc34)cccc2c1=O] | 385.46 | 386.35 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1152 | 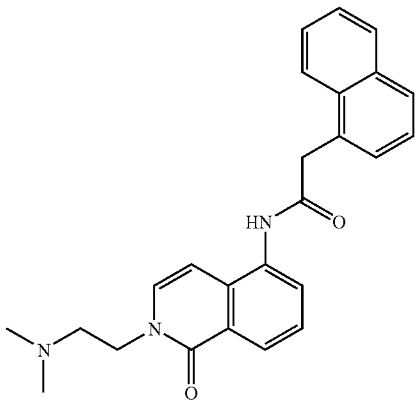 [SMILES: CN(C)CCn1ccc2c(NC(=O)Cc3cccc4ccccc34)cccc2c1=O] | 399.49 | 400.42 | + |
| 1153 | 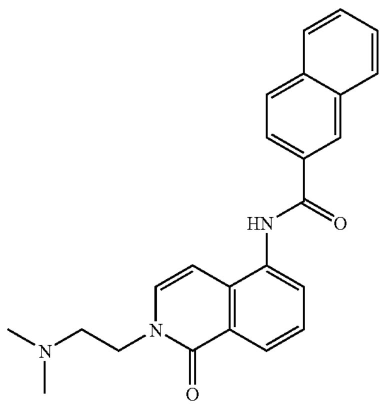 [SMILES: CN(C)CCn1ccc2c(NC(=O)c3ccc4ccccc4c3)cccc2c1=O] | 385.46 | 386.35 | + |
| 1154 | 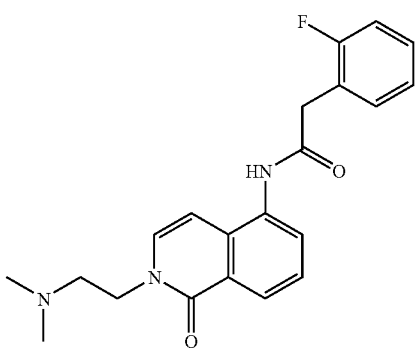 [SMILES: CN(C)CCn1ccc2c(NC(=O)Cc3ccccc3F)cccc2c1=O] | 367.42 | 368.27 | + |
| 1155 | 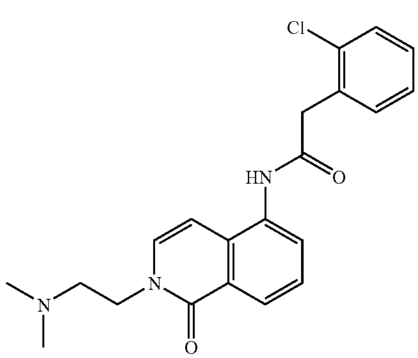 [SMILES: CN(C)CCn1ccc2c(NC(=O)Cc3ccccc3Cl)cccc2c1=O] | 383.88 | 384.50 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1156 | 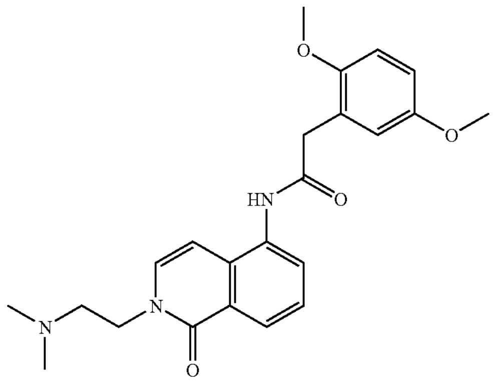 | 409.48 | 410.56 | + |
| 1157 | 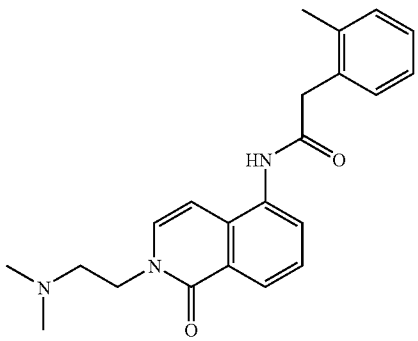 [SMILES: Cc1ccccc1CC(=O)Nc1cccc2c(=O)n(CCN(C)C)ccc12] | 363.46 | 364.40 | + |
| 1158 | 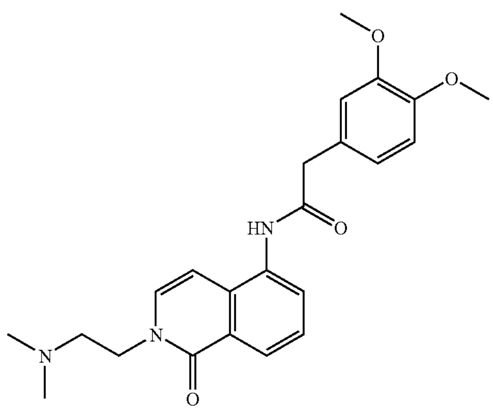 | 409.48 | 410.49 | + |
| 1159 | 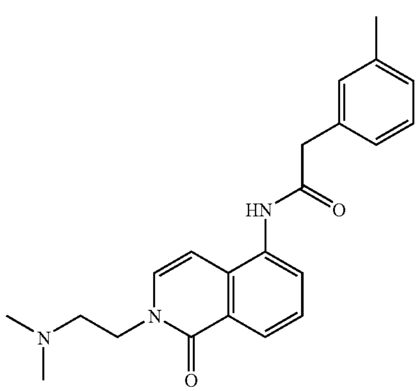 [SMILES: Cc1cccc(CC(=O)Nc2cccc3c(=O)n(CCN(C)C)ccc23)c1] | 363.46 | 364.41 | + |

TABLE 1-continued

IL-1β % Inhibition of Exemplary Compounds

| ID | Structure | MW | MS (obs) | IL-1β % Inhib. @ 0.3 µM |
|---|---|---|---|---|
| 1160 | 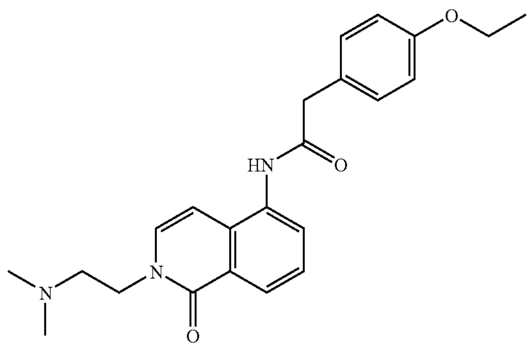 [SMILES: CCOc1ccc(CC(=O)Nc2cccc3c(=O)n(CCN(C)C)ccc23)cc1] | 393.48 | 394.36 | + |
| 1161 | 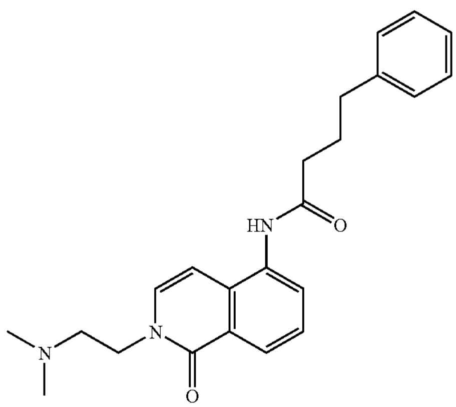 [SMILES: CN(C)CCn1ccc2c(NC(=O)CCCc3ccccc3)cccc2c1=O] | 377.49 | 378.50 | + |
| 1162 | 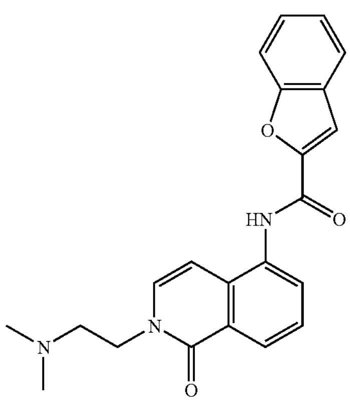 [SMILES: CN(C)CCn1ccc2c(NC(=O)c3cc4ccccc4o3)cccc2c1=O] | 375.43 | 376.29 | + |
| 1163 | 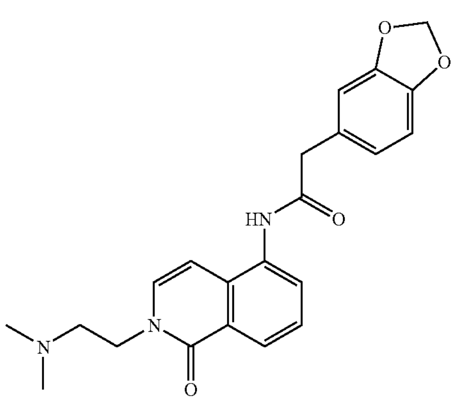 [SMILES: CN(C)CCn1ccc2c(NC(=O)Cc3ccc4c(c3)OCO4)cccc2c1=O] | 393.44 | 394.34 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1164 | 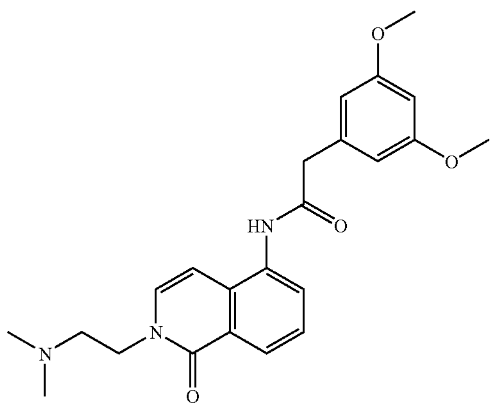 | 409.48 | 410.50 | + |
| 1165 | 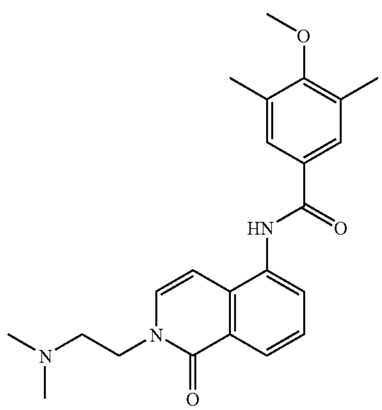 | 393.48 | 394.36 | + |
| 1166 | 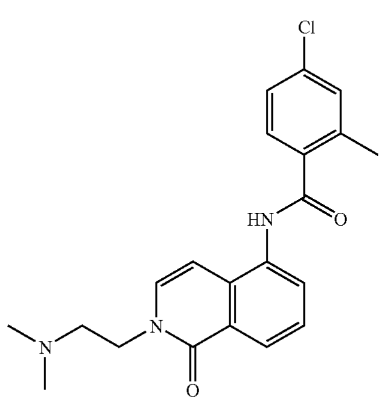 | 383.88 | 384.50 | + |

TABLE 1-continued

IL-1β % Inhibition of Exemplary Compounds

| ID | Structure | MW | MS (obs) | IL-1β % Inhib. @ 0.3 µM |
|---|---|---|---|---|
| 1167 | 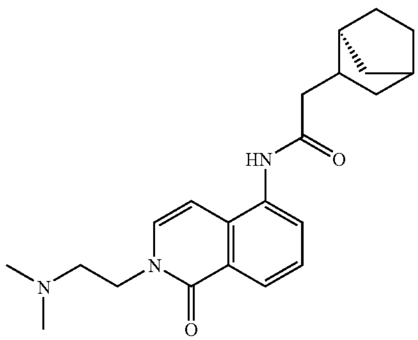 [SMILES: CN(C)CCn1ccc2c(NC(=O)CC3CC4CC[C@H]3C4)cccc2c1=O] | 367.49 | 368.31 | ++ |
| 1168 | 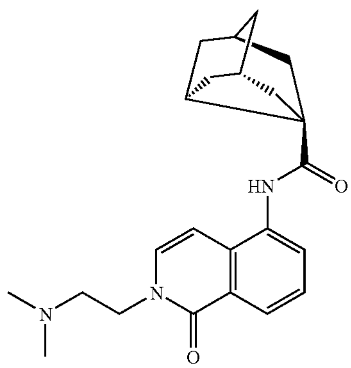 [SMILES: CN(C)CCn1ccc2c(NC(=O)[C@@]34C[C@@H]5C[C@@H](C[C@@H]3C5)C4)cccc2c1=O] | 379.50 | 380.57 | + |
| 1169 | 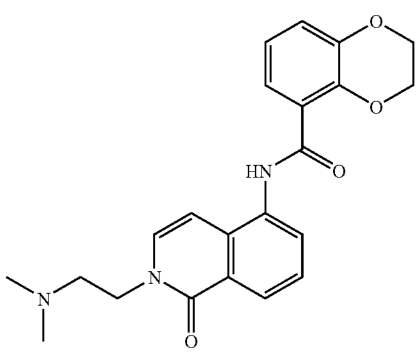 [SMILES: CN(C)CCn1ccc2c(NC(=O)c3cccc4c3OCCO4)cccc2c1=O] | 393.44 | 394.35 | + |
| 1170 | 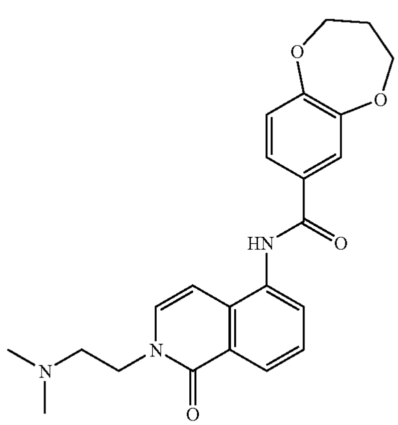 [SMILES: CN(C)CCn1ccc2c(NC(=O)c3ccc4c(c3)OCCCO4)cccc2c1=O] | 407.47 | 408.50 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1171 | 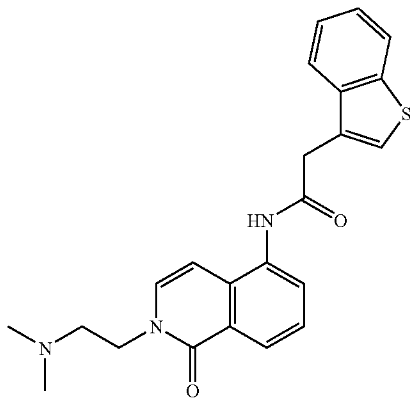 | 405.52 | 406.56 | + |
| 1172 | 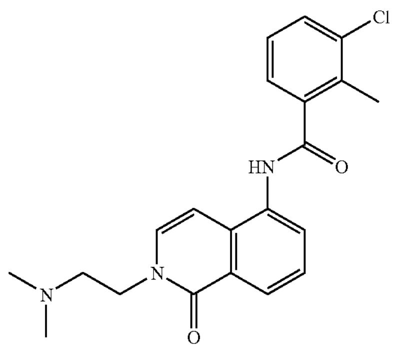 [SMILES: Cc1c(Cl)cccc1C(=O)Nc1cccc2c(=O)n(CCN(C)C)ccc12] | 383.88 | 384.50 | + |
| 1173 | 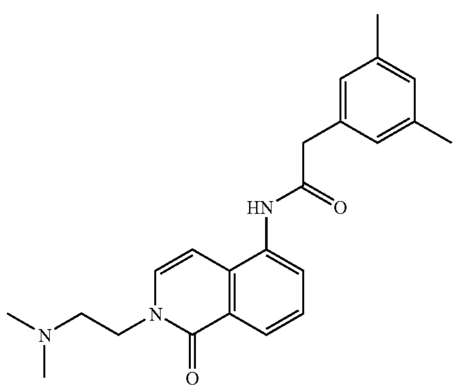 | 377.49 | 378.49 | + |
| 1174 | 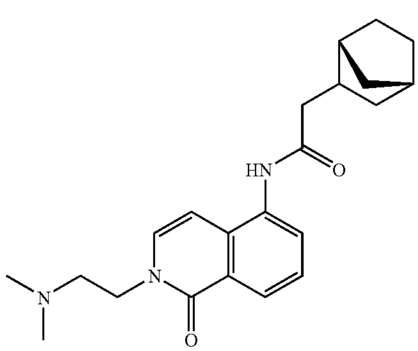 [SMILES: CN(C)CCn1ccc2c(NC(=O)CC3C[C@H]4CC[C@@H]3C4)cccc2c1=O] | 353.46 | 354.52 | + |

TABLE 1-continued

IL-1β % Inhibition of Exemplary Compounds

| ID | Structure | MW | MS (obs) | IL-1β % Inhib. @ 0.3 μM |
|----|-----------|------|----------|-------------------------|
| 1175 | 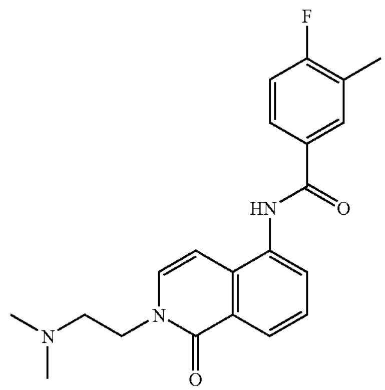 | 367.42 | 368.26 | + |
| 1176 | 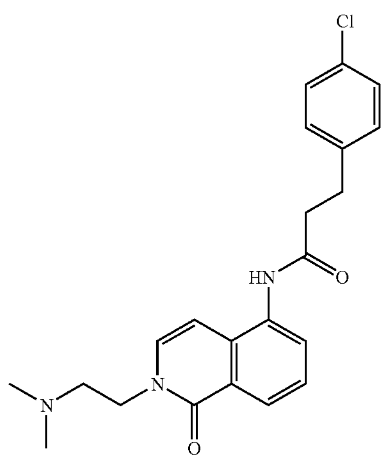 [SMILES: CN(C)CCn1ccc2c(NC(=O)CCc3ccc(Cl)cc3)cccc2c1=O] | 397.90 | 398.10 | + |
| 1177 | 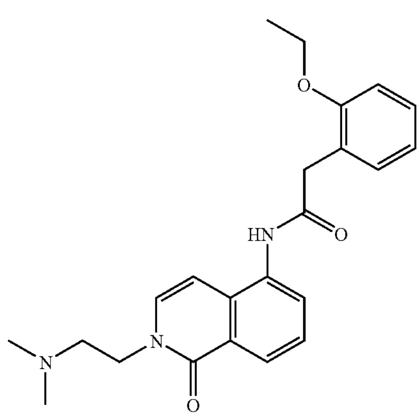 [SMILES: CCOc1ccccc1CC(=O)Nc1cccc2c(=O)n(CCN(C)C)ccc12] | 393.48 | 394.37 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1178 | 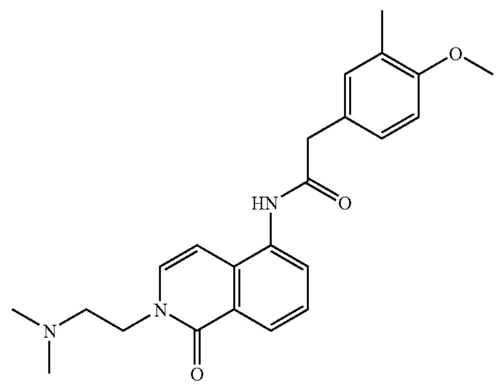 | 393.48 | 394.36 | + |
| 1179 | 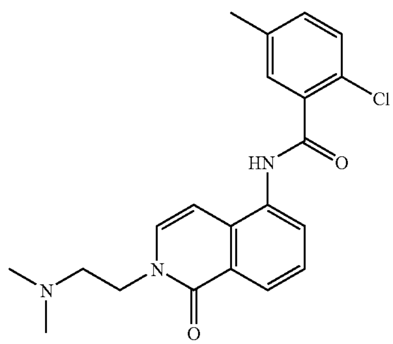 [SMILES: Cc1ccc(Cl)c(C(=O)Nc2cccc3c(=O)n(CCN(C)C)ccc23)c1] | 383.88 | 384.51 | + |
| 1180 | 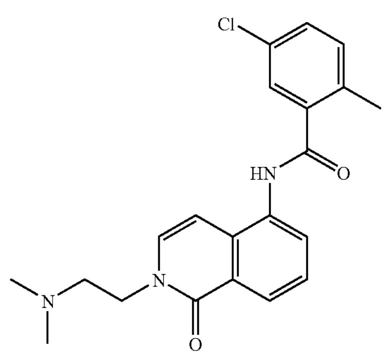 | 383.88 | 384.49 | + |
| 1181 | 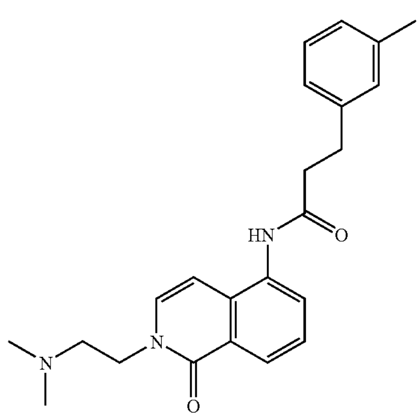 | 377.49 | 378.48 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1182 | 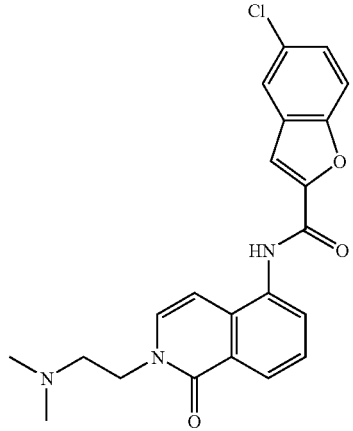 [SMILES: CN(C)CCn1ccc2c(NC(=O)c3cc4cc(Cl)ccc4o3)cccc2c1=O] | 409.87 | 410.41 | + |
| 1183 | 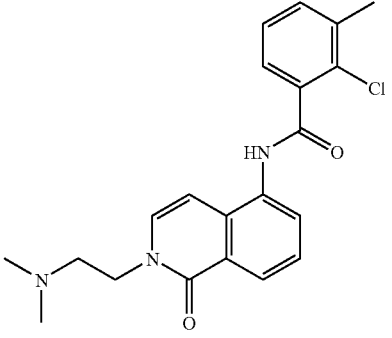 | 383.88 | 384.49 | + |
| 1184 | 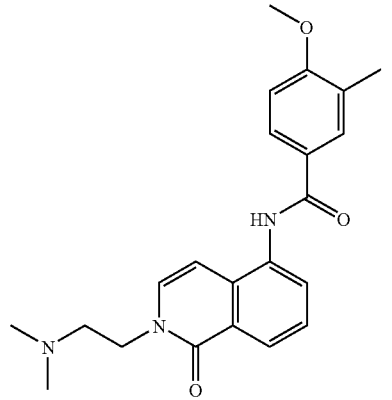 | 379.46 | 380.56 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1185 | 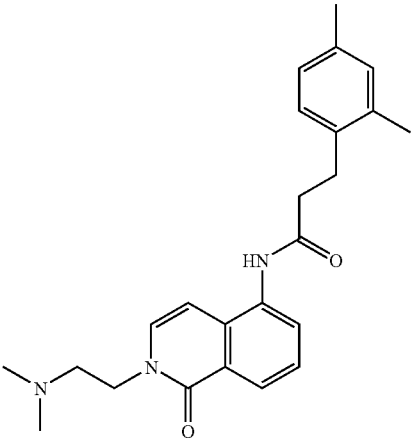 | 391.51 | 392.41 | + |
| 1186 | 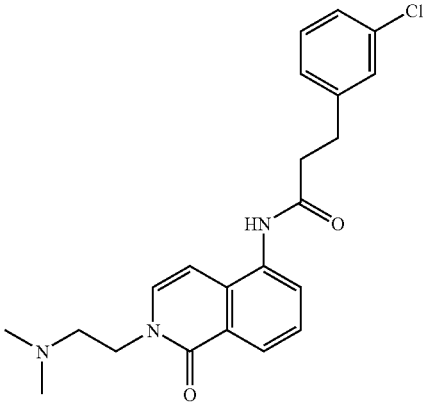 [SMILES: CN(C)CCn1ccc2c(NC(=O)CCc3cccc(Cl)c3)cccc2c1=O] | 397.90 | 398.24 | +++ |
| 1187 | 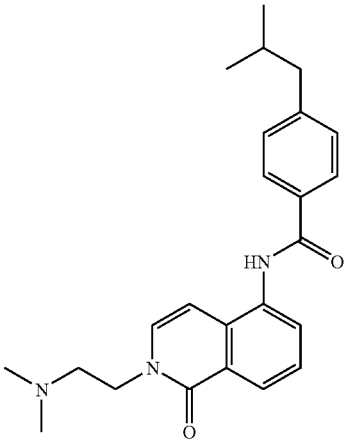 [SMILES: CC(C)Cc1ccc(C(=O)Nc2cccc3c(=O)n(CCN(C)C)ccc23)cc1] | 391.51 | 392.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1188 | 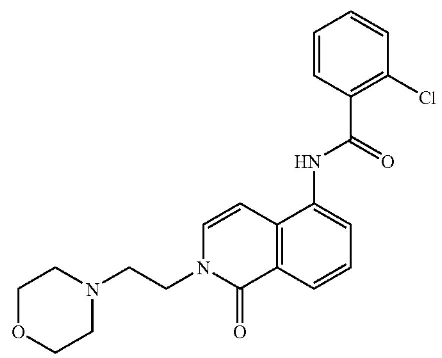 [SMILES: O=C(Nc1cccc2c(=O)n(CCN3CCOCC3)ccc12)c1ccccc1Cl] | 411.89 | 412.20 | + |
| 1189 | 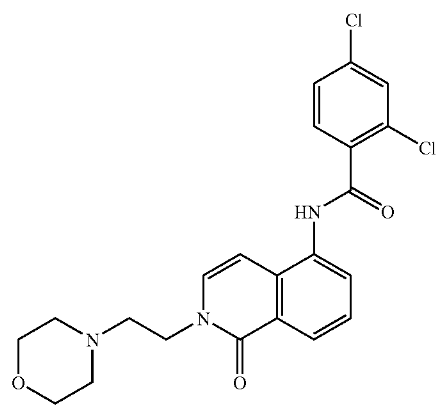 [SMILES: O=C(Nc1cccc2c(=O)n(CCN3CCOCC3)ccc12)c1ccc(Cl)cc1Cl] | 446.33 | 446.16 | + |
| 1190 | 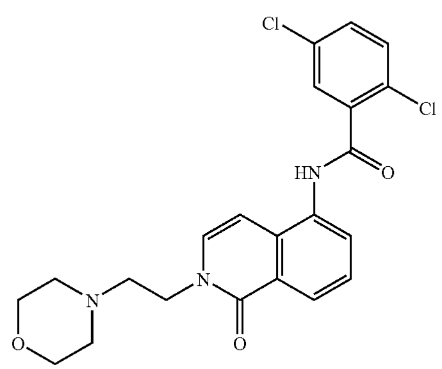 [SMILES: O=C(Nc1cccc2c(=O)n(CCN3CCOCC3)ccc12)c1cc(Cl)ccc1Cl] | 446.33 | 446.16 | + |
| 1191 | 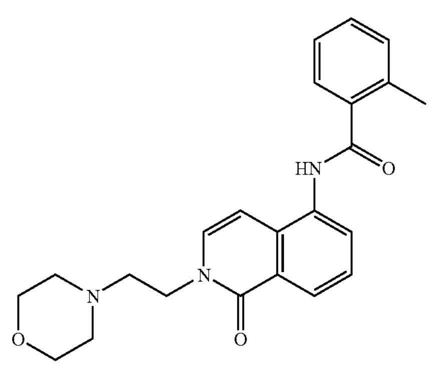 [SMILES: Cc1ccccc1C(=O)Nc1cccc2c(=O)n(CCN3CCOCC3)ccc12] | 391.47 | 392.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1192 | 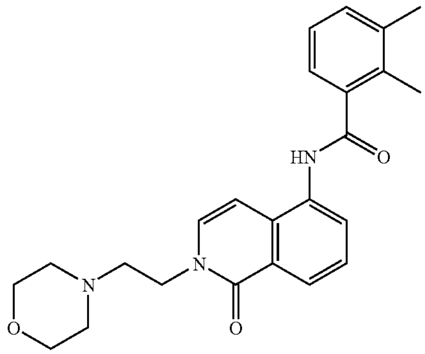 [SMILES: Cc1cccc(C(=O)Nc2cccc3c(=O)n(CCN4CCOCC4)ccc23)c1C] | 405.50 | 406.47 | ++ |
| 1193 | 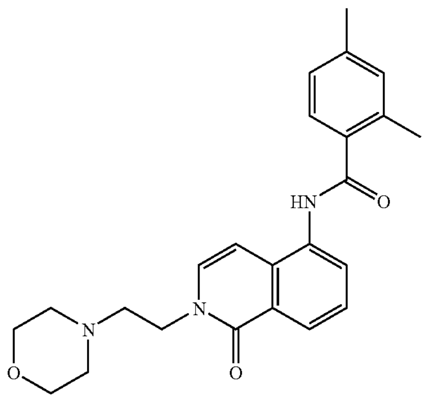 [SMILES: Cc1ccc(C(=O)Nc2cccc3c(=O)n(CCN4CCOCC4)ccc23)c(C)c1] | 405.50 | 406.48 | + |
| 1194 | 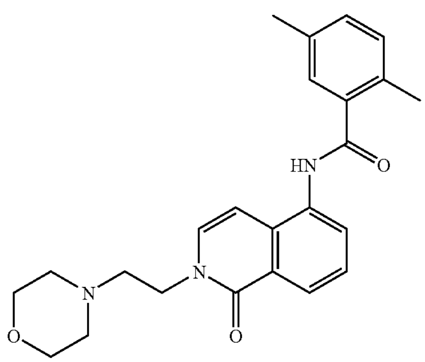 [SMILES: Cc1ccc(C)c(C(=O)Nc2cccc3c(=O)n(CCN4CCOCC4)ccc23)c1] | 405.50 | 406.48 | + |
| 1195 | 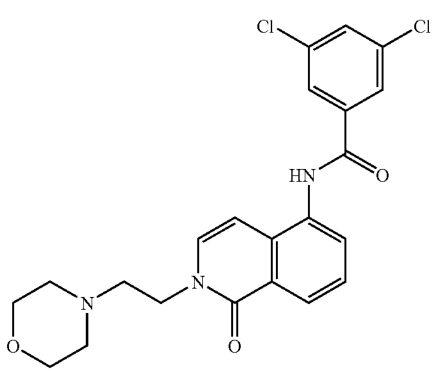 [SMILES: O=C(Nc1cccc2c(=O)n(CCN3CCOCC3)ccc12)c1cc(Cl)cc(Cl)c1] | 446.33 | 446.38 | * |

TABLE 1-continued

IL-1β % Inhibition of Exemplary Compounds

| ID | Structure | MW | MS (obs) | IL-1β % Inhib. @ 0.3 µM |
|---|---|---|---|---|
| 1196 | 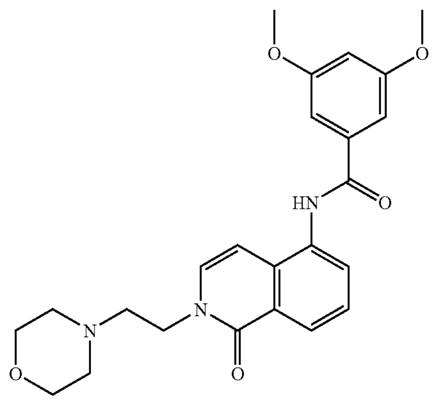 [SMILES: COc1cc(OC)cc(C(=O)Nc2cccc3c(=O)n(CCN4CCOCC4)ccc23)c1] | 437.49 | 438.60 | * |
| 1197 | 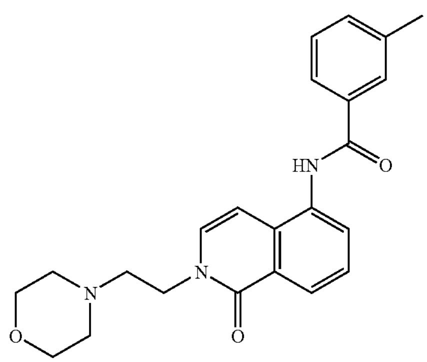 [SMILES: Cc1cccc(C(=O)Nc2cccc3c(=O)n(CCN4CCOCC4)ccc23)c1] | 391.47 | 392.38 | * |
| 1198 | 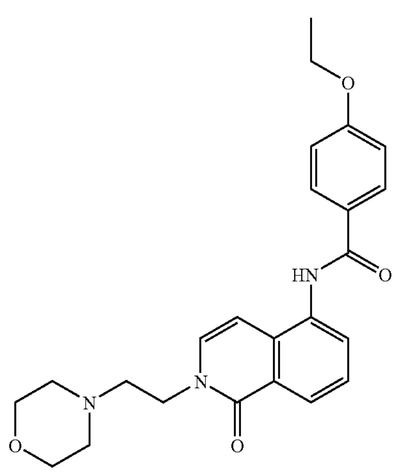 [SMILES: CCOc1ccc(C(=O)Nc2cccc3c(=O)n(CCN4CCOCC4)ccc23)cc1] | 421.49 | 422.34 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1199 | 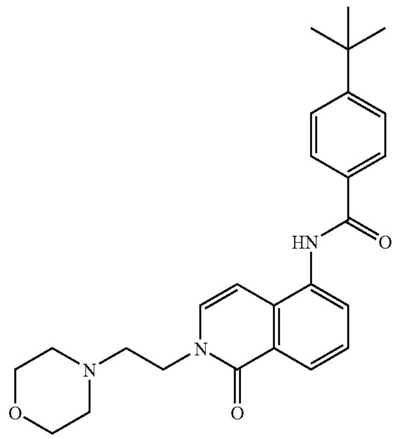 [SMILES: CC(C)(C)c1ccc(C(=O)Nc2cccc3c(=O)n(CCN4CCOCC4)ccc23)cc1] | 433.55 | 434.63 | * |
| 1200 | 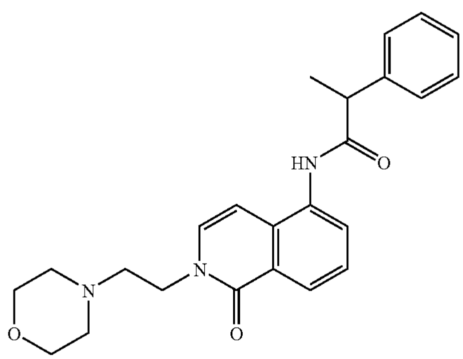 [SMILES: CC(C(=O)Nc1cccc2c(=O)n(CCN3CCOCC3)ccc12)c1ccccc1] | 405.50 | 406.64 | + |
| 1201 | 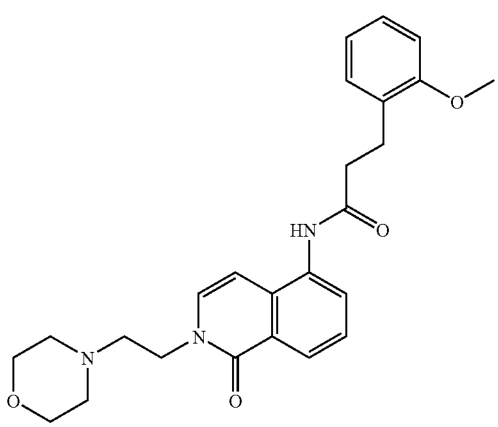 [SMILES: COc1ccccc1CCC(=O)Nc1cccc2c(=O)n(CCN3CCOCC3)ccc12] | 435.52 | 436.50 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1202 | 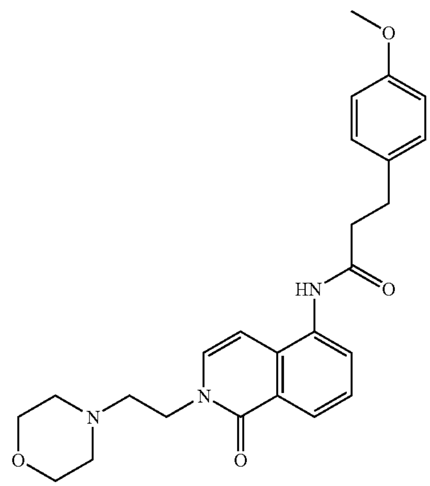 [SMILES: COc1ccc(CCC(=O)Nc2cccc3c(=O)n(CCN4CCOCC4)ccc23)cc1] | 435.52 | 436.54 | + |
| 1203 | 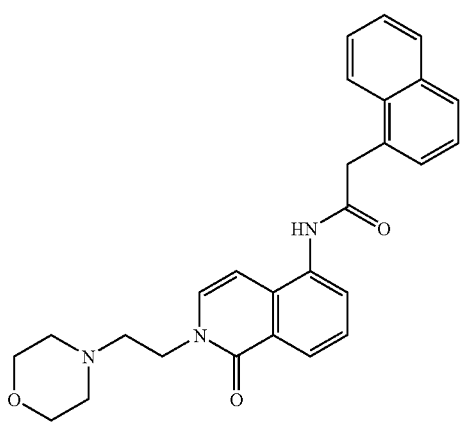 [SMILES: O=C(Cc1cccc2ccccc12)Nc1cccc2c(=O)n(CCN3CCOCC3)ccc12] | 441.53 | 442.31 | + |
| 1204 | 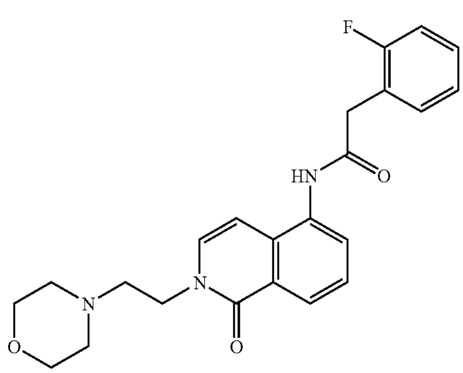 [SMILES: O=C(Cc1ccccc1F)Nc1cccc2c(=O)n(CCN3CCOCC3)ccc12] | 409.46 | 410.51 | + |

TABLE 1-continued

IL-1β % Inhibition of Exemplary Compounds

| ID | Structure | MW | MS (obs) | IL-1β % Inhib. @ 0.3 μM |
|----|-----------|------|----------|------------------------|
| 1205 | 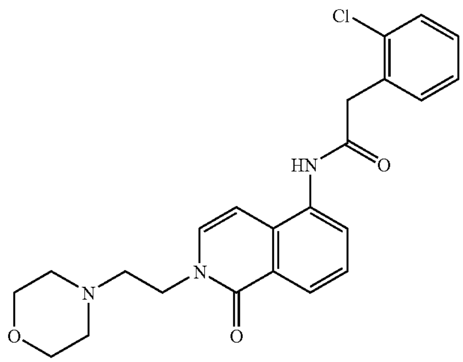 | 425.91 | 426.22 | + |
| 1206 | 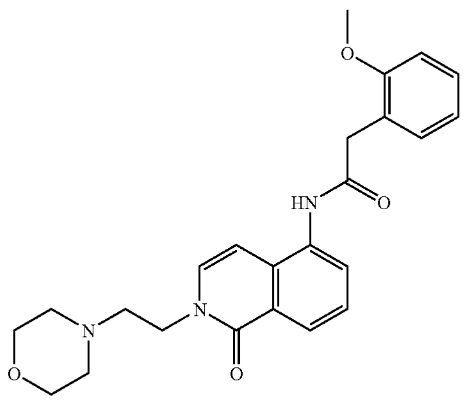 [SMILES: COc1ccccc1CC(=O)Nc1cccc2c(=O)n(CCN3CCOCC3)ccc12] | 421.49 | 422.35 | + |
| 1207 | 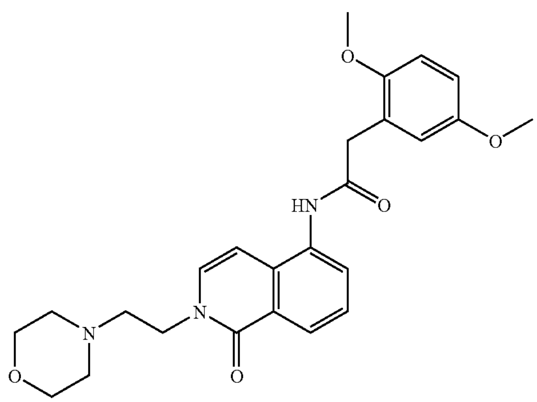 [SMILES: COc1ccc(OC)c(CC(=O)Nc2cccc3c(=O)n(CCN4CCOCC4)ccc23)c1] | 451.52 | 452.22 | + |
| 1208 | 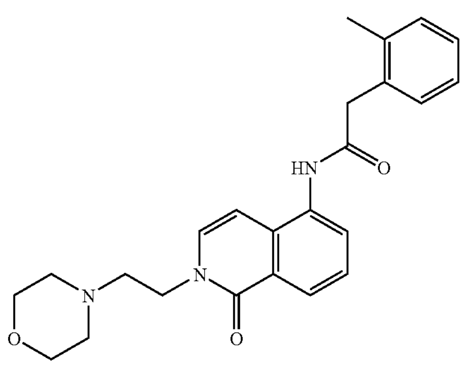 [SMILES: Cc1ccccc1CC(=O)Nc1cccc2c(=O)n(CCN3CCOCC3)ccc12] | 405.50 | 406.61 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1209 | 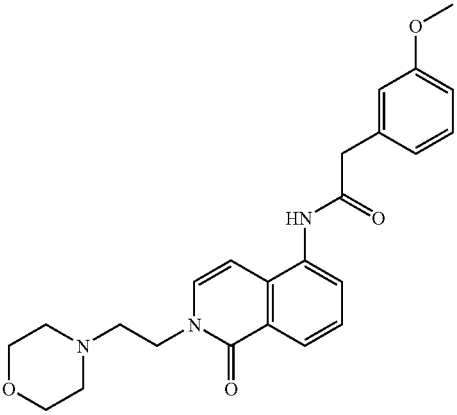 [SMILES: COc1cccc(CC(=O)Nc2cccc3c(=O)n(CCN4CCOCC4)ccc23)c1] | 421.49 | 422.36 | + |
| 1210 | 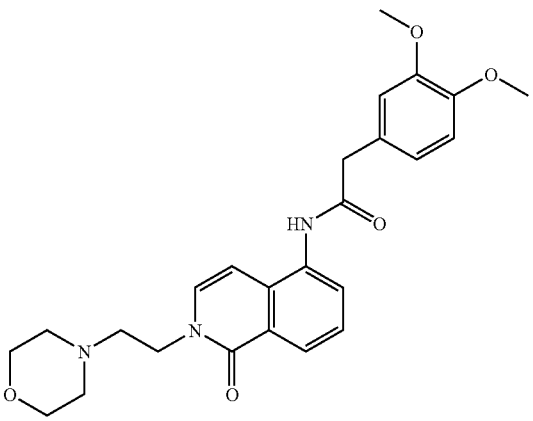 [SMILES: COc1ccc(CC(=O)Nc2cccc3c(=O)n(CCN4CCOCC4)ccc23)cc1OC] | 451.52 | 452.20 | + |
| 1211 | 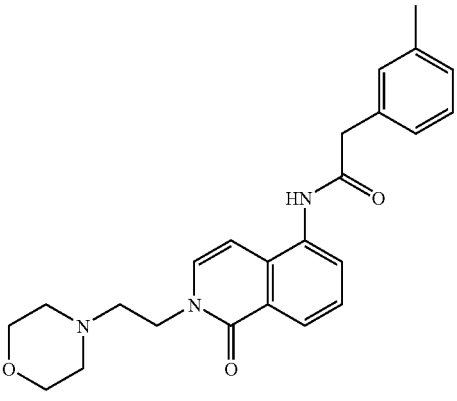 [SMILES: Cc1cccc(CC(=O)Nc2cccc3c(=O)n(CCN4CCOCC4)ccc23)c1] | 405.50 | 406.62 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1212 | 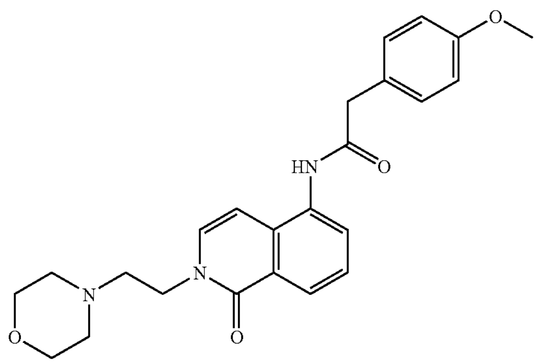 [SMILES: COc1ccc(CC(=O)Nc2cccc3c(=O)n(CCN4CCOCC4)ccc23)cc1] | 421.49 | 422.38 | + |
| 1213 | 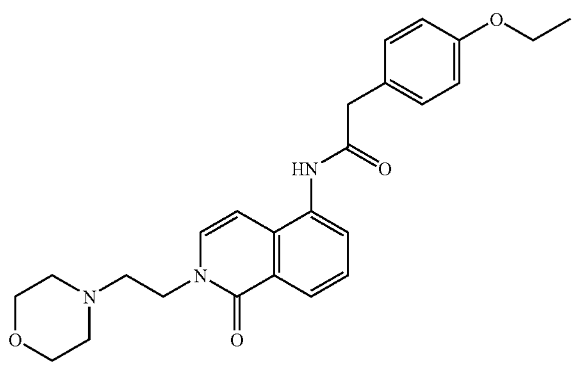 [SMILES: CCOc1ccc(CC(=O)Nc2cccc3c(=O)n(CCN4CCOCC4)ccc23)cc1] | 435.52 | 436.55 | + |
| 1214 | 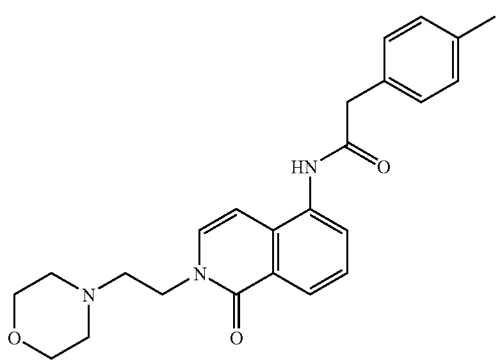 [SMILES: Cc1ccc(CC(=O)Nc2cccc3c(=O)n(CCN4CCOCC4)ccc23)cc1] | 405.50 | 406.63 | + |
| 1215 | 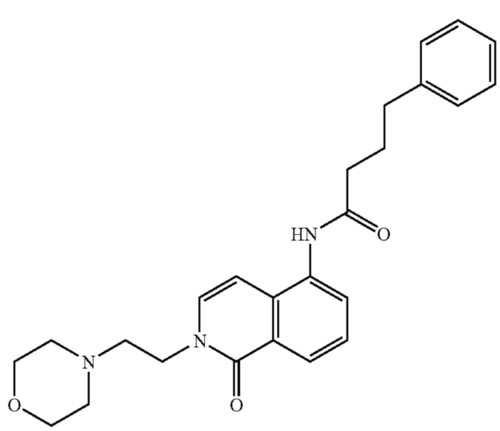 [SMILES: O=C(CCCc1ccccc1)Nc1cccc2c(=O)n(CCN3CCOCC3)ccc12] | 419.52 | 420.47 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1216 | 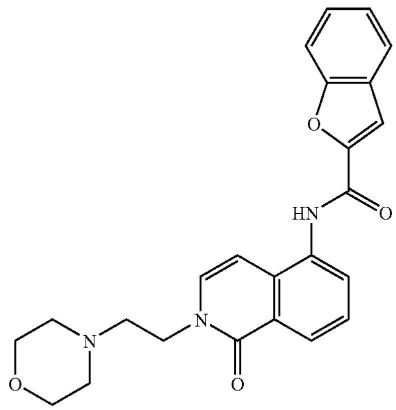 [SMILES: O=C(Nc1cccc2c(=O)n(CCN3CCOCC3)ccc12)c1cc2ccccc2o1] | 417.46 | 418.42 | + |
| 1217 | 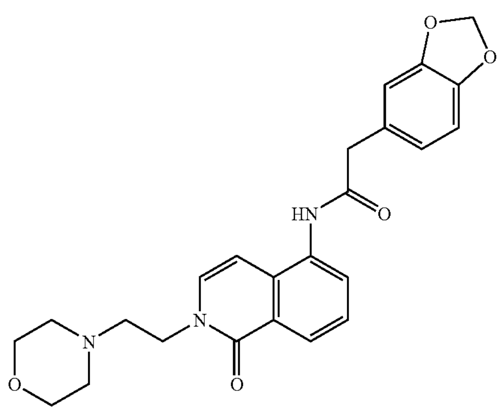 [SMILES: O=C(Cc1ccc2c(c1)OCO2)Nc1cccc2c(=O)n(CCN3CCOCC3)ccc12] | 435.48 | 436.49 | + |
| 1218 | 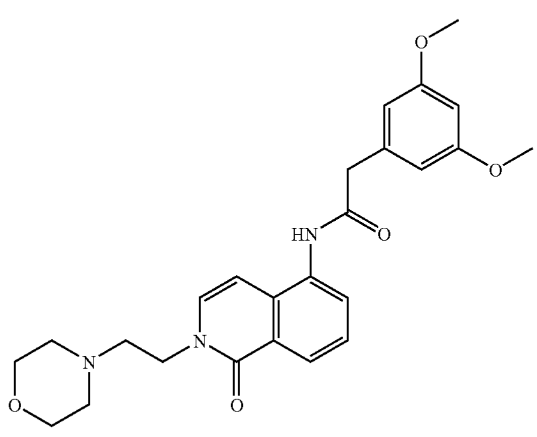 [SMILES: COc1cc(CC(=O)Nc2cccc3c(=O)n(CCN4CCOCC4)ccc23)cc(OC)c1] | 451.52 | 452.22 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1219 | 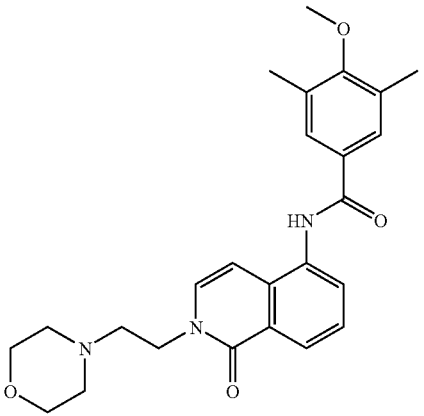 [SMILES: COc1c(C)cc(C(=O)Nc2cccc3c(=O)n(CCN4CCOCC4)ccc23)cc1C] | 435.52 | 436.54 | ++ |
| 1220 | 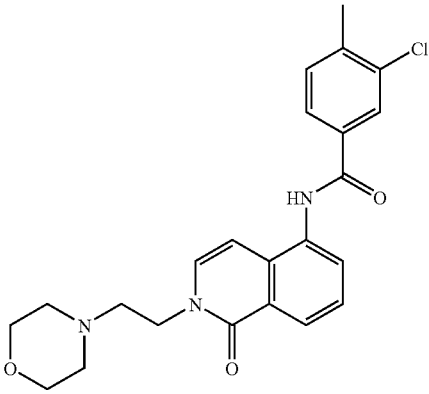 [SMILES: Cc1ccc(C(=O)Nc2cccc3c(=O)n(CCN4CCOCC4)ccc23)cc1Cl] | 425.91 | 426.26 | + |
| 1221 | 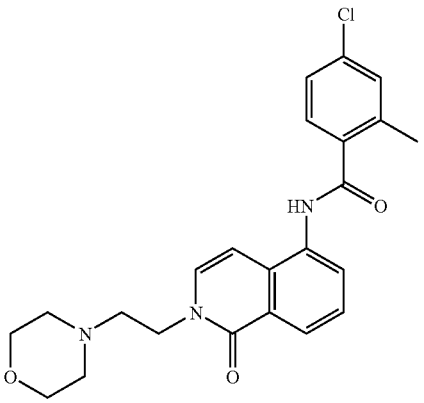 [SMILES: Cc1cc(Cl)ccc1C(=O)Nc1cccc2c(=O)n(CCN3CCOCC3)ccc12] | 425.91 | 426.23 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1222 | 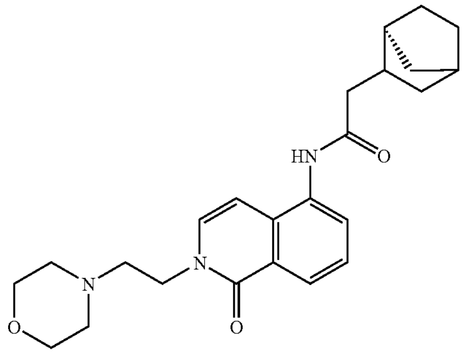 [SMILES: O=C(CC1CC2CC[C@H]1C2)Nc1cccc2c(=O)n(CCN3CCOCC3)ccc12] | 409.53 | 410.57 | + |
| 1223 | 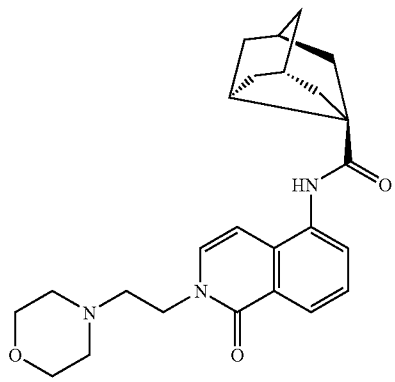 [SMILES: O=C(Nc1cccc2c(=O)n(CCN3CCOCC3)ccc12)[C@@]12C[C@@H]3C[C@@H](C[C@@H]1C3)C2] | 421.54 | 422.41 | + |
| 1224 | 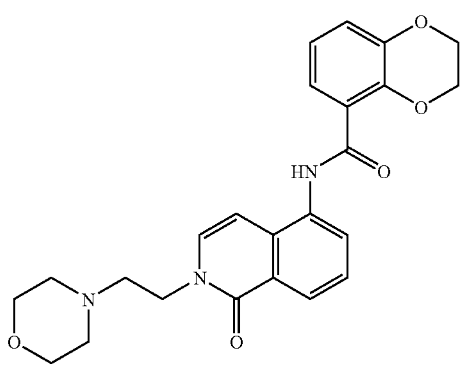 [SMILES: O=C(Nc1cccc2c(=O)n(CCN3CCOCC3)ccc12)c1cccc2c1OCCO2] | 435.48 | 436.48 | + |
| 1225 | 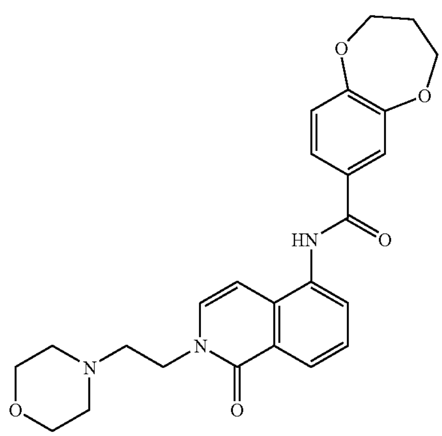 [SMILES: O=C(Nc1cccc2c(=O)n(CCN3CCOCC3)ccc12)c1ccc2c(c1)OCCCO2] | 449.50 | 450.41 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1226 | 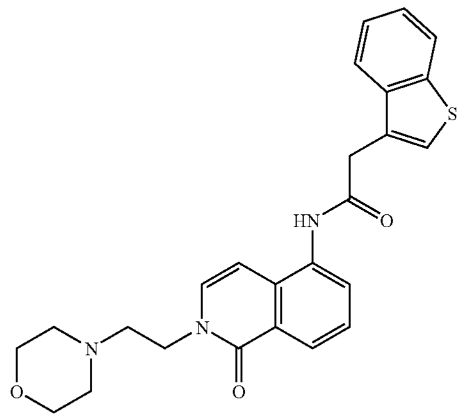 [SMILES: O=C(Cc1csc2ccccc12)Nc1cccc2c(=O)n(CCN3CCOCC3)ccc12] | 447.56 | 448.38 | + |
| 1227 | 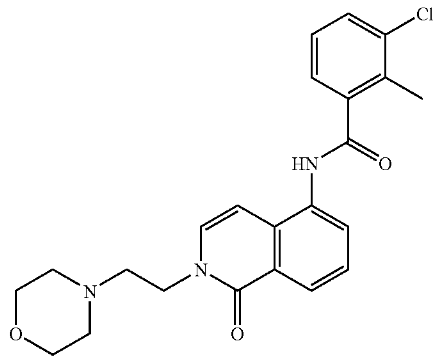 [SMILES: Cc1c(Cl)cccc1C(=O)Nc1cccc2c(=O)n(CCN3CCOCC3)ccc12] | 425.91 | 426.24 | + |
| 1228 | 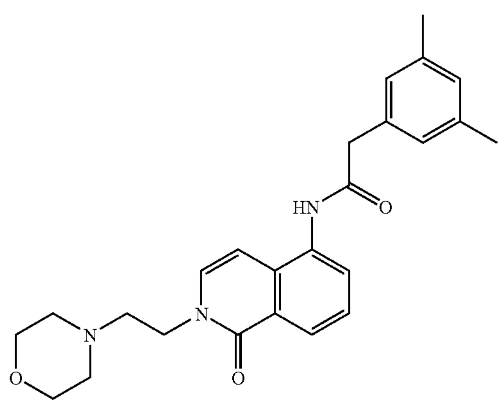 [SMILES: Cc1cc(C)cc(CC(=O)Nc2cccc3c(=O)n(CCN4CCOCC4)ccc23)c1] | 419.52 | 420.46 | + |
| 1229 | 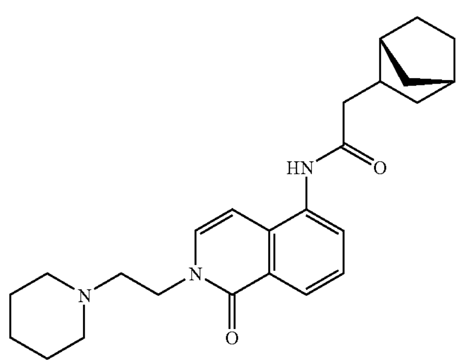 [SMILES: O=C(CC1C[C@H]2CC[C@@H]1C2)Nc1cccc2c(=O)n(CCN3CCCCC3)ccc12] | 395.50 | 396.32 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1230 | 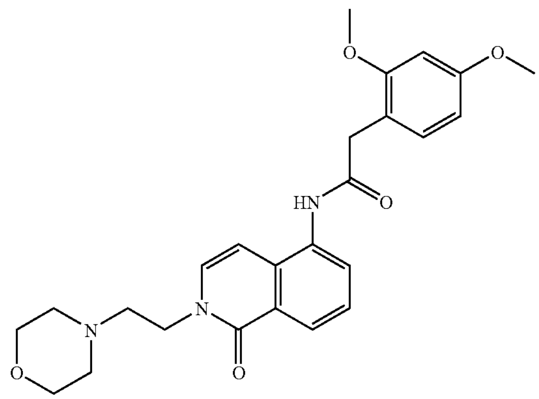 [SMILES: COc1ccc(CC(=O)Nc2cccc3c(=O)n(CCN4CCOCC4)ccc23)c(OC)c1] | 451.52 | 452.23 | + |
| 1231 | 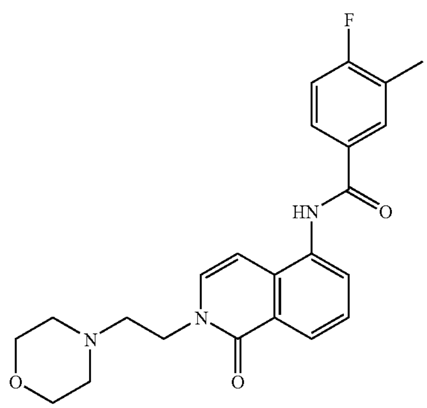 [SMILES: Cc1cc(C(=O)Nc2cccc3c(=O)n(CCN4CCOCC4)ccc23)ccc1F] | 409.46 | 410.51 | + |
| 1232 | 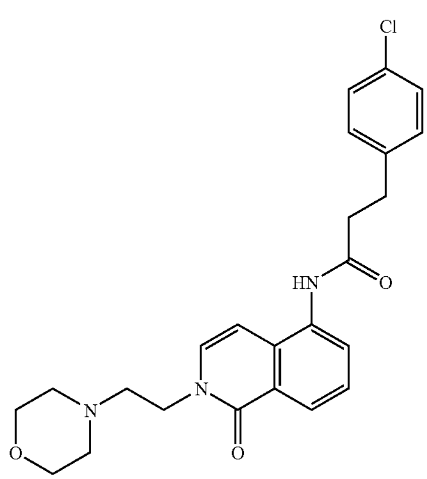 [SMILES: O=C(CCc1ccc(Cl)cc1)Nc1cccc2c(=O)n(CCN3CCOCC3)ccc12] | 439.94 | 440.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1233 | 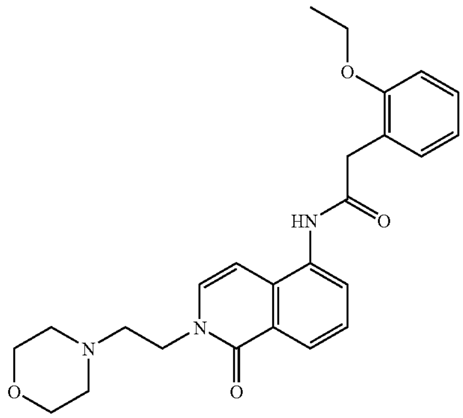 [SMILES: CCOc1ccccc1CC(=O)Nc1cccc2c(=O)n(CCN3CCOCC3)ccc12] | 435.52 | 436.52 | + |
| 1234 | 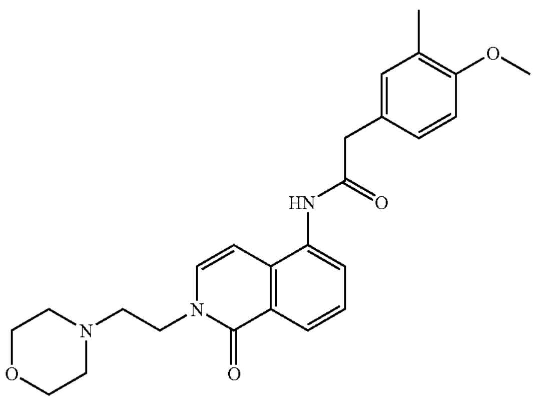 [SMILES: COc1ccc(CC(=O)Nc2cccc3c(=O)n(CCN4CCOCC4)ccc23)cc1C] | 435.52 | 436.53 | + |
| 1235 | 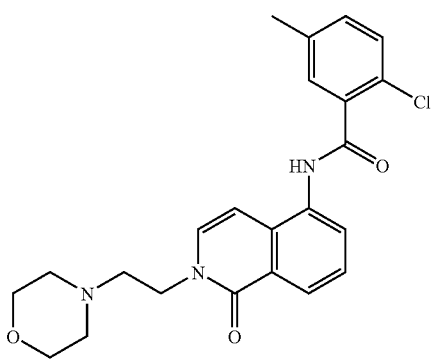 [SMILES: Cc1ccc(Cl)c(C(=O)Nc2cccc3c(=O)n(CCN4CCOCC4)ccc23)c1] | 425.91 | 426.22 | + |
| 1236 | 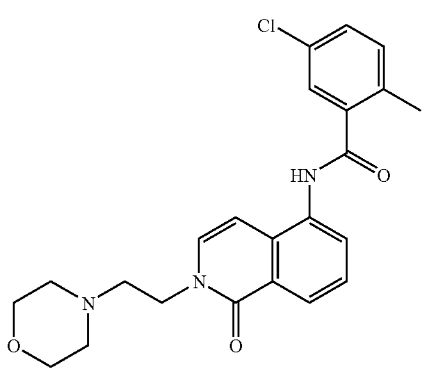 [SMILES: Cc1ccc(Cl)cc1C(=O)Nc1cccc2c(=O)n(CCN3CCOCC3)ccc12] | 425.91 | 426.21 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1237 | 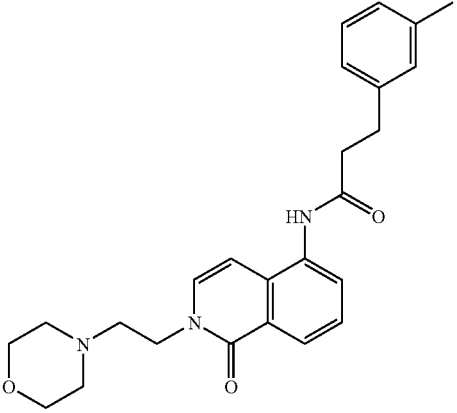 [SMILES: Cc1cccc(CCC(=O)Nc2cccc3c(=O)n(CCN4CCOCC4)ccc23)c1] | 419.52 | 420.46 | ++ |
| 1238 | 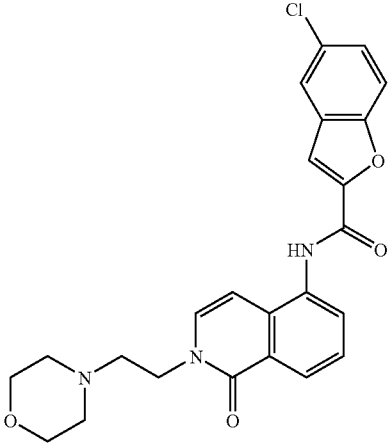 [SMILES: O=C(Nc1cccc2c(=O)n(CCN3CCOCC3)ccc12)c1cc2cc(Cl)ccc2o1] | 451.91 | 452.15 | ++ |
| 1239 | 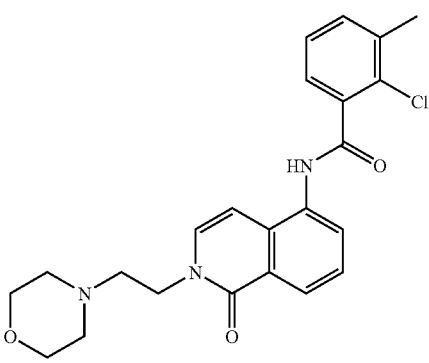 [SMILES: Cc1cccc(C(=O)Nc2cccc3c(=O)n(CCN4CCOCC4)ccc23)c1Cl] | 425.91 | 426.23 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1240 | 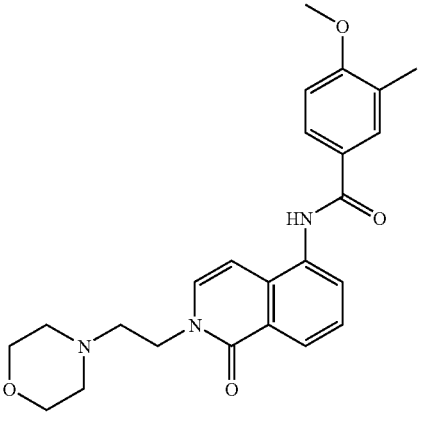 [SMILES: COc1ccc(C(=O)Nc2cccc3c(=O)n(CCN4CCOCC4)ccc23)cc1C] | 421.49 | 422.34 | ++ |
| 1241 | 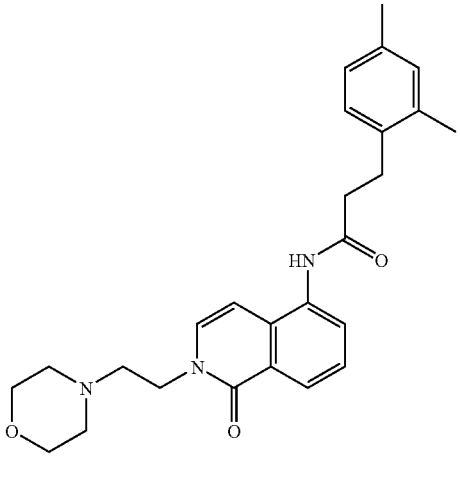 [SMILES: Cc1ccc(CCC(=O)Nc2cccc3c(=O)n(CCN4CCOCC4)ccc23)c(C)c1] | 433.55 | 434.62 | + |
| 1242 | 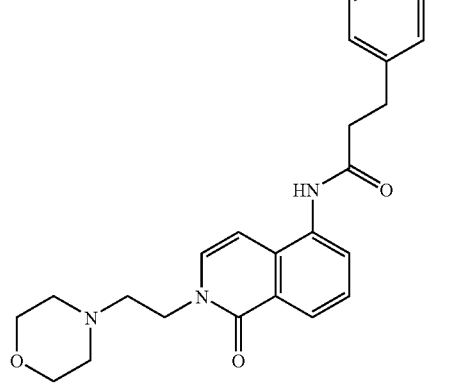 | 439.94 | 440.40 | ++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1243 | 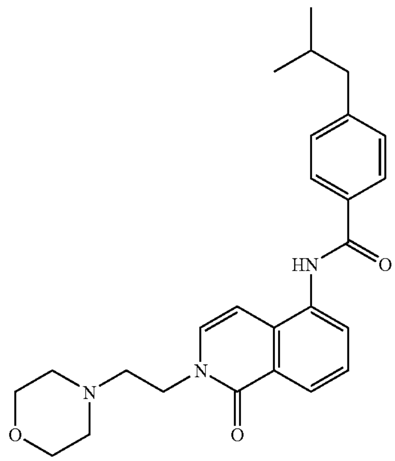 [SMILES: CC(C)Cc1ccc(C(=O)Nc2cccc3c(=O)n(CCN4CCOCC4)ccc23)cc1] | 433.55 | 434.67 | + |
| 1244 | 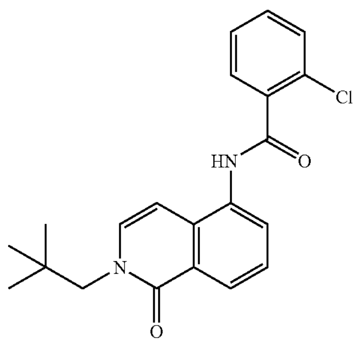 [SMILES: CC(C)(C)Cn1ccc2c(NC(=O)c3ccccc3Cl)cccc2c1=O] | 368.86 | 368.99 | + |
| 1245 | 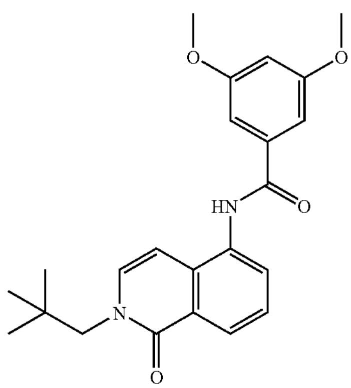 [SMILES: COc1cc(OC)cc(C(=O)Nc2cccc3c(=O)n(CC(C)(C)C)ccc23)c1] | 394.47 | 395.29 | * |
| 1246 | 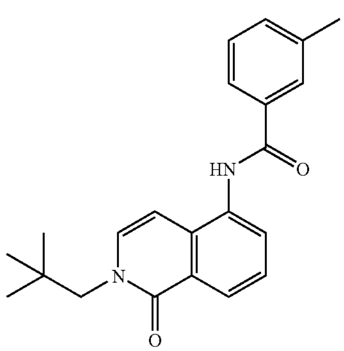 [SMILES: Cc1cccc(C(=O)Nc2cccc3c(=O)n(CC(C)(C)C)ccc23)c1] | 348.44 | 349.37 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1247 | 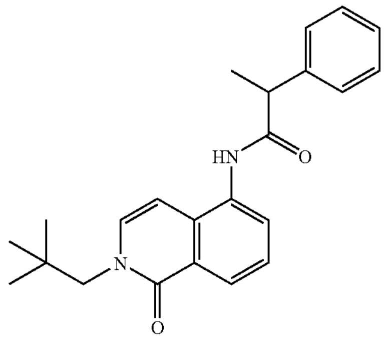 [SMILES: CC(C(=O)Nc1cccc2c(=O)n(CC(C)(C)C)ccc12)c1ccccc1] | 362.47 | 363.43 | * |
| 1248 | 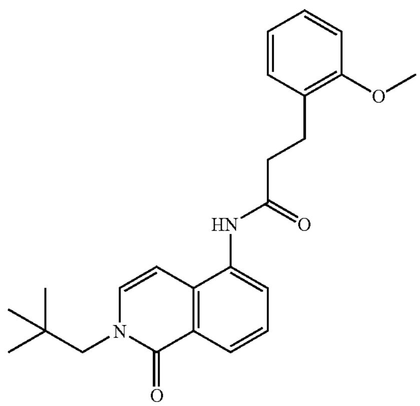 [SMILES: COc1ccccc1CCC(=O)Nc1cccc2c(=O)n(CC(C)(C)C)ccc12] | 392.50 | 393.35 | + |
| 1249 | 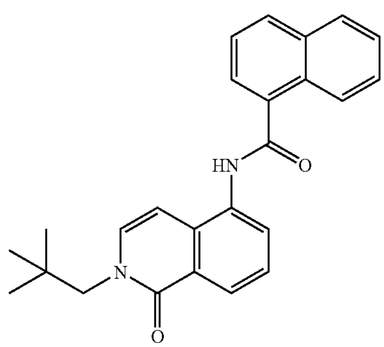 [SMILES: CC(C)(C)Cn1ccc2c(NC(=O)c3cccc4ccccc34)cccc2c1=O] | 384.48 | 385.48 | + |
| 1250 | 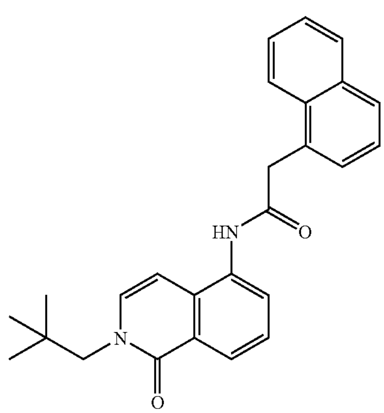 [SMILES: CC(C)(C)Cn1ccc2c(NC(=O)Cc3cccc4ccccc34)cccc2c1=O] | 398.50 | 399.26 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1251 | 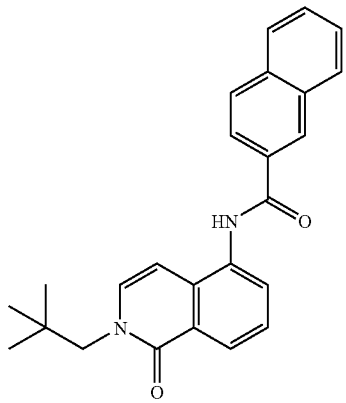 [SMILES: CC(C)(C)Cn1ccc2c(NC(=O)c3ccc4ccccc4c3)cccc2c1=O] | 384.48 | 385.48 | + |
| 1252 | 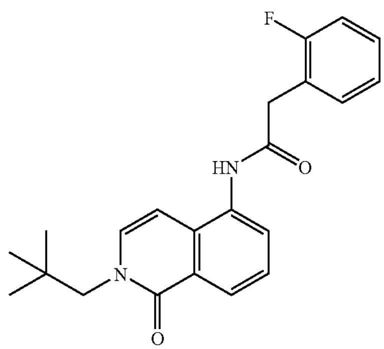 [SMILES: CC(C)(C)Cn1ccc2c(NC(=O)Cc3ccccc3F)cccc2c1=O] | 366.43 | 367.34 | + |
| 1253 | 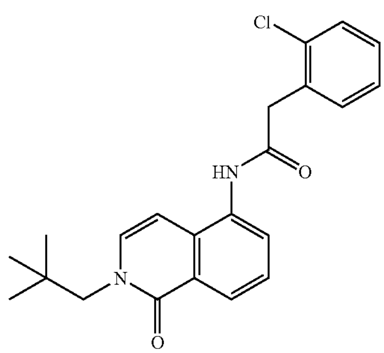 [SMILES: CC(C)(C)Cn1ccc2c(NC(=O)Cc3ccccc3Cl)cccc2c1=O] | 382.89 | 383.38 | + |
| 1254 | 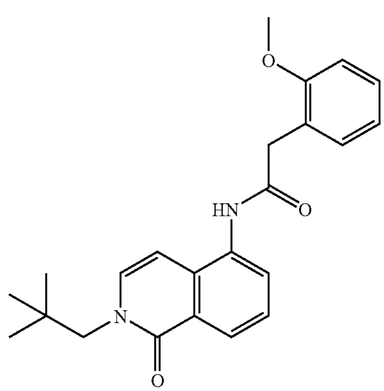 [SMILES: COc1ccccc1CC(=O)Nc1cccc2c(=O)n(CC(C)(C)C)ccc12] | 378.47 | 379.44 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1255 | 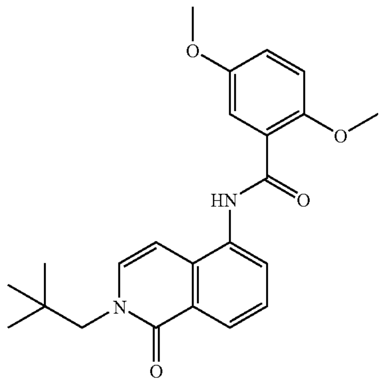 [SMILES: COc1ccc(OC)c(C(=O)Nc2cccc3c(=O)n(CC(C)(C)C)ccc23)c1] | 408.50 | 409.53 | + |
| 1256 | 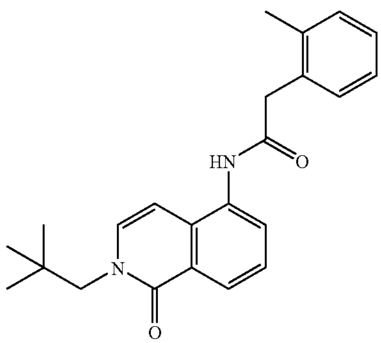 [SMILES: Cc1ccccc1CC(=O)Nc1cccc2c(=O)n(CC(C)(C)C)ccc12] | 362.47 | 363.40 | + |
| 1257 | 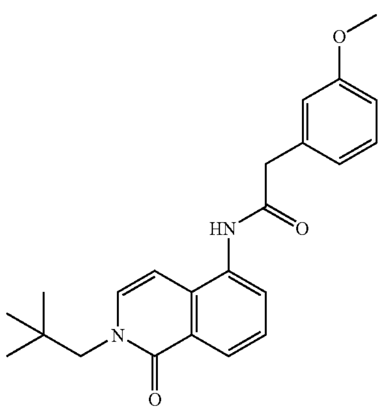 [SMILES: COc1cccc(CC(=O)Nc2cccc3c(=O)n(CC(C)(C)C)ccc23)c1] | 378.47 | 379.44 | + |
| 1258 | 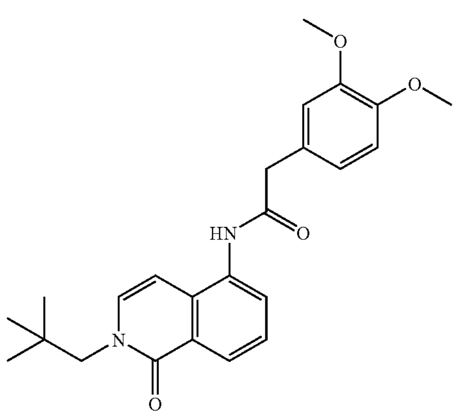 [SMILES: COc1ccc(CC(=O)Nc2cccc3c(=O)n(CC(C)(C)C)ccc23)cc1OC] | 408.50 | 409.55 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1259 | 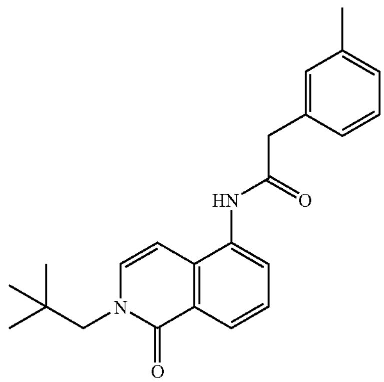 [SMILES: Cc1cccc(CC(=O)Nc2cccc3c(=O)n(CC(C)(C)C)ccc23)c1] | 362.47 | 363.41 | + |
| 1260 | 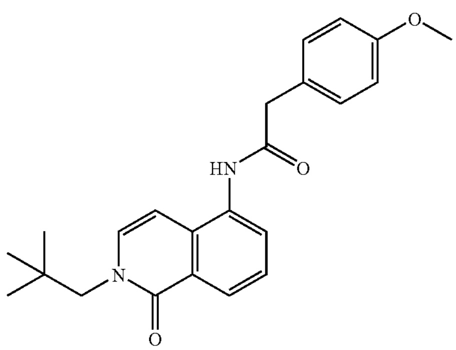 [SMILES: COc1ccc(CC(=O)Nc2cccc3c(=O)n(CC(C)(C)C)ccc23)cc1] | 378.47 | 379.45 | + |
| 1261 | 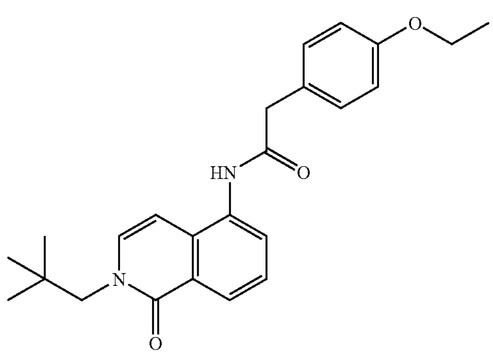 [SMILES: CCOc1ccc(CC(=O)Nc2cccc3c(=O)n(CC(C)(C)C)ccc23)cc1] | 392.50 | 393.37 | + |
| 1262 | 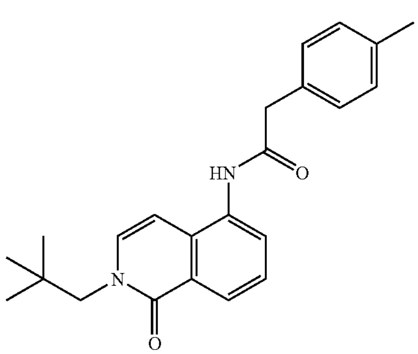 [SMILES: Cc1ccc(CC(=O)Nc2cccc3c(=O)n(CC(C)(C)C)ccc23)cc1] | 362.47 | 363.40 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1263 | 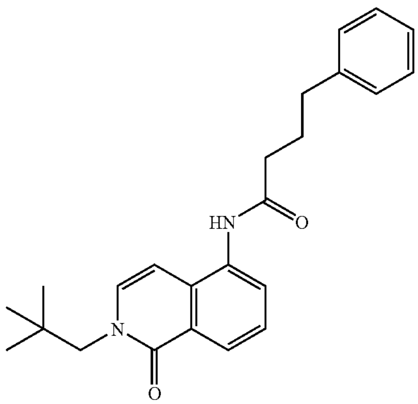 [SMILES: CC(C)(C)Cn1ccc2c(NC(=O)CCCc3ccccc3)cccc2c1=O] | 376.50 | 377.45 | + |
| 1264 | 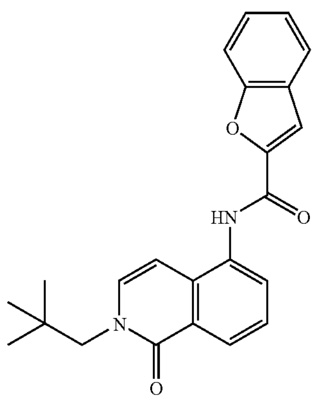 [SMILES: CC(C)(C)Cn1ccc2c(NC(=O)c3cc4ccccc4o3)cccc2c1=O] | 374.44 | 375.20 | + |
| 1265 | 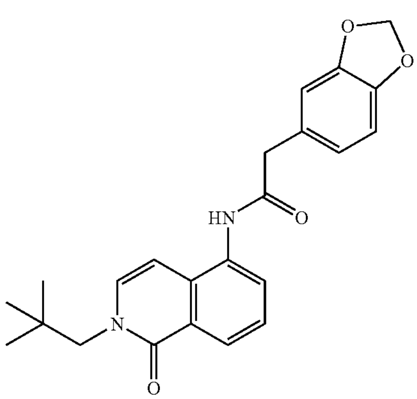 [SMILES: CC(C)(C)Cn1ccc2c(NC(=O)Cc3ccc4c(c3)OCO4)cccc2c1=O] | 392.45 | 393.31 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1266 | 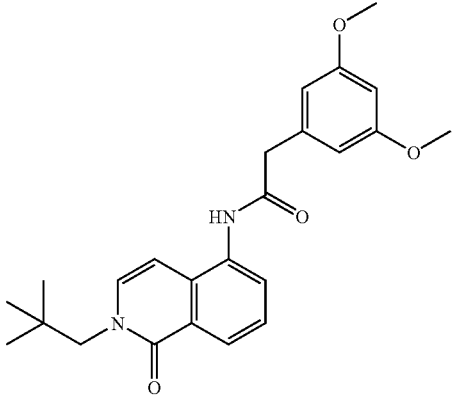 [SMILES: COc1cc(CC(=O)Nc2cccc3c(=O)n(CC(C)(C)C)ccc23)cc(OC)c1] | 408.50 | 409.54 | + |
| 1267 | 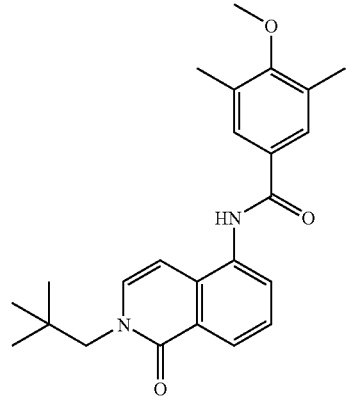 [SMILES: COc1c(C)cc(C(=O)Nc2cccc3c(=O)n(CC(C)(C)C)ccc23)cc1C] | 392.50 | 393.36 | + |
| 1268 | 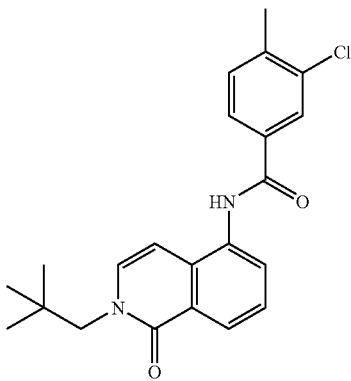 [SMILES: Cc1ccc(C(=O)Nc2cccc3c(=O)n(CC(C)(C)C)ccc23)cc1Cl] | 382.89 | 383.38 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1269 | 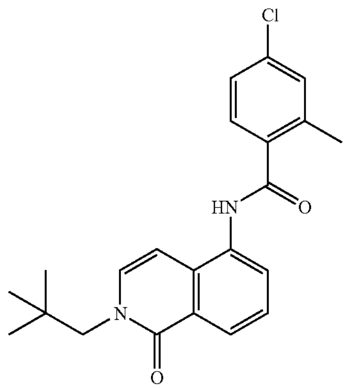 [SMILES: Cc1cc(Cl)ccc1C(=O)Nc1cccc2c(=O)n(CC(C)(C)C)ccc12] | 382.89 | 383.40 | + |
| 1270 | 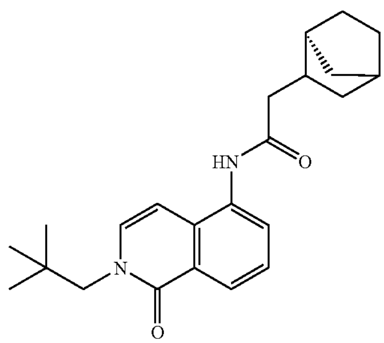 [SMILES: CC(C)(C)Cn1ccc2c(NC(=O)CC3CC4CC[C@H]3C4)cccc2c1=O] | 366.50 | 367.36 | + |
| 1271 | 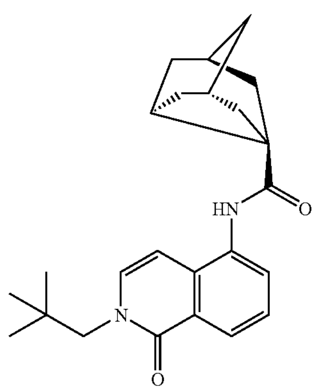 [SMILES: CC(C)(C)Cn1ccc2c(NC(=O)[C@@]34C[C@@H]5C[C@@H](C[C@@H]3C5)C4)cccc2c1=O] | 378.51 | 379.48 | + |
| 1272 | 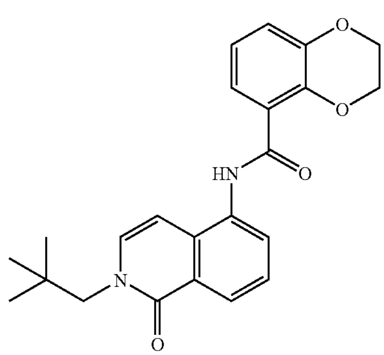 [SMILES: CC(C)(C)Cn1ccc2c(NC(=O)c3cccc4c3OCCO4)cccc2c1=O] | 392.45 | 393.32 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1273 | 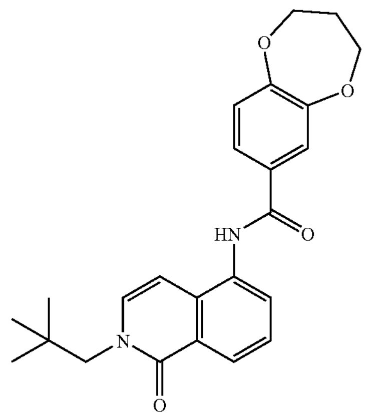 [SMILES: CC(C)(C)Cn1ccc2c(NC(=O)c3ccc4c(c3)OCCCO4)cccc2c1=O] | 406.48 | 407.59 | + |
| 1274 | 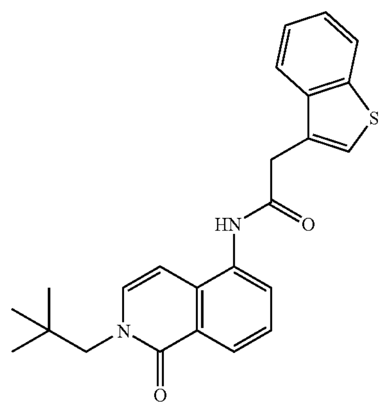 [SMILES: CC(C)(C)Cn1ccc2c(NC(=O)Cc3csc4ccccc34)cccc2c1=O] | 404.53 | 405.45 | + |
| 1275 | 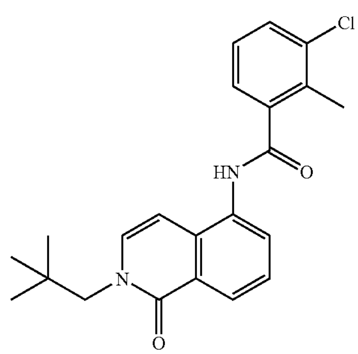 [SMILES: Cc1c(Cl)cccc1C(=O)Nc1cccc2c(=O)n(CC(C)(C)C)ccc12] | 382.89 | 383.38 | + |
| 1276 | 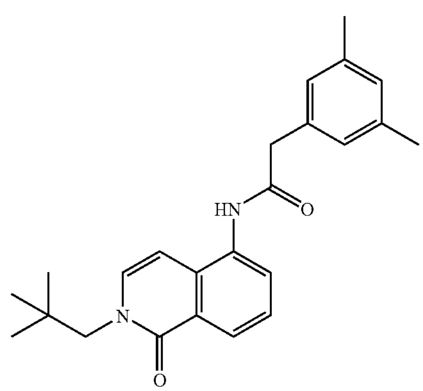 [SMILES: Cc1cc(C)cc(CC(=O)Nc2cccc3c(=O)n(CC(C)(C)C)ccc23)c1] | 376.50 | 377.45 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1277 | 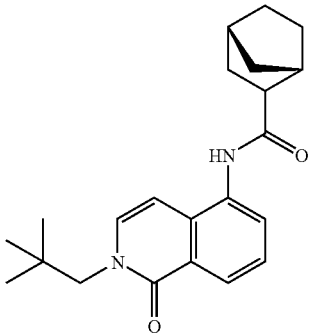 [SMILES: CC(C)(C)Cn1ccc2c(NC(=O)C3C[C@@H]4CC[C@H]3C4)cccc2c1=O] | 352.48 | 353.62 | ++++ |
| 1278 | 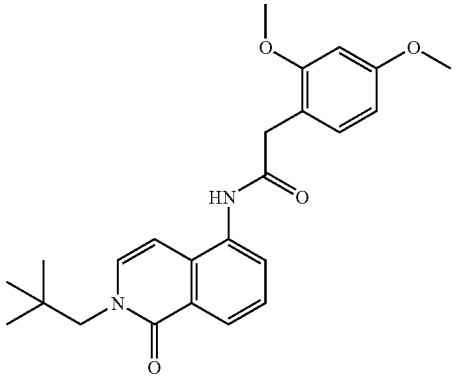 [SMILES: COc1ccc(CC(=O)Nc2cccc3c(=O)n(CC(C)(C)C)ccc23)c(OC)c1] | 408.50 | 409.52 | + |
| 1279 | 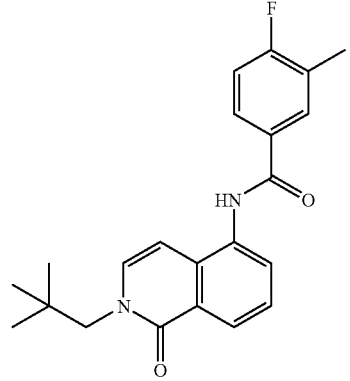 [SMILES: Cc1cc(C(=O)Nc2cccc3c(=O)n(CC(C)(C)C)ccc23)ccc1F] | 366.43 | 367.35 | + |
| 1280 | 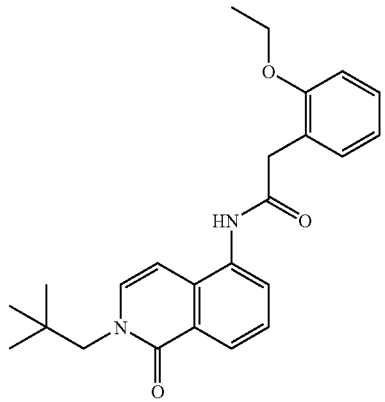 [SMILES: CCOc1ccccc1CC(=O)Nc1cccc2c(=O)n(CC(C)(C)C)ccc12] | 392.50 | 393.36 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1281 | 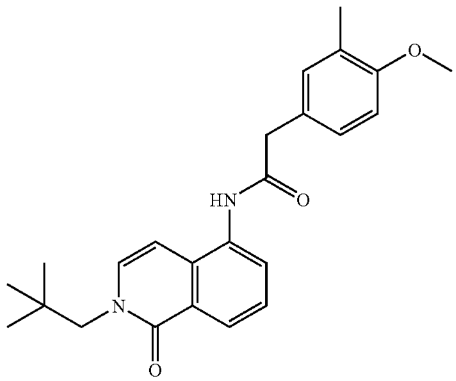 [SMILES: COc1ccc(CC(=O)Nc2cccc3c(=O)n(CC(C)(C)C)ccc23)cc1C] | 392.50 | 393.37 | ++ |
| 1282 | 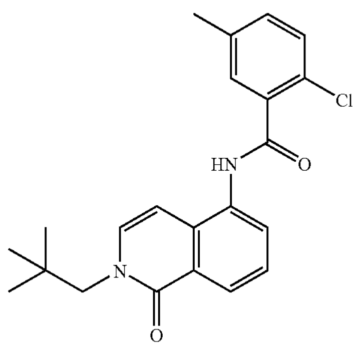 [SMILES: Cc1ccc(Cl)c(C(=O)Nc2cccc3c(=O)n(CC(C)(C)C)ccc23)c1] | 382.89 | 383.40 | + |
| 1283 | 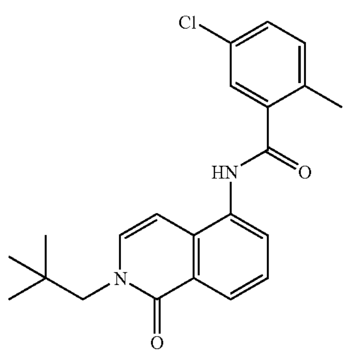 [SMILES: Cc1ccc(Cl)cc1C(=O)Nc1cccc2c(=O)n(CC(C)(C)C)ccc12] | 382.89 | 383.23 | ++ |
| 1284 | 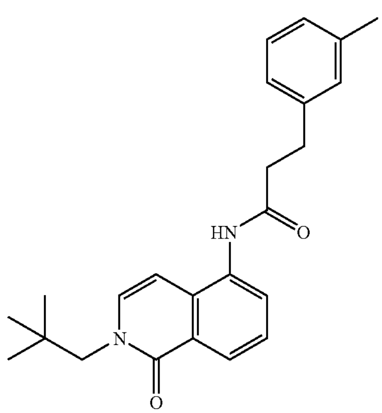 [SMILES: Cc1cccc(CCC(=O)Nc2cccc3c(=O)n(CC(C)(C)C)ccc23)c1] | 376.50 | 377.33 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1285 | 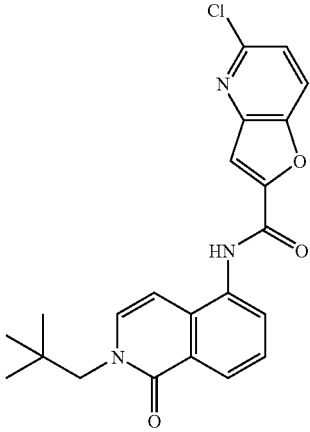 [SMILES: CC(C)(C)Cn1ccc2c(NC(=O)c3cc4nc(Cl)ccc4o3)cccc2c1=O] | 408.88 | 409.24 | + |
| 1286 | 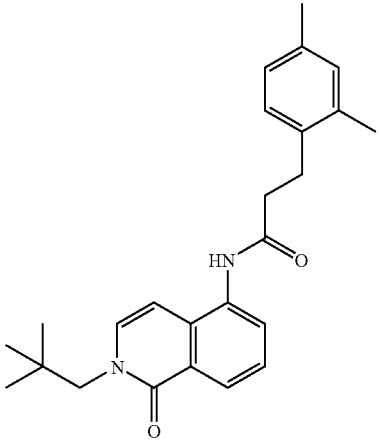 [SMILES: Cc1ccc(CCC(=O)Nc2cccc3c(=O)n(CC(C)(C)C)ccc23)c(C)c1] | 390.52 | 391.50 | + |
| 1287 | 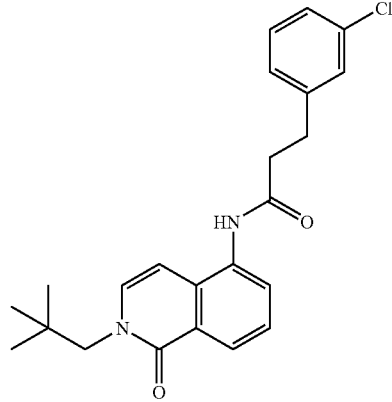 [SMILES: CC(C)(C)Cn1ccc2c(NC(=O)CCc3cccc(Cl)c3)cccc2c1=O] | 396.92 | 397.26 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1288 | 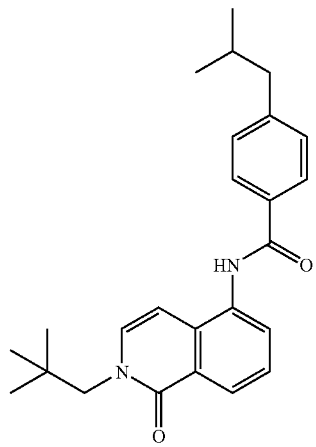 [SMILES: CC(C)Cc1ccc(C(=O)Nc2cccc3c(=O)n(CC(C)(C)C)ccc23)cc1] | 390.52 | 391.41 | + |
| 1289 | 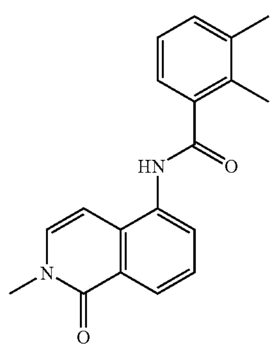 | 306.36 | 307.20 | + |
| 1290 | 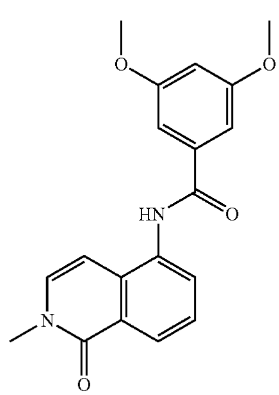 | 338.36 | 339.36 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1291 | 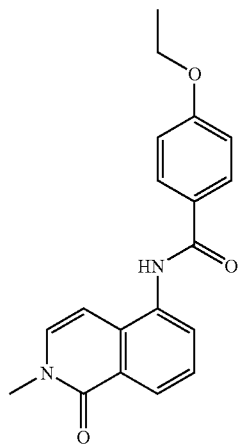 [SMILES: CCOc1ccc(C(=O)Nc2cccc3c(=O)n(C)ccc23)cc1] | 322.36 | 323.47 | + |
| 1292 | 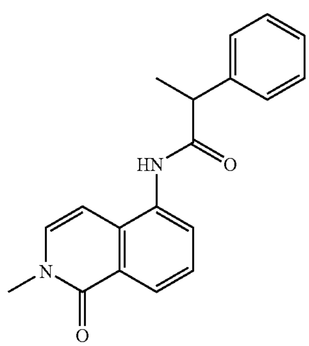 [SMILES: CC(C(=O)Nc1cccc2c(=O)n(C)ccc12)c1ccccc1] | 306.36 | 307.32 | + |
| 1293 | 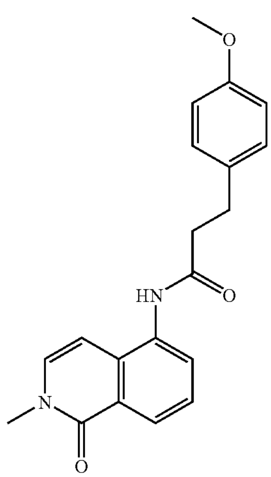 [SMILES: COc1ccc(CCC(=O)Nc2cccc3c(=O)n(C)ccc23)cc1] | 336.39 | 337.43 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1294 | 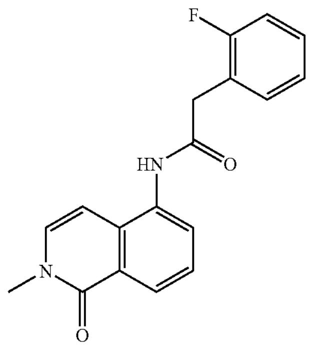 [SMILES: Cn1ccc2c(NC(=O)Cc3ccccc3F)cccc2c1=O] | 310.33 | 311.44 | + |
| 1295 | 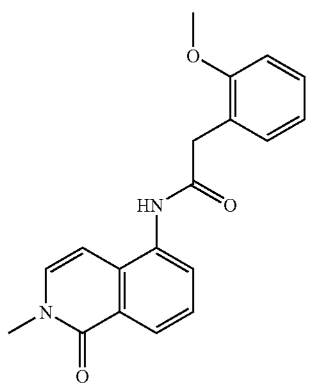 [SMILES: COc1ccccc1CC(=O)Nc1cccc2c(=O)n(C)ccc12] | 322.36 | 323.54 | + |
| 1296 | 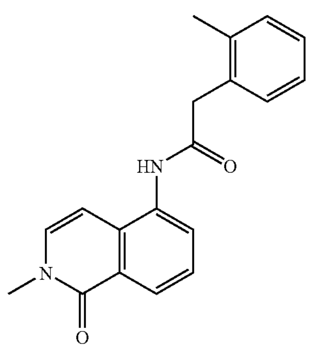 [SMILES: Cc1ccccc1CC(=O)Nc1cccc2c(=O)n(C)ccc12] | 306.36 | 307.38 | + |
| 1297 | 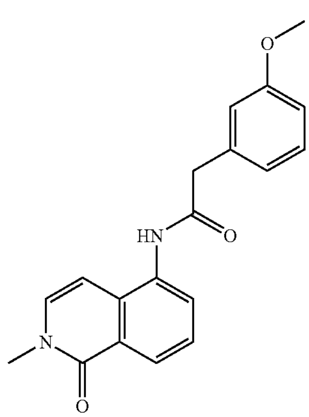 | 322.36 | 323.55 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1298 | 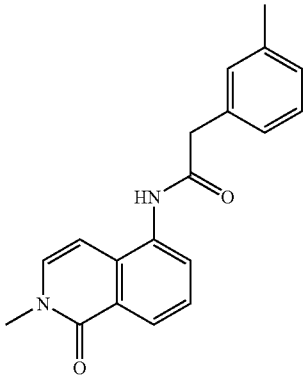 [SMILES: Cc1cccc(CC(=O)Nc2cccc3c(=O)n(C)ccc23)c1] | 306.36 | 307.39 | + |
| 1299 | 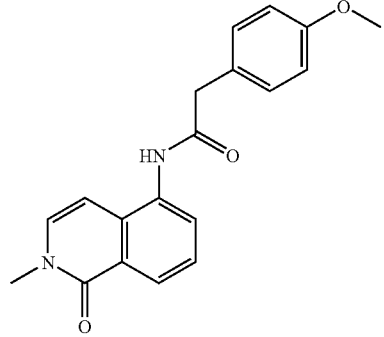 | 322.36 | 323.55 | + |
| 1300 | 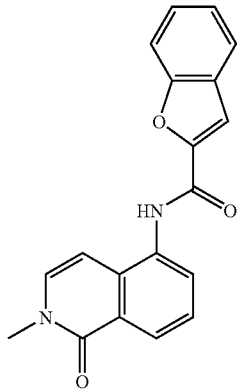 [SMILES: Cn1ccc2c(NC(=O)c3cc4ccccc4o3)cccc2c1=O] | 318.33 | 319.41 | + |
| 1301 | 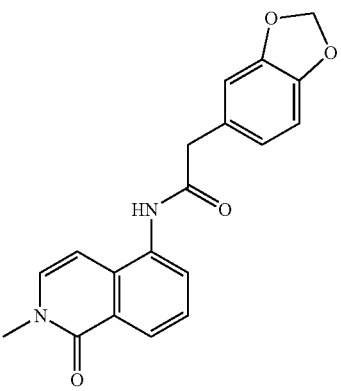 [SMILES: Cn1ccc2c(NC(=O)Cc3ccc4c(c3)OCO4)cccc2c1=O] | 336.35 | 337.42 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1302 | 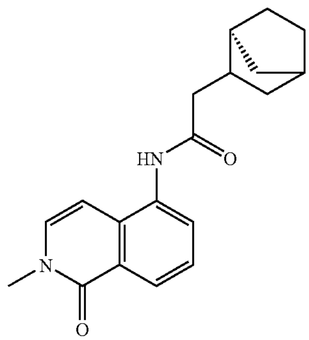 [SMILES: Cn1ccc2c(NC(=O)CC3CC4CC[C@H]3C4)cccc2c1=O] | 310.39 | 311.52 | + |
| 1303 | 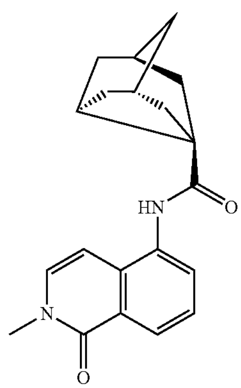 [SMILES: Cn1ccc2c(NC(=O)[C@@]34C[C@@H]5C[C@@H](C[C@@H]3C5)C4)cccc2c1=O] | 322.41 | 323.56 | + |
| 1304 | 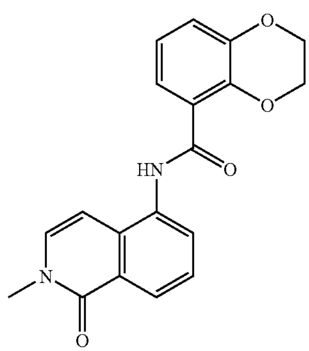 [SMILES: Cn1ccc2c(NC(=O)c3cccc4c3OCCO4)cccc2c1=O] | 336.35 | 337.41 | + |
| 1305 | 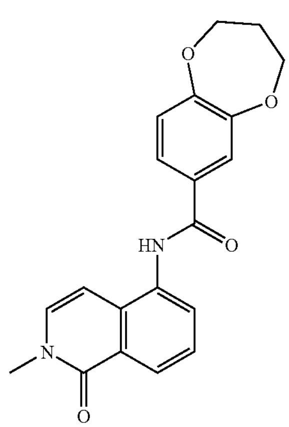 [SMILES: Cn1ccc2c(NC(=O)c3ccc4c(c3)OCCCO4)cccc2c1=O] | 350.37 | 351.47 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1306 | 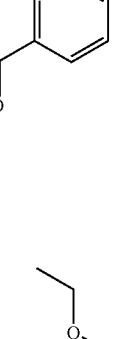 | 296.37 | 297.51 | + |
| 1307 | 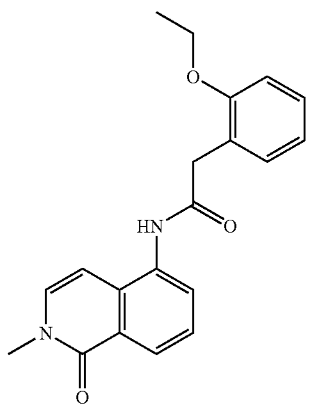 [SMILES: CCOc1ccccc1CC(=O)Nc1cccc2c(=O)n(C)ccc12] | 336.39 | 337.36 | + |
| 1308 | 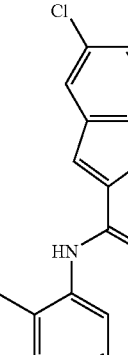 | 352.78 | 353.17 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1309 | 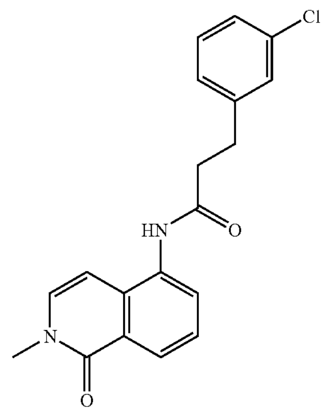 [SMILES: Cn1ccc2c(NC(=O)CCc3cccc(Cl)c3)cccc2c1=O] | 340.81 | 341.31 | ++++ |
| 1310 | 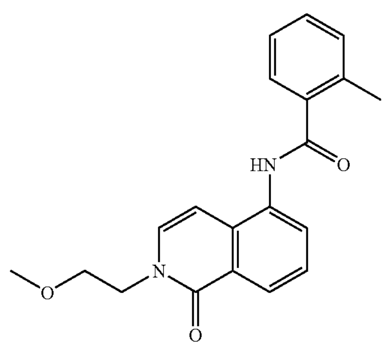 | 336.39 | 337.36 | + |
| 1311 | 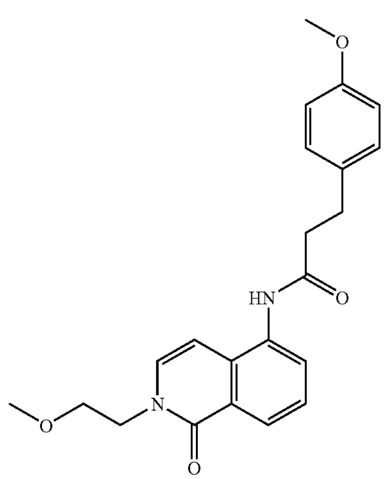 [SMILES: COCCn1ccc2c(NC(=O)CCc3ccc(OC)cc3)cccc2c1=O] | 380.44 | 381.47 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1312 | 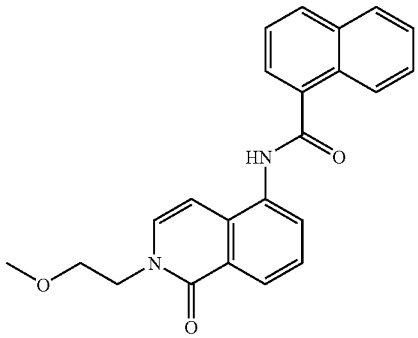 | 372.42 | 373.32 | + |
| 1313 | 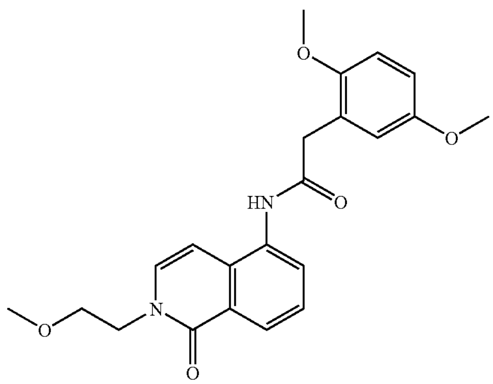 | 396.44 | 397.28 | * |
| 1314 | 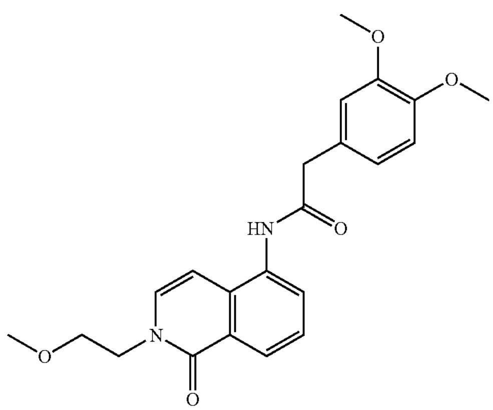 | 396.44 | 397.27 | + |
| 1315 | 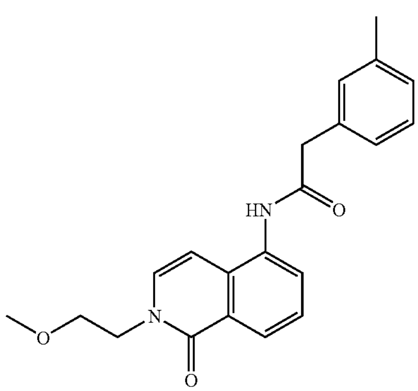 [SMILES: COCCn1ccc2c(NC(=O)Cc3cccc(C)c3)cccc2c1=O] | 350.42 | 351.48 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1316 | 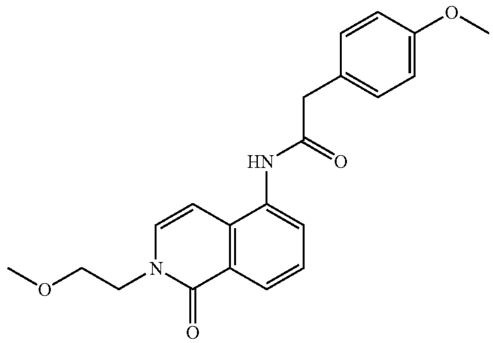 | 366.41 | 367.34 | + |
| 1317 | 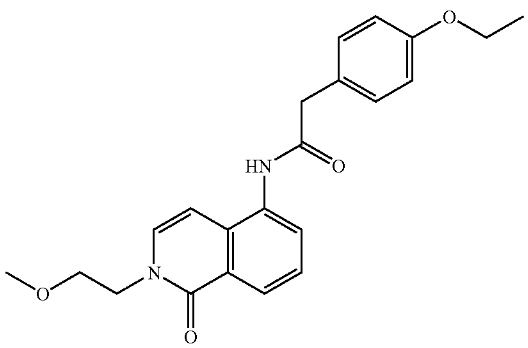 [SMILES: CCOc1ccc(CC(=O)Nc2cccc3c(=O)n(CCOC)ccc23)cc1] | 380.44 | 381.48 | + |
| 1318 | 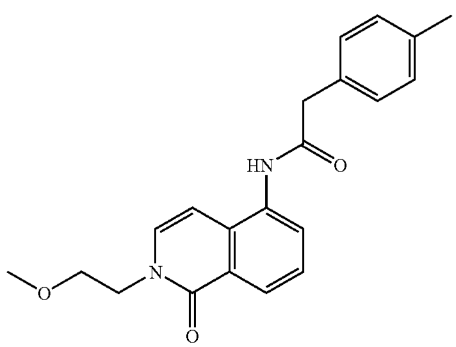 | 350.42 | 351.48 | + |
| 1319 | 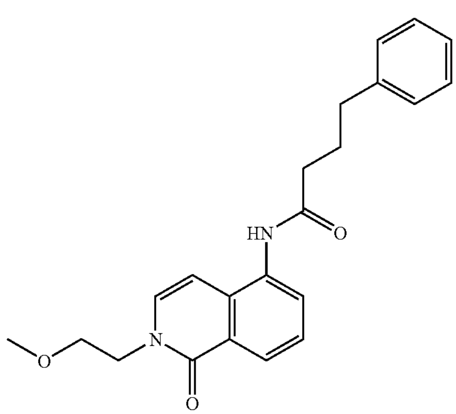 [SMILES: COCCn1ccc2c(NC(=O)CCCc3ccccc3)cccc2c1=O] | 364.44 | 365.37 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1320 | 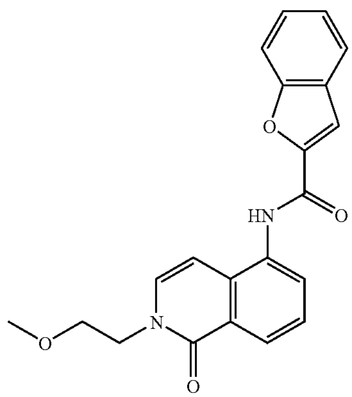 [SMILES: COCCn1ccc2c(NC(=O)c3cc4ccccc4o3)cccc2c1=O] | 362.38 | 363.27 | + |
| 1321 | 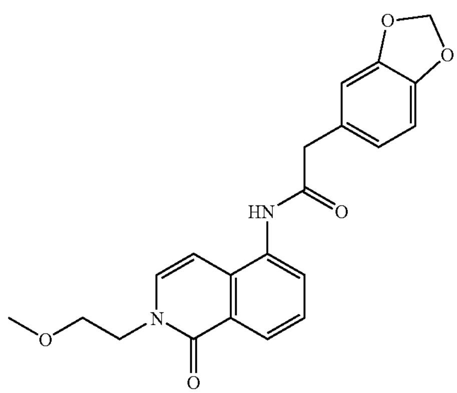 [SMILES: COCCn1ccc2c(NC(=O)Cc3ccc4c(c3)OCO4)cccc2c1=O] | 380.40 | 381.45 | + |
| 1322 | 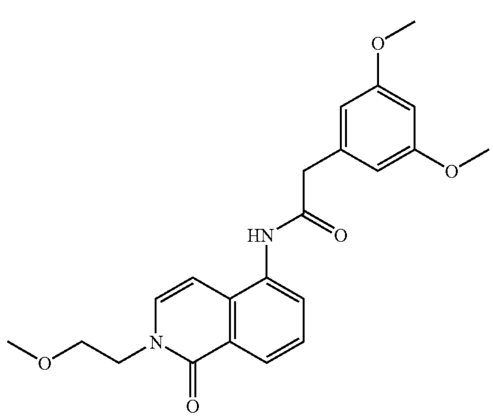 | 396.44 | 397.27 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1323 | 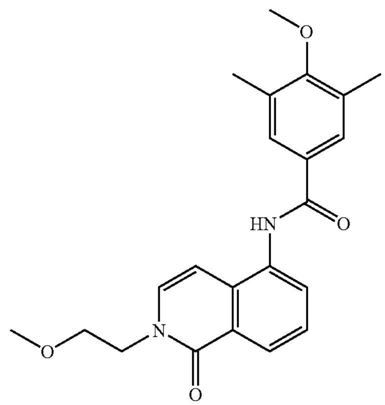 | 380.44 | 381.48 | + |
| 1324 | 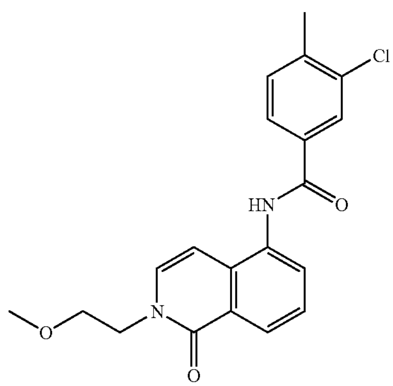 [SMILES: COCCn1ccc2c(NC(=O)c3ccc(C)c(Cl)c3)cccc2c1=O] | 370.83 | 371.09 | ++ |
| 1325 | 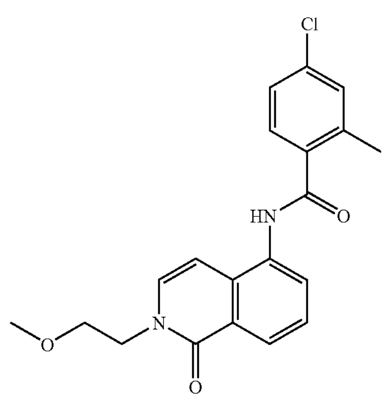 | 370.83 | 371.09 | ++ |
| 1326 | 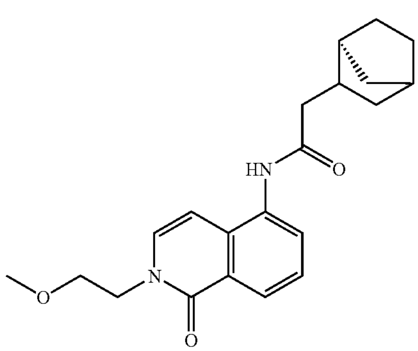 | 354.45 | 355.53 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1327 | 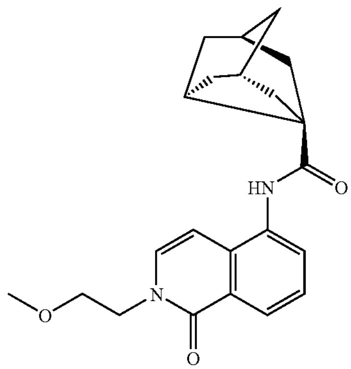 [SMILES: COCCn1ccc2c(NC(=O)[C@@]34C[C@@H]5C[C@@H](C[C@@H]3C5)C4)cccc2c1=O] | 366.46 | 367.36 | + |
| 1328 | 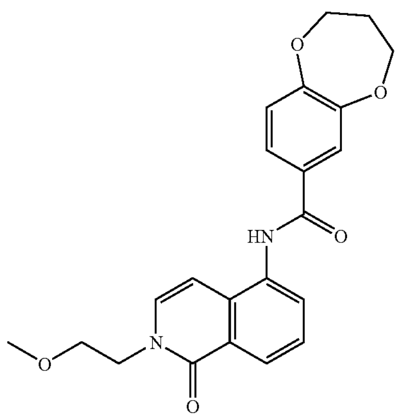 [SMILES: COCCn1ccc2c(NC(=O)c3ccc4c(c3)OCCCO4)cccc2c1=O] | 394.42 | 395.27 | + |
| 1329 | 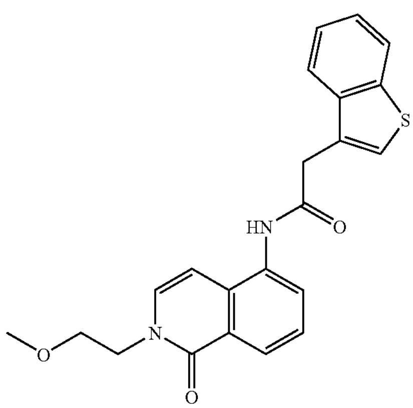 [SMILES: COCCn1ccc2c(NC(=O)Cc3csc4ccccc34)cccc2c1=O] | 392.48 | 393.25 | + |
| 1330 | 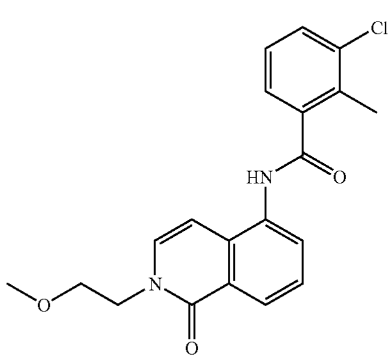 | 370.83 | 371.10 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1331 | 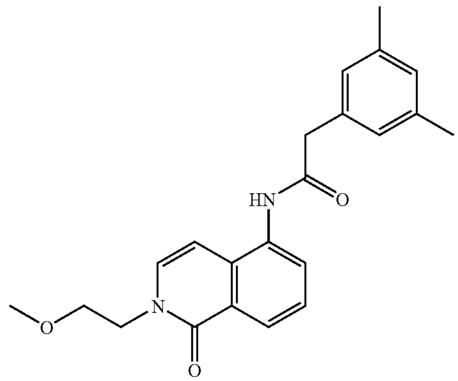 | 364.44 | 365.37 | + |
| 1332 | 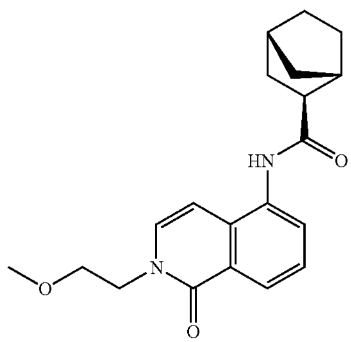 [SMILES: COCCn1ccc2c(NC(=O)[C@H]3C[C@@H]4CC[C@H]3C4)cccc2c1=O] | 340.42 | 341.39 | + |
| 1333 | 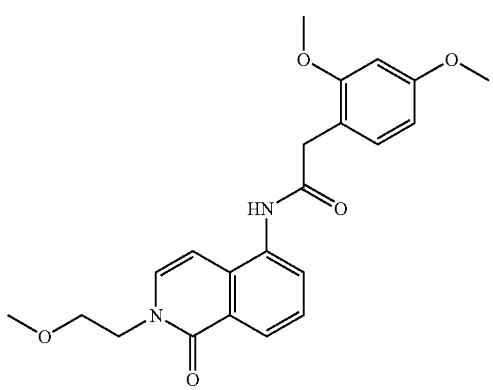 | 396.44 | 397.20 | + |
| 1334 | 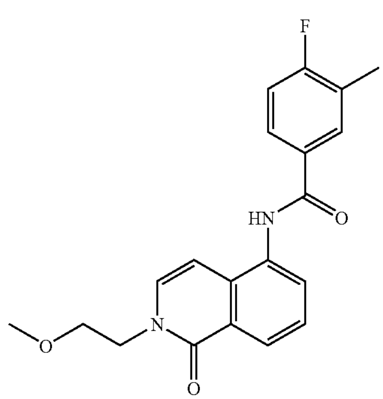 | 354.38 | 355.22 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1335 | 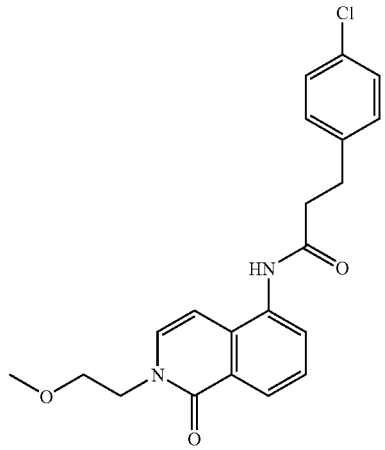 [SMILES: COCCn1ccc2c(NC(=O)CCc3ccc(Cl)cc3)cccc2c1=O] | 384.86 | 385.13 | + |
| 1336 | 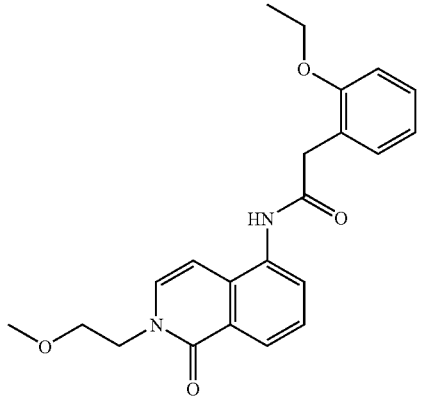 [SMILES: CCOc1ccccc1CC(=O)Nc1cccc2c(=O)n(CCOC)ccc12] | 380.44 | 381.30 | + |
| 1337 | 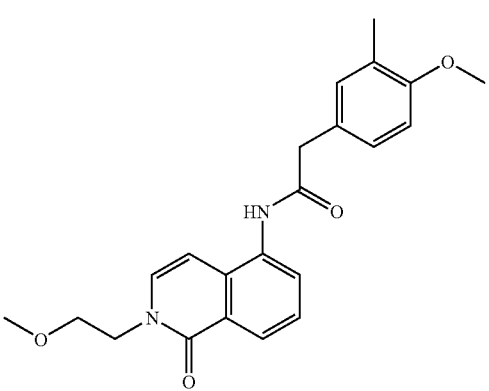 | 380.44 | 381.30 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1338 | 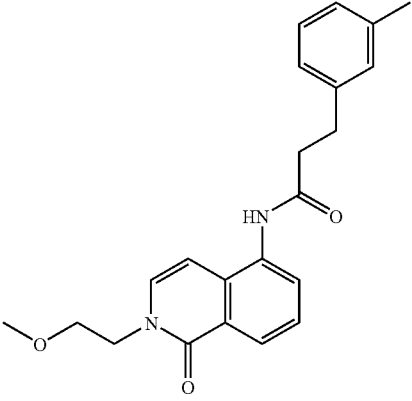 | 364.44 | 365.32 | + |
| 1339 | 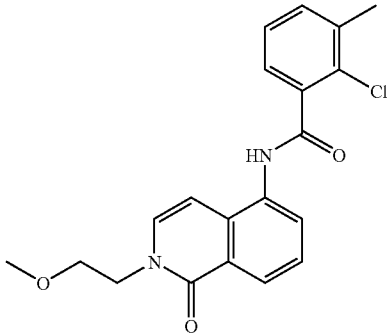 [SMILES: COCCn1ccc2c(NC(=O)c3cccc(C)c3Cl)cccc2c1=O] | 370.83 | 371.10 | + |
| 1340 | 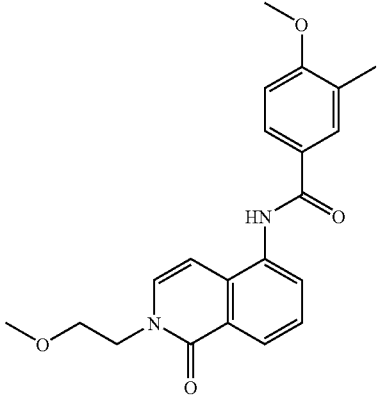 | 366.41 | 367.12 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1341 | 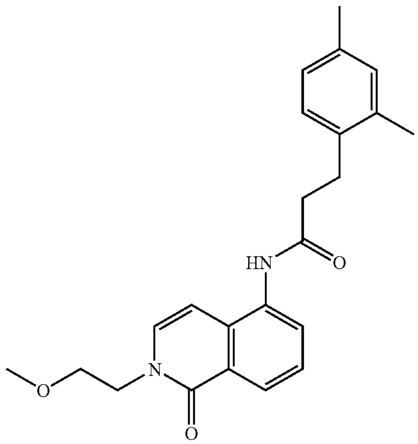 | 378.47 | 379.37 | + |
| 1342 | 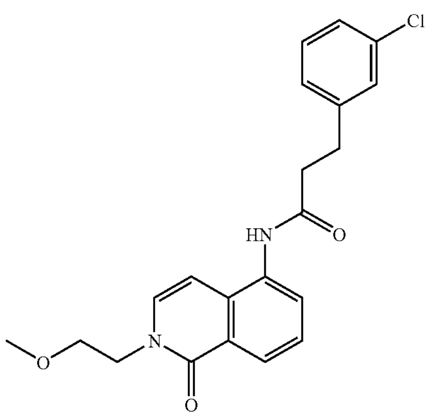 [SMILES: COCCn1ccc2c(NC(=O)CCc3cccc(Cl)c3)cccc2c1=O] | 384.86 | 385.43 | + |
| 1343 | 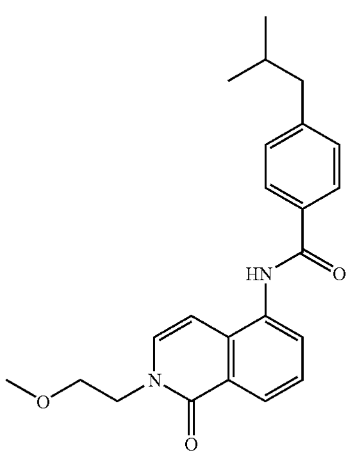 [SMILES: COCCn1ccc2c(NC(=O)c3ccc(CC(C)C)cc3)cccc2c1=O] | 378.47 | 379.45 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1344 | 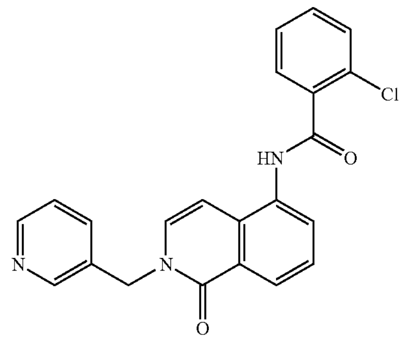 [SMILES: O=C(Nc1cccc2c(=O)n(Cc3cccnc3)ccc12)c1ccccc1Cl] | 389.84 | 390.23 | ++ |
| 1345 | 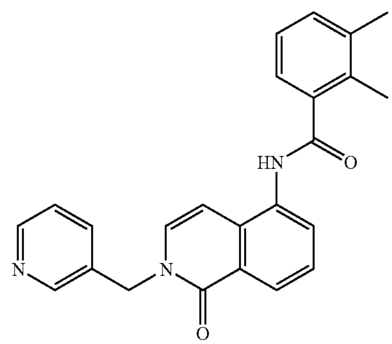 [SMILES: Cc1cccc(C(=O)Nc2cccc3c(=O)n(Cc4cccnc4)ccc23)c1C] | 383.45 | 384.53 | + |
| 1346 | 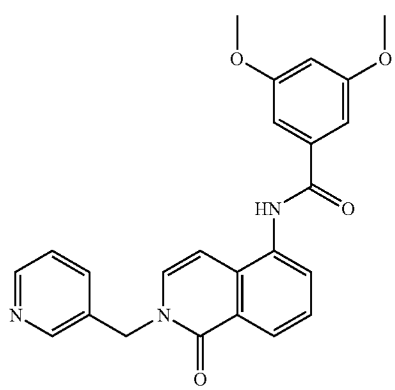 [SMILES: COc1cc(OC)cc(C(=O)Nc2cccc3c(=O)n(Cc4cccnc4)ccc23)c1] | 415.45 | 416.34 | *** |
| 1347 | 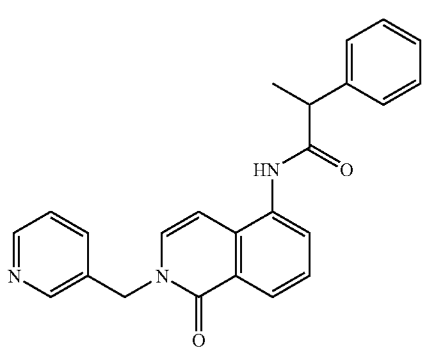 [SMILES: CC(C(=O)Nc1cccc2c(=O)n(Cc3cccnc3)ccc12)c1ccccc1] | 383.45 | 384.50 | ** |

TABLE 1-continued
IL-1β % Inhibition of Exemplary Compounds
| ID | Structure | MW | MS (obs) | IL-1β % Inhib. @ 0.3 μM |
|---|---|---|---|---|
| 1348 | 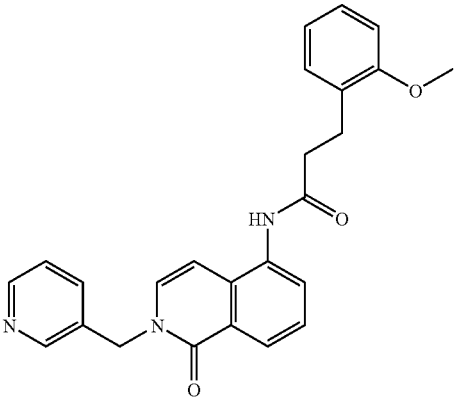 [SMILES: COc1ccccc1CCC(=O)Nc1cccc2c(=O)n(Cc3cccnc3)ccc12] | 413.47 | 414.34 | * |
| 1349 | 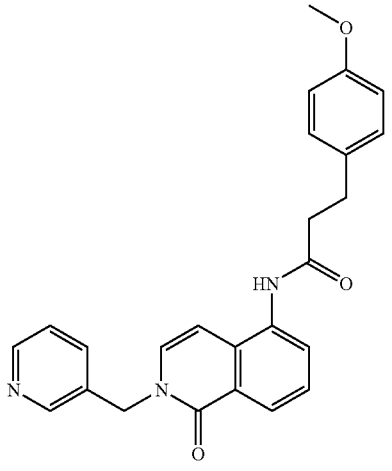 [SMILES: COc1ccc(CCC(=O)Nc2cccc3c(=O)n(Cc4cccnc4)ccc23)cc1] | 413.47 | 414.33 | * |
| 1350 | 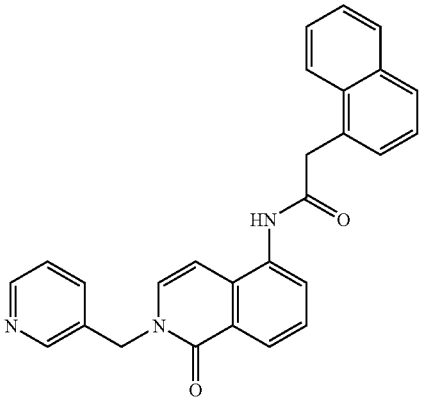 [SMILES: O=C(Cc1cccc2ccccc12)Nc1cccc2c(=O)n(Cc3cccnc3)ccc12] | 419.48 | 420.42 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1351 | 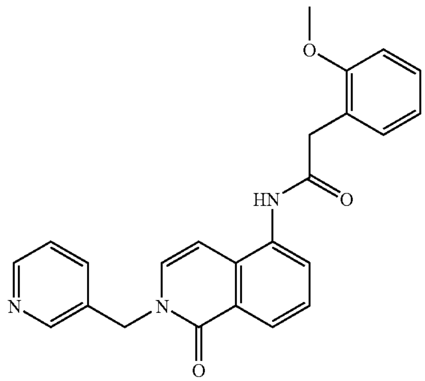 [SMILES: COc1ccccc1CC(=O)Nc1cccc2c(=O)n(Cc3cccnc3)ccc12] | 399.45 | 400.40 | + |
| 1352 | 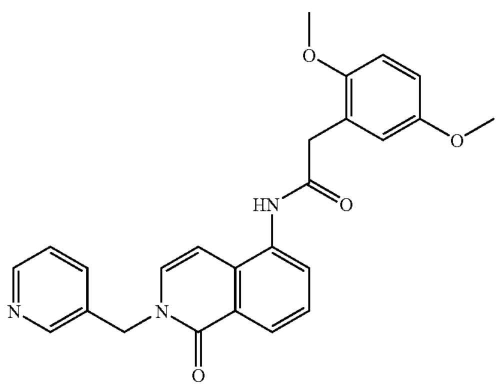 [SMILES: COc1ccc(OC)c(CC(=O)Nc2cccc3c(=O)n(Cc4cccnc4)ccc23)c1] | 429.47 | 430.32 | + |
| 1353 | 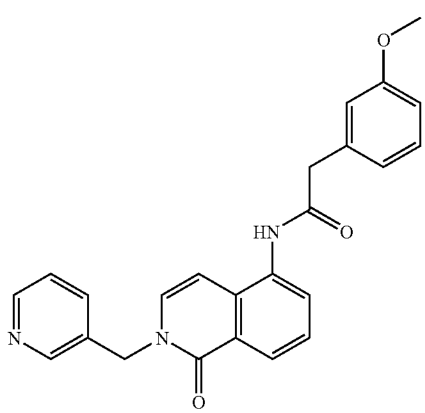 [SMILES: COc1cccc(CC(=O)Nc2cccc3c(=O)n(Cc4cccnc4)ccc23)c1] | 399.45 | 400.41 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1354 | 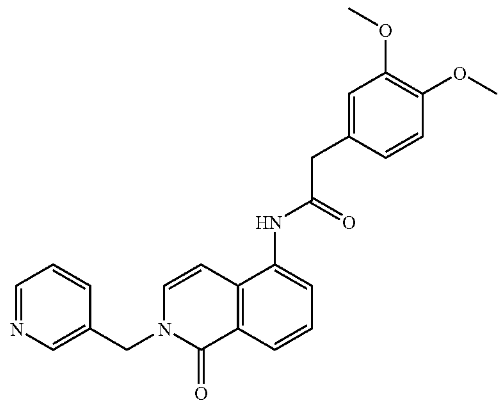 [SMILES: COc1ccc(CC(=O)Nc2cccc3c(=O)n(Cc4cccnc4)ccc23)cc1OC] | 429.47 | 430.35 | + |
| 1355 | 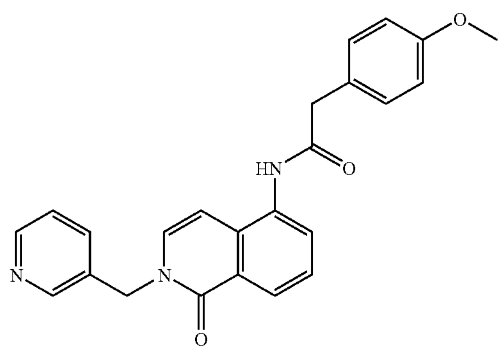 [SMILES: COc1ccc(CC(=O)Nc2cccc3c(=O)n(Cc4cccnc4)ccc23)cc1] | 399.45 | 400.40 | + |
| 1356 | 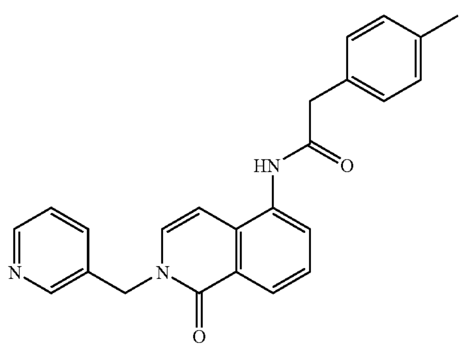 [SMILES: Cc1ccc(CC(=O)Nc2cccc3c(=O)n(Cc4cccnc4)ccc23)cc1] | 383.45 | 384.51 | + |
| 1357 | 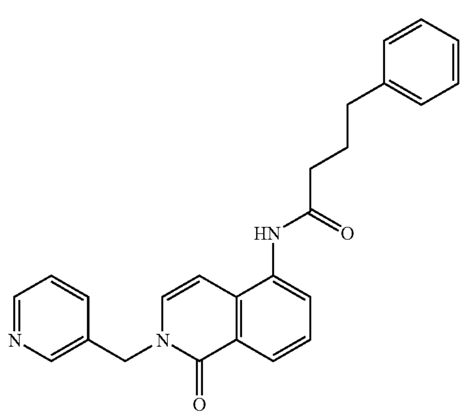 [SMILES: O=C(CCCc1ccccc1)Nc1cccc2c(=O)n(Cc3cccnc3)ccc12] | 397.48 | 398.13 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1358 | 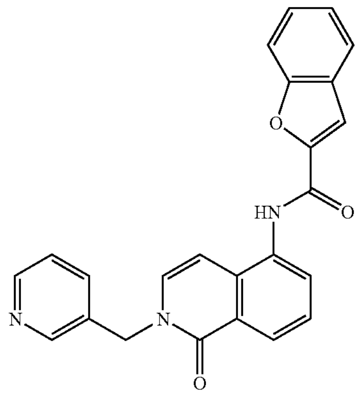 [SMILES: O=C(Nc1cccc2c(=O)n(Cc3cccnc3)ccc12)c1cc2ccccc2o1] | 395.42 | 396.21 | + |
| 1359 | 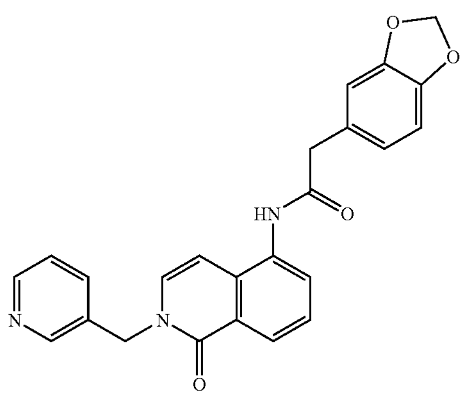 [SMILES: O=C(Cc1ccc2c(c1)OCO2)Nc1cccc2c(=O)n(Cc3cccnc3)ccc12] | 413.43 | 414.29 | ++ |
| 1360 | 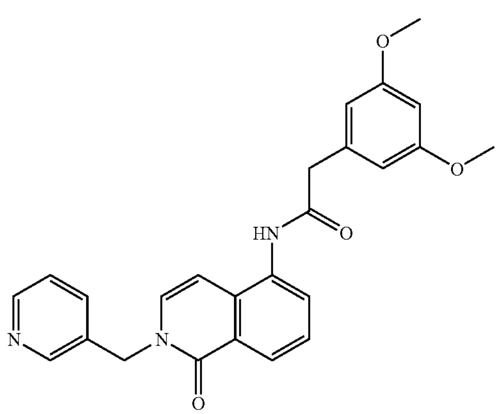 [SMILES: COc1cc(CC(=O)Nc2cccc3c(=O)n(Cc4cccnc4)ccc23)cc(OC)c1] | 429.47 | 430.36 | ++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1361 | 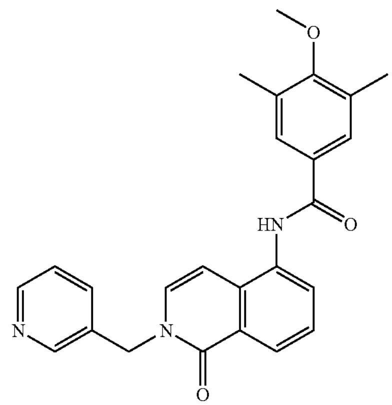 [SMILES: COc1c(C)cc(C(=O)Nc2cccc3c(=O)n(Cc4cccnc4)ccc23)cc1C] | 413.47 | 414.31 | + |
| 1362 | 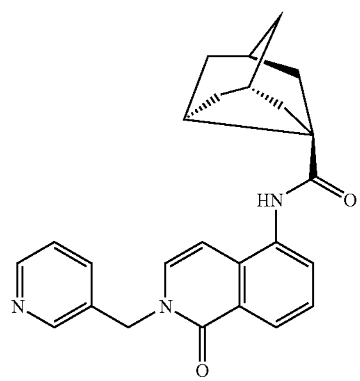 [SMILES: O=C(Nc1cccc2c(=O)n(Cc3cccnc3)ccc12)[C@@]12C[C@@H]3C[C@@H](C[C@@H]1C3)C2] | 399.49 | 400.41 | + |
| 1363 | 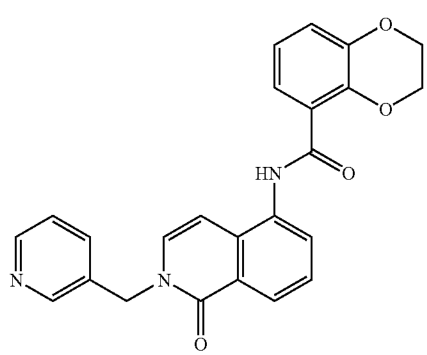 [SMILES: O=C(Nc1cccc2c(=O)n(Cc3cccnc3)ccc12)c1cccc2c1OCCO2] | 413.43 | 414.31 | + |
| 1364 | 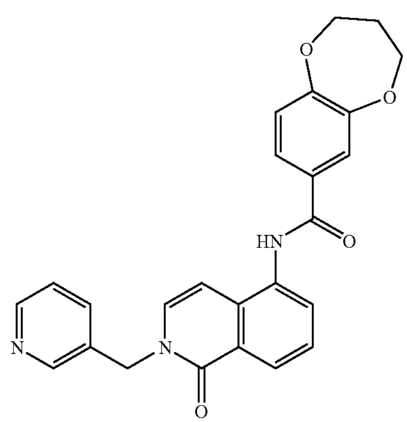 [SMILES: O=C(Nc1cccc2c(=O)n(Cc3cccnc3)ccc12)c1ccc2c(c1)OCCCO2] | 427.46 | 428.36 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1365 | 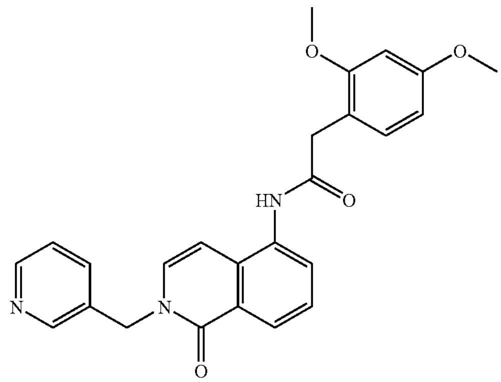 [SMILES: COc1ccc(CC(=O)Nc2cccc3c(=O)n(Cc4cccnc4)ccc23)c(OC)c1] | 429.47 | 430.36 | + |
| 1366 | 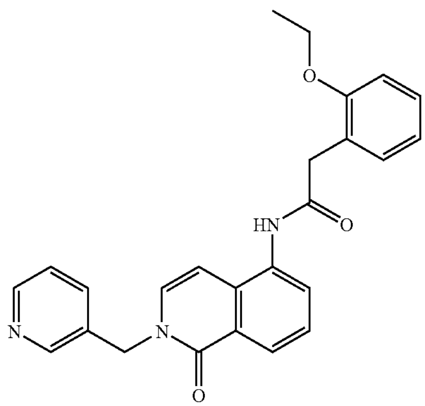 [SMILES: CCOc1ccccc1CC(=O)Nc1cccc2c(=O)n(Cc3cccnc3)ccc12] | 413.47 | 414.35 | ++ |
| 1367 | 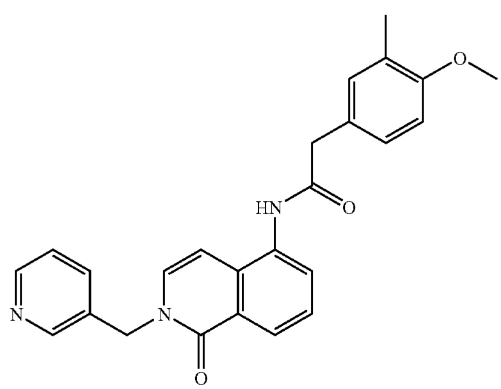 [SMILES: COc1ccc(CC(=O)Nc2cccc3c(=O)n(Cc4cccnc4)ccc23)cc1C] | 413.47 | 414.33 | + |
| 1368 | 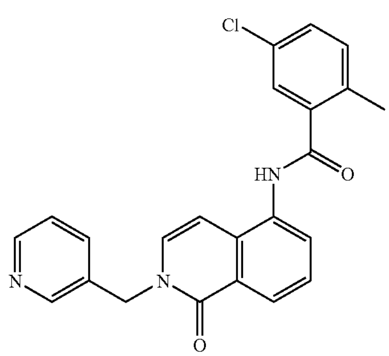 [SMILES: Cc1ccc(Cl)cc1C(=O)Nc1cccc2c(=O)n(Cc3cccnc3)ccc12] | 403.87 | 404.40 | + |

TABLE 1-continued
IL-1β % Inhibition of Exemplary Compounds
| ID | Structure | MW | MS (obs) | IL-1β % Inhib. @ 0.3 μM |
|---|---|---|---|---|
| 1369 | 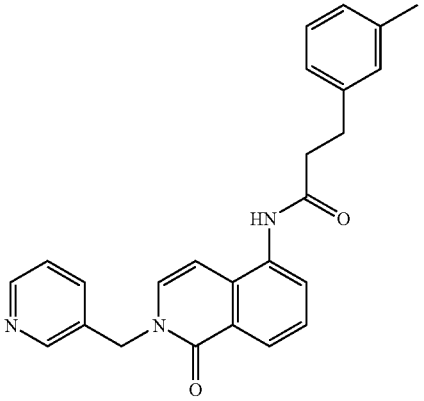 [SMILES: Cc1cccc(CCC(=O)Nc2cccc3c(=O)n(Cc4cccnc4)ccc23)c1] | 397.48 | 398.12 | + |
| 1370 | 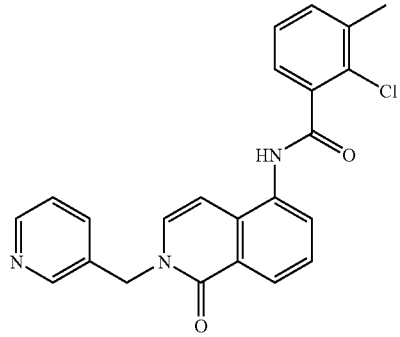 [SMILES: Cc1cccc(C(=O)Nc2cccc3c(=O)n(Cc4cccnc4)ccc23)c1Cl] | 403.87 | 404.40 | + |
| 1371 | 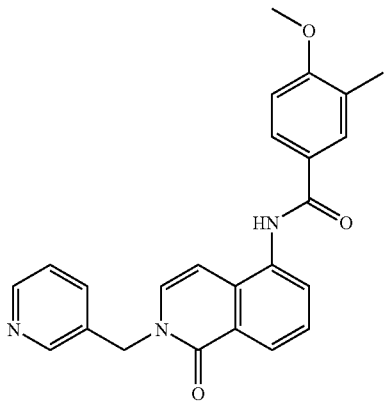 [SMILES: COc1ccc(C(=O)Nc2cccc3c(=O)n(Cc4cccnc4)ccc23)cc1C] | 399.45 | 400.37 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1372 | 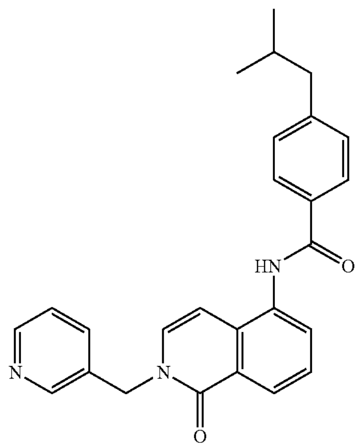 [SMILES: CC(C)Cc1ccc(C(=O)Nc2cccc3c(=O)n(Cc4cccnc4)ccc23)cc1] | 411.50 | 412.54 | + |
| 1373 | 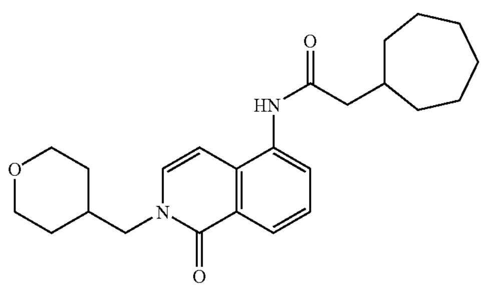 [SMILES: O=C(CC1CCCCCC1)Nc1cccc2c(=O)n(CC3CCOCC3)ccc12] | 396.53 | 397.10 | ++++ |
| 1374 | 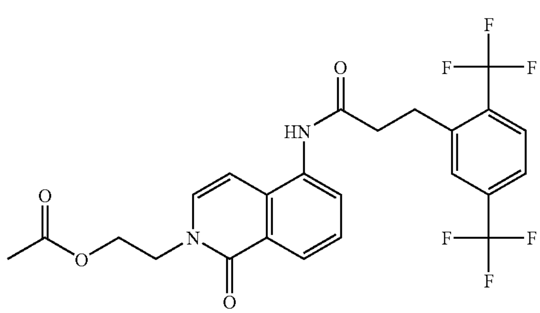 [SMILES: CC(=O)OCCn1ccc2c(NC(=O)CCc3cc(C(F)(F)F)ccc3C(F)(F)F)cccc2c1=O] | 514.42 | 515.20 | ++++ |
| 1375 | 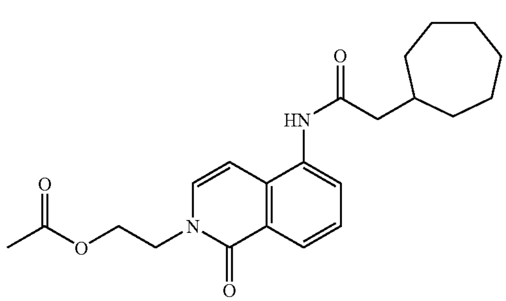 [SMILES: CC(=O)OCCn1ccc2c(NC(=O)CC3CCCCCC3)cccc2c1=O] | 384.47 | 385.10 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1376 | 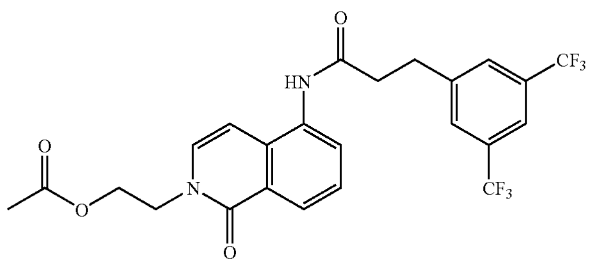 [SMILES: CC(=O)OCCn1ccc2c(NC(=O)CCc3cc(C(F)(F)F)cc(C(F)(F)F)c3)cccc2c1=O] | 514.42 | 515.00 | + |
| 1377 | 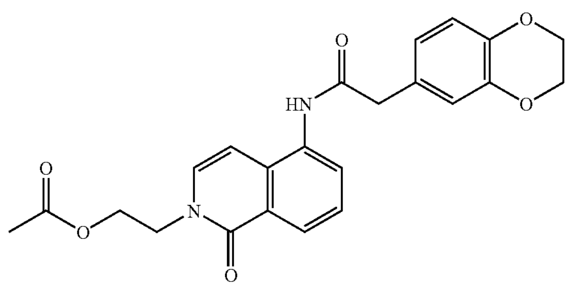 [SMILES: CC(=O)OCCn1ccc2c(NC(=O)Cc3ccc4c(c3)OCCO4)cccc2c1=O] | 422.43 | 423.30 | + |
| 1378 | 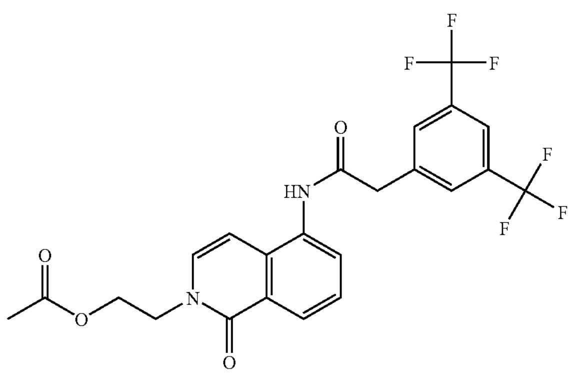 [SMILES: CC(=O)OCCn1ccc2c(NC(=O)Cc3cc(C(F)(F)F)cc(C(F)(F)F)c3)cccc2c1=O] | 500.39 | 501.30 | +++ |
| 1379 | 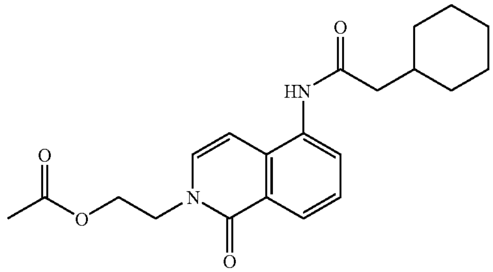 [SMILES: CC(=O)OCCn1ccc2c(NC(=O)CC3CCCCC3)cccc2c1=O] | 370.45 | 371.10 | ++++ |
| 1380 | 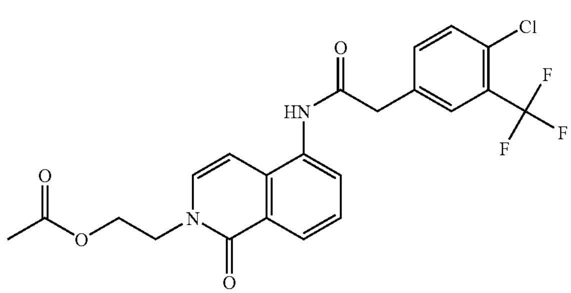 [SMILES: CC(=O)OCCn1ccc2c(NC(=O)Cc3ccc(Cl)c(C(F)(F)F)c3)cccc2c1=O] | 466.84 | 467.30 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1381 | 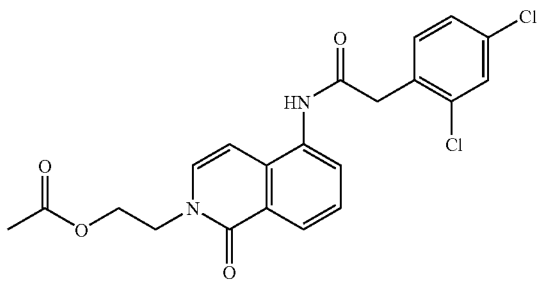 [SMILES: CC(=O)OCCn1ccc2c(NC(=O)Cc3ccc(Cl)cc3Cl)cccc2c1=O] | 433.29 | 433.10 | ++++ |
| 1382 | 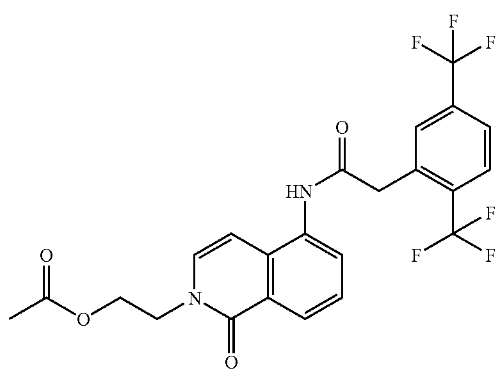 [SMILES: CC(=O)OCCn1ccc2c(NC(=O)Cc3cc(C(F)(F)F)ccc3C(F)(F)F)cccc2c1=O] | 500.39 | 501.20 | ++ |
| 1383 | 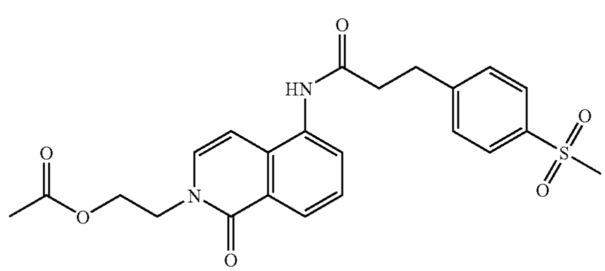 [SMILES: CC(=O)OCCn1ccc2c(NC(=O)CCc3ccc(S(C)(=O)=O)cc3)cccc2c1=O] | 456.52 | 457.00 | + |
| 1384 | 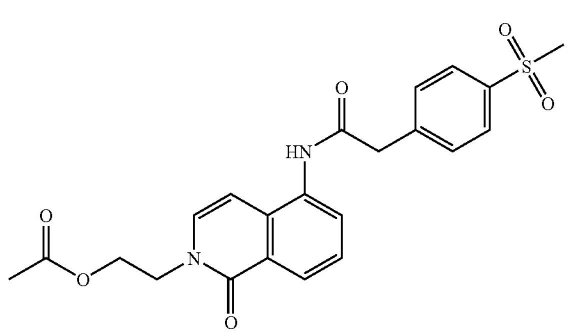 [SMILES: CC(=O)OCCn1ccc2c(NC(=O)Cc3ccc(S(C)(=O)=O)cc3)cccc2c1=O] | 442.49 | 443.30 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1385 | 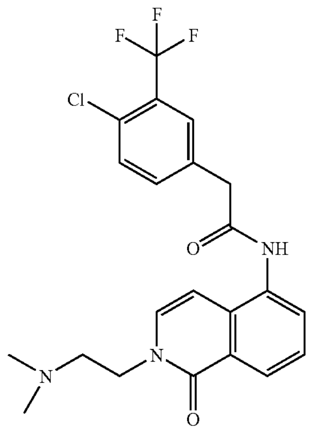 [SMILES: CN(C)CCn1ccc2c(NC(=O)Cc3ccc(Cl)c(C(F)(F)F)c3)cccc2c1=O] | 451.87 | 452.00 | ++++ |
| 1386 | 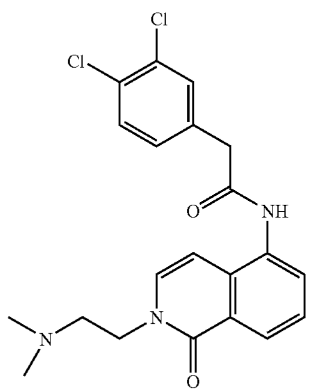 [SMILES: CN(C)CCn1ccc2c(NC(=O)Cc3ccc(Cl)c(Cl)c3)cccc2c1=O] | 418.32 | 417.90 | +++ |
| 1387 | 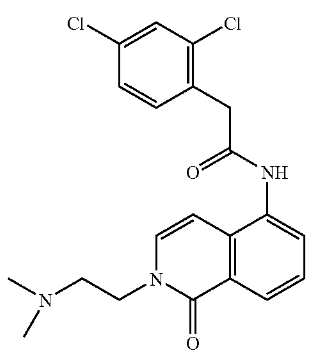 [SMILES: CN(C)CCn1ccc2c(NC(=O)Cc3ccc(Cl)cc3Cl)cccc2c1=O] | 418.02 | 418.30 | +++ |
| 1388 | 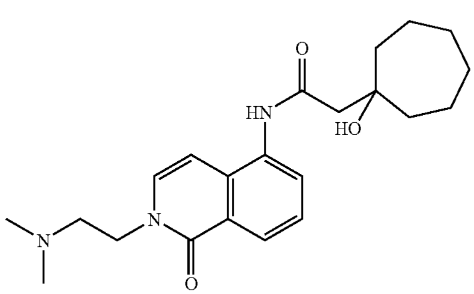 [SMILES: CN(C)CCn1ccc2c(NC(=O)CC3(O)CCCCCC3)cccc2c1=O] | 385.50 | 385.60 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1389 | 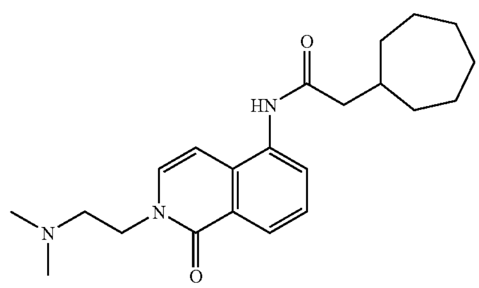 [SMILES: CN(C)CCn1ccc2c(NC(=O)CC3CCCCCC3)cccc2c1=O] | 369.51 | 370.00 | ++ |
| 1390 | 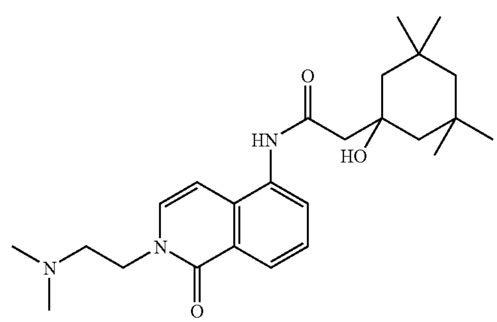 | 427.59 | 428.20 | ++++ |
| 1391 | 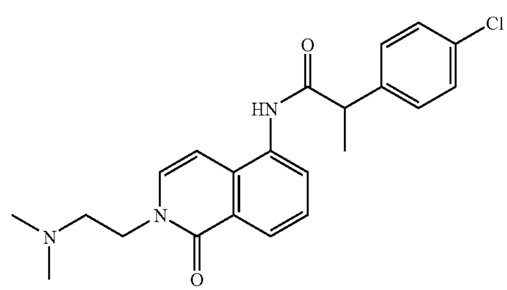 [SMILES: CC(C(=O)Nc1cccc2c(=O)n(CCN(C)C)ccc12)c1ccc(Cl)cc1] | 397.90 | 398.20 | ++++ |
| 1392 | 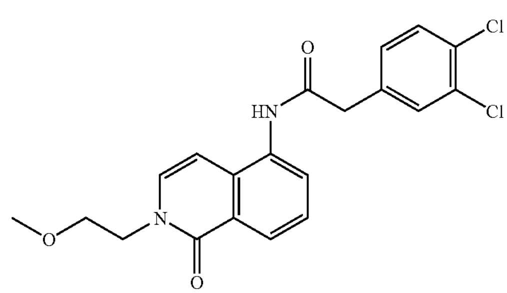 [SMILES: COCCn1ccc2c(NC(=O)Cc3ccc(Cl)c(Cl)c3)cccc2c1=O] | 405.28 | 405.00 | +++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1393 | 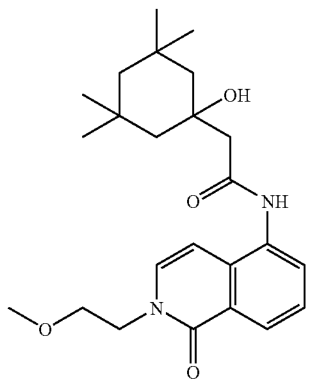 [SMILES: COCCn1ccc2c(NC(=O)CC3(O)CC(C)(C)CC(C)(C)C3)cccc2c1=O] | 414.54 | 415.20 | ++++ |
| 1394 | 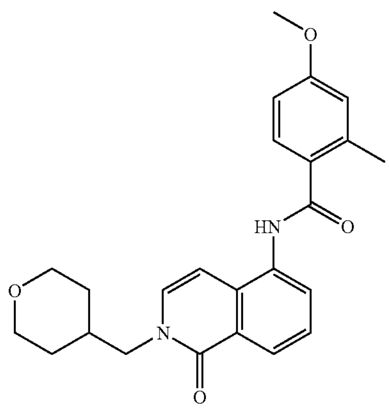 | 406.48 | 407.61 | * |
| 1395 | 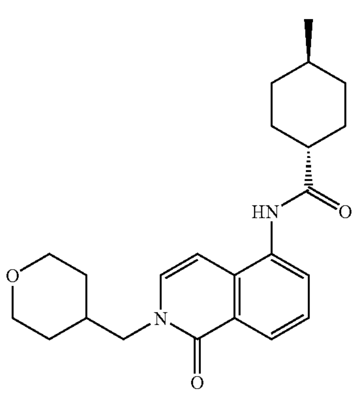 | 382.50 | 383.44 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1396 | 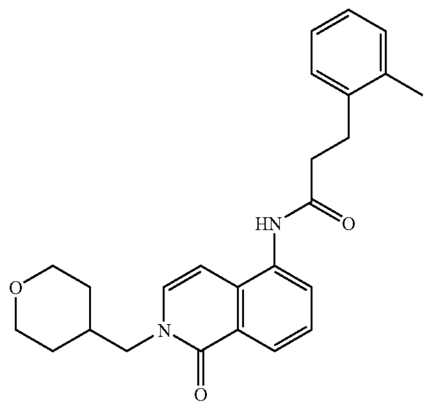 [SMILES: Cc1ccccc1CCC(=O)Nc1cccc2c(=O)n(CC3CCOCC3)ccc12] | 404.51 | 405.54 | * |
| 1397 | 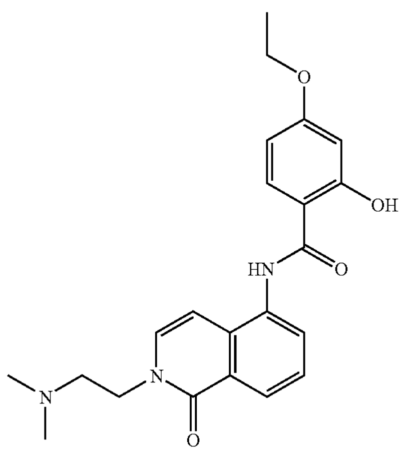 | 395.46 | 396.31 | * |
| 1398 | 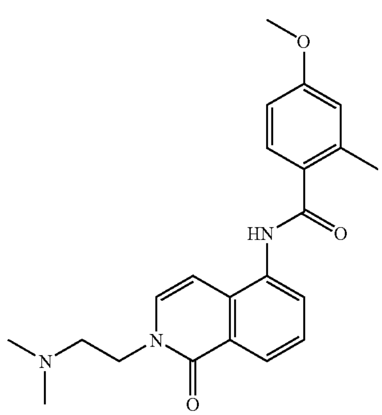 | 379.46 | 380.56 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1399 | 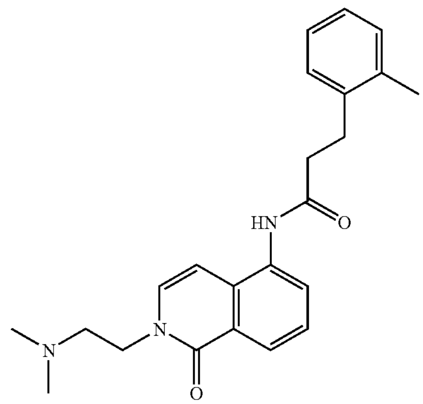 | 377.49 | 378.51 | * |
| 1400 | 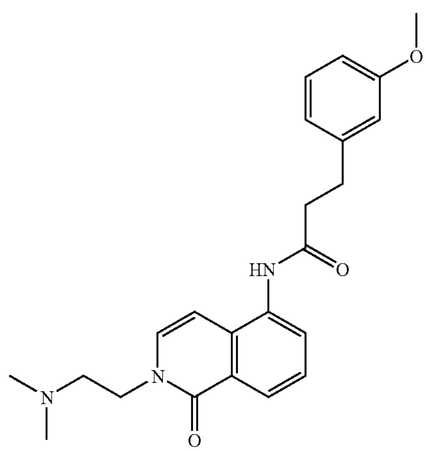 | 393.48 | 394.36 | ** |
| 1401 | 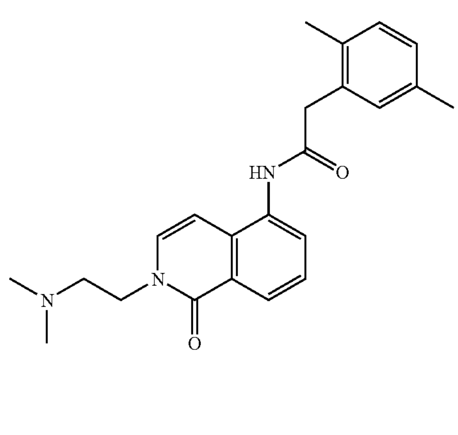 | 377.49 | 378.51 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1402 | 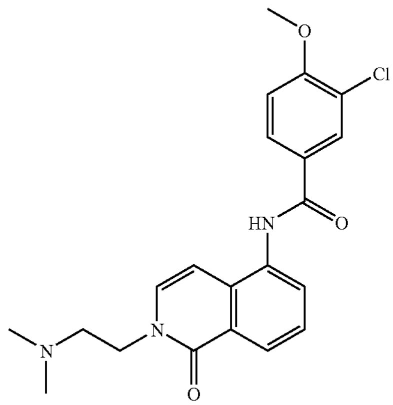 [SMILES: COc1ccc(C(=O)Nc2cccc3c(=O)n(CCN(C)C)ccc23)cc1Cl] | 399.88 | 400.35 | * |
| 1403 | 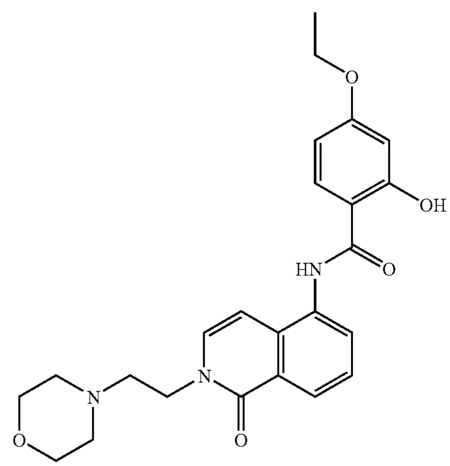 [SMILES: CCOc1ccc(C(=O)Nc2cccc3c(=O)n(CCN4CCOCC4)ccc23)c(O)c1] | 437.49 | 438.60 | * |
| 1404 | 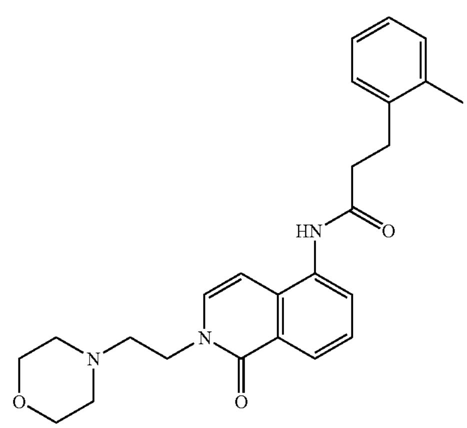 [SMILES: Cc1ccccc1CCC(=O)Nc1cccc2c(=O)n(CCN3CCOCC3)ccc12] | 419.52 | 420.46 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1405 | 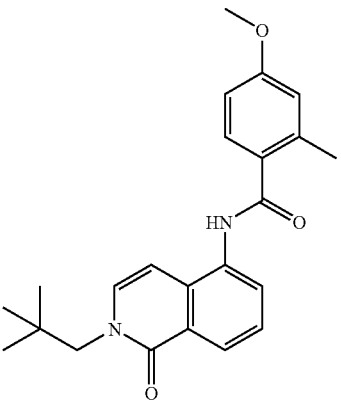 [SMILES: COc1ccc(C(=O)Nc2cccc3c(=O)n(CC(C)(C)C)ccc23)c(C)c1] | 378.47 | 379.46 | * |
| 1406 | 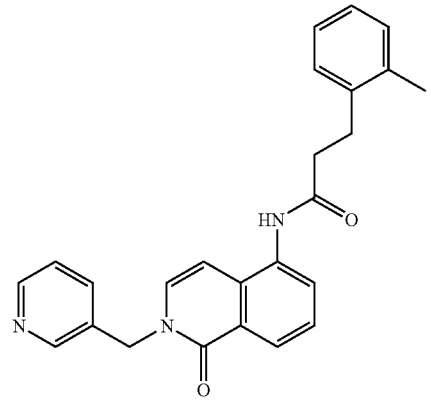 [SMILES: Cc1ccccc1CCC(=O)Nc1cccc2c(=O)n(Cc3cccnc3)ccc12] | 397.48 | 399.33 | * |
| 1407 | 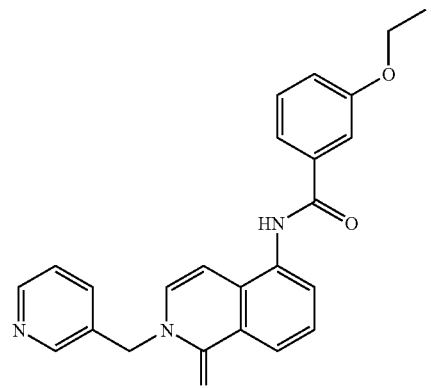 | 399.45 | 400.40 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1408 | 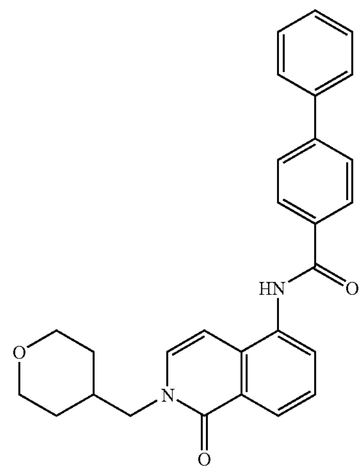 [SMILES: O=C(Nc1cccc2c(=O)n(CC3CCOCC3)ccc12)c1ccc(-c2ccccc2)cc1] | 438.52 | 439.57 | * |
| 1409 | 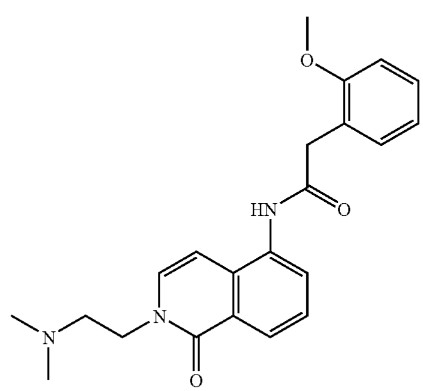 [SMILES: COc1ccccc1CC(=O)Nc1cccc2c(=O)n(CCN(C)C)ccc12] | 379.46 | 380.55 | * |
| 1410 | 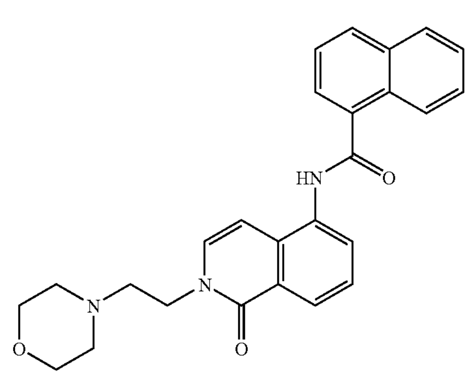 [SMILES: O=C(Nc1cccc2c(=O)n(CCN3CCOCC3)ccc12)c1cccc2ccccc12] | 427.50 | 428.27 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1411 | 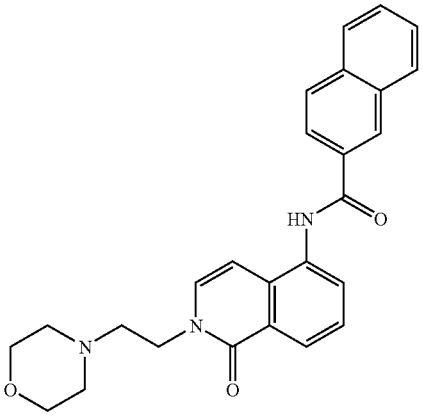 [SMILES: O=C(Nc1cccc2c(=O)n(CCN3CCOCC3)ccc12)c1ccc2ccccc2c1] | 427.50 | 428.38 | * |
| 1412 | 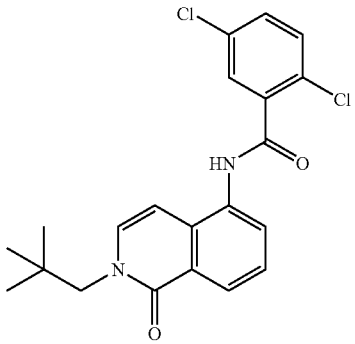 [SMILES: CC(C)(C)Cn1ccc2c(NC(=O)c3cc(Cl)ccc3Cl)cccc2c1=O] | 403.31 | 403.26 | * |
| 1413 | 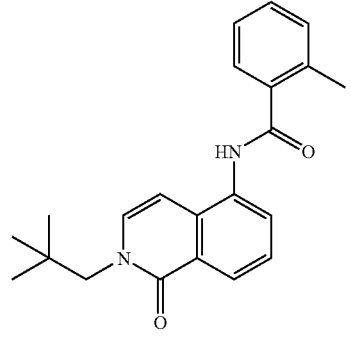 [SMILES: Cc1ccccc1C(=O)Nc1cccc2c(=O)n(CC(C)(C)C)ccc12] | 348.44 | 349.35 | * |
| 1414 | 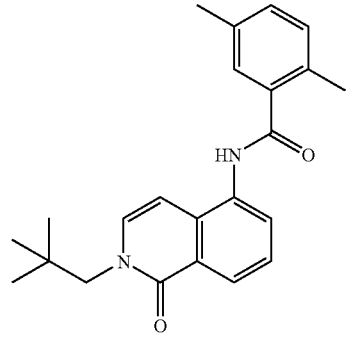 [SMILES: Cc1ccc(C)c(C(=O)Nc2cccc3c(=O)n(CC(C)(C)C)ccc23)c1] | 362.47 | 363.38 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1415 | 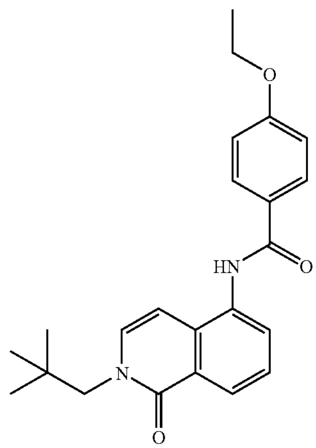 [SMILES: CCOc1ccc(C(=O)Nc2cccc3c(=O)n(CC(C)(C)C)ccc23)cc1] | 378.47 | 379.45 | * |
| 1416 | 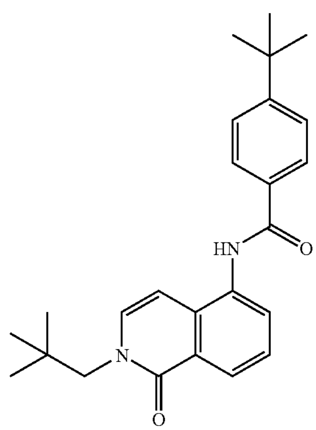 [SMILES: CC(C)(C)Cn1ccc2c(NC(=O)c3ccc(C(C)(C)C)cc3)cccc2c1=O] | 390.52 | 391.42 | * |
| 1417 | 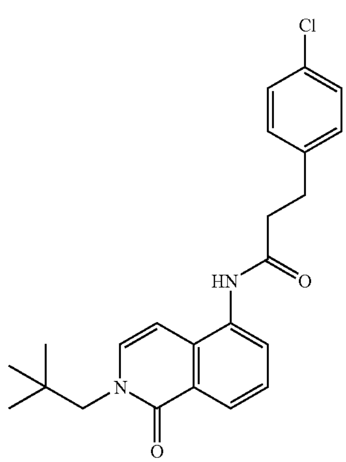 [SMILES: CC(C)(C)Cn1ccc2c(NC(=O)CCc3ccc(Cl)cc3)cccc2c1=O] | 396.92 | 397.29 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1418 | 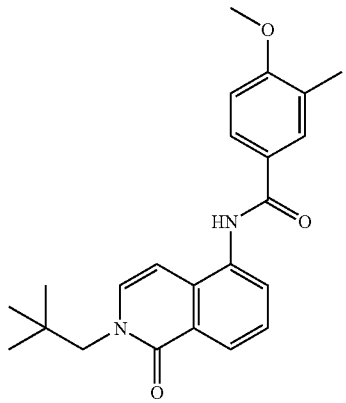 [SMILES: COc1ccc(C(=O)Nc2cccc3c(=O)n(CC(C)(C)C)ccc23)cc1C] | 378.47 | 379.46 | * |
| 1419 | 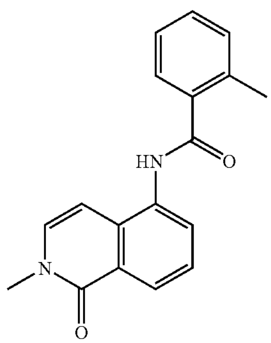 | 292.34 | 293.28 | * |
| 1420 | 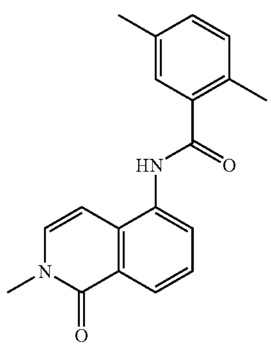 | 306.36 | 307.32 | * |
| 1421 | 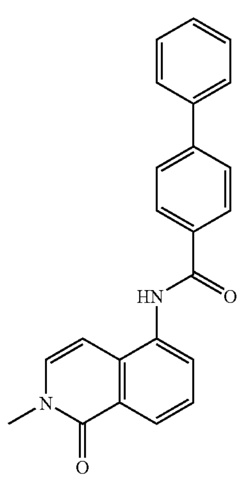 [SMILES: Cn1ccc2c(NC(=O)c3ccc(-c4ccccc4)cc3)cccc2c1=O] | 354.41 | 355.41 | |

TABLE 1-continued

IL-1β % Inhibition of Exemplary Compounds

| ID | Structure | MW | MS (obs) | IL-1β % Inhib. @ 0.3 μM |
|---|---|---|---|---|
| 1422 | 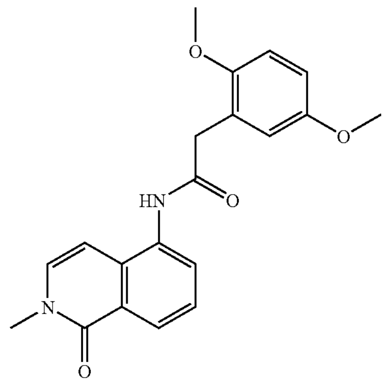 | 352.39 | 353.34 | * |
| 1423 | 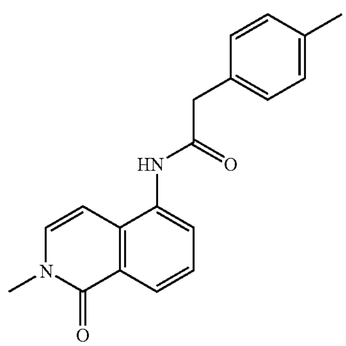 | 306.36 | 307.32 | * |
| 1424 | 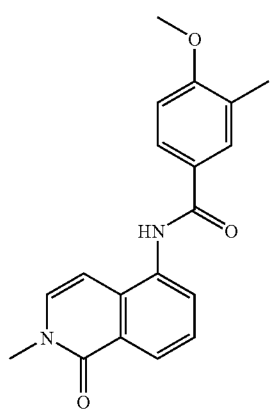 | 322.36 | 323.46 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1425 | 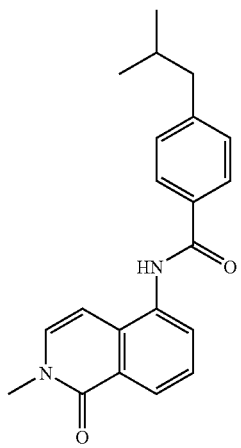 [SMILES: CC(C)Cc1ccc(C(=O)Nc2cccc3c(=O)n(C)ccc23)cc1] | 334.42 | 335.49 | * |
| 1426 | 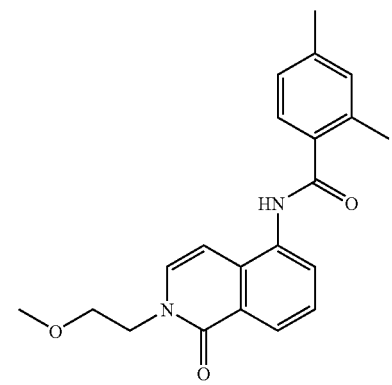 | 350.42 | 351.47 | * |
| 1427 | 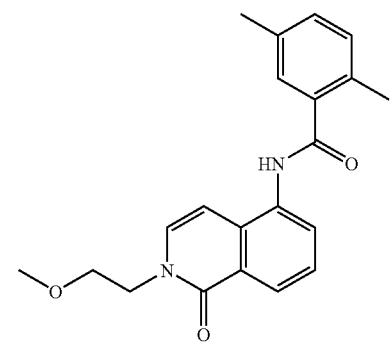 | 350.42 | 351.47 | ** |
| 1428 | 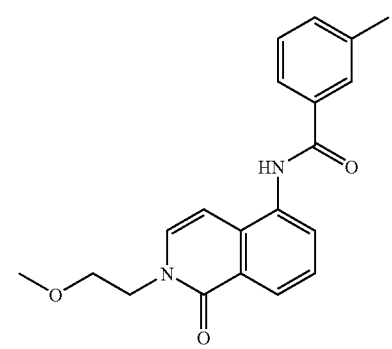 | 336.39 | 337.39 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1429 | 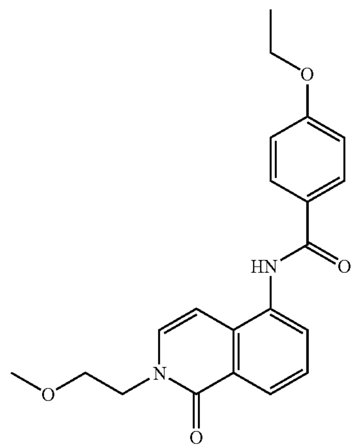 [SMILES: CCOc1ccc(C(=O)Nc2cccc3c(=O)n(CCOC)ccc23)cc1] | 366.41 | 367.33 | * |
| 1430 | 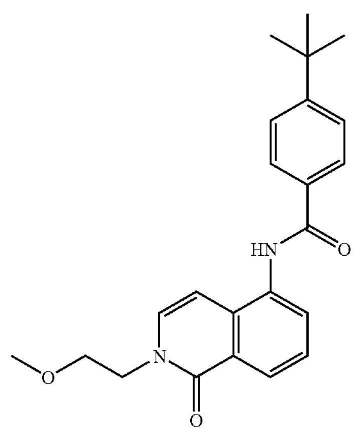 [SMILES: COCCn1ccc2c(NC(=O)c3ccc(C(C)(C)C)cc3)cccc2c1=O] | 378.47 | 379.45 | * |
| 1431 | 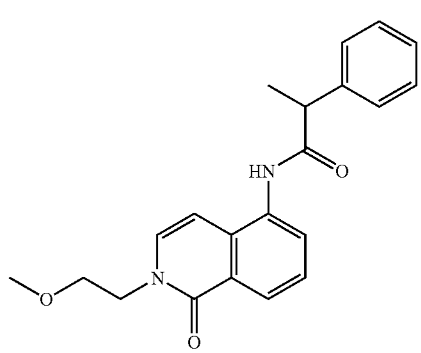 [SMILES: COCCn1ccc2c(NC(=O)C(C)c3ccccc3)cccc2c1=O] | 350.42 | 351.47 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1432 | 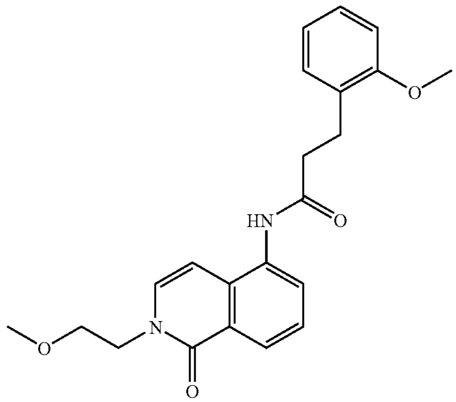 | 380.44 | 381.46 | * |
| 1433 | 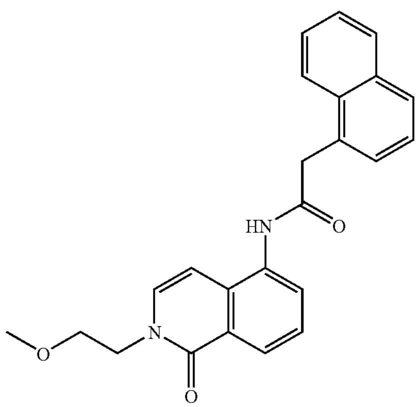 [SMILES: COCCn1ccc2c(NC(=O)Cc3cccc4ccccc34)cccc2c1=O] | 386.45 | 387.26 | * |
| 1434 | 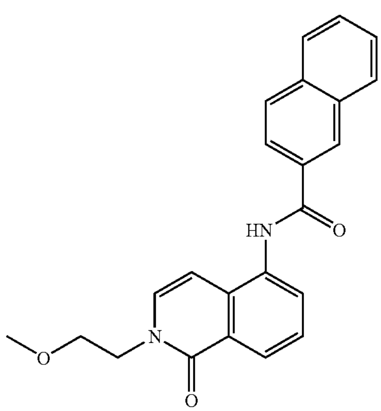 [SMILES: COCCn1ccc2c(NC(=O)c3ccc4ccccc4c3)cccc2c1=O] | 372.42 | 373.29 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1435 | 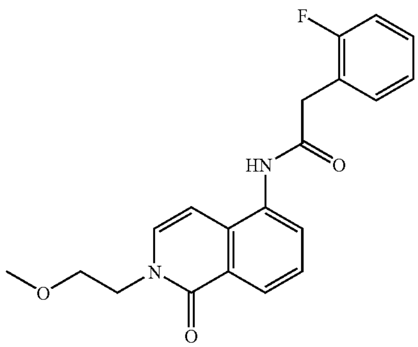 [SMILES: COCCn1ccc2c(NC(=O)Cc3ccccc3F)cccc2c1=O] | 354.38 | 355.19 | * |
| 1436 | 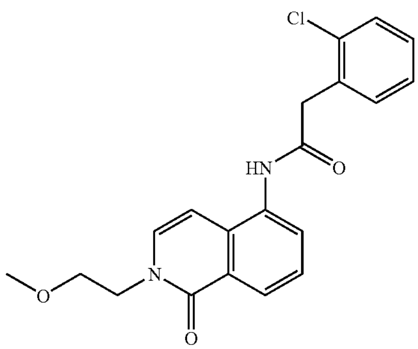 [SMILES: COCCn1ccc2c(NC(=O)Cc3ccccc3Cl)cccc2c1=O] | 370.83 | 371.12 | * |
| 1437 | 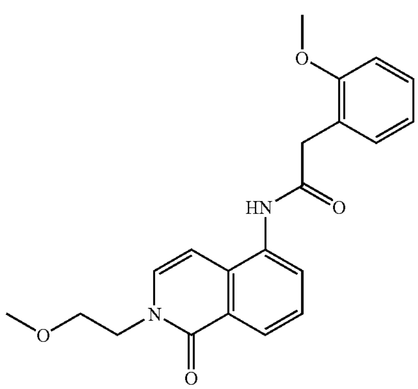 [SMILES: COCCn1ccc2c(NC(=O)Cc3ccccc3OC)cccc2c1=O] | 366.41 | 367.35 | * |
| 1438 | 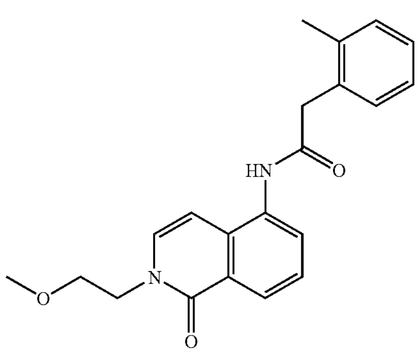 [SMILES: COCCn1ccc2c(NC(=O)Cc3ccccc3C)cccc2c1=O] | 350.42 | 352.38 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1439 | 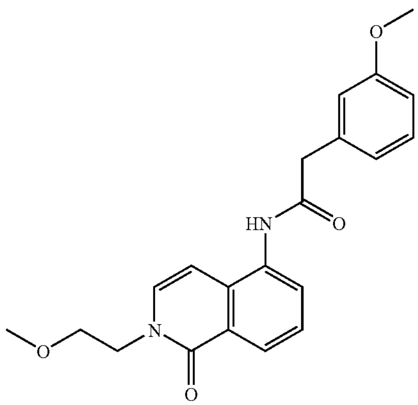 | 366.41 | 367.34 | * |
| 1440 | 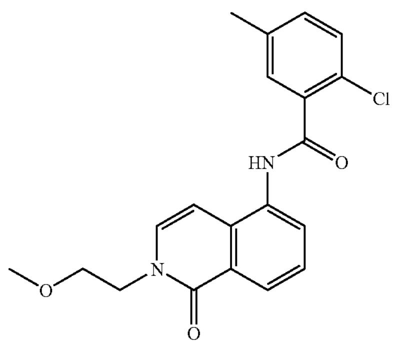 [SMILES: COCCn1ccc2c(NC(=O)c3cc(C)ccc3Cl)cccc2c1=O] | 370.83 | 371.10 | * |
| 1441 | 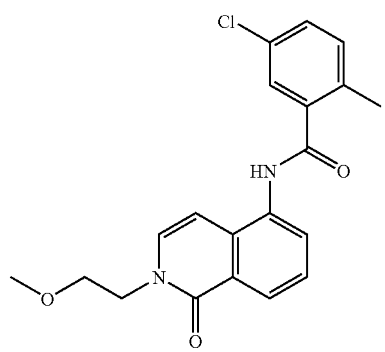 | 370.83 | 371.06 | * |
| 1442 | 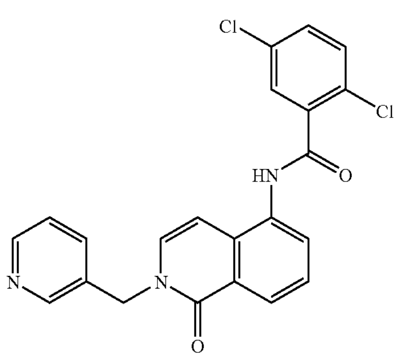 [SMILES: O=C(Nc1cccc2c(=O)n(Cc3cccnc3)ccc12)c1cc(Cl)ccc1Cl] | 424.29 | 424.22 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1443 | 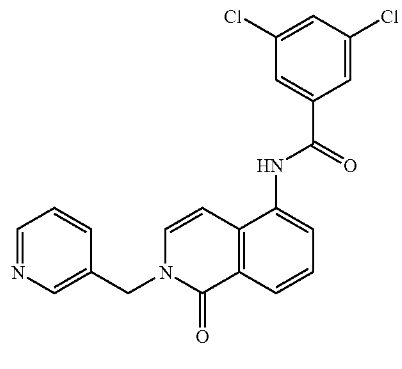 [SMILES: O=C(Nc1cccc2c(=O)n(Cc3cccnc3)ccc12)c1cc(Cl)cc(Cl)c1] | 424.29 | 424.20 | * |
| 1444 | 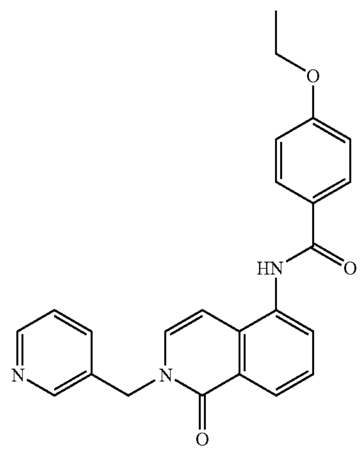 [SMILES: CCOc1ccc(C(=O)Nc2cccc3c(=O)n(Cc4cccnc4)ccc23)cc1] | 399.45 | 399.33 | * |
| 1445 | 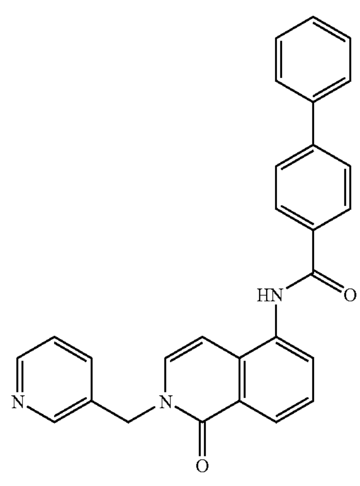 [SMILES: O=C(Nc1cccc2c(=O)n(Cc3cccnc3)ccc12)c1ccc(-c2ccccc2)cc1] | 431.49 | 432.50 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1446 | 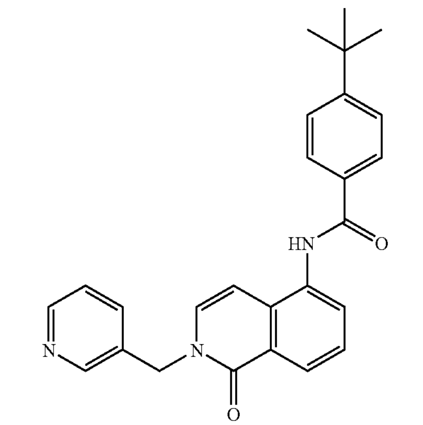 [SMILES: CC(C)(C)c1ccc(C(=O)Nc2cccc3c(=O)n(Cc4cccnc4)ccc23)cc1] | 411.50 | 412.56 | * |
| 1447 | 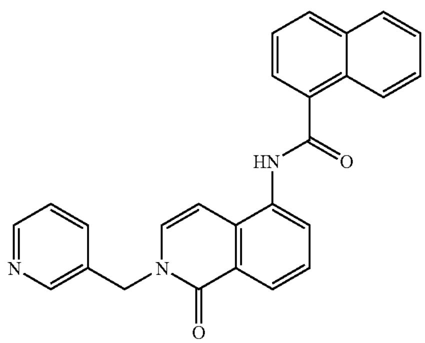 [SMILES: O=C(Nc1cccc2c(=O)n(Cc3cccnc3)ccc12)c1cccc2ccccc12] | 405.46 | 406.59 | * |
| 1448 | 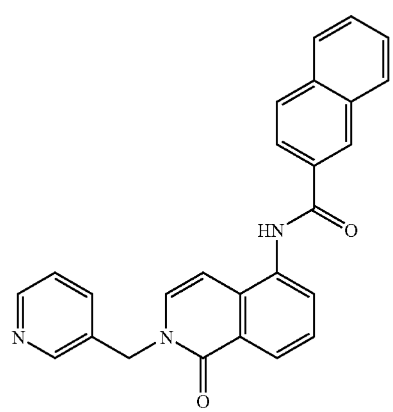 [SMILES: O=C(Nc1cccc2c(=O)n(Cc3cccnc3)ccc12)c1ccc2ccccc2c1] | 405.46 | 406.42 | * |
| 1449 | 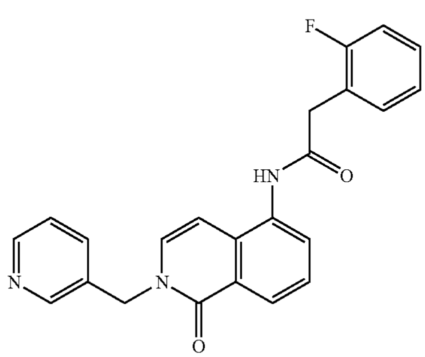 [SMILES: O=C(Cc1ccccc1F)Nc1cccc2c(=O)n(Cc3cccnc3)ccc12] | 387.41 | 388.25 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1450 | 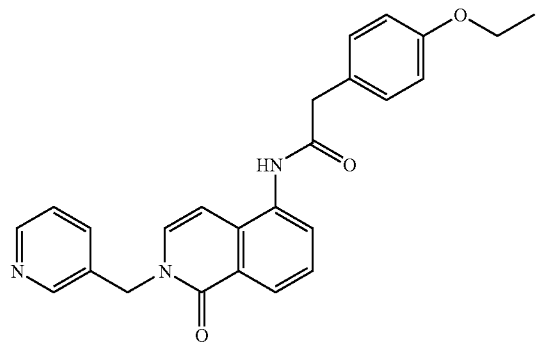 [SMILES: CCOc1ccc(CC(=O)Nc2cccc3c(=O)n(Cc4cccnc4)ccc23)cc1] | 413.47 | 414.34 | * |
| 1451 | 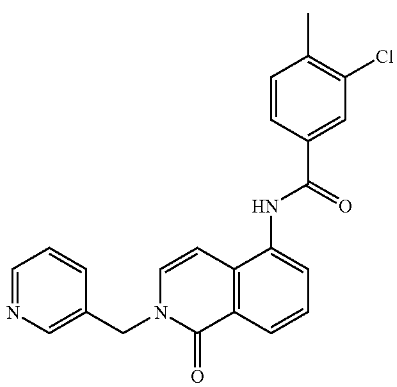 [SMILES: Cc1ccc(C(=O)Nc2cccc3c(=O)n(Cc4cccnc4)ccc23)cc1Cl] | 403.87 | 404.35 | * |
| 1452 | 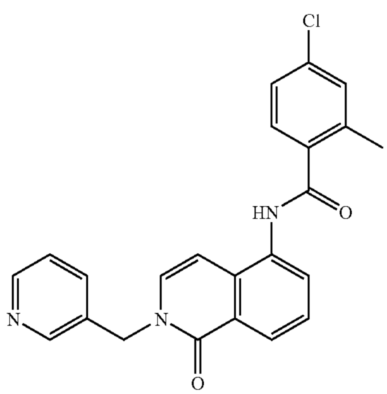 [SMILES: Cc1cc(Cl)ccc1C(=O)Nc1cccc2c(=O)n(Cc3cccnc3)ccc12] | 403.87 | 404.23 | * |
| 1453 | 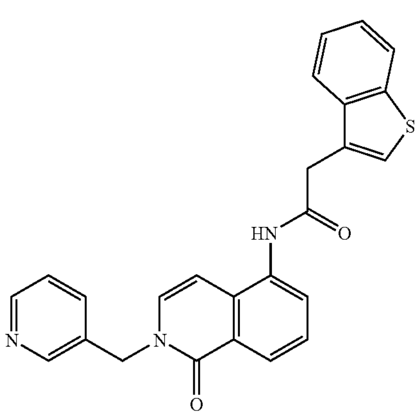 [SMILES: O=C(Cc1csc2ccccc12)Nc1cccc2c(=O)n(Cc3cccnc3)ccc12] | 425.51 | 426.18 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1454 | 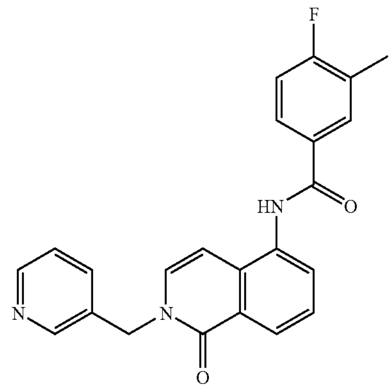 [SMILES: Cc1cc(C(=O)Nc2cccc3c(=O)n(Cc4cccnc4)ccc23)ccc1F] | 387.41 | 388.28 | * |
| 1455 | 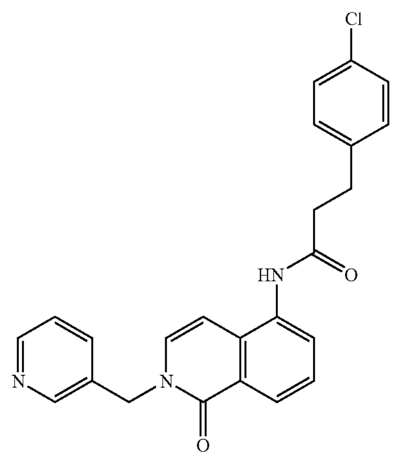 [SMILES: O=C(CCc1ccc(Cl)cc1)Nc1cccc2c(=O)n(Cc3cccnc3)ccc12] | 417.89 | 418.39 | * |
| 1456 | 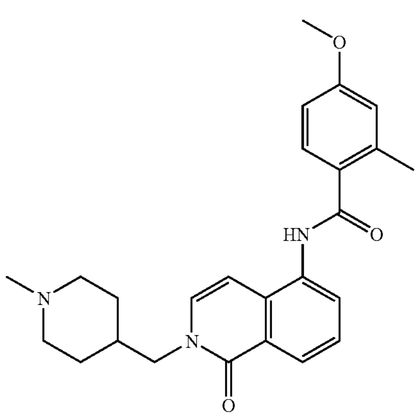 | 419.52 | 420.47 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1457 | 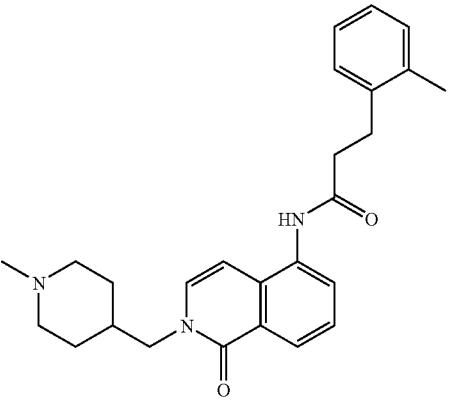 | 417.55 | 418.50 | * |
| 1458 | 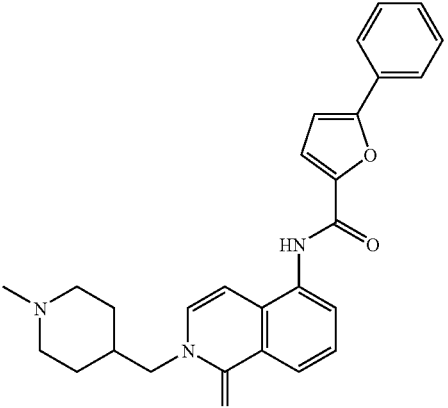 | 441.53 | 442.37 | * |
| 1459 | 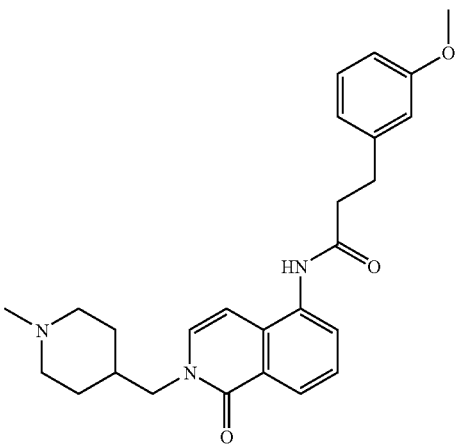 | 433.55 | 434.43 | ** |

TABLE 1-continued
IL-1β % Inhibition of Exemplary Compounds
| ID | Structure | MW | MS (obs) | IL-1β % Inhib. @ 0.3 µM |
|---|---|---|---|---|
| 1460 | 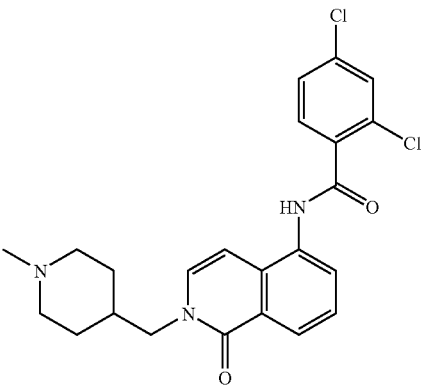 [SMILES: CN1CCC(Cn2ccc3c(NC(=O)c4ccc(Cl)cc4Cl)cccc3c2=O)CC1] | 444.36 | 444.35 | * |
| 1461 | 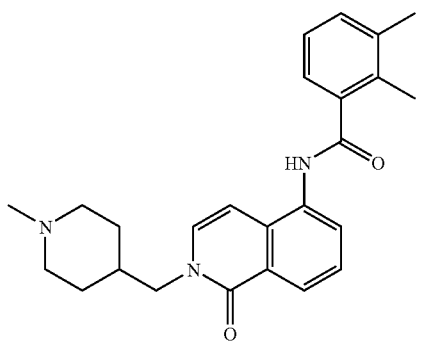 | 403.52 | 404.49 | * |
| 1462 | 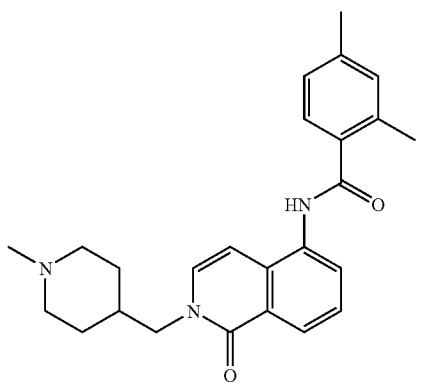 | 403.52 | 404.38 | * |
| 1463 | 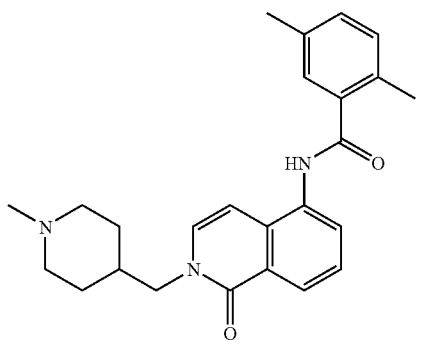 | 403.52 | 404.50 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1464 | 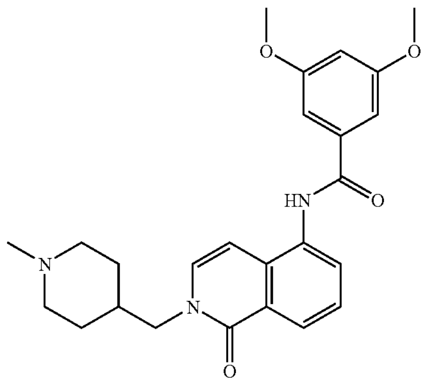 | 435.52 | 436.58 | * |
| 1465 | 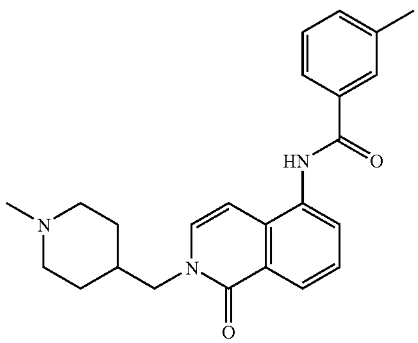 | 389.50 | 390.43 | * |
| 1466 | 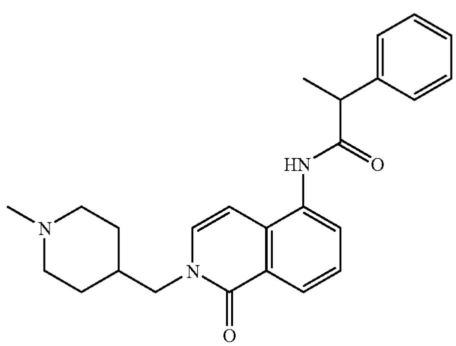 [SMILES: CC(C(=O)Nc1cccc2c(=O)n(CC3CCN(C)CC3)ccc12)c1ccccc1] | 403.52 | 404.37 | * |
| 1467 | 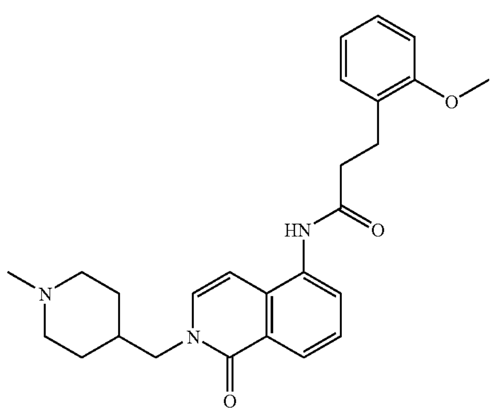 | 433.55 | 434.42 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1468 | 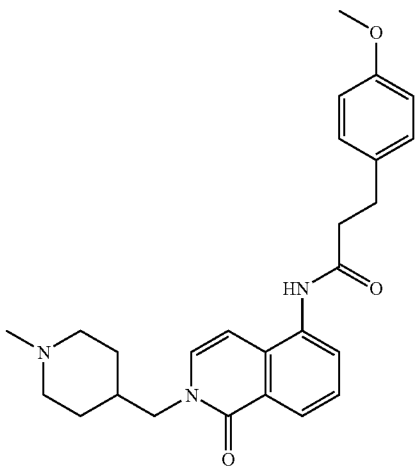 [SMILES: COc1ccc(CCC(=O)Nc2cccc3c(=O)n(CC4CCN(C)CC4)ccc23)cc1] | 433.55 | 434.65 | * |
| 1469 | 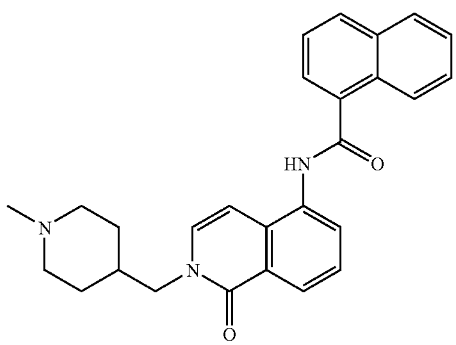 [SMILES: CN1CCC(Cn2ccc3c(NC(=O)c4cccc5ccccc45)cccc3c2=O)CC1] | 425.53 | 426.26 | * |
| 1470 | 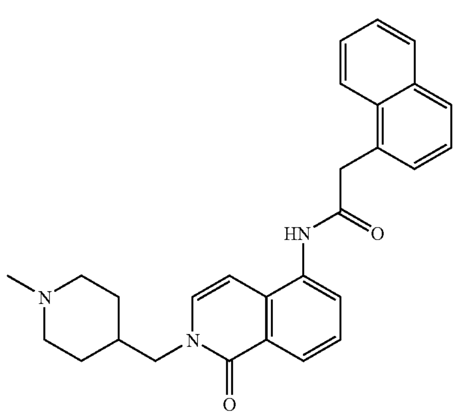 [SMILES: CN1CCC(Cn2ccc3c(NC(=O)Cc4cccc5ccccc45)cccc3c2=O)CC1] | 439.56 | 440.43 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1471 | 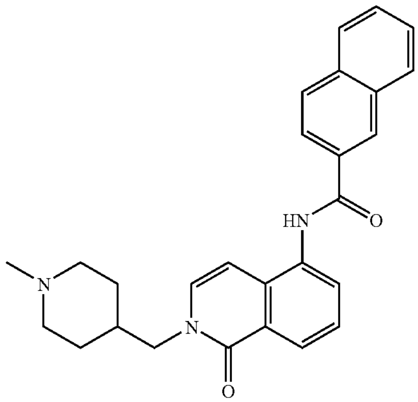 [SMILES: CN1CCC(Cn2ccc3c(NC(=O)c4ccc5ccccc5c4)cccc3c2=O)CC1] | 425.53 | 426.25 | * |
| 1472 | 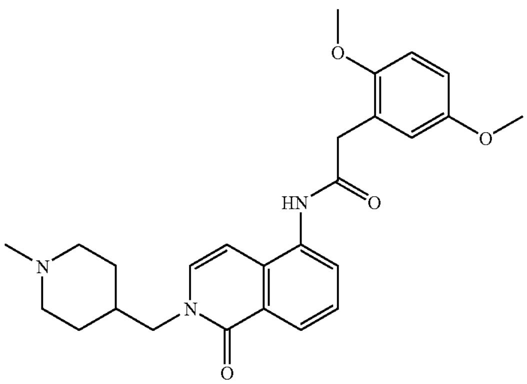 | 449.55 | 450.43 | * |
| 1473 | 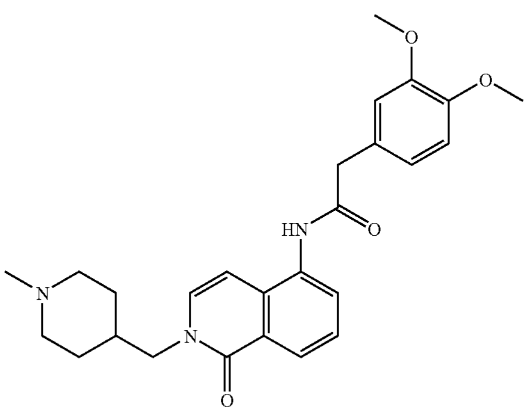 | 449.55 | 450.43 | * |
| 1474 | 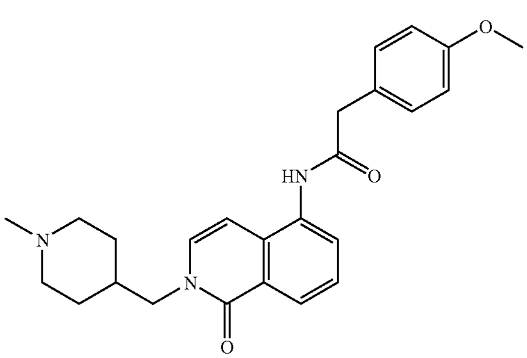 | 419.52 | 420.46 | * |

TABLE 1-continued
IL-1β % Inhibition of Exemplary Compounds
| ID | Structure | MW | MS (obs) | IL-1β % Inhib. @ 0.3 μM |
|----|-----------|------|----------|-------------------------|
| 1475 | 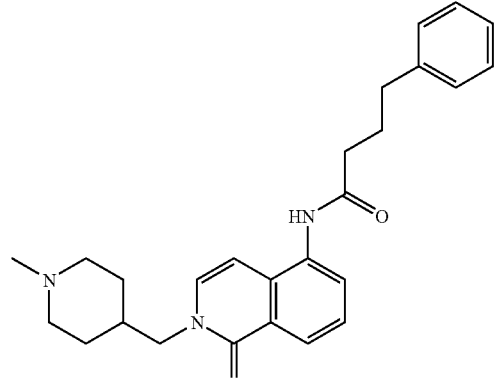 | 417.55 | 418.54 | * |
| 1476 | 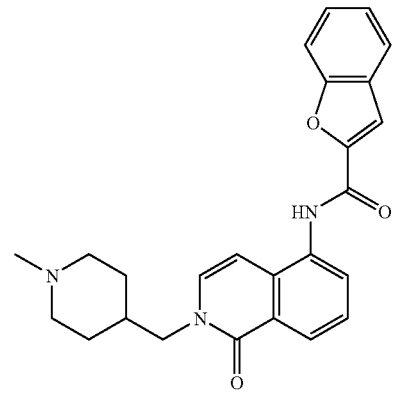 [SMILES: CN1CCC(Cn2ccc3c(NC(=O)c4cc5ccccc5o4)cccc3c2=O)CC1] | 415.49 | 416.40 | * |
| 1477 | 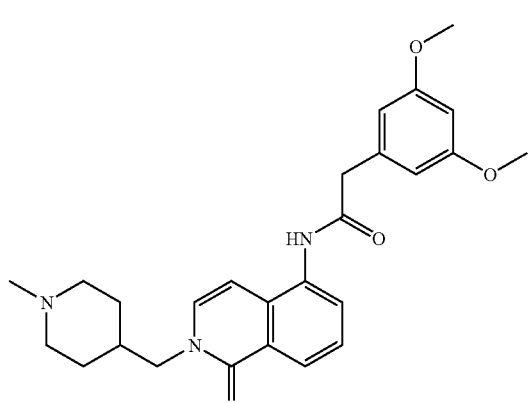 | 449.55 | 450.43 | * |

TABLE 1-continued
IL-1β % Inhibition of Exemplary Compounds
| ID | Structure | MW | MS (obs) | IL-1β % Inhib. @ 0.3 μM |
|----|-----------|-----|----------|-------------------------|
| 1478 | 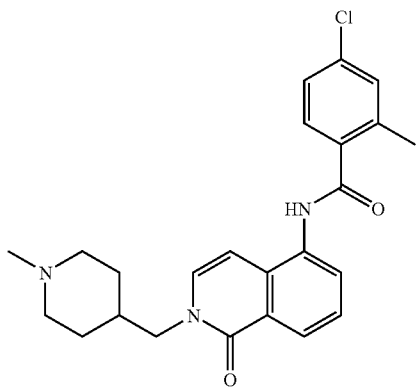 | 423.94 | 424.14 | * |
| 1479 | 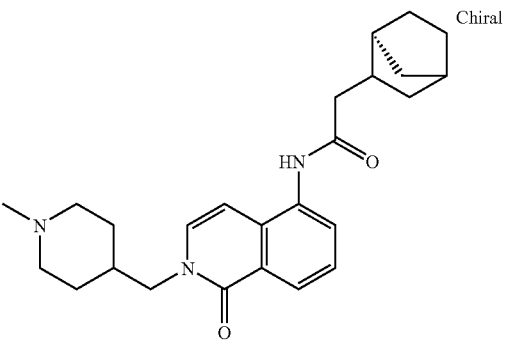 [SMILES: CN1CCC(Cn2ccc3c(NC(=O)CC4CC5CC[C@H]4C5)cccc3c2=O)CC1] Chiral | 407.55 | 408.46 | * |
| 1480 | 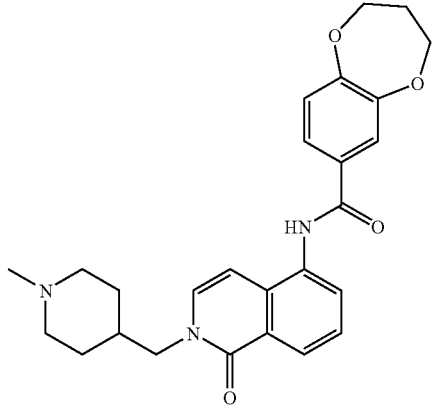 [SMILES: CN1CCC(Cn2ccc3c(NC(=O)c4ccc5c(c4)OCCCO5)cccc3c2=O)CC1] | 447.53 | 448.37 | * |
| 1481 | 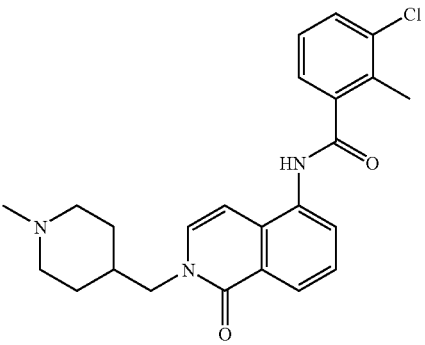 | 423.94 | 424.14 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1482 | 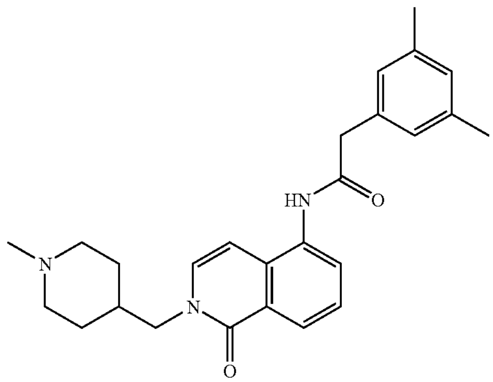 | 417.55 | 418.51 | ** |
| 1483 | 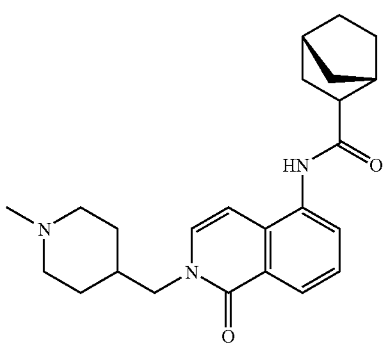 | 393.53 | 394.37 | ** |
| 1484 | 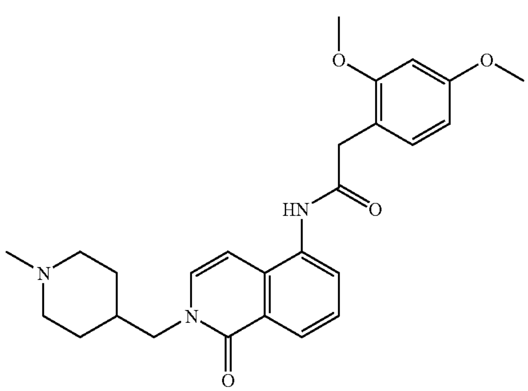 | 449.55 | 450.42 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1485 | 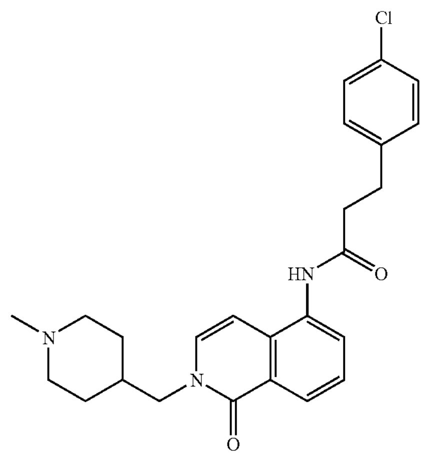 [SMILES: CN1CCC(Cn2ccc3c(NC(=O)CCc4ccc(Cl)cc4)cccc3c2=O)CC1] | 437.97 | 438.39 | * |
| 1486 | 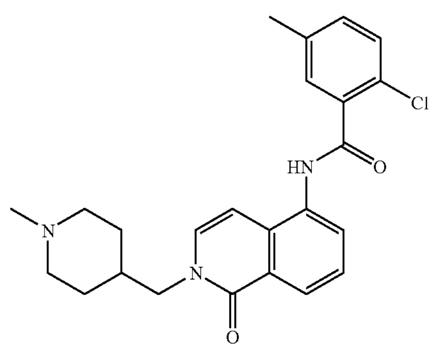 [SMILES: Cc1ccc(Cl)c(C(=O)Nc2cccc3c(=O)n(CC4CCN(C)CC4)ccc23)c1] | 423.94 | 424.15 | * |
| 1487 | 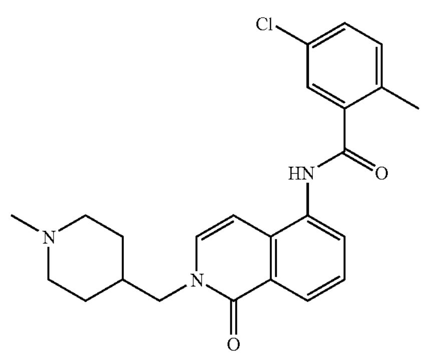 | 423.94 | 424.14 | * |
| 1488 | 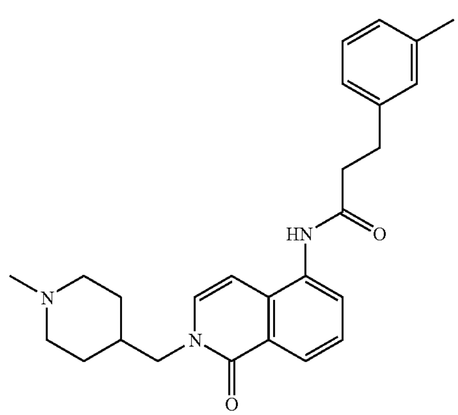 | 417.55 | 418.53 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1489 | 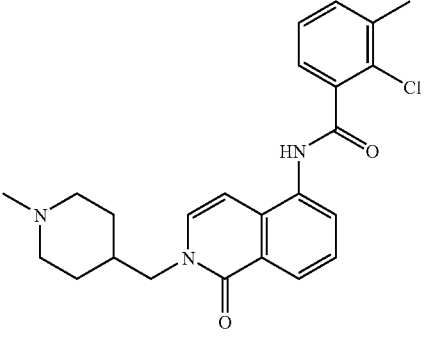 [SMILES: Cc1cccc(C(=O)Nc2cccc3c(=O)n(CC4CCN(C)CC4)ccc23)c1Cl] | 423.94 | 424.33 | * |
| 1490 | 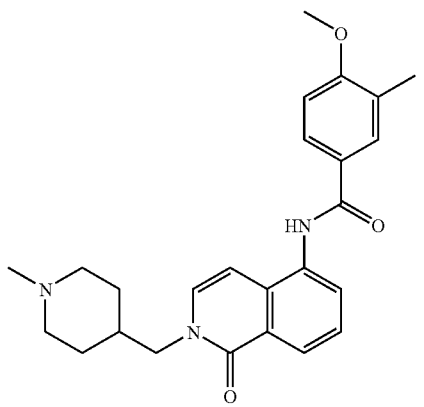 | 419.52 | 420.47 | * |
| 1491 | 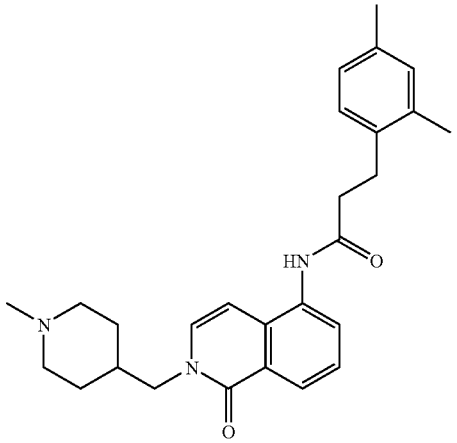 | 431.58 | 432.39 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1492 | 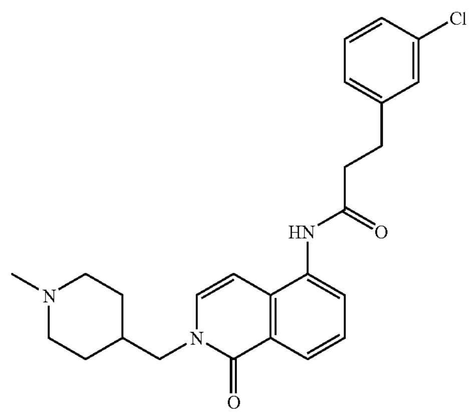 [SMILES: CN1CCC(Cn2ccc3c(NC(=O)CCc4cccc(Cl)c4)cccc3c2=O)CC1] | 437.97 | 438.60 | * |
| 1493 | 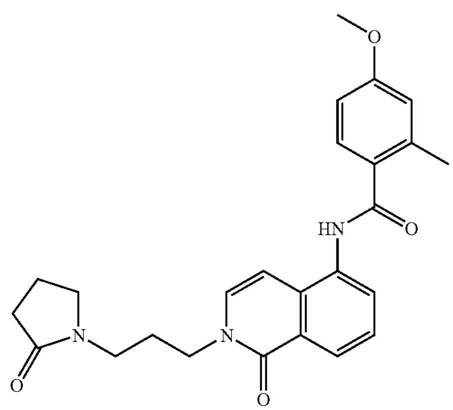 [SMILES: COc1ccc(C(=O)Nc2cccc3c(=O)n(CCCN4CCCC4=O)ccc23)c(C)c1] | 433.51 | 434.39 | * |
| 1494 | 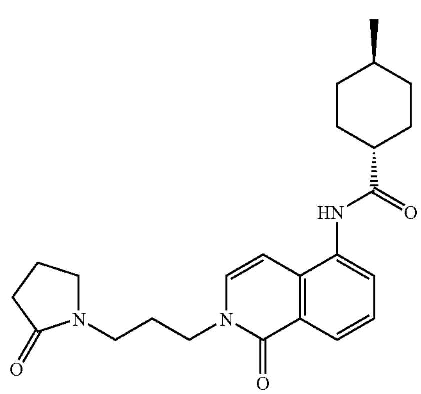 | 409.53 | 410.57 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1495 | 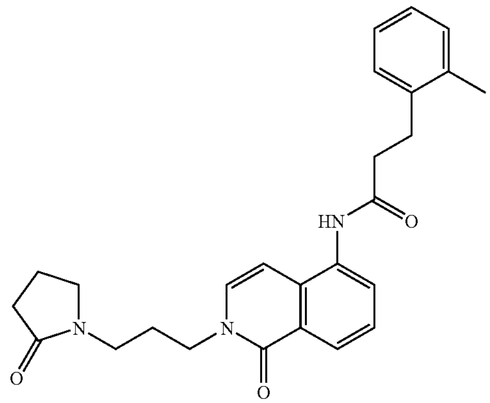 [SMILES: Cc1ccccc1CCC(=O)Nc1cccc2c(=O)n(CCCN3CCCC3=O)ccc12] | 431.53 | 432.36 | * |
| 1496 | 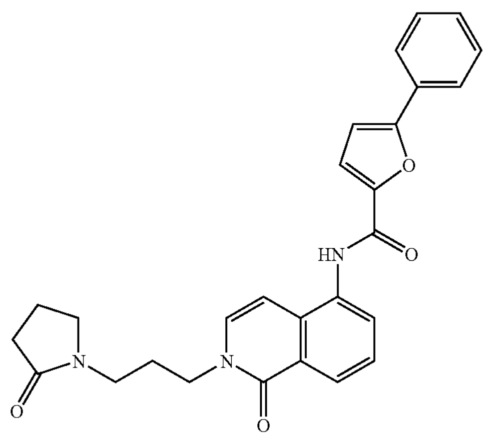 [SMILES: O=C(Nc1cccc2c(=O)n(CCCN3CCCC3=O)ccc12)c1ccc(-c2ccccc2)o1] | 455.51 | 456.17 | * |
| 1497 | 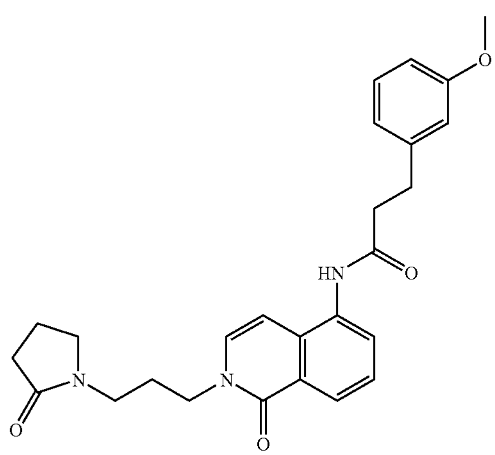 [SMILES: COc1cccc(CCC(=O)Nc2cccc3c(=O)n(CCCN4CCCC4=O)ccc23)c1] | 447.53 | 448.36 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1498 | 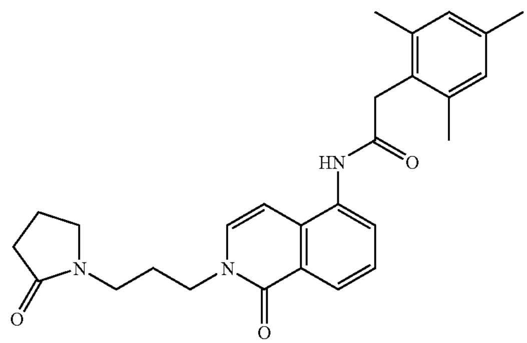 [SMILES: Cc1cc(C)c(CC(=O)Nc2cccc3c(=O)n(CCCN4CCCC4=O)ccc23)c(C)c1] | 445.56 | 446.54 | * |
| 1499 | 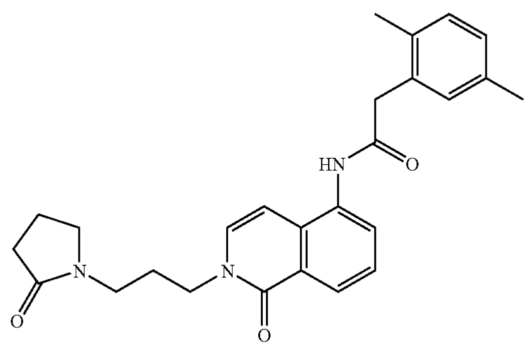 [SMILES: Cc1ccc(C)c(CC(=O)Nc2cccc3c(=O)n(CCCN4CCCC4=O)ccc23)c1] | 431.53 | 432.59 | * |
| 1500 | 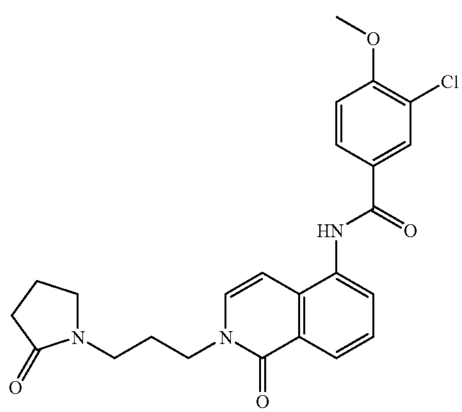 [SMILES: COc1ccc(C(=O)Nc2cccc3c(=O)n(CCCN4CCCC4=O)ccc23)cc1Cl] | 453.92 | 454.31 | * |
| 1501 | 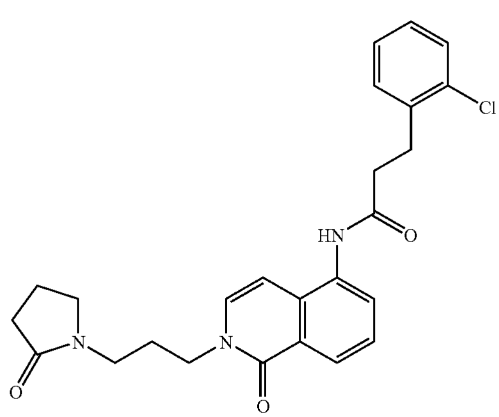 [SMILES: O=C(CCc1ccccc1Cl)Nc1cccc2c(=O)n(CCCN3CCCC3=O)ccc12] | 451.95 | 452.17 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1502 | 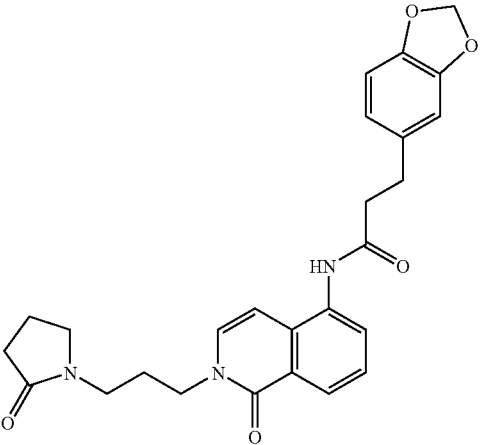 [SMILES: O=C(CCc1ccc2c(c1)OCO2)Nc1cccc2c(=O)n(CCCN3CCCC3=O)ccc12] | 461.52 | 462.54 | * |
| 1503 | 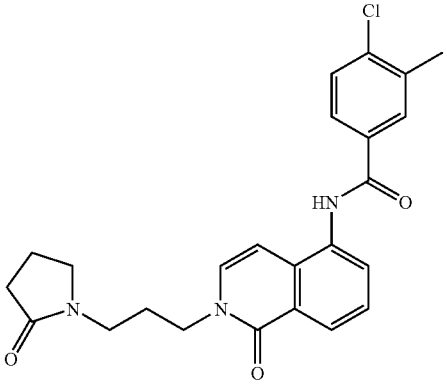 [SMILES: Cc1cc(C(=O)Nc2cccc3c(=O)n(CCCN4CCCC4=O)ccc23)ccc1Cl] | 437.92 | 438.55 | * |
| 1504 | 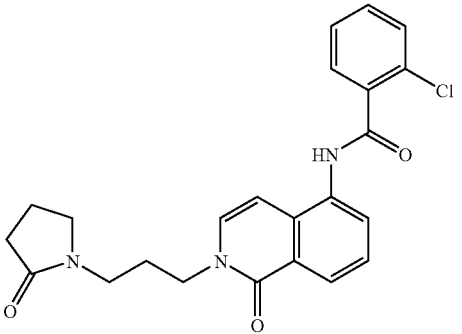 [SMILES: O=C(Nc1cccc2c(=O)n(CCCN3CCCC3=O)ccc12)c1ccccc1Cl] | 423.90 | 424.31 | *** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1505 | 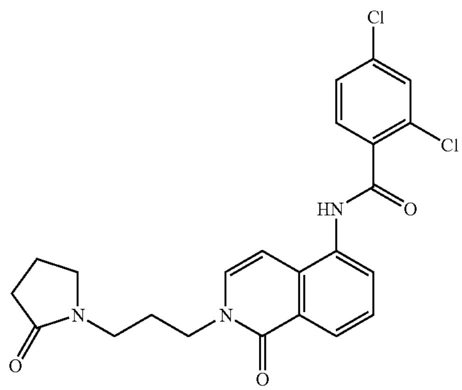 [SMILES: O=C(Nc1cccc2c(=O)n(CCCN3CCCC3=O)ccc12)c1ccc(Cl)cc1Cl] | 458.34 | 458.34 | ** |
| 1506 | 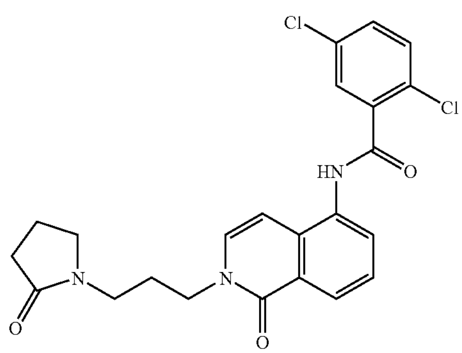 [SMILES: O=C(Nc1cccc2c(=O)n(CCCN3CCCC3=O)ccc12)c1cc(Cl)ccc1Cl] | 458.34 | 458.34 | ** |
| 1507 | 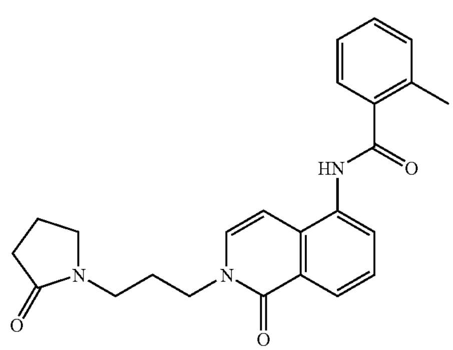 [SMILES: Cc1ccccc1C(=O)Nc1cccc2c(=O)n(CCCN3CCCC3=O)ccc12] | 403.48 | 404.46 | * |
| 1508 | 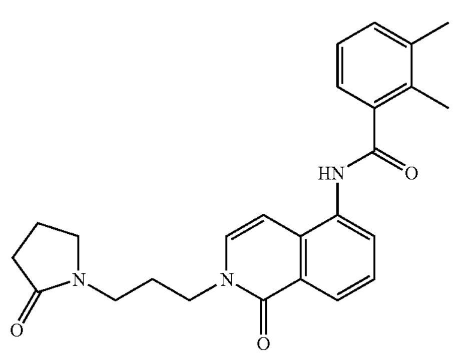 [SMILES: Cc1cccc(C(=O)Nc2cccc3c(=O)n(CCCN4CCCC4=O)ccc23)c1C] | 417.51 | 418.44 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1509 | 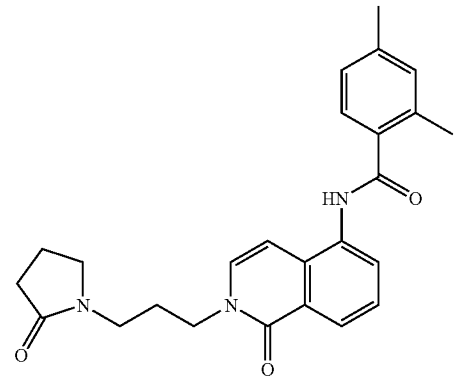 [SMILES: Cc1ccc(C(=O)Nc2cccc3c(=O)n(CCCN4CCCC4=O)ccc23)c(C)c1] | 417.51 | 418.46 | * |
| 1510 | 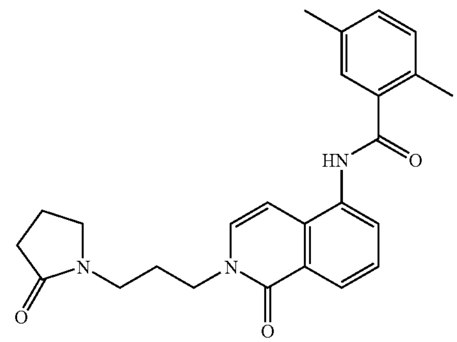 [SMILES: Cc1ccc(C)c(C(=O)Nc2cccc3c(=O)n(CCCN4CCCC4=O)ccc23)c1] | 417.51 | 418.43 | * |
| 1511 | 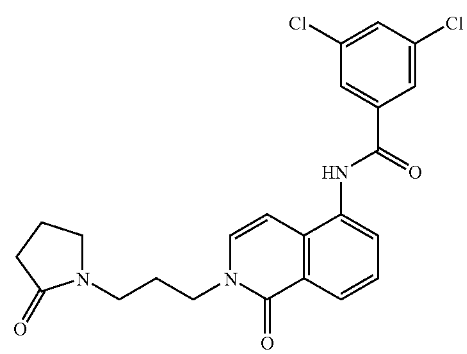 [SMILES: O=C(Nc1cccc2c(=O)n(CCCN3CCCC3=O)ccc12)c1cc(Cl)cc(Cl)c1] | 458.34 | 458.10 | * |
| 1512 | 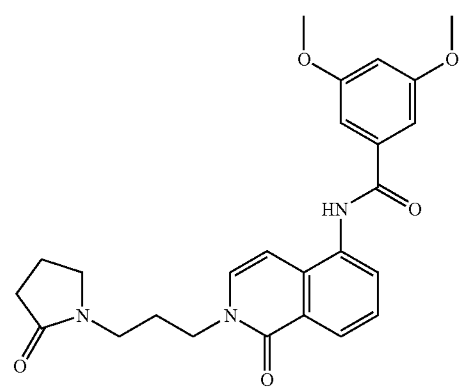 [SMILES: COc1cc(OC)cc(C(=O)Nc2cccc3c(=O)n(CCCN4CCCC4=O)ccc23)c1] | 449.50 | 450.27 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1513 | 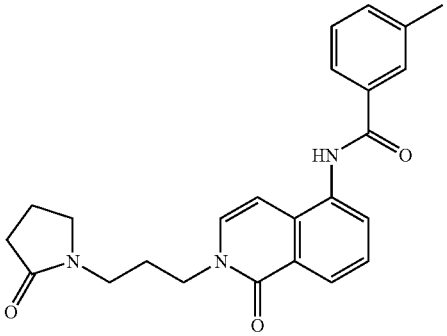 [SMILES: Cc1cccc(C(=O)Nc2cccc3c(=O)n(CCCN4CCCC4=O)ccc23)c1] | 403.48 | 404.35 | * |
| 1514 | 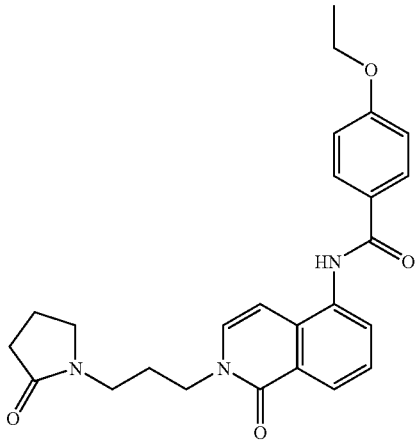 [SMILES: CCOc1ccc(C(=O)Nc2cccc3c(=O)n(CCCN4CCCC4=O)ccc23)cc1] | 433.51 | 434.39 | * |
| 1515 | 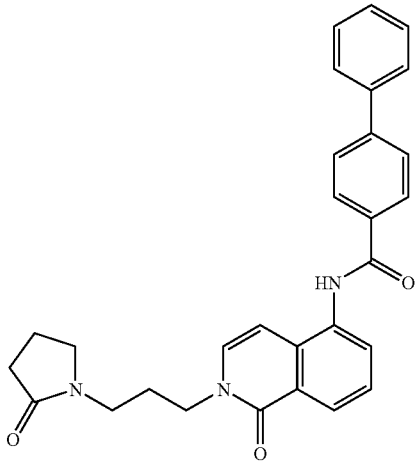 [SMILES: O=C(Nc1cccc2c(=O)n(CCCN3CCCC3=O)ccc12)c1ccc(-c2ccccc2)cc1] | 465.55 | 466.29 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1516 | 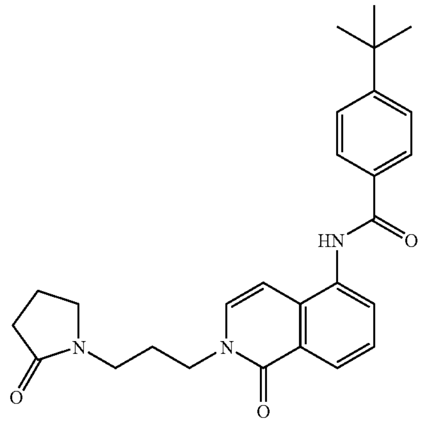 [SMILES: CC(C)(C)c1ccc(C(=O)Nc2cccc3c(=O)n(CCCN4CCCC4=O)ccc23)cc1] | 445.56 | 446.48 | * |
| 1517 | 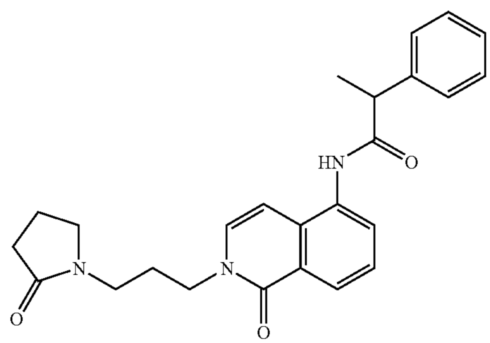 [SMILES: CC(C(=O)Nc1cccc2c(=O)n(CCCN3CCCC3=O)ccc12)c1ccccc1] | 417.51 | 418.49 | * |
| 1518 | 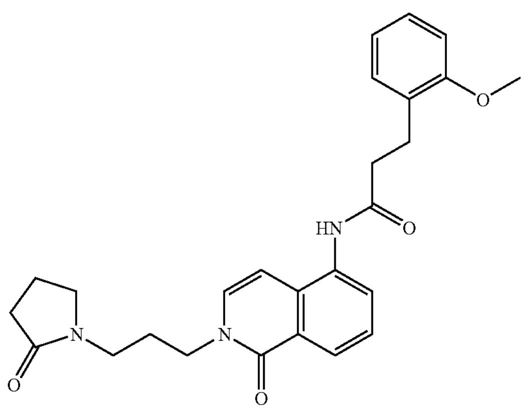 [SMILES: COc1ccccc1CCC(=O)Nc1cccc2c(=O)n(CCCN3CCCC3=O)ccc12] | 447.53 | 448.37 | * |
| 1519 | 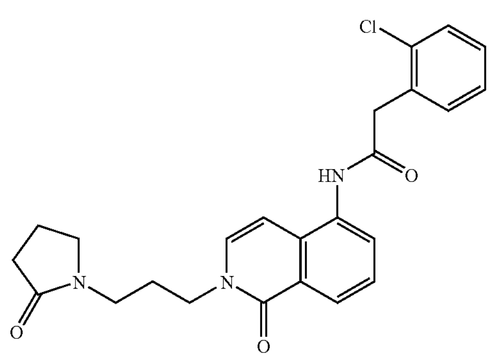 [SMILES: O=C(Cc1ccccc1Cl)Nc1cccc2c(=O)n(CCCN3CCCC3=O)ccc12] | 437.92 | 438.57 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1520 | 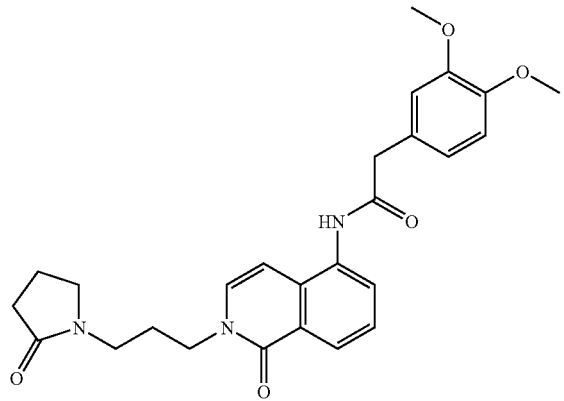 [SMILES: COc1ccc(CC(=O)Nc2cccc3c(=O)n(CCCN4CCCC4=O)ccc23)cc1OC] | 463.53 | 464.55 | * |
| 1521 | 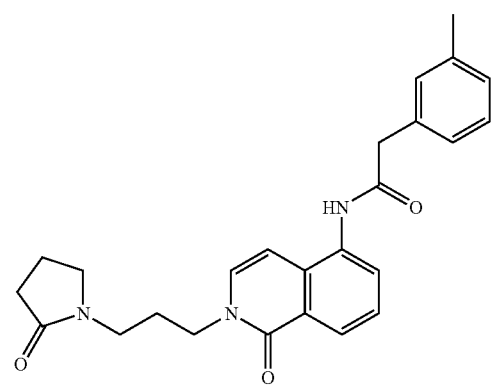 [SMILES: Cc1cccc(CC(=O)Nc2cccc3c(=O)n(CCCN4CCCC4=O)ccc23)c1] | 417.51 | 418.45 | * |
| 1522 | 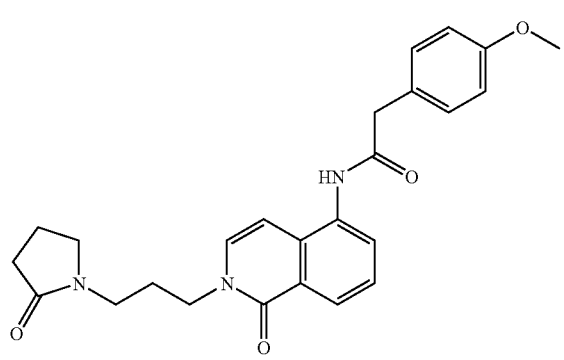 [SMILES: COc1ccc(CC(=O)Nc2cccc3c(=O)n(CCCN4CCCC4=O)ccc23)cc1] | 433.51 | 434.61 | * |
| 1523 | 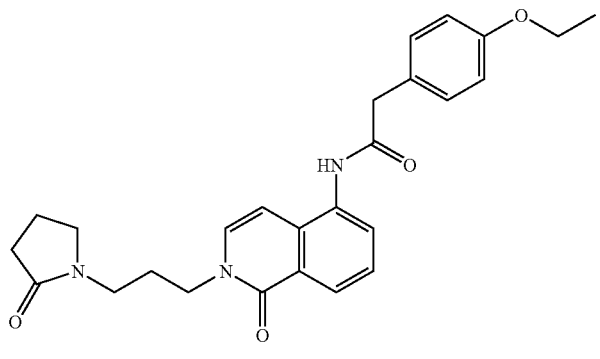 [SMILES: CCOc1ccc(CC(=O)Nc2cccc3c(=O)n(CCCN4CCCC4=O)ccc23)cc1] | 447.53 | 448.40 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1524 | 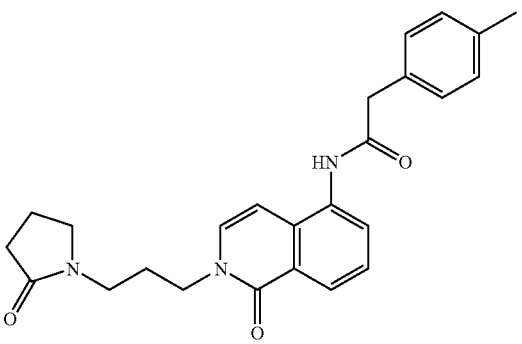 [SMILES: Cc1ccc(CC(=O)Nc2cccc3c(=O)n(CCCN4CCCC4=O)ccc23)cc1] | 417.51 | 418.47 | * |
| 1525 | 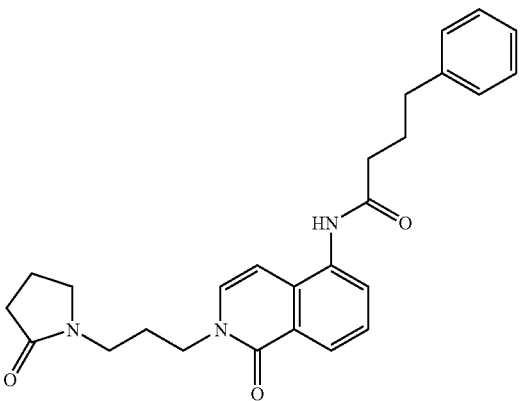 [SMILES: O=C(CCCc1ccccc1)Nc1cccc2c(=O)n(CCCN3CCCC3=O)ccc12] | 431.53 | 432.57 | * |
| 1526 | 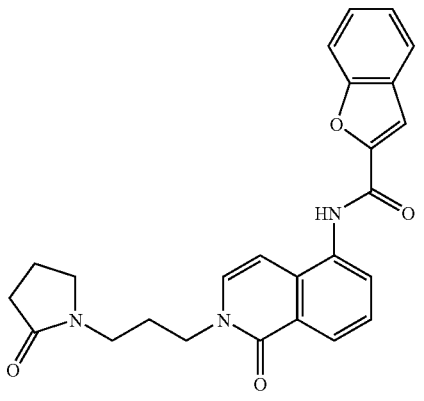 [SMILES: O=C(Nc1cccc2c(=O)n(CCCN3CCCC3=O)ccc12)c1cc2ccccc2o1] | 429.47 | 430.35 | * |
| 1527 | 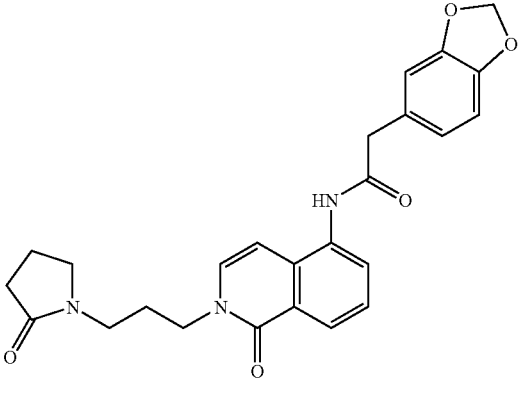 [SMILES: O=C(Cc1ccc2c(c1)OCO2)Nc1cccc2c(=O)n(CCCN3CCCC3=O)ccc12] | 447.49 | 448.38 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1528 | 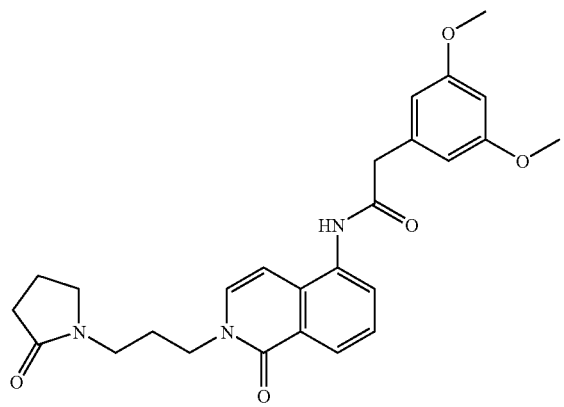 [SMILES: COc1cc(CC(=O)Nc2cccc3c(=O)n(CCCN4CCCC4=O)ccc23)cc(OC)c1] | 463.53 | 464.55 | * |
| 1529 | 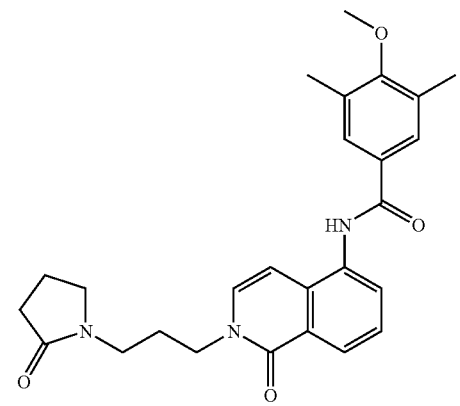 [SMILES: COc1c(C)cc(C(=O)Nc2cccc3c(=O)n(CCCN4CCCC4=O)ccc23)cc1C] | 447.53 | 448.40 | * |
| 1530 | 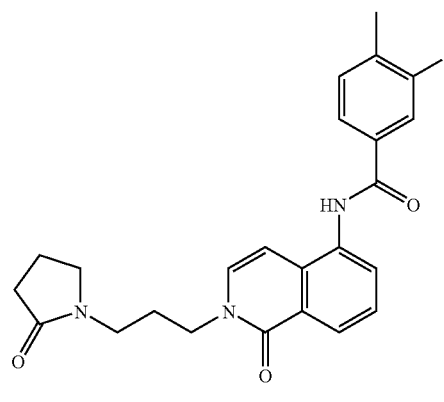 | 437.92 | 438.54 | ** |
| 1531 | 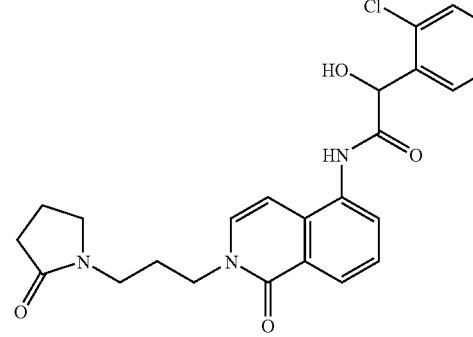 | 453.92 | 454.22 | ** |

TABLE 1-continued
IL-1β % Inhibition of Exemplary Compounds
| ID | Structure | MW | MS (obs) | IL-1β % Inhib. @ 0.3 μM |
|---|---|---|---|---|
| 1532 | 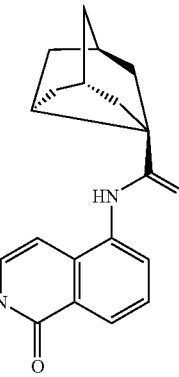 Chiral | 433.55 | 434.63 | * |
| 1533 | 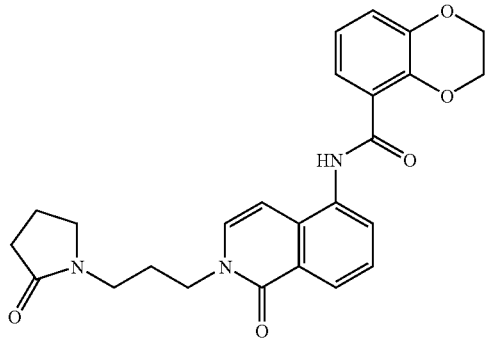 [SMILES: O=C(Nc1cccc2c(=O)n(CCCN3CCCC3=O)ccc12)c1cccc2c1OCCO2] | 447.49 | 448.37 | ** |
| 1534 | 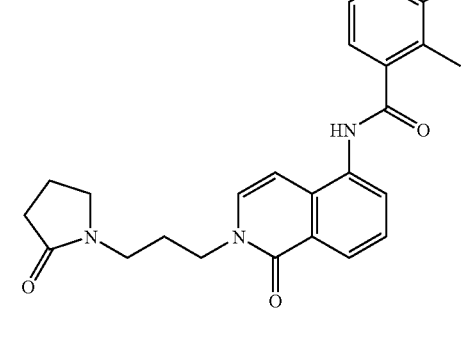 | 437.92 | 438.53 | *** |
| 1535 | 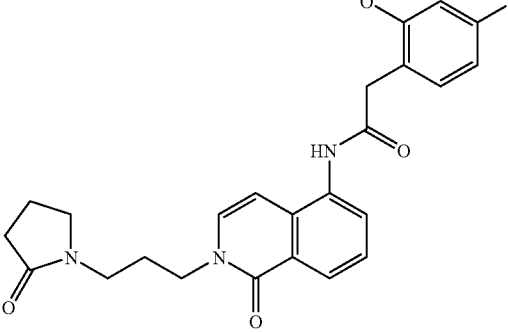 | 463.53 | 464.57 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1536 | 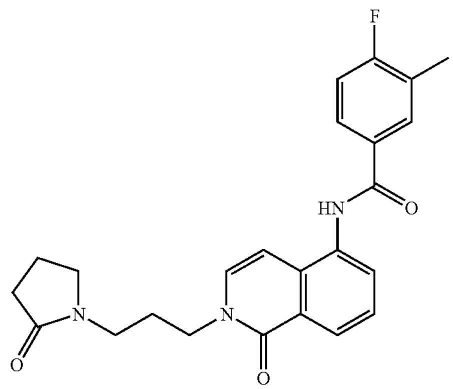 | 421.47 | 422.32 | * |
| 1537 | 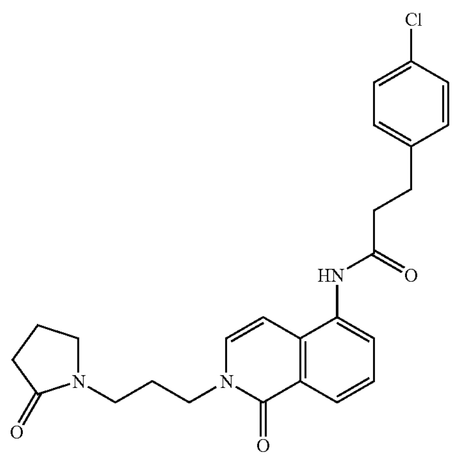 [SMILES: O=C(CCc1ccc(Cl)cc1)Nc1cccc2c(=O)n(CCCN3CCCC3=O)ccc12] | 451.95 | 452.20 | ** |
| 1538 | 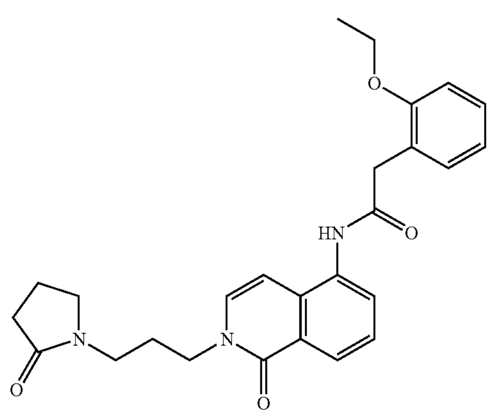 [SMILES: CCOc1ccccc1CC(=O)Nc1cccc2c(=O)n(CCCN3CCCC3=O)ccc12] | 447.53 | 448.41 | ** |

TABLE 1-continued

IL-1β % Inhibition of Exemplary Compounds

| ID | Structure | MW | MS (obs) | IL-1β % Inhib. @ 0.3 μM |
|----|-----------|------|----------|------------------------|
| 1539 | 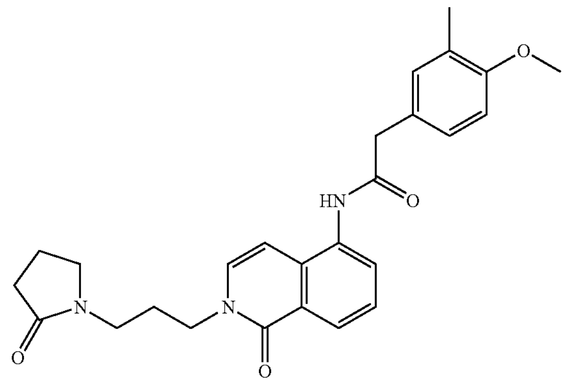 [SMILES: COc1ccc(CC(=O)Nc2cccc3c(=O)n(CCCN4CCCC4=O)ccc23)cc1C] | 447.53 | 448.41 | * |
| 1540 | 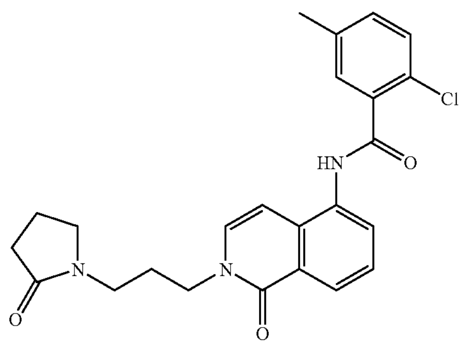 [SMILES: Cc1ccc(Cl)c(C(=O)Nc2cccc3c(=O)n(CCCN4CCCC4=O)ccc23)c1] | 437.92 | 438.57 | * |
| 1541 | 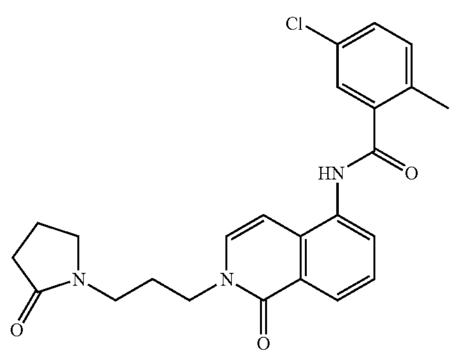 [SMILES: Cc1ccc(Cl)cc1C(=O)Nc1cccc2c(=O)n(CCCN3CCCC3=O)ccc12] | 437.92 | 438.60 | * |
| 1542 | 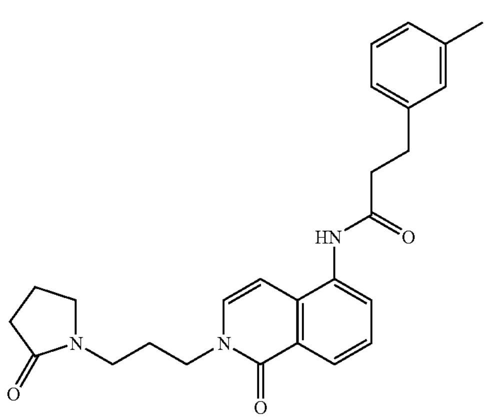 [SMILES: Cc1cccc(CCC(=O)Nc2cccc3c(=O)n(CCCN4CCCC4=O)ccc23)c1] | 431.53 | 432.59 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1543 | 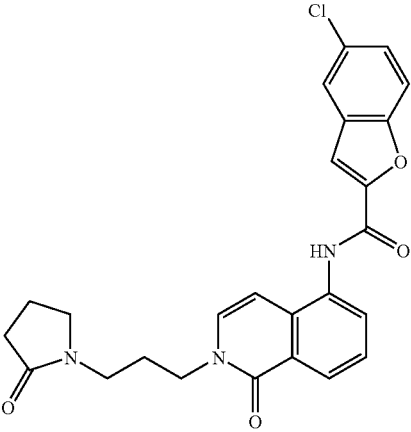 [SMILES: O=C(Nc1cccc2c(=O)n(CCCN3CCCC3=O)ccc12)c1cc2cc(Cl)ccc2o1] | 463.92 | 464.48 | * |
| 1544 | 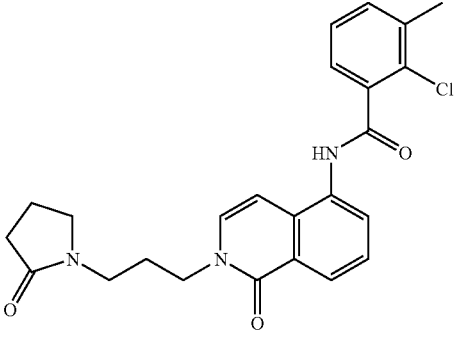 [SMILES: Cc1cccc(C(=O)Nc2cccc3c(=O)n(CCCN4CCCC4=O)ccc23)c1Cl] | 437.92 | 438.58 | * |
| 1545 | 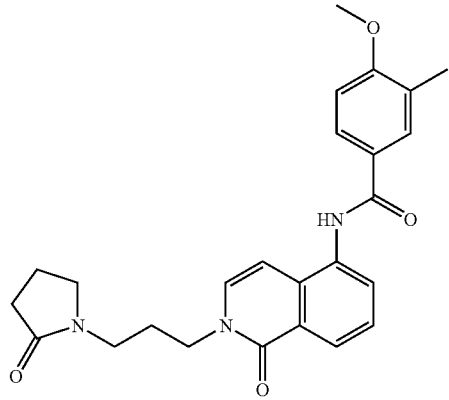 [SMILES: COc1ccc(C(=O)Nc2cccc3c(=O)n(CCCN4CCCC4=O)ccc23)cc1C] | 433.51 | 434.60 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1546 | 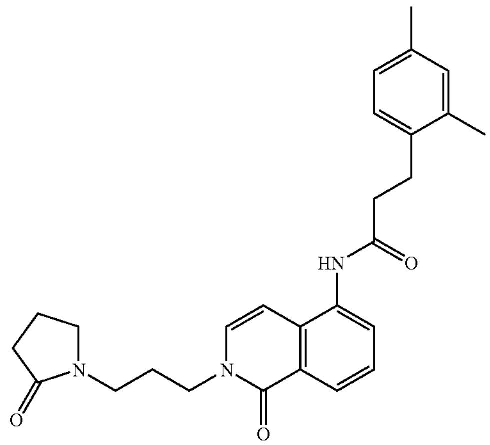 [SMILES: Cc1ccc(CCC(=O)Nc2cccc3c(=O)n(CCCN4CCCC4=O)ccc23)c(C)c1] | 445.56 | 446.56 | * |
| 1547 | 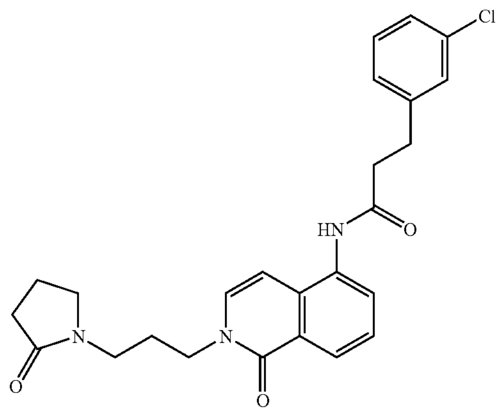 [SMILES: O=C(CCc1cccc(Cl)c1)Nc1cccc2c(=O)n(CCCN3CCCC3=O)ccc12] | 451.95 | 452.21 | * |
| 1548 | 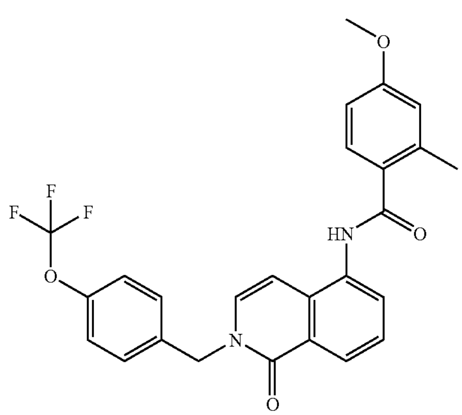 [SMILES: COc1ccc(C(=O)Nc2cccc3c(=O)n(Cc4ccc(OC(F)(F)F)cc4)ccc23)c(C)c1] | 482.46 | 483.35 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1549 | 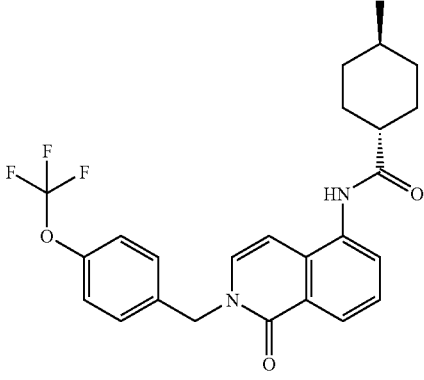 | 458.48 | 459.50 | * |
| 1550 | 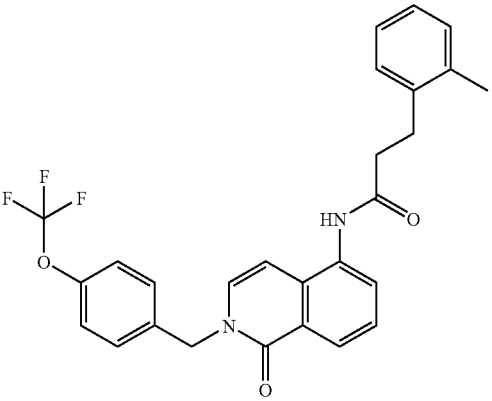 [SMILES: Cc1ccccc1CCC(=O)Nc1cccc2c(=O)n(Cc3ccc(OC(F)(F)F)cc3)ccc12] | 480.48 | 481.40 | * |
| 1551 | 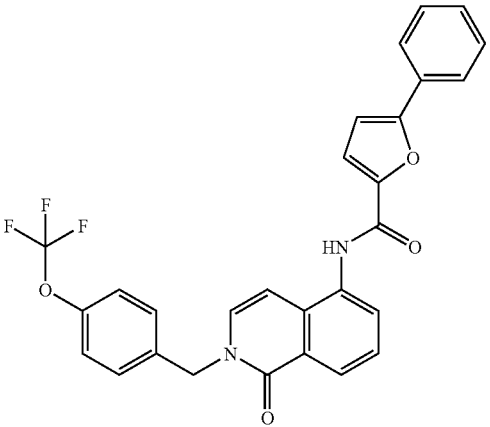 [SMILES: O=C(Nc1cccc2c(=O)n(Cc3ccc(OC(F)(F)F)cc3)ccc12)c1ccc(-c2ccccc2)o1] | 504.46 | 505.31 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1552 | 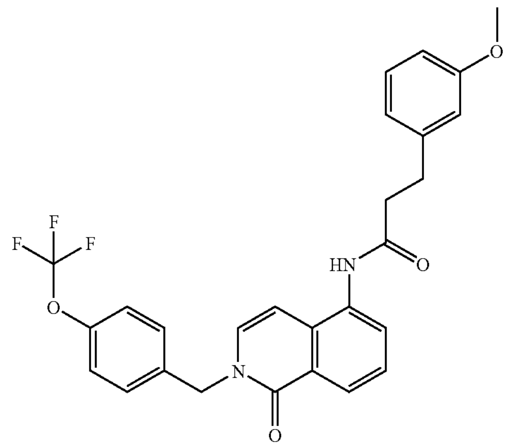 [SMILES: COc1cccc(CCC(=O)Nc2cccc3c(=O)n(Cc4ccc(OC(F)(F)F)cc4)ccc23)c1] | 496.48 | 497.40 | * |
| 1553 | 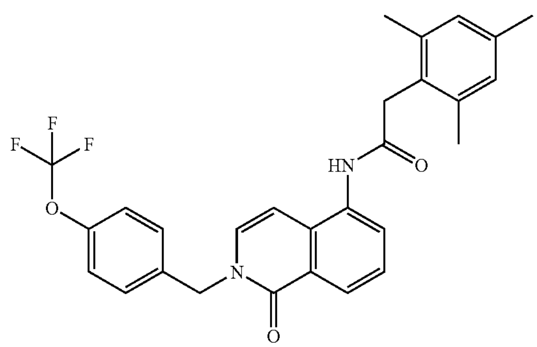 [SMILES: Cc1cc(C)c(CC(=O)Nc2cccc3c(=O)n(Cc4ccc(OC(F)(F)F)cc4)ccc23)c(C)c1] | 494.51 | 495.38 | * |
| 1554 | 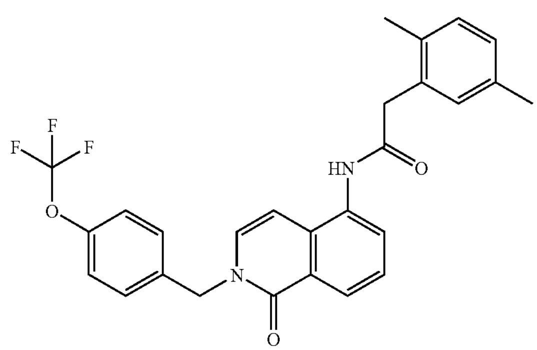 [SMILES: Cc1ccc(C)c(CC(=O)Nc2cccc3c(=O)n(Cc4ccc(OC(F)(F)F)cc4)ccc23)c1] | 480.48 | 481.38 | * |
| 1555 | 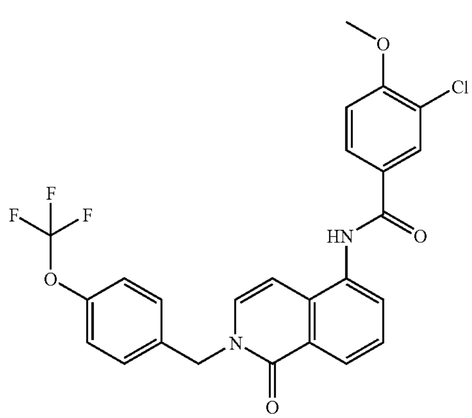 [SMILES: COc1ccc(C(=O)Nc2cccc3c(=O)n(Cc4ccc(OC(F)(F)F)cc4)ccc23)cc1Cl] | 502.87 | 503.28 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1556 | 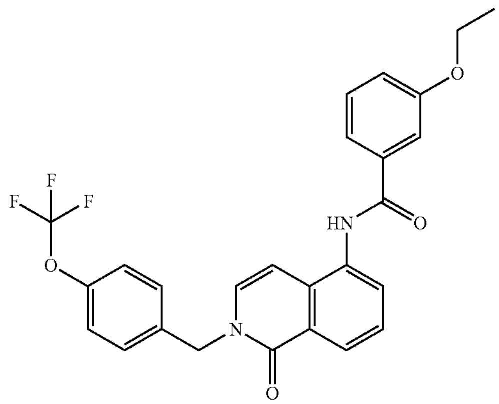 [SMILES: CCOc1cccc(C(=O)Nc2cccc3c(=O)n(Cc4ccc(OC(F)(F)F)cc4)ccc23)c1] | 482.46 | 483.35 | * |
| 1557 | 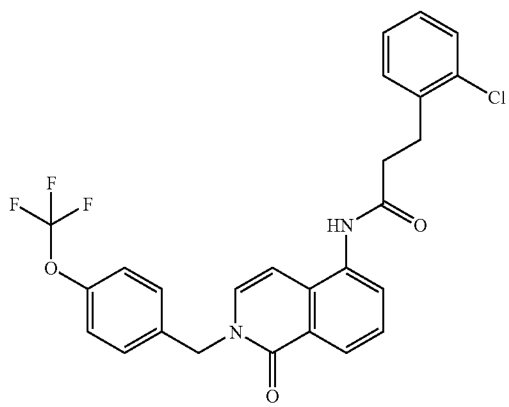 [SMILES: O=C(CCc1ccccc1Cl)Nc1cccc2c(=O)n(Cc3ccc(OC(F)(F)F)cc3)ccc12] | 500.90 | 501.42 | * |
| 1558 | 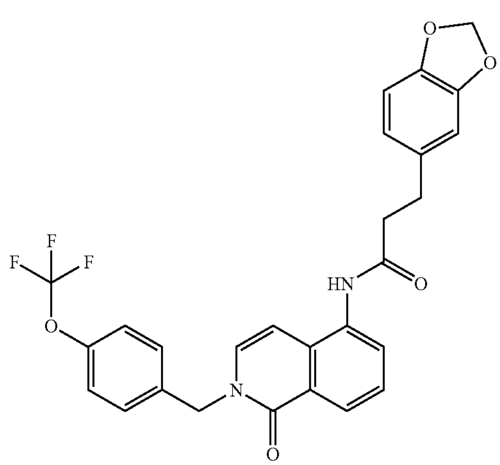 [SMILES: O=C(CCc1ccc2c(c1)OCO2)Nc1cccc2c(=O)n(Cc3ccc(OC(F)(F)F)cc3)ccc12] | 510.47 | 511.35 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1559 | 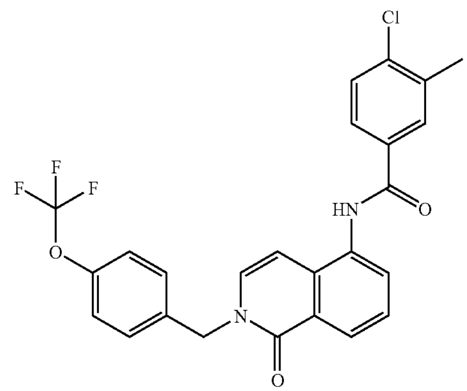 [SMILES: Cc1cc(C(=O)Nc2cccc3c(=O)n(Cc4ccc(OC(F)(F)F)cc4)ccc23)ccc1Cl] | 486.88 | 487.46 | * |
| 1560 | 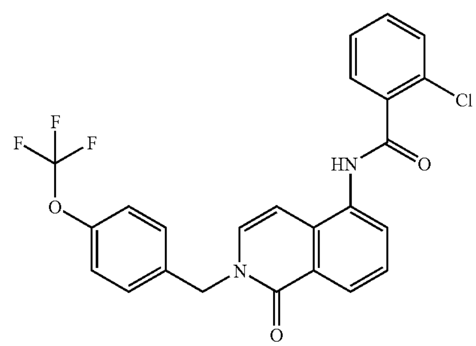 [SMILES: O=C(Nc1cccc2c(=O)n(Cc3ccc(OC(F)(F)F)cc3)ccc12)c1ccccc1Cl] | 472.85 | 473.40 | * |
| 1561 | 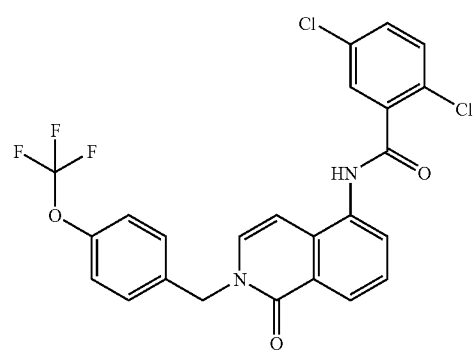 [SMILES: O=C(Nc1cccc2c(=O)n(Cc3ccc(OC(F)(F)F)cc3)ccc12)c1cc(Cl)ccc1Cl] | 507.29 | 507.40 | * |
| 1562 | 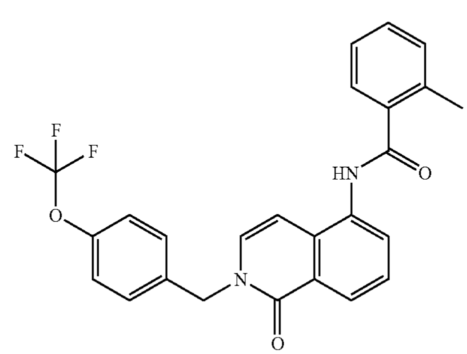 [SMILES: Cc1ccccc1C(=O)Nc1cccc2c(=O)n(Cc3ccc(OC(F)(F)F)cc3)ccc12] | 452.43 | 453.24 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1563 | 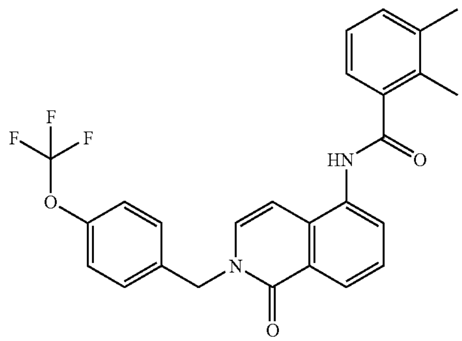 [SMILES: Cc1cccc(C(=O)Nc2cccc3c(=O)n(Cc4ccc(OC(F)(F)F)cc4)ccc23)c1C] | 466.46 | 467.40 | * |
| 1564 | 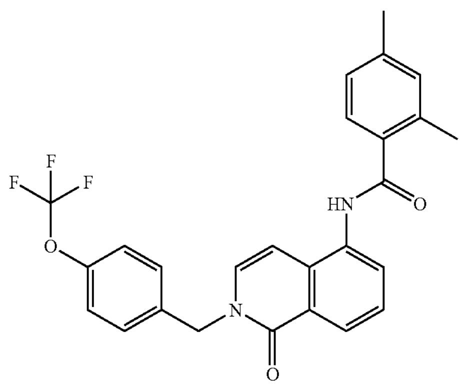 [SMILES: Cc1ccc(C(=O)Nc2cccc3c(=O)n(Cc4ccc(OC(F)(F)F)cc4)ccc23)c(C)c1] | 466.46 | 467.40 | * |
| 1565 | 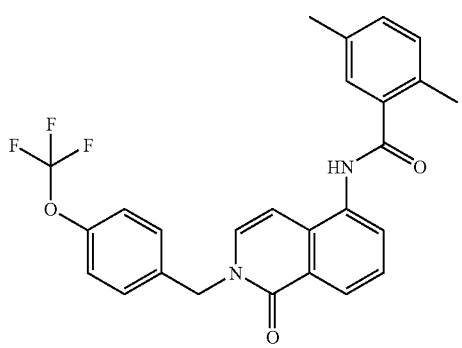 [SMILES: Cc1ccc(C)c(C(=O)Nc2cccc3c(=O)n(Cc4ccc(OC(F)(F)F)cc4)ccc23)c1] | 466.46 | 467.40 | * |
| 1566 | 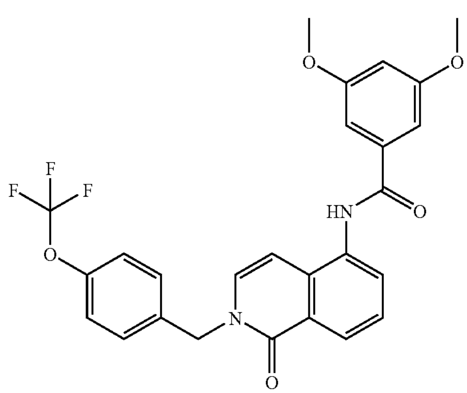 [SMILES: COc1cc(OC)cc(C(=O)Nc2cccc3c(=O)n(Cc4ccc(OC(F)(F)F)cc4)ccc23)c1] | 498.45 | 499.37 | ** |

TABLE 1-continued

IL-1β % Inhibition of Exemplary Compounds

| ID | Structure | MW | MS (obs) | IL-1β % Inhib. @ 0.3 μM |
|---|---|---|---|---|
| 1567 | 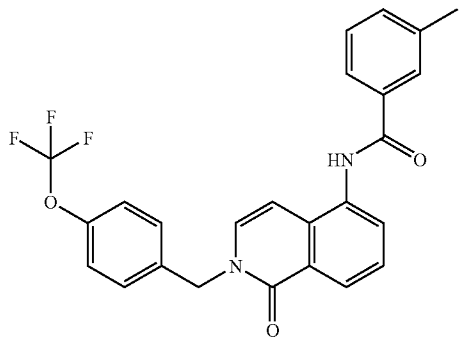 [SMILES: Cc1cccc(C(=O)Nc2cccc3c(=O)n(Cc4ccc(OC(F)(F)F)cc4)ccc23)c1] | 452.43 | 453.17 | * |
| 1568 | 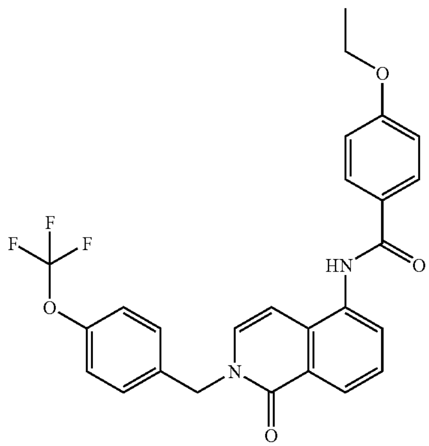 [SMILES: CCOc1ccc(C(=O)Nc2cccc3c(=O)n(Cc4ccc(OC(F)(F)F)cc4)ccc23)cc1] | 482.46 | 483.35 | * |
| 1569 | 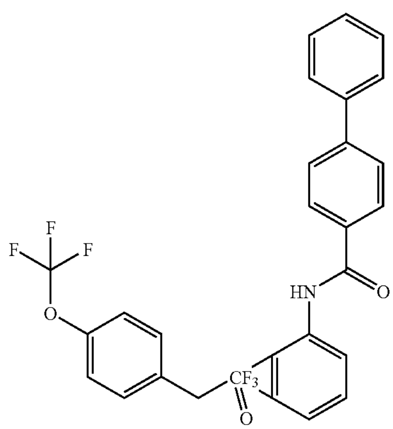 | 514.50 | 515.61 | * |
| 1570 | 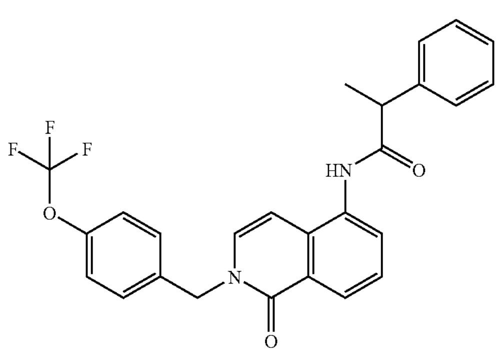 [SMILES: CC(C(=O)Nc1cccc2c(=O)n(Cc3ccc(OC(F)(F)F)cc3)ccc12)c1ccccc1] | 466.46 | 467.40 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1571 | 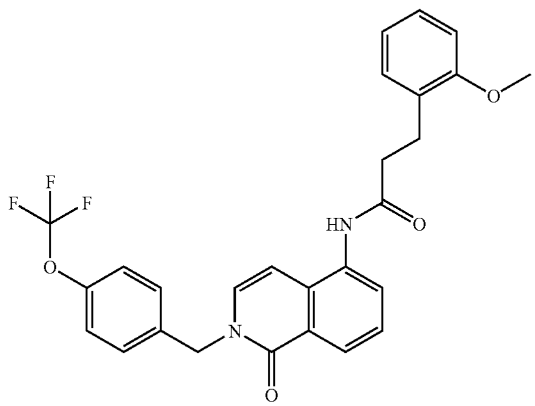 [SMILES: COc1ccccc1CCC(=O)Nc1cccc2c(=O)n(Cc3ccc(OC(F)(F)F)cc3)ccc12] | 496.48 | 497.34 | * |
| 1572 | 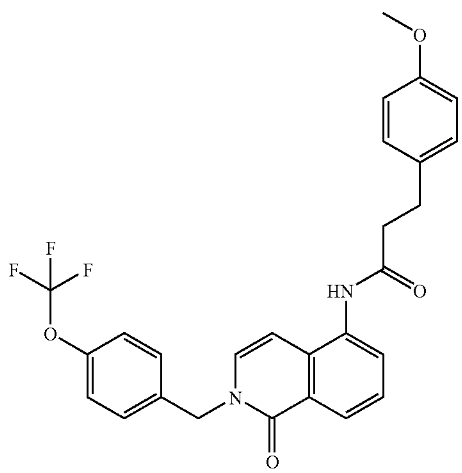 [SMILES: COc1ccc(CCC(=O)Nc2cccc3c(=O)n(Cc4ccc(OC(F)(F)F)cc4)ccc23)cc1] | 496.48 | 497.34 | * |
| 1573 | 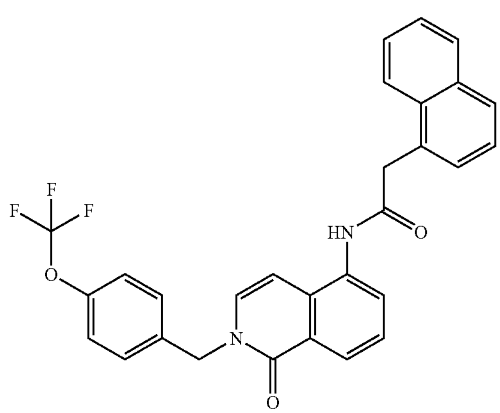 [SMILES: O=C(Cc1cccc2ccccc12)Nc1cccc2c(=O)n(Cc3ccc(OC(F)(F)F)cc3)ccc12] | 502.49 | 503.33 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1574 | 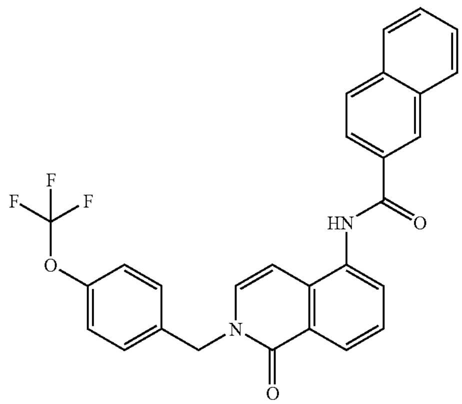 [SMILES: O=C(Nc1cccc2c(=O)n(Cc3ccc(OC(F)(F)F)cc3)ccc12)c1ccc2ccccc2c1] | 488.46 | 489.52 | * |
| 1575 | 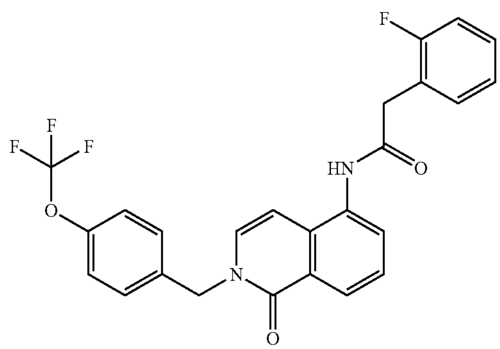 | 470.42 | 471.38 | * |
| 1576 | 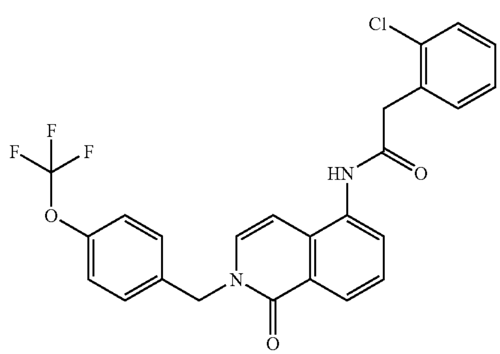 | 486.88 | 487.47 | * |
| 1577 | 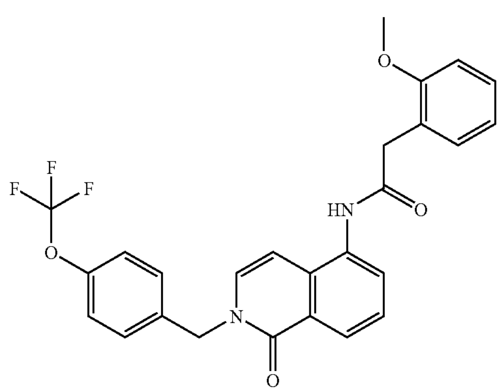 [SMILES: COc1ccccc1CC(=O)Nc1cccc2c(=O)n(Cc3ccc(OC(F)(F)F)cc3)ccc12] | 482.46 | 483.36 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1578 | 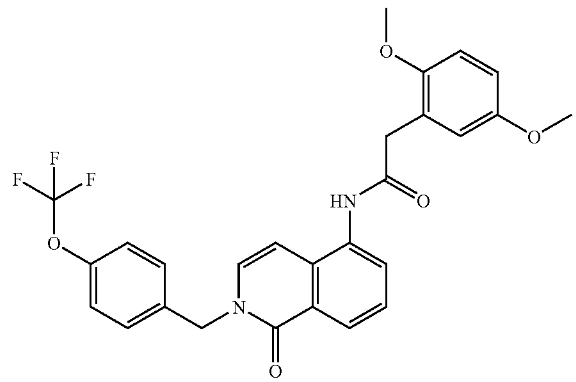 [SMILES: COc1ccc(OC)c(CC(=O)Nc2cccc3c(=O)n(Cc4ccc(OC(F)(F)F)cc4)ccc23)c1] | 512.48 | 513.49 | * |
| 1579 | 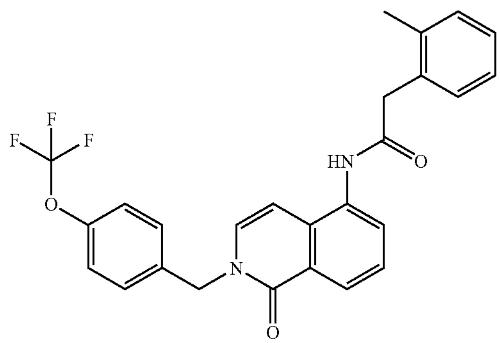 [SMILES: Cc1ccccc1CC(=O)Nc1cccc2c(=O)n(Cc3ccc(OC(F)(F)F)cc3)ccc12] | 466.46 | 467.40 | * |
| 1580 | 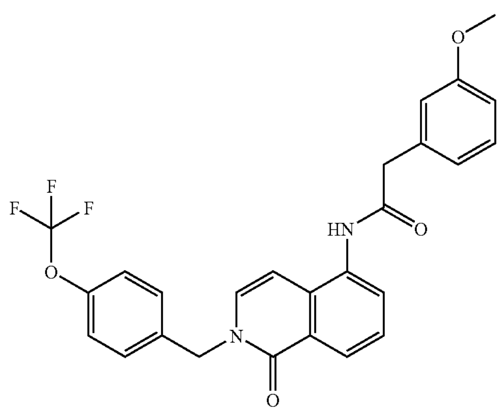 [SMILES: COc1cccc(CC(=O)Nc2cccc3c(=O)n(Cc4ccc(OC(F)(F)F)cc4)ccc23)c1] | 482.46 | 483.34 | * |
| 1581 | 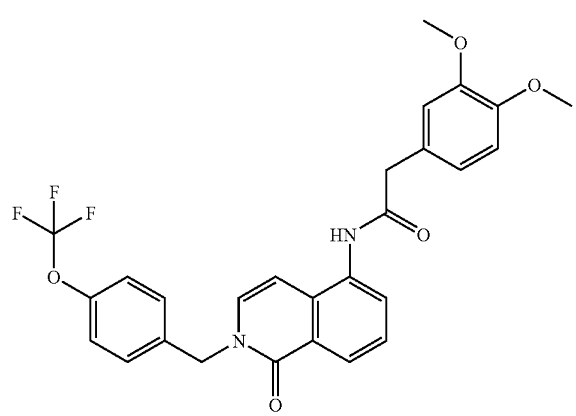 [SMILES: COc1ccc(CC(=O)Nc2cccc3c(=O)n(Cc4ccc(OC(F)(F)F)cc4)ccc23)cc1OC] | 512.48 | 513.49 | * |

TABLE 1-continued

IL-1β % Inhibition of Exemplary Compounds

| ID | Structure | MW | MS (obs) | IL-1β % Inhib. @ 0.3 µM |
|----|-----------|-----|----------|-------------------------|
| 1582 | 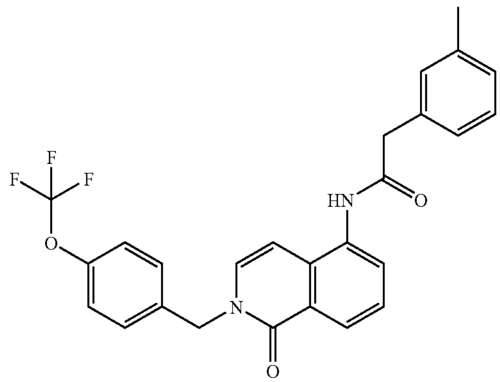 [SMILES: Cc1cccc(CC(=O)Nc2cccc3c(=O)n(Cc4ccc(OC(F)(F)F)cc4)ccc23)c1] | 466.46 | 467.40 | * |
| 1583 | 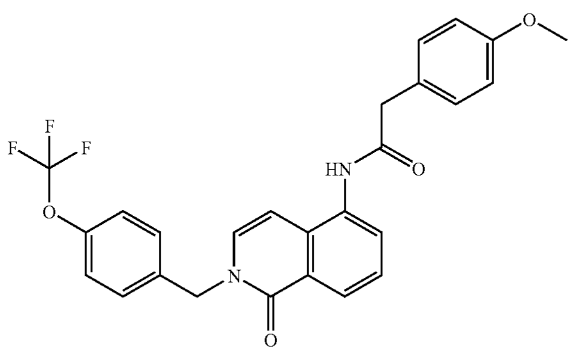 [SMILES: COc1ccc(CC(=O)Nc2cccc3c(=O)n(Cc4ccc(OC(F)(F)F)cc4)ccc23)cc1] | 482.46 | 483.35 | ** |
| 1584 | 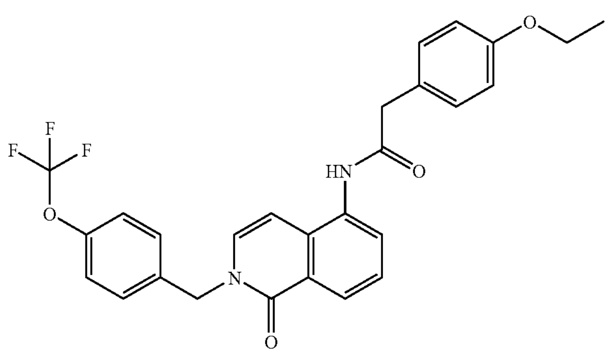 [SMILES: CCOc1ccc(CC(=O)Nc2cccc3c(=O)n(Cc4ccc(OC(F)(F)F)cc4)ccc23)cc1] | 496.48 | 497.35 | * |
| 1585 | 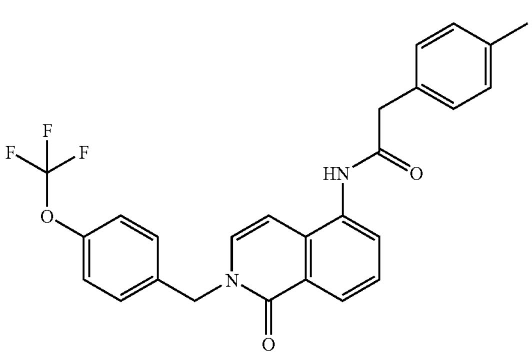 [SMILES: Cc1ccc(CC(=O)Nc2cccc3c(=O)n(Cc4ccc(OC(F)(F)F)cc4)ccc23)cc1] | 466.46 | 467.40 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1586 | 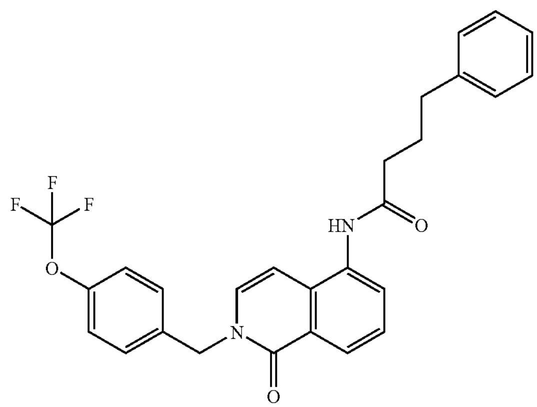 [SMILES: O=C(CCCc1ccccc1)Nc1cccc2c(=O)n(Cc3ccc(OC(F)(F)F)cc3)ccc12] | 480.48 | 481.39 | * |
| 1587 | 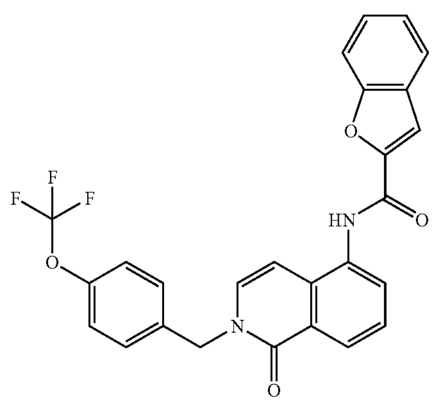 [SMILES: O=C(Nc1cccc2c(=O)n(Cc3ccc(OC(F)(F)F)cc3)ccc12)c1cc2ccccc2o1] | 478.42 | 479.10 | * |
| 1588 | 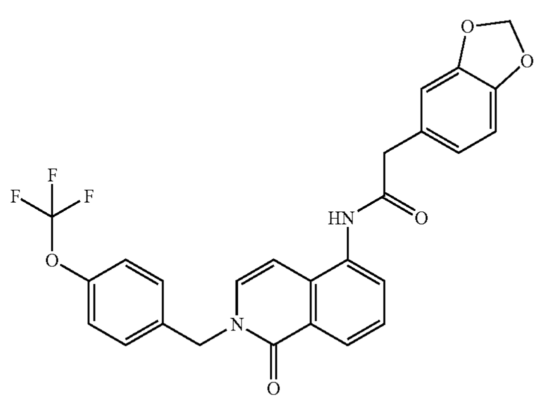 [SMILES: O=C(Cc1ccc2c(c1)OCO2)Nc1cccc2c(=O)n(Cc3ccc(OC(F)(F)F)cc3)ccc12] | 496.44 | 497.32 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1589 | 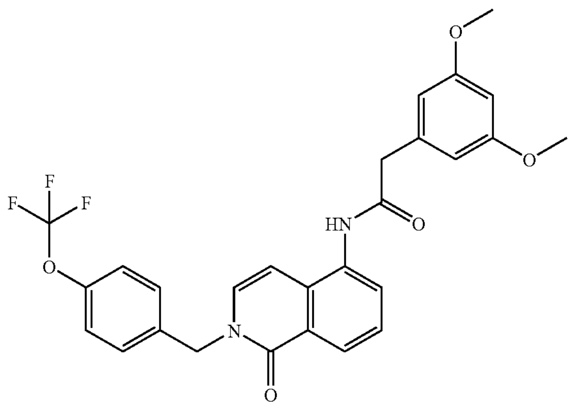 [SMILES: COc1cc(CC(=O)Nc2cccc3c(=O)n(Cc4ccc(OC(F)(F)F)cc4)ccc23)cc(OC)c1] | 512.48 | 513.50 | * |
| 1590 | 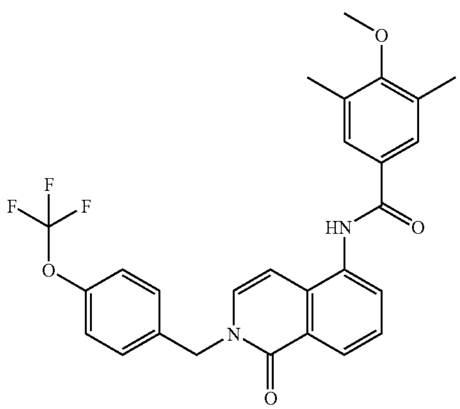 [SMILES: COc1c(C)cc(C(=O)Nc2cccc3c(=O)n(Cc4ccc(OC(F)(F)F)cc4)ccc23)cc1C] | 496.48 | 497.21 | ** |
| 1591 | 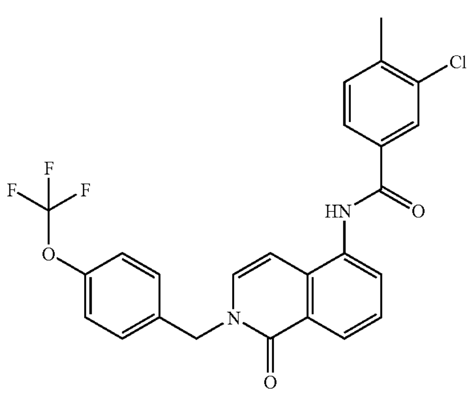 [SMILES: Cc1ccc(C(=O)Nc2cccc3c(=O)n(Cc4ccc(OC(F)(F)F)cc4)ccc23)cc1Cl] | 486.88 | 487.47 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1592 | 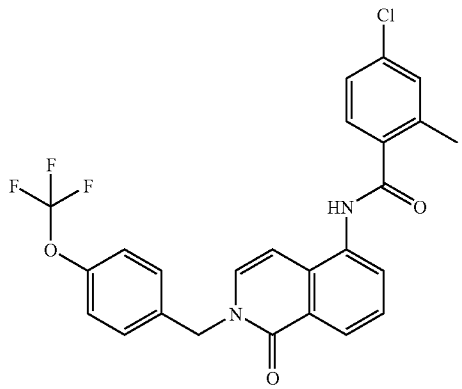 [SMILES: Cc1cc(Cl)ccc1C(=O)Nc1cccc2c(=O)n(Cc3ccc(OC(F)(F)F)cc3)ccc12] | 486.88 | 487.43 | * |
| 1593 | 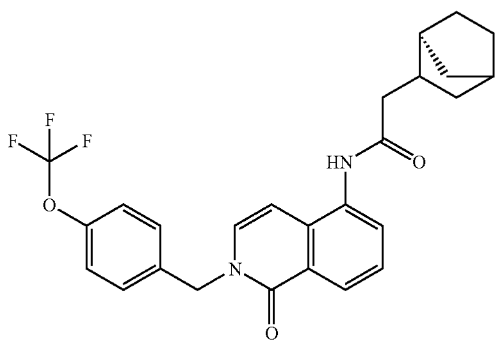 | 470.49 | 471.45 | * |
| 1594 | 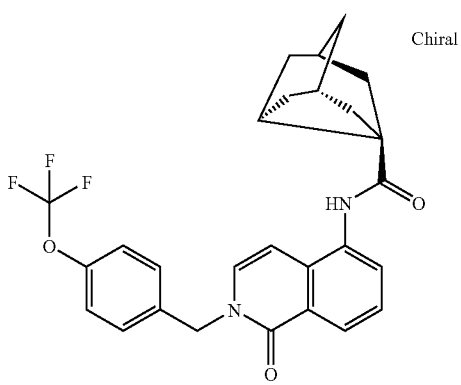 [SMILES: O=C(Nc1cccc2c(=O)n(Cc3ccc(OC(F)(F)F)cc3)ccc12)[C@@]12C[C@@H]3C[C@@H](C[C@@H]1C3)C2] | 482.50 | 483.38 | * |
| 1595 | 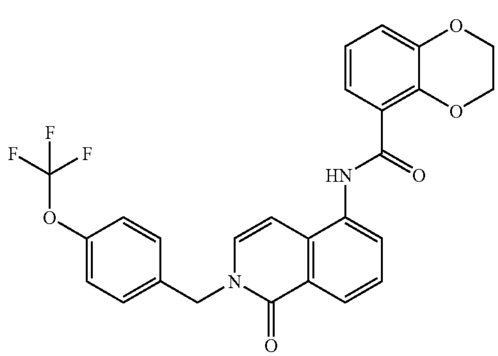 [SMILES: O=C(Nc1cccc2c(=O)n(Cc3ccc(OC(F)(F)F)cc3)ccc12)c1cccc2c1OCCO2] | 496.44 | 497.34 | * |

TABLE 1-continued

IL-1β % Inhibition of Exemplary Compounds

| ID | Structure | MW | MS (obs) | IL-1β % Inhib. @ 0.3 µM |
|---|---|---|---|---|
| 1596 | 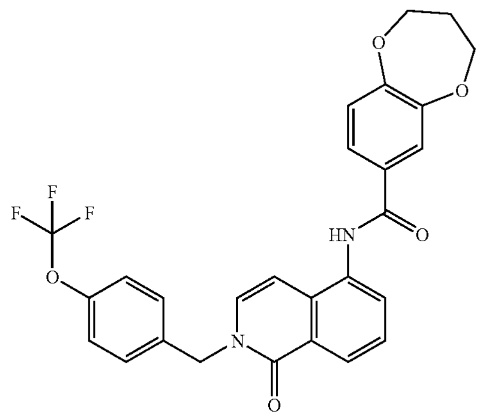 [SMILES: O=C(Nc1cccc2c(=O)n(Cc3ccc(OC(F)(F)F)cc3)ccc12)c1ccc2c(c1)OCCCO2] | 510.47 | 511.35 | * |
| 1597 | 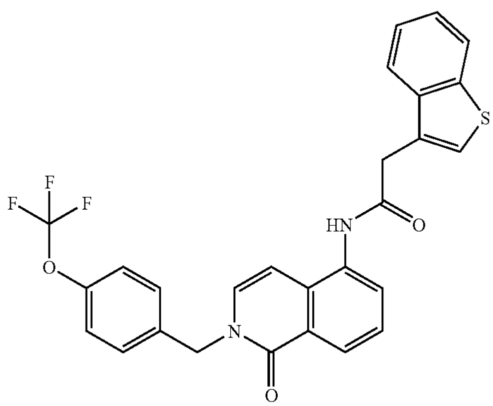 [SMILES: O=C(Cc1csc2ccccc12)Nc1cccc2c(=O)n(Cc3ccc(OC(F)(F)F)cc3)ccc12] | 508.52 | 509.36 | * |
| 1598 | 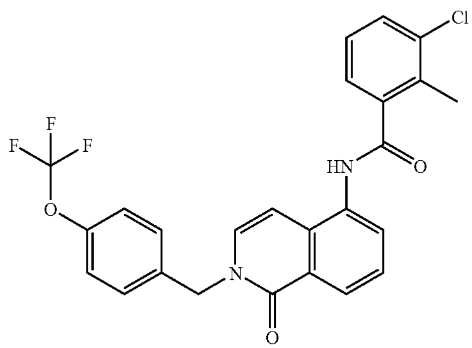 [SMILES: Cc1c(Cl)cccc1C(=O)Nc1cccc2c(=O)n(Cc3ccc(OC(F)(F)F)cc3)ccc12] | 486.88 | 487.40 | ** |
| 1599 | 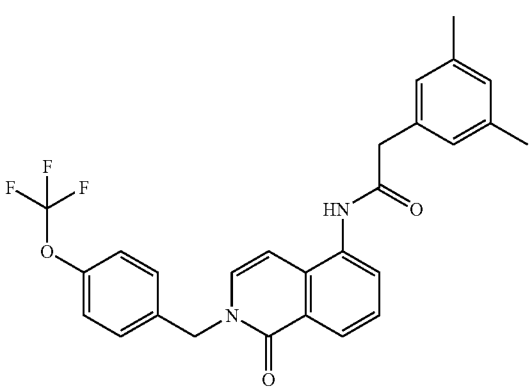 [SMILES: Cc1cc(C)cc(CC(=O)Nc2cccc3c(=O)n(Cc4ccc(OC(F)(F)F)cc4)ccc23)c1] | 480.48 | 481.38 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1600 | 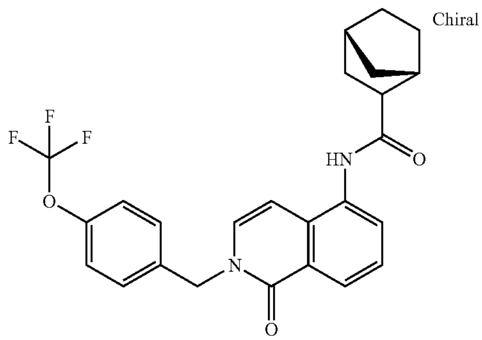 [SMILES: O=C(Nc1cccc2c(=O)n(Cc3ccc(OC(F)(F)F)cc3)ccc12)C1C[C@@H]2CC[C@H]1C2] | 456.46 | 457.36 | * |
| 1601 | 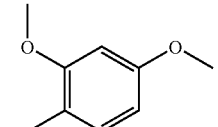 | 512.48 | 513.53 | * |
| 1602 | 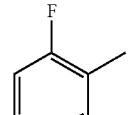 | 470.42 | 471.40 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1603 | 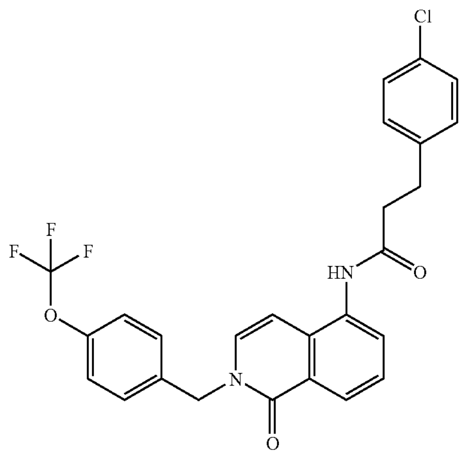 [SMILES: O=C(CCc1ccc(Cl)cc1)Nc1cccc2c(=O)n(Cc3ccc(OC(F)(F)F)cc3)ccc12] | 500.90 | 501.42 | * |
| 1604 | 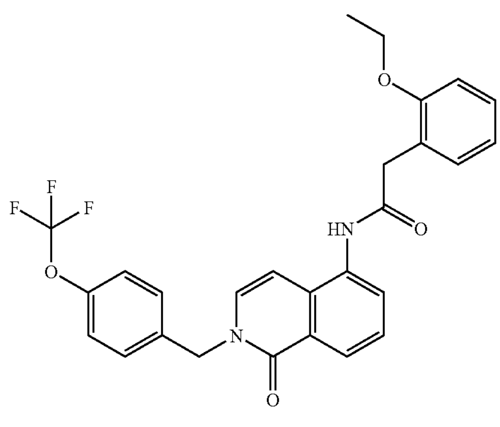 [SMILES: CCOc1ccccc1CC(=O)Nc1cccc2c(=O)n(Cc3ccc(OC(F)(F)F)cc3)ccc12] | 496.48 | 497.34 | * |
| 1605 | 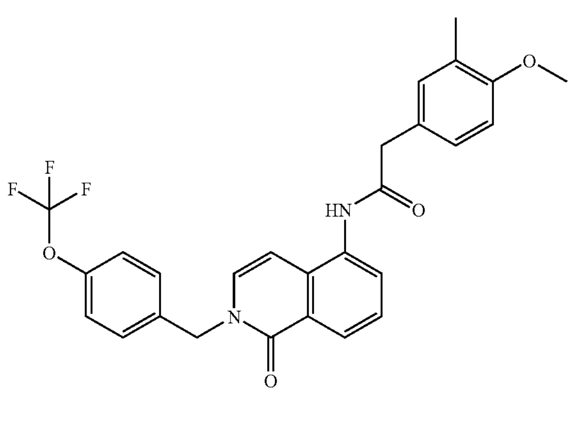 | 496.48 | 497.35 | * |

TABLE 1-continued

IL-1β % Inhibition of Exemplary Compounds

| ID | Structure | MW | MS (obs) | IL-1β % Inhib. @ 0.3 μM |
|---|---|---|---|---|
| 1606 | 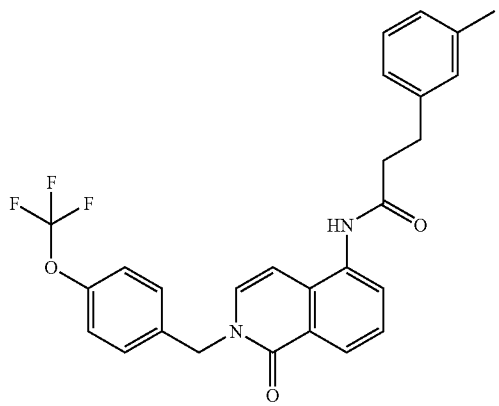 [SMILES: Cc1cccc(CCC(=O)Nc2cccc3c(=O)n(Cc4ccc(OC(F)(F)F)cc4)ccc23)c1] | 480.48 | 481.39 | * |
| 1607 | 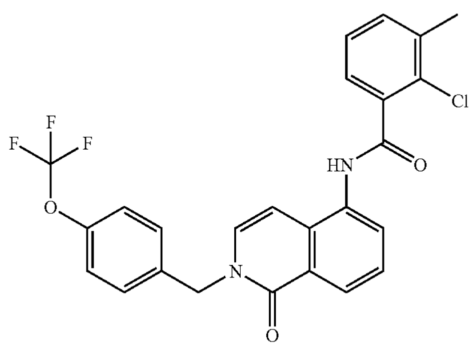 [SMILES: Cc1cccc(C(=O)Nc2cccc3c(=O)n(Cc4ccc(OC(F)(F)F)cc4)ccc23)c1Cl] | 486.88 | 487.48 | * |
| 1608 | 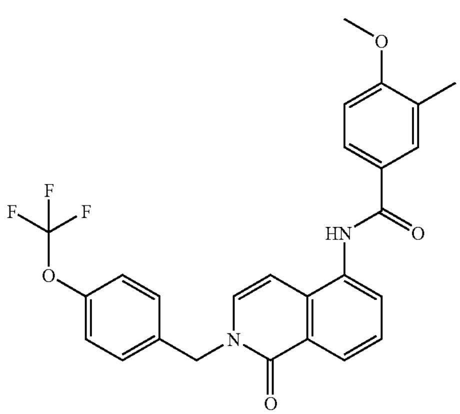 [SMILES: COc1ccc(C(=O)Nc2cccc3c(=O)n(Cc4ccc(OC(F)(F)F)cc4)ccc23)cc1C] | 482.46 | 483.34 | * |

TABLE 1-continued
IL-1β % Inhibition of Exemplary Compounds
| ID | Structure | MW | MS (obs) | IL-1β % Inhib. @ 0.3 μM |
|---|---|---|---|---|
| 1609 | 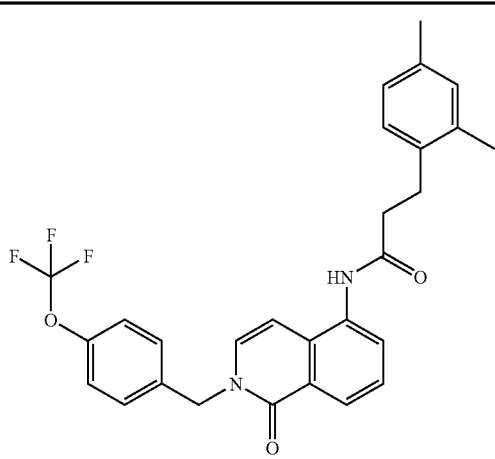 | 494.51 | 495.41 | * |
| 1610 | 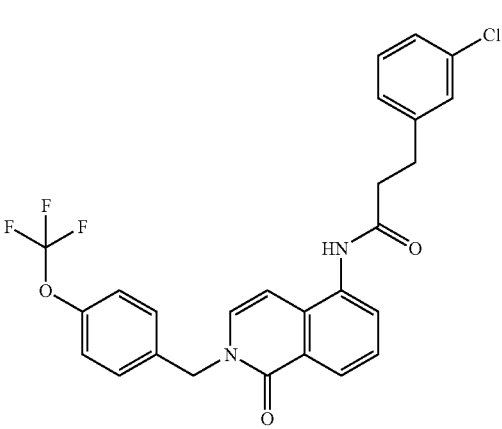 [SMILES: O=C(CCc1cccc(Cl)c1)Nc1cccc2c(=O)n(Cc3ccc(OC(F)(F)F)cc3)ccc12] | 500.90 | 501.39 | * |
| 1611 | 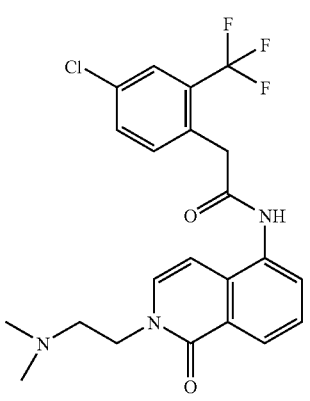 [SMILES: CN(C)CCn1ccc2c(NC(=O)Cc3ccc(Cl)cc3C(F)(F)F)cccc2c1=O] | 451.87 | 452.30 | + |
| 1612 | 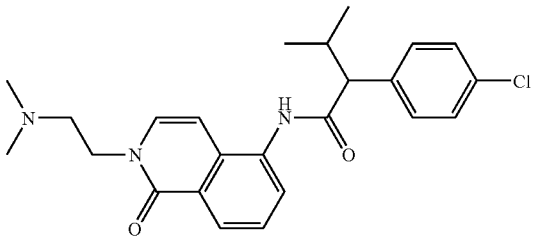 [SMILES: CC(C)C(C(=O)Nc1cccc2c(=O)n(CCN(C)C)ccc12)c1ccc(Cl)cc1] | 425.96 | 426.20 | + |

TABLE 1-continued

IL-1β % Inhibition of Exemplary Compounds

| ID | Structure | MW | MS (obs) | IL-1β % Inhib. @ 0.3 μM |
|---|---|---|---|---|
| 1613 | 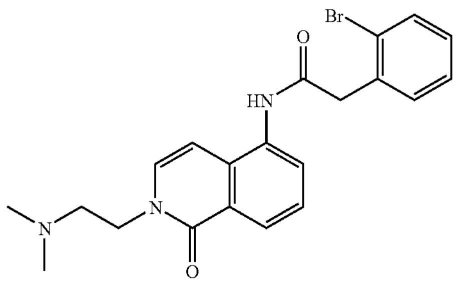 [SMILES: CN(C)CCn1ccc2c(NC(=O)Cc3ccccc3Br)cccc2c1=O] | 428.33 | 427.70 | + |
| 1614 | 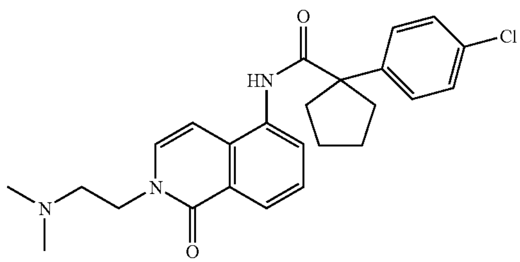 [SMILES: CN(C)CCn1ccc2c(NC(=O)C3(c4ccc(Cl)cc4)CCCC3)cccc2c1=O] | 437.97 | 438.10 | + |
| 1615 | Chiral | 447.45 | 447.70 | + |
| 1616 | Chiral | 447.45 | 447.40 | + |
| 1617 | 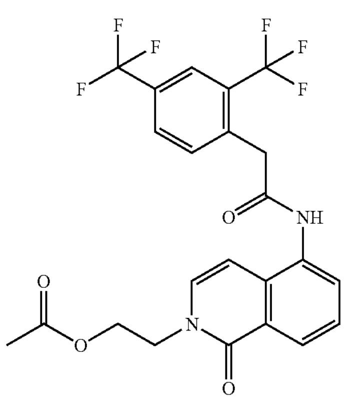 [SMILES: CC(=O)OCCn1ccc2c(NC(=O)Cc3ccc(C(F)(F)F)cc3C(F)(F)F)cccc2c1=O] | 500.39 | 501.50 | ++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1618 | 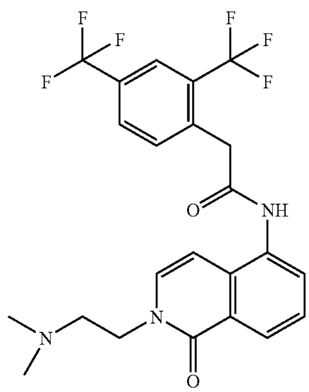 [SMILES: CN(C)CCn1ccc2c(NC(=O)Cc3ccc(C(F)(F)F)cc3C(F)(F)F)cccc2c1=O] | 485.43 | 485.60 | + |
| 1619 | Chiral | 481.63 | 482.20 | ++++ |
| 1620 | Chiral | 564.00 | 564.00 | ++++ |
| 1621 | Chiral | 564.00 | 564.00 | ++++ |

TABLE 1-continued
IL-1β % Inhibition of Exemplary Compounds
| ID | Structure | MW | MS (obs) | IL-1β % Inhib. @ 0.3 µM |
|---|---|---|---|---|
| 1622 | 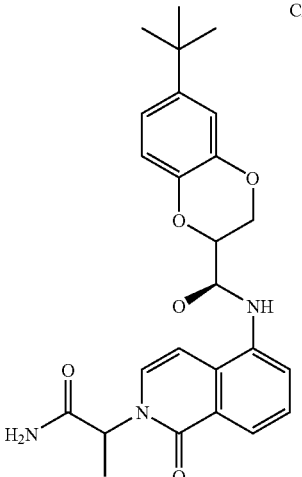 Chiral | 449.50 | 450.10 | + |
| 1623 | 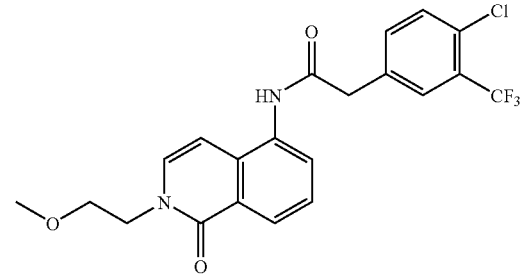 [SMILES: COCCn1ccc2c(NC(=O)Cc3ccc(Cl)c(C(F)(F)F)c3)cccc2c1=O] | 438.83 | 439.20 | ++++ |
| 1624 | 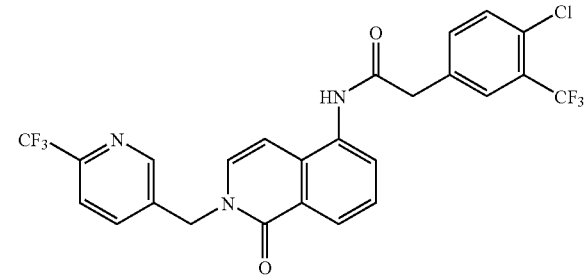 [SMILES: O=C(Cc1ccc(Cl)c(C(F)(F)F)c1)Nc1cccc2c(=O)n(Cc3ccc(C(F)(F)F)nc3)ccc12] | 539.86 | 540.10 | ++ |
| 1625 | 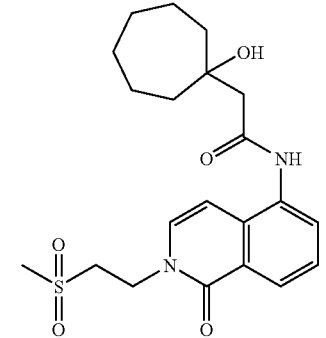 [SMILES: CS(=O)(=O)CCn1ccc2c(NC(=O)CC3(O)CCCCCC3)cccc2c1=O] | 420.53 | 421.20 | + |

TABLE 1-continued

IL-1β % Inhibition of Exemplary Compounds

| ID | Structure | MW | MS (obs) | IL-1β % Inhib. @ 0.3 μM |
|----|-----------|------|----------|-------------------------|
| 1626 | 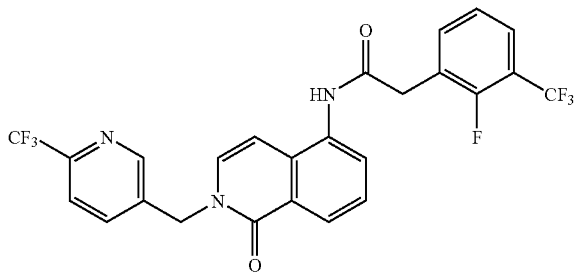 [SMILES: O=C(Cc1cccc(C(F)(F)F)c1F)Nc1cccc2c(=O)n(Cc3ccc(C(F)(F)F)nc3)ccc12] | 523.41 | 524.30 | + |
| 1627 | 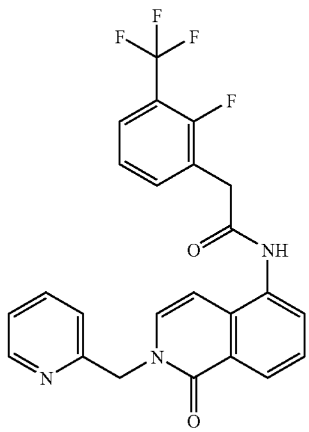 [SMILES: O=C(Cc1cccc(C(F)(F)F)c1F)Nc1cccc2c(=O)n(Cc3ccccn3)ccc12] | 455.41 | 455.90 | ++ |
| 1628 | 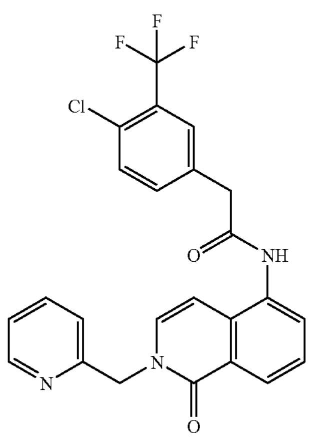 [SMILES: O=C(Cc1ccc(Cl)c(C(F)(F)F)c1)Nc1cccc2c(=O)n(Cc3ccccn3)ccc12] | 471.86 | 472.30 | ++++ |
| 1629 | 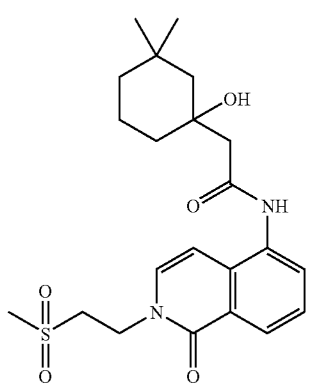 [SMILES: CC1(C)CCCC(O)(CC(=O)Nc2cccc3c(=O)n(CCS(C)(=O)=O)ccc23)C1] | 434.55 | 435.20 | ++ |

TABLE 1-continued
IL-1β % Inhibition of Exemplary Compounds
| ID | Structure | MW | MS (obs) | IL-1β % Inhib. @ 0.3 μM |
|---|---|---|---|---|
| 1630 | 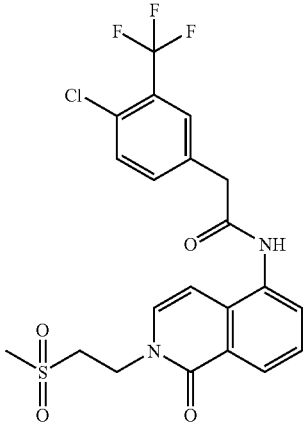 [SMILES: CS(=O)(=O)CCn1ccc2c(NC(=O)Cc3ccc(Cl)c(C(F)(F)F)c3)cccc2c1=O] | 486.90 | 487.00 | ++++ |
| 1631 | 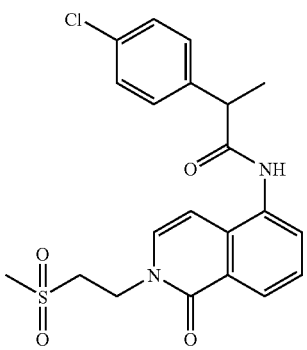 [SMILES: CC(C(=O)Nc1cccc2c(=O)n(CCS(C)(=O)=O)ccc12)c1ccc(Cl)cc1] | 432.93 | 433.10 | + |
| 1632 | 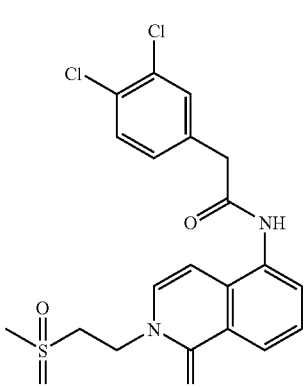 | 453.34 | 453.10 | ++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1633 | 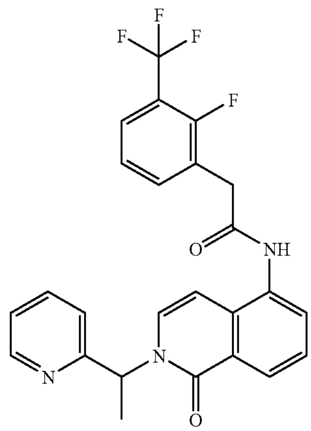 [SMILES: CC(c1ccccn1)n1ccc2c(NC(=O)Cc3cccc(C(F)(F)F)c3F)cccc2c1=O] | 469.44 | 468.30 | ++++ |
| 1634 | 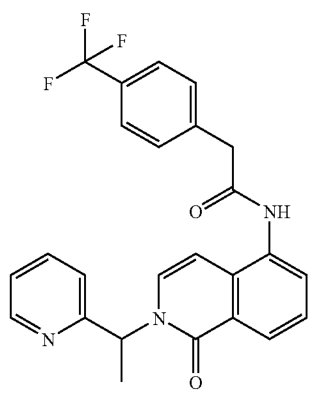 [SMILES: CC(c1ccccn1)n1ccc2c(NC(=O)Cc3ccc(C(F)(F)F)cc3)cccc2c1=O] | 451.45 | 451.80 | +++ |
| 1635 | 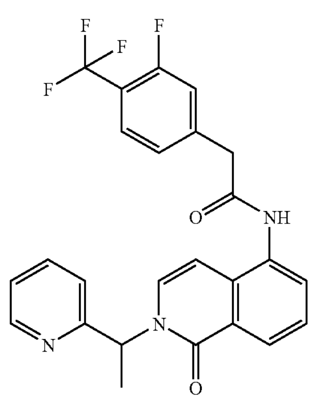 [SMILES: CC(c1ccccn1)n1ccc2c(NC(=O)Cc3ccc(C(F)(F)F)c(F)c3)cccc2c1=O] | 469.44 | 470.20 | ++++ |

TABLE 1-continued

IL-1β % Inhibition of Exemplary Compounds

| ID | Structure | MW | MS (obs) | IL-1β % Inhib. @ 0.3 μM |
|---|---|---|---|---|
| 1636 | Chiral | 466.37 | 466.10 | ** |
| 1637 | 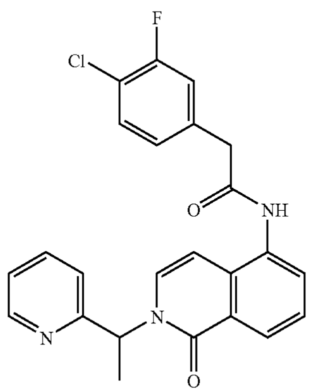 [SMILES: CC(c1ccccn1)n1ccc2c(NC(=O)Cc3ccc(Cl)c(F)c3)cccc2c1=O] | 435.88 | 437.30 | ** |

IC$_{50}$ Determinations

The compounds set forth in Table 1 were tested for activity in a cellular model as described herein. Specifically, cells were pretreated with differing amounts of the compound under test and released IL-1β determined as in Example 9, above. Measurements were made and IC$_{50}$ values, presented in Table 2, below, were determined by fitting the data to a four parameter logistic equation using GraphPad Prism software (GraphPad Software, Inc). The equation may be expressed by the following formula:

$$Y = \text{Bottom} + (\text{Top} - \text{Bottom})/(1 + 10\char`\^((\text{Log } EC50 - X) * \text{HillSlope}))$$

Where X is the logarithm of concentration, Y is the response and Y starts at Bottom and goes to Top with a sigmoid shape.

TABLE 2

IL-1β IC$_{50}$ for Exemplary Compounds

| ID | IL-1β IC$_{50}$ (nM) |
|---|---|
| 1001 | 240 |
| 1002 | 72.33 |
| 1003 | >1000 |
| 1004 | 108.4 |
| 1005 | 39.59 |
| 1006 | 99.22 |
| 1007 | >1000 |
| 1008 | >1000 |

TABLE 2-continued

IL-1β IC$_{50}$ for Exemplary Compounds

| ID | IL-1β IC$_{50}$ (nM) |
|---|---|
| 1009 | >1000 |
| 1010 | >1000 |
| 1011 | >1000 |
| 1012 | 421.5 |
| 1013 | 0.355 |
| 1014 | 326.2 |
| 1015 | 171.1 |
| 1016 | 338.5 |
| 1017 | 367.5 |
| 1018 | >1000 |
| 1019 | >1000 |
| 1020 | >1000 |
| 1021 | >1000 |
| 1022 | >1000 |
| 1023 | 53.45 |
| 1024 | 31.5 |
| 1366 | 409.6 |
| 1373 | 72.12 |
| 1374 | 40.57 |
| 1375 | 86.66 |
| 1376 | 731.3 |
| 1377 | >1000 |
| 1378 | 120.8 |
| 1379 | 41.55 |
| 1380 | 5.332 |
| 1381 | 34.14 |
| 1382 | 602.3 |

TABLE 2-continued

IL-1β IC$_{50}$ for Exemplary Compounds

| ID | IL-1β IC$_{50}$ (nM) |
|---|---|
| 1383 | >1000 |
| 1384 | >1000 |
| 1385 | 151.6 |
| 1386 | 237.9 |
| 1387 | 146.4 |
| 1388 | >1000 |
| 1389 | 310.5 |
| 1390 | 79.25 |
| 1391 | 45.68 |
| 1392 | 123.1 |
| 1393 | 77.81 |
| 1611 | 929.7 |
| 1612 | >1000 |
| 1613 | >1000 |
| 1614 | >1000 |
| 1615 | >1000 |
| 1616 | >1000 |
| 1617 | 417.5 |
| 1618 | >1000 |
| 1619 | 67.18 |
| 1620 | 41.08 |
| 1621 | 6.864 |
| 1622 | >1000 |
| 1623 | 9.24 |
| 1624 | 365 |
| 1625 | >1000 |
| 1626 | >1000 |
| 1627 | 416.1 |
| 1628 | 55.87 |
| 1629 | 456.6 |
| 1630 | 108.5 |
| 1631 | >1000 |
| 1632 | 314.5 |
| 1633 | 25.54 |
| 1634 | 261.9 |
| 1635 | 111.7 |

Half-Life in Human Liver Microsomes (HLM)

Test compounds (1 μM) are incubated with 3.3 mM MgCl$_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

$$\text{Half-life} = \ln 2/k$$

Pharmacokinetic Evaluation of Compounds Following Intravenous and Oral Administration in Rats.

Male Sprague-Dawley rats are acclimatized for at least 24 hours prior to experiment initiation. During the acclimation period, all animals receive food and water ad libitum. However, food but not water is removed from the animals' cages at least 12 hours before initiation of the experiment. During the first 3 hours of experimentation, the animals receive only water ad libitum. At least three animals each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). The animals are weighed before dosing. The determined body weight is used to calculate the dose volume for each animal.

$$\text{Dose volume (mL/kg)} = 1 \text{ mg/kg/formulation concentration (mg/mL)}$$

In instances where the formulation concentrations are less than 0.5 mg/mL, the dosing volume is about 2 mL/kg.

For oral formulation, compounds of this invention are suspended (0.5 to 0.75 mg/mL) in a mixture of 5% of 10% Tween 80 in water (v/v) and 95% of 0.5% methyl cellulose in water (w/v). PO rats are typically dosed through oral gavage following the same dose volume formula as IV to achieve a dose level of 1 to 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite (AUC$_{inf}$). The AUC$_{inf}$ is averaged and the oral bioavailability (% F) for individual animal is calculated as:

$$\text{AUC}_{inf}(\text{PO})/\text{AUC}_{inf}(\text{IV}), \text{ normalized to their respective dose levels.}$$

The % F can be reported as the mean % F of all animals dosed orally with the compound of the invention at the specified level.

From the foregoing description, various modifications and changes in the compositions and methods of this invention will occur to those skilled in the art. All such modifications coming within the scope of the appended claims are intended to be included therein.

All publications, including but not limited to patents and patent applications, cited' in this specification are herein incorporated by reference as if each individual publication were specifically and individually indicated to be incorporated by reference herein as though fully set forth.

The chemical names of compounds of the invention given in this application are generated using Open Eye Software's Lexichem naming tool, Symyx Renaissance Software's Reaction Planner or MDL's ISIS Draw Autonom Software tool and not verified.

What is claimed is:

1. A bicycloheteroaryl compound having a formula:

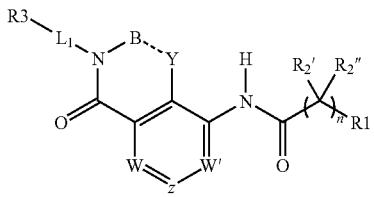

wherein
B and Y are independently selected from $CR^{2a}$;
W, W' and Z are each independently $CR^4$;
$L^1$ is substituted or unsubstituted $C_1C_5$ alkylene;
n is 1, 2, 3 or 4;
$R^1$ is selected from a substituted or unsubstituted heterocycloalkyl, aryl and heteroaryl ring;
each of $R^{2a}$, $R^{2'}$ and $R^{2''}$ is independently selected from hydrogen, halo, and substituted or unsubstituted $C_1$-$C_6$ alkyl; or any of $R^{2'}$ and $R^{2''}$ join together to form a cycloalkyl or cycloheteroalkyl ring of 3-7 atoms;
$R^3$ is hydrogen or a functional group selected from acyl, substituted acyl, substituted or unsubstituted acylamino, substituted or unsubstituted alkylamino, substituted or unsubstituted dialkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, aryl, substituted aryl, arylalkyl, substituted or unsubstituted sulfone, substituted or unsubstituted sulfanyl, substituted or unsubstituted aminosulfonyl, substituted or unsubstituted arylsulfonyl, substituted or unsubstituted carbamoyl, cyano, substituted or unsubstituted cycloalkyl, substituted or unsubstituted cycloheteroalkyl, halo, heteroaryloxy, substituted or unsubstituted heteroaryl, substituted or unsubstituted heteroalkyl, nitro, and thio;
provided that $R^3$ is other than hydrogen bond donor group;
$R^4$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfone, substituted or unsubstituted sulfanyl, substituted or unsubstituted aminosulfonyl, substituted or unsubstituted arylsulfonyl, substituted or unsubstituted dihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
and the dotted bond is a double bond;
or a pharmaceutically acceptable salt thereof;
and stereoisomers, isotopic variants and tautomers thereof.

2. A compound according to claim 1 wherein each of B and Y is CH; and the dotted bond is a double bond.

3. A compound according to claim 1 wherein each of $R^{2'}$ and $R^{2''}$ is H.

4. A compound according to claim 1 wherein one of $R^{2'}$ and $R^{2''}$ is independently Me and the other is H.

5. A compound according to claim 1 wherein $R^1$ is substituted or unsubstituted aryl or substituted or unsubstituted heteroaryl.

6. A compound according to claim 1 wherein $R^1$ is substituted or unsubstituted phenyl, pyridyl, quinoline, or benzodioxole, benzodioxane, benzofuran, benzothiophene, and benzodioxepine.

7. A compound according to claim 1 wherein the compound is according to formula III or IV:

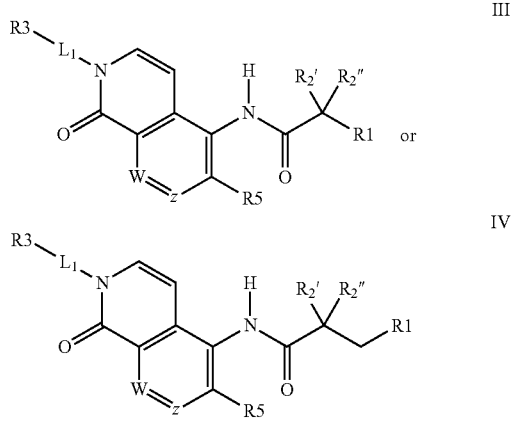

wherein
W is $CR^4$; Z is $CR^4$;
$L^1$, $R^1$, $R^{2'}$, $R^{2''}$, $R^3$ and $R^4$ are as in claim 1;
and $R^5$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, arylalkyl, substituted or unsubstituted sulfone, substituted or unsubstituted sulfanyl, substituted or unsubstituted aminosulfonyl, substituted or unsubstituted arylsulfonyl, substituted or unsubstituted dihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroalkyl, hydroxy, nitro, and thio;
or a pharmaceutically acceptable salt thereof;
and stereoisomers, isotopic variants and tautomers thereof.

8. A compound according to claim 1 wherein the compound is according to formula IX or X:

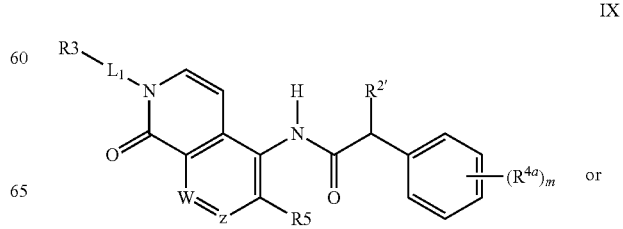

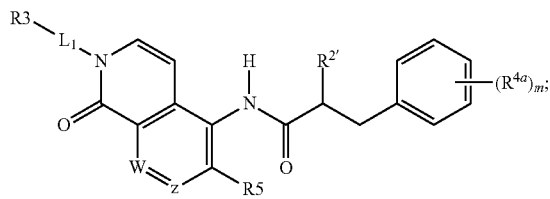

wherein
W is CR⁴; Z is CR⁴;
L¹, R³ and R⁴ are as in claim 1;
R⁵ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, arylalkyl, substituted or unsubstituted sulfone, substituted or unsubstituted sulfanyl, substituted or unsubstituted aminosulfonyl, substituted or unsubstituted arylsulfonyl, substituted or unsubstituted dihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroalkyl, hydroxy, nitro, and thio; R²' is H or Me;
each R⁴ᵃ is selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfone, substituted or unsubstituted sulfanyl, substituted or unsubstituted aminosulfonyl, substituted or unsubstituted arylsulfonyl, substituted or unsubstituted dihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5;
or a pharmaceutically acceptable salt thereof;
and stereoisomers, isotopic variants and tautomers thereof.

9. A compound according to any one of claims 1, 7 and 8, wherein L¹ is a C₁-C₅ alkylene unsubstituted or substituted by one or more substituents independently selected from alkyl and oxo.

10. A compound according to any one of claims 1, 7 and 8, wherein R³ is selected from alkyl, dialkylamino, acyloxy, alkoxy, and —SO₂-alkyl.

11. A compound according to any one of claims 1, 7 and 8, wherein R³ is selected from t-Bu, NMe₂, SO₂Me, OMe, and OCOMe.

12. A compound according to any one of claims 1, 7 and 8, wherein R³ is substituted or unsubstituted aryl, heteroaryl, cycloalkyl or cycloheteroalkyl.

13. A compound according to any one of claims 1, 7 and 8, wherein R³ is substituted or unsubstituted phenyl, pyridyl, pyran, tetrahydropyran, piperidine, morpholine, pyrrolidine, pyrrolidinone and benzodioxane.

14. A compound according to any one of claims 1, 7 and 8, wherein the group -L₁-R³ is selected from

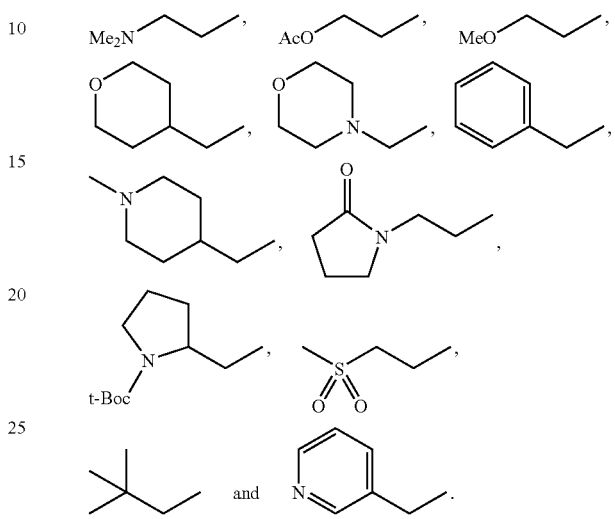

15. A compound according to claim 1 wherein the compound is according to formula XIa, XIb, XIc, XId, XIe, XIf, XIg, XIh or XIj:

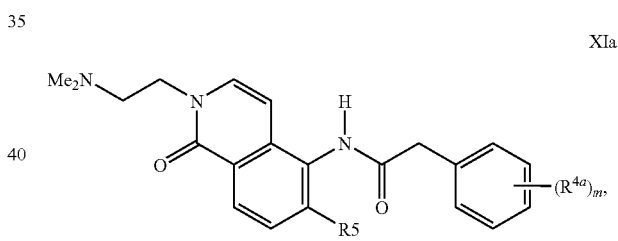

XIa

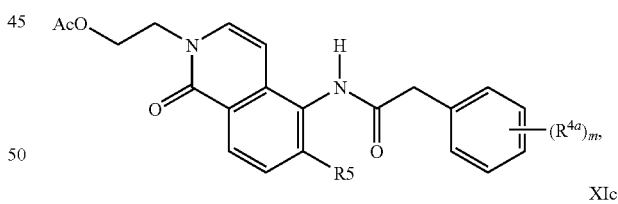

XIb

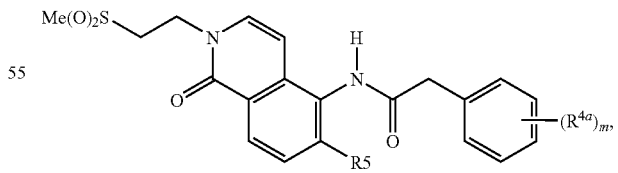

XIc

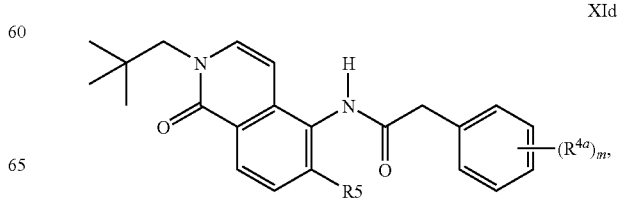

XId

-continued

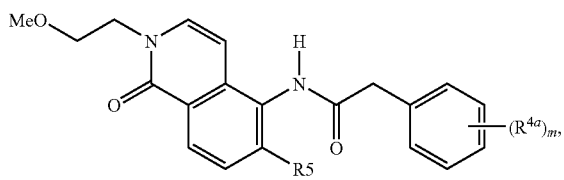
XIe

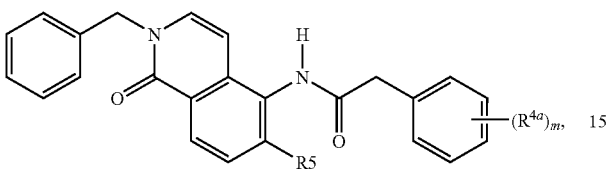
XIf

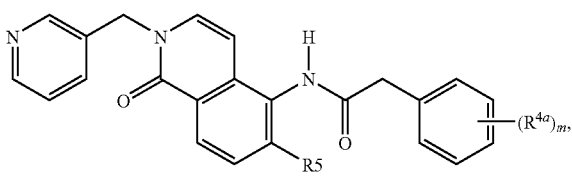
XIg

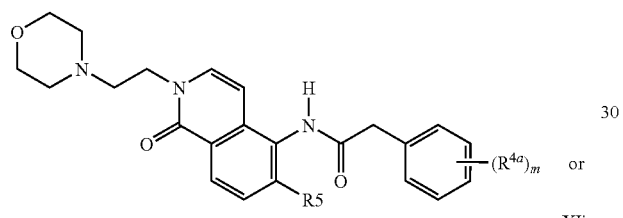
XIh or

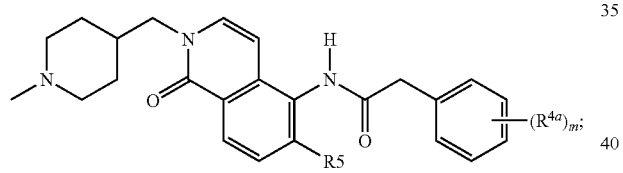
XIj wherein
each R$^{4a}$ is selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfone, substituted or unsubstituted sulfanyl, substituted or unsubstituted aminosulfonyl, substituted or unsubstituted arylsulfonyl, substituted or unsubstituted dihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; m is selected from 0-5; and R$^5$ is selected from H, alkyl, or halo.

16. A compound according to any one of claims 8 and 15, wherein m is 1 or 2; and each R$^{4a}$ is independently selected from Me, Et, Ph, Cl, F, Br, CN, OH, OMe, OEt, OPh, COPh, CF$_3$, CHF$_2$, OCF$_3$, i-Pr, i-Bu, t-Bu, SMe, CH=CH—CO$_2$H, SOMe, SO$_2$Me, SO$_3$H, SO$_3$Me, and pyridyl.

17. A compound according to any one of claims 1, 7 and 8, wherein each of W and Z is independently CH.

18. A compound according to any one of claims 7, 8 and 15, wherein R$^5$ is H, Me, Cl, F, or CF$_3$.

19. A compound according to claim 1 wherein the compound is selected from table below:

| ID | Structure |
|---|---|
| 1001 | 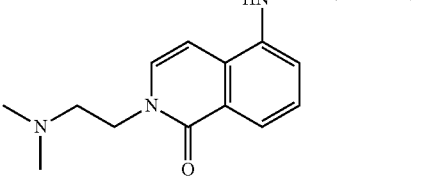 |
| 1002 | 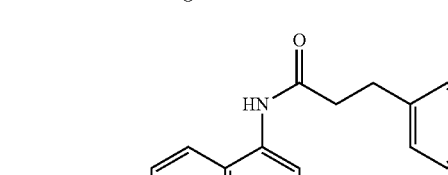 |
| 1003 | 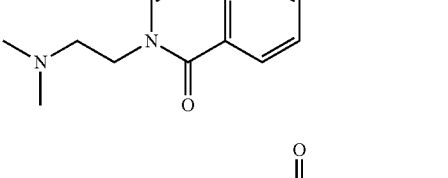 |
| 1004 | 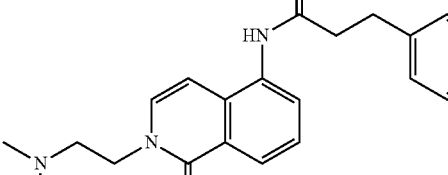 |
| 1005 | 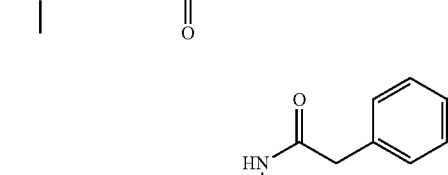 |

435
-continued
| ID | Structure |
|---|---|
| 1009 | 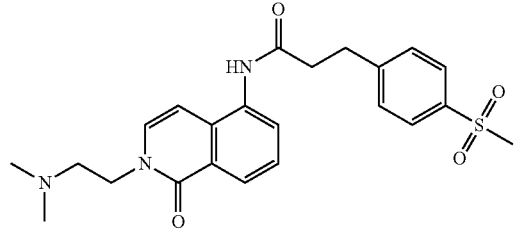 |
| 1010 | 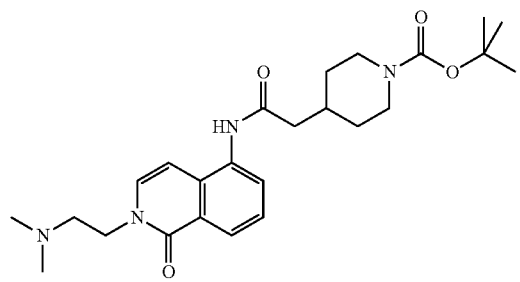 [SMILES: CN(C)CCn1ccc2c(NC(=O)CC3CCN(C(=O)OC(C)(C)C)CC3)cccc2c1=O] |
| 1011 | 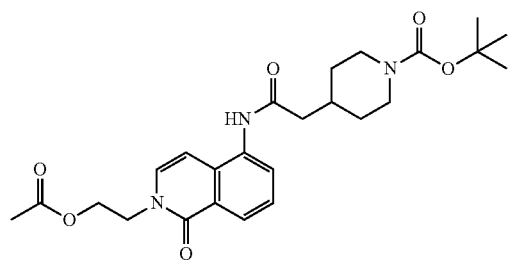 [SMILES: CC(=O)OCCn1ccc2c(NC(=O)CC3CCN(C(=O)OC(C)(C)C)CC3)cccc2c1=O] |
| 1016 | 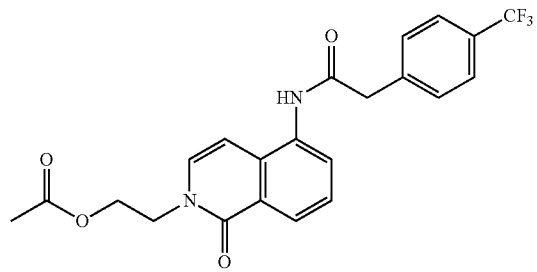 [SMILES: CC(=O)OCCn1ccc2c(NC(=O)Cc3ccc(C(F)(F)F)cc3)cccc2c1=O] |
| 1017 | 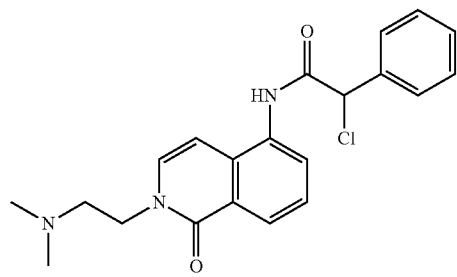 [SMILES: CN(C)CCn1ccc2c(NC(=O)C(Cl)c3ccccc3)cccc2c1=O] |
436
-continued
| ID | Structure |
|---|---|
| 1018 | 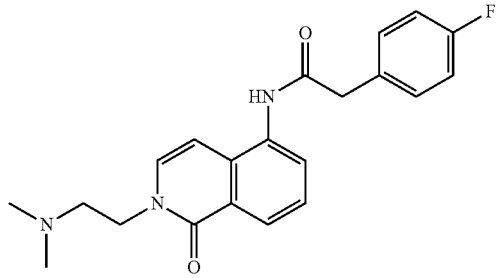 [SMILES: CN(C)CCn1ccc2c(NC(=O)Cc3ccc(F)cc3)cccc2c1=O] |
| 1019 | 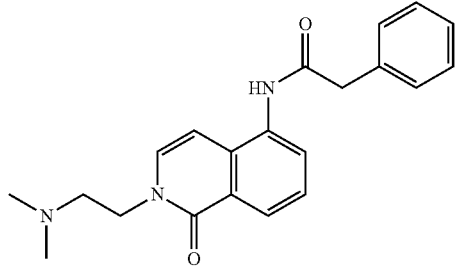 [SMILES: CN(C)CCn1ccc2c(NC(=O)Cc3ccccc3)cccc2c1=O] |
| 1020 | 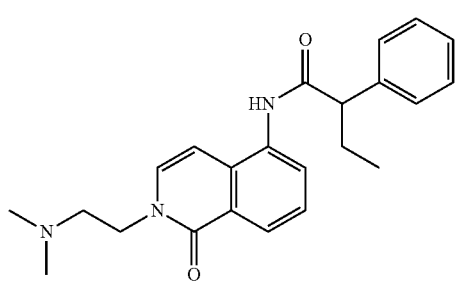 [SMILES: CCC(C(=O)Nc1cccc2c(=O)n(CCN(C)C)ccc12)c1ccccc1] |
| 1021 | 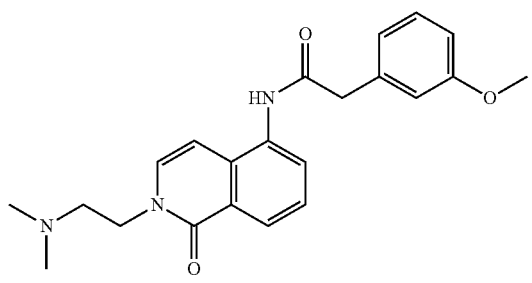 |
| 1022 | 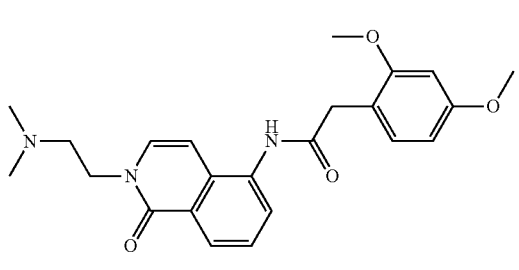 |

| ID | Structure | | ID | Structure |
|---|---|---|---|---|
| 1023 | 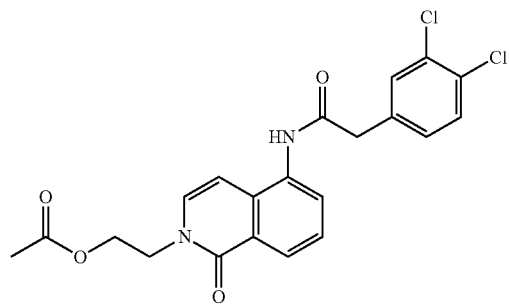 [SMILES: CC(=O)OCCn1ccc2c(NC(=O)Cc3ccc(Cl)c(Cl)c3)cccc2c1=O] | | 1032 | 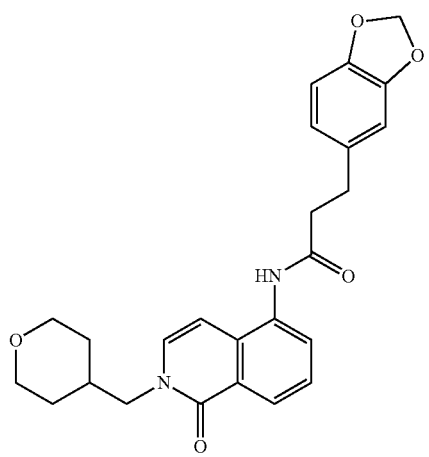 |
| 1027 | 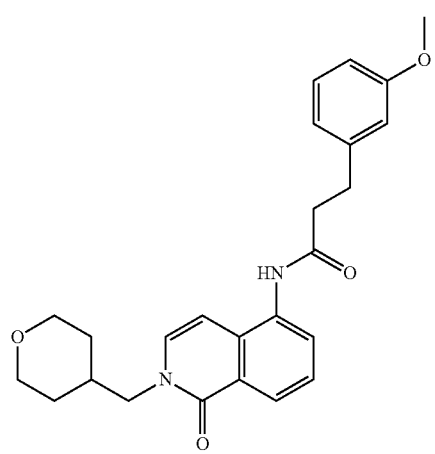 [SMILES: COc1cccc(CCC(=O)Nc2cccc3c(=O)n(CC4CCOCC4)ccc23)c1] | | 1036 | |
| 1028 | 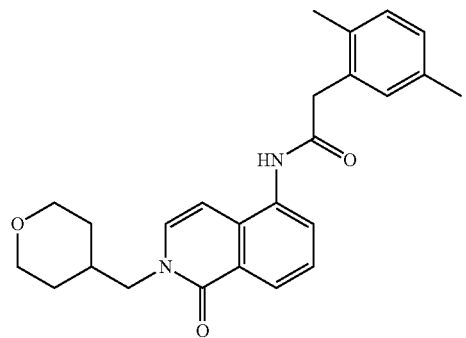 [SMILES: Cc1ccc(C)c(CC(=O)Nc2cccc3c(=O)n(CC4CCOCC4)ccc23)c1] | | 1037 | |
| 1031 | 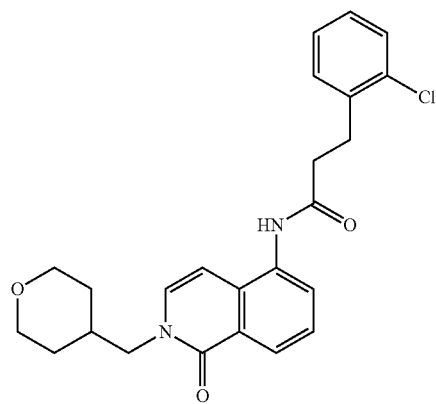 [SMILES: O=C(CCc1ccccc1Cl)Nc1cccc2c(=O)n(CC3CCOCC3)ccc12] | | | 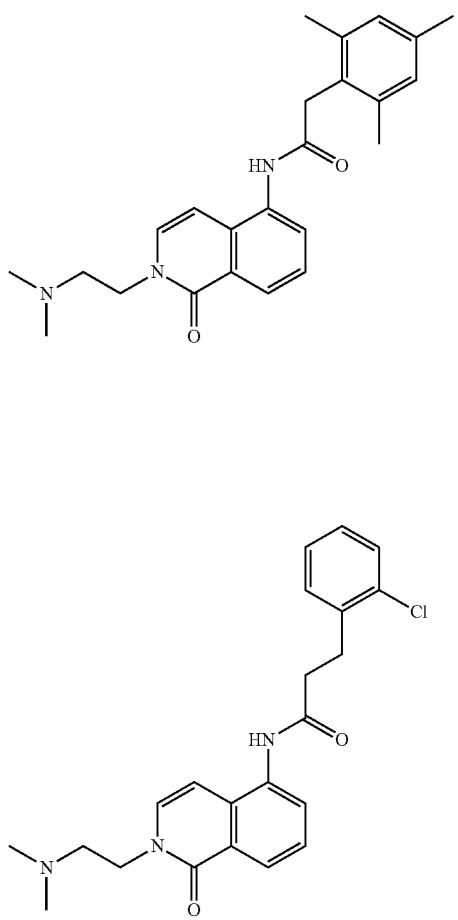 |

| ID | Structure | | ID | Structure |
|---|---|---|---|---|
| 1038 | 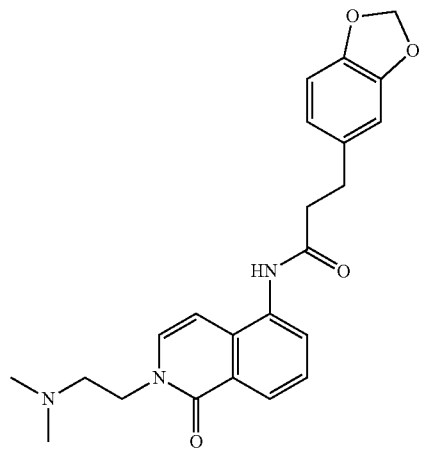 [SMILES: CN(C)CCn1ccc2c(NC(=O)CCc3ccc4c(c3)OCO4)cccc2c1=O] | | 1045 | 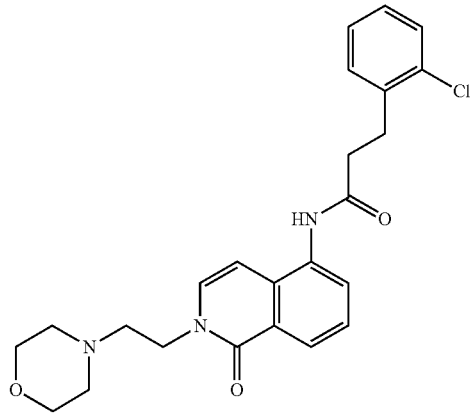 |
| 1041 | 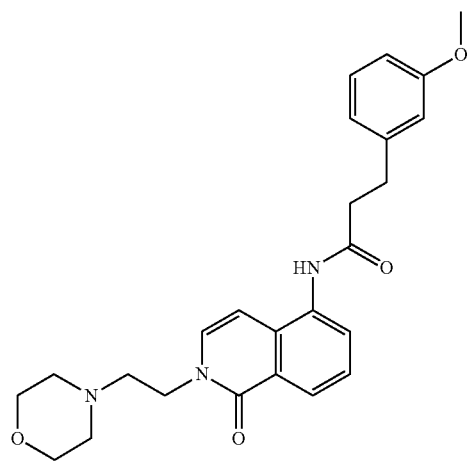 [SMILES: COc1cccc(CCC(=O)Nc2cccc3c(=O)n(CCN4CCOCC4)ccc23)c1] | | 1046 | 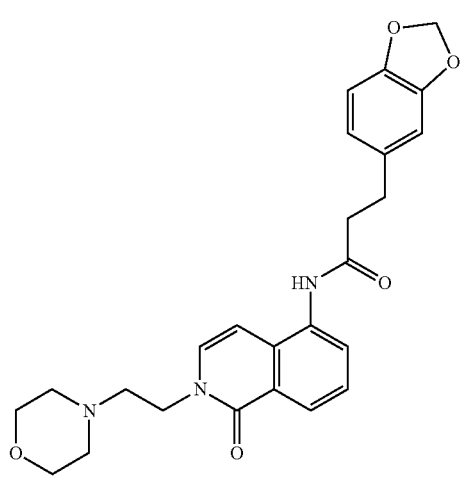 |
| 1042 | 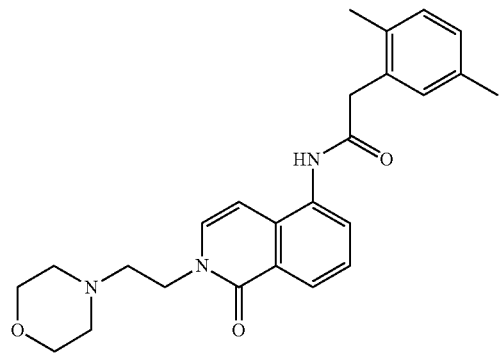 [SMILES: Cc1ccc(C)c(CC(=O)Nc2cccc3c(=O)n(CCN4CCOCC4)ccc23)c1] | | 1048 | 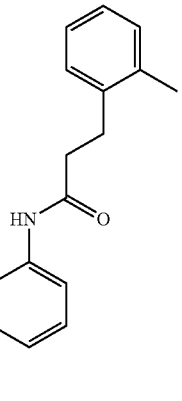 |

| ID | Structure |
|---|---|
| 1049 | 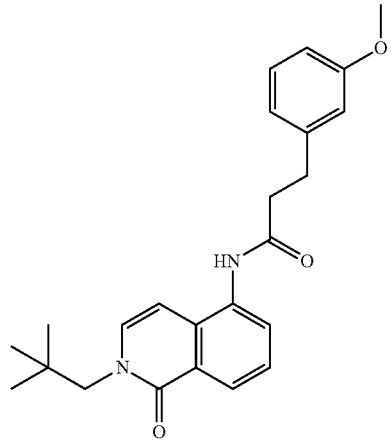 [SMILES: COc1cccc(CCC(=O)Nc2cccc3c(=O)n(CC(C)(C)C)ccc23)c1] |
| 1050 | 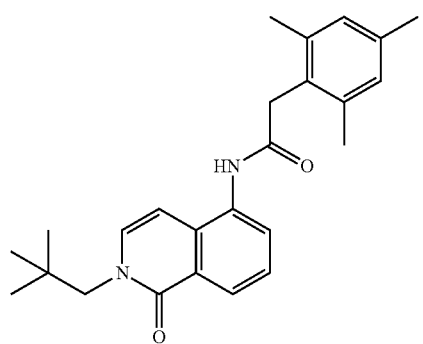 [SMILES: Cc1cc(C)c(CC(=O)Nc2cccc3c(=O)n(CC(C)(C)C)ccc23)c(C)c1] |
| 1051 | 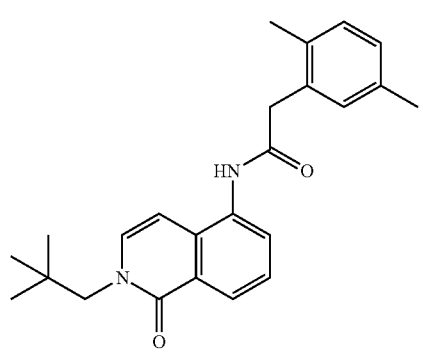 [SMILES: Cc1ccc(C)c(CC(=O)Nc2cccc3c(=O)n(CC(C)(C)C)ccc23)c1] |
| 1054 | 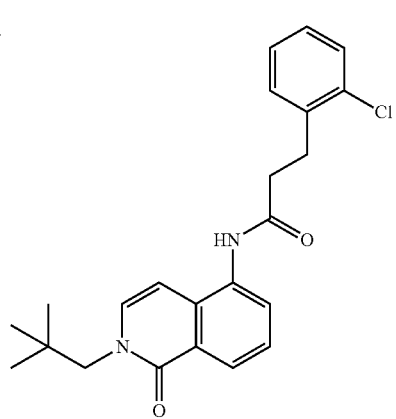 |
| ID | Structure |
|---|---|
| 1055 | 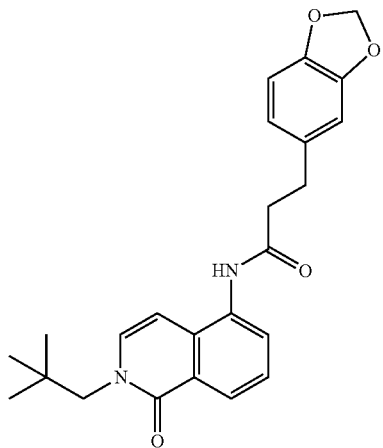 [SMILES: CC(C)(C)Cn1ccc2c(NC(=O)CCc3ccc4c(c3)OCO4)cccc2c1=O] |
| 1057 | 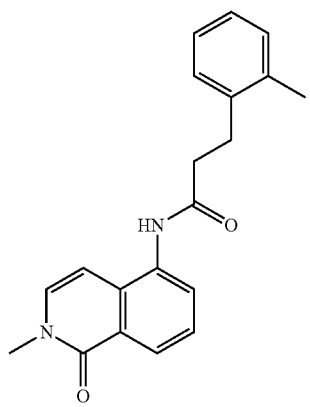 |
| 1058 | 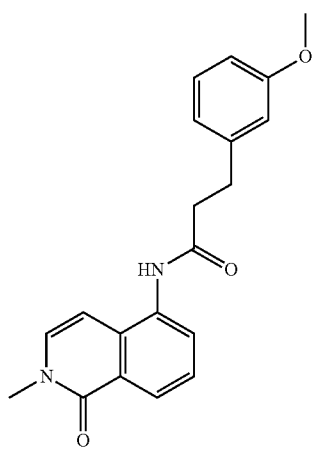 |

| ID | Structure |
|---|---|
| 1062 | 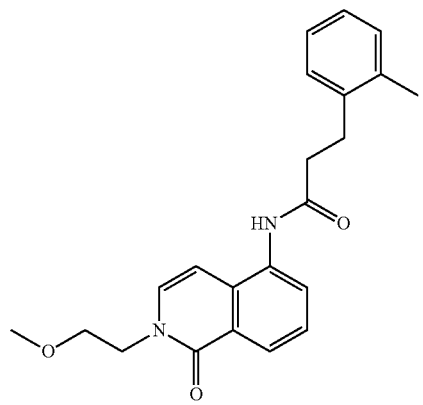 |
| 1064 | 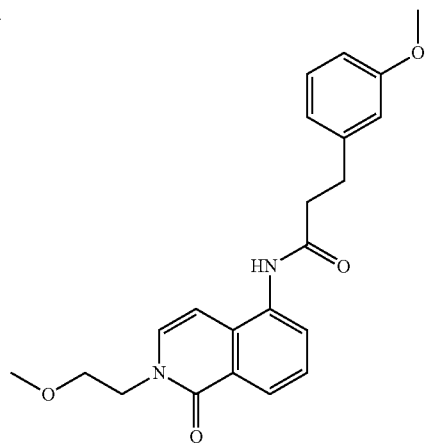 |
| 1065 | 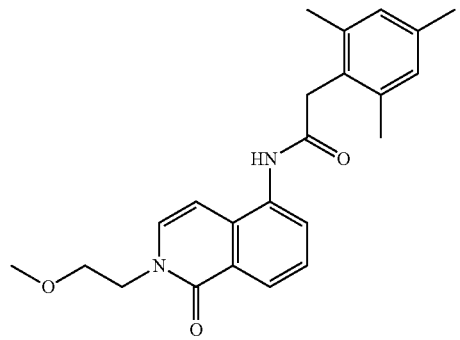 |
| 1066 | 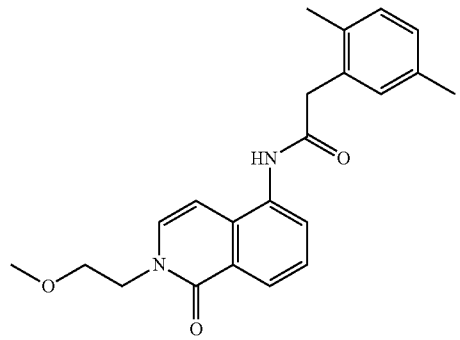 |
| ID | Structure |
|---|---|
| 1069 | 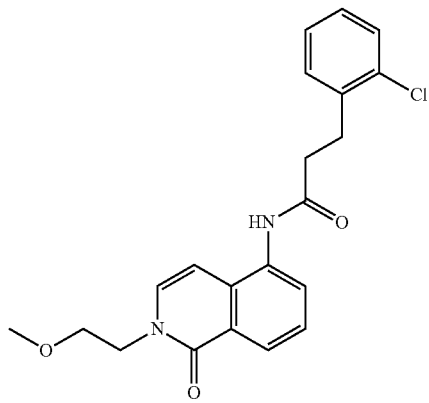 |
| 1070 | 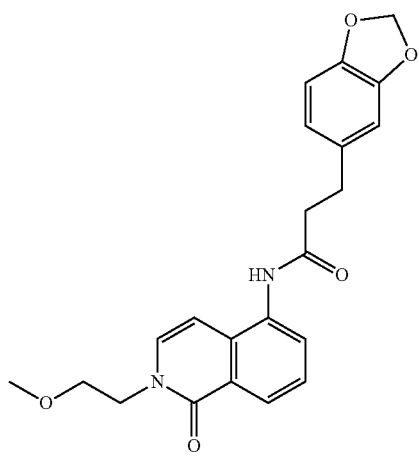 [SMILES: COCCn1ccc2c(NC(=O)CCc3ccc4c(c3)OCO4)cccc2c1=O] |
| 1075 | 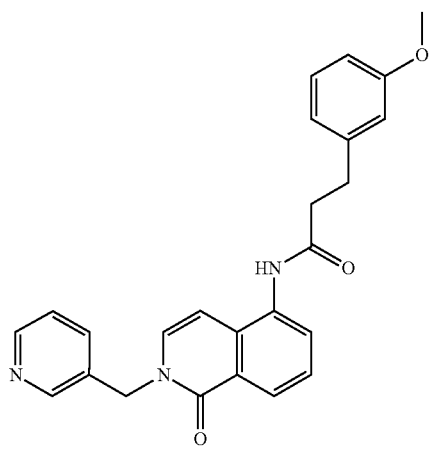 [SMILES: COc1cccc(CCC(=O)Nc2cccc3c(=O)n(Cc4cccnc4)ccc23)c1] |

| ID | Structure | | ID | Structure |
|---|---|---|---|---|
| 1076 | 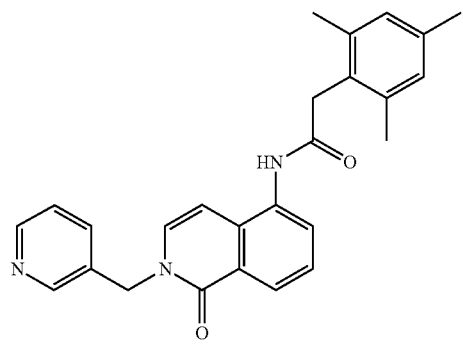 [SMILES: Cc1cc(C)c(CC(=O)Nc2cccc3c(=O)n(Cc4cccnc4)ccc23)c(C)c1] | | 1093 | 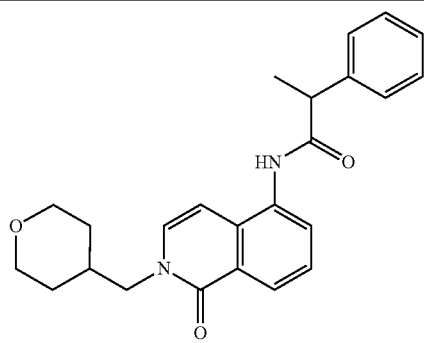 |
| 1077 | 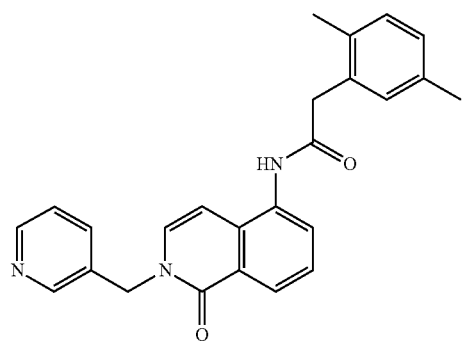 [SMILES: Cc1ccc(C)c(CC(=O)Nc2cccc3c(=O)n(Cc4cccnc4)ccc23)c1] | | 1094 | 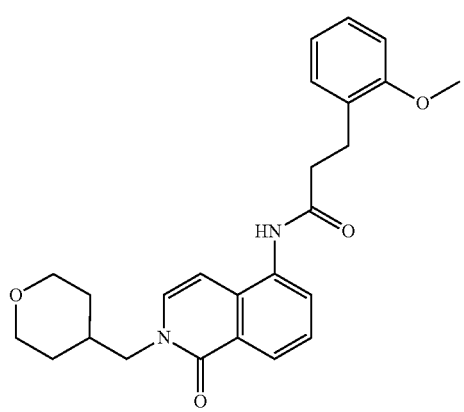 |
| 1079 | 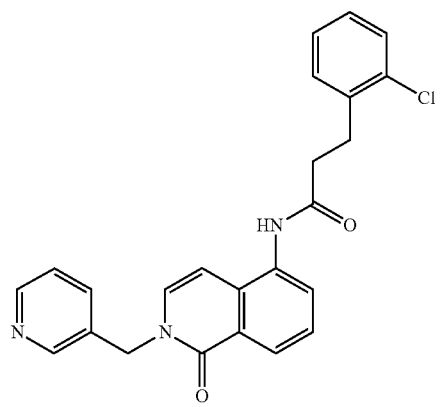 [SMILES: O=C(CCc1ccccc1Cl)Nc1cccc2c(=O)n(Cc3cccnc3)ccc12] | | 1095 | 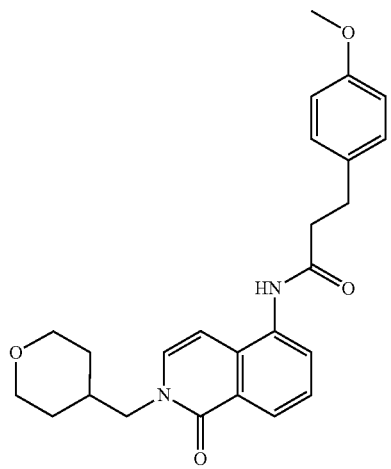 |
| 1080 | 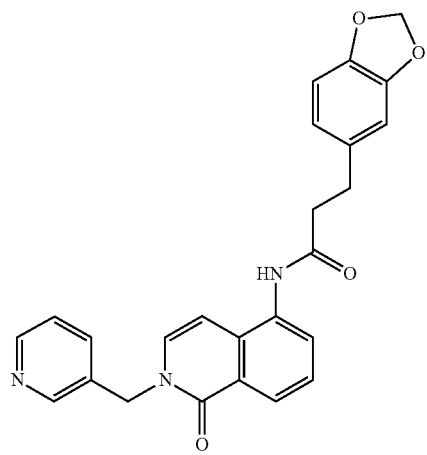 [SMILES: O=C(CCc1ccc2c(c1)OCO2)Nc1cccc2c(=O)n(Cc3cccnc3)ccc12] | | 1097 | 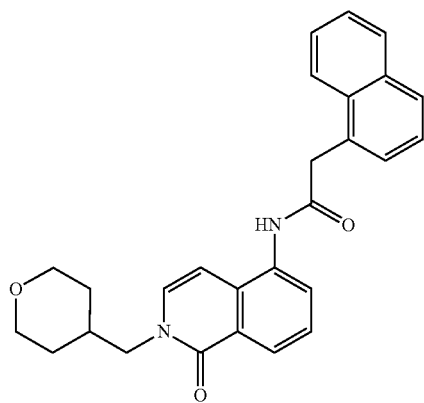 [SMILES: O=C(Cc1cccc2ccccc12)Nc1cccc2c(=O)n(CC3CCOCC3)ccc12] |

| ID | Structure |
|---|---|
| 1099 | 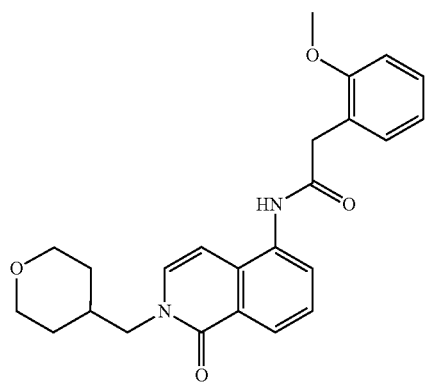 [SMILES: COc1ccccc1CC(=O)Nc1cccc2c(=O)n(CC3CCOCC3)ccc12] |
| 1100 | 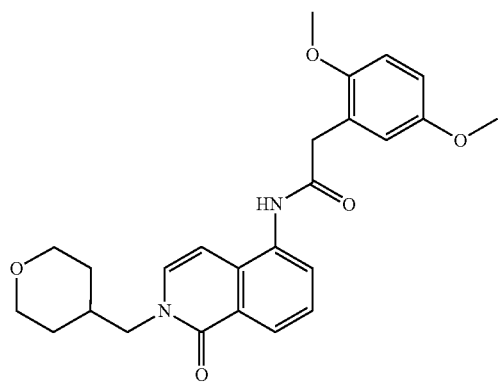 [SMILES: COc1ccc(OC)c(CC(=O)Nc2cccc3c(=O)n(CC4CCOCC4)ccc23)c1] |
| 1101 | 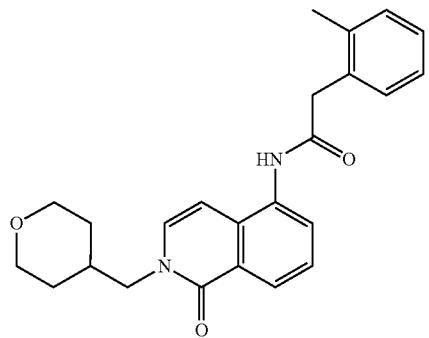 [SMILES: Cc1ccccc1CC(=O)Nc1cccc2c(=O)n(CC3CCOCC3)ccc12] |
| 1102 | 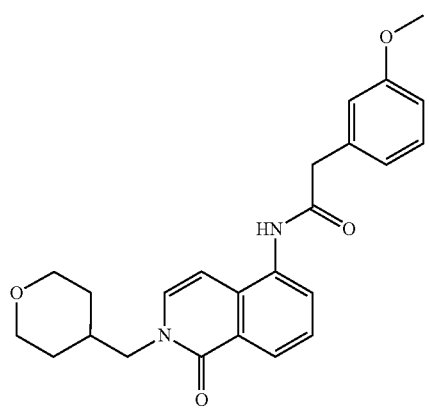 [SMILES: COc1cccc(CC(=O)Nc2cccc3c(=O)n(CC4CCOCC4)ccc23)c1] |
| ID | Structure |
|---|---|
| 1103 | 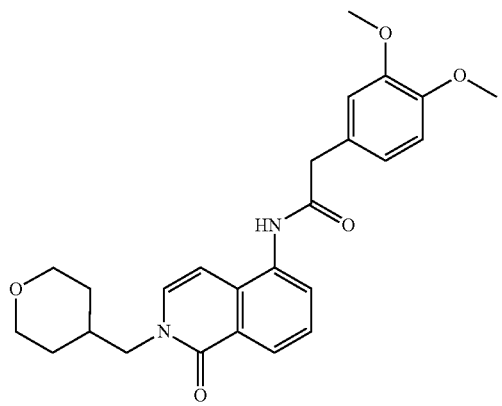 [SMILES: COc1ccc(CC(=O)Nc2cccc3c(=O)n(CC4CCOCC4)ccc23)cc1OC] |
| 1104 | 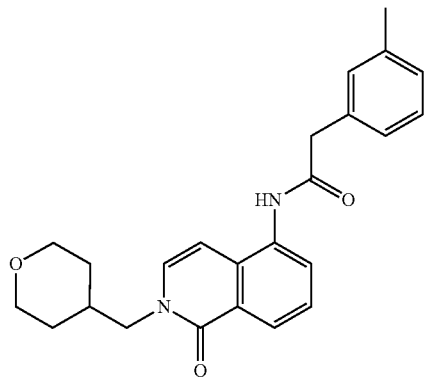 [SMILES: Cc1cccc(CC(=O)Nc2cccc3c(=O)n(CC4CCOCC4)ccc23)c1] |
| 1105 | 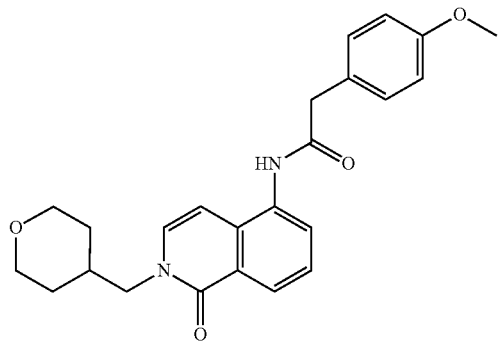 [SMILES: COc1ccc(CC(=O)Nc2cccc3c(=O)n(CC4CCOCC4)ccc23)cc1] |
| 1106 | 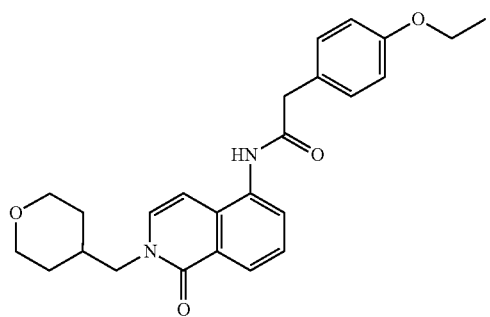 [SMILES: CCOc1ccc(CC(=O)Nc2cccc3c(=O)n(CC4CCOCC4)ccc23)cc1] |

-continued
| ID | Structure |
|---|---|
| 1107 | 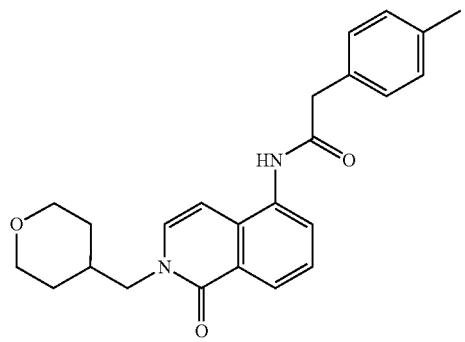 [SMILES: Cc1ccc(CC(=O)Nc2cccc3c(=O)n(CC4CCOCC4)ccc23)cc1] |
| 1108 | 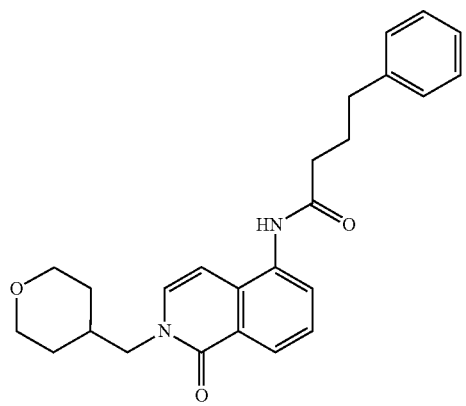 [SMILES: O=C(CCCc1ccccc1)Nc1cccc2c(=O)n(CC3CCOCC3)ccc12] |
| 1110 | 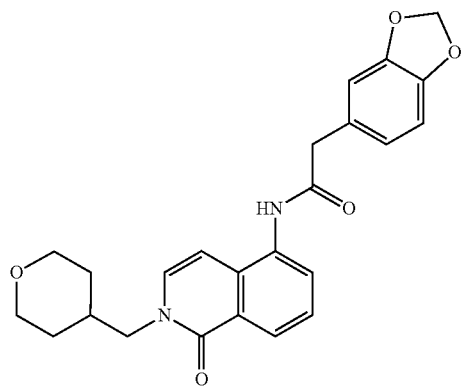 [SMILES: O=C(Cc1ccc2c(c1)OCO2)Nc1cccc2c(=O)n(CC3CCOCC3)ccc12] |
| 1111 | 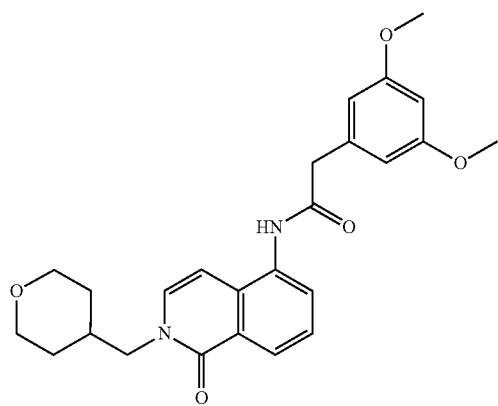 [SMILES: COc1cc(CC(=O)Nc2cccc3c(=O)n(CC4CCOCC4)ccc23)cc(OC)c1] |
-continued
| ID | Structure |
|---|---|
| 1119 | 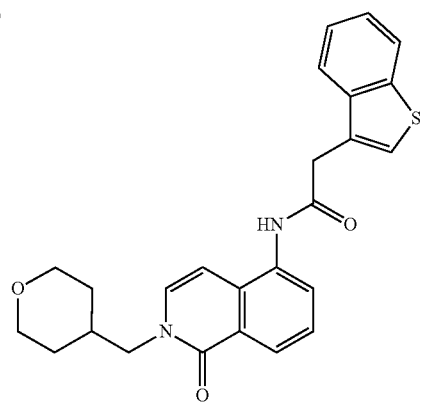 [SMILES: O=C(Cc1csc2ccccc12)Nc1cccc2c(=O)n(CC3CCOCC3)ccc12] |
| 1121 | 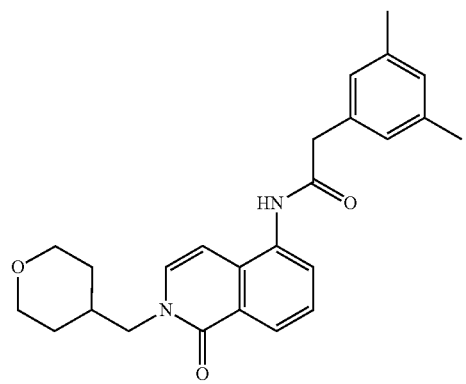 [SMILES: Cc1cc(C)cc(CC(=O)Nc2cccc3c(=O)n(CC4CCOCC4)ccc23)c1] |
| 1123 | 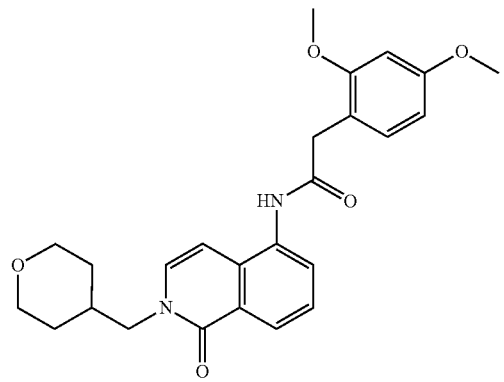 [SMILES: COc1ccc(CC(=O)Nc2cccc3c(=O)n(CC4CCOCC4)ccc23)c(OC)c1] |

| ID | Structure | | ID | Structure |
|---|---|---|---|---|
| 1125 | 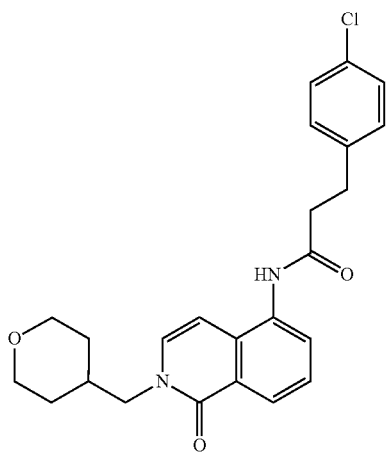 [SMILES: O=C(CCc1ccc(Cl)cc1)Nc1cccc2c(=O)n(CC3CCOCC3)ccc12] | | 1130 | 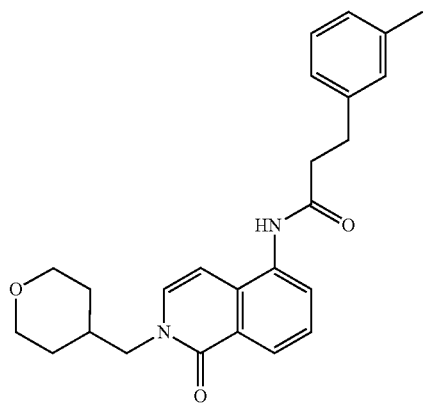 |
| 1126 | 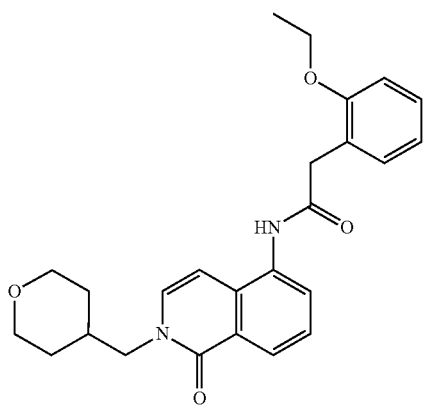 [SMILES: CCOc1ccccc1CC(=O)Nc1cccc2c(=O)n(CC3CCOCC3)ccc12] | | 1134 | 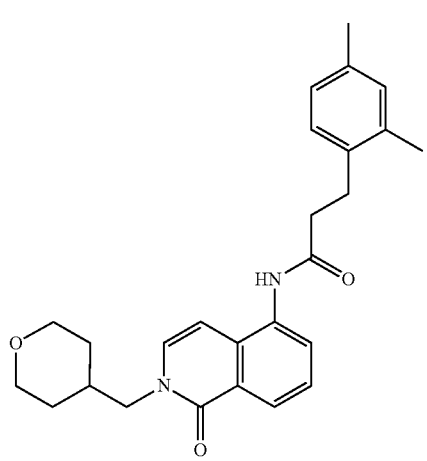 |
| 1127 | 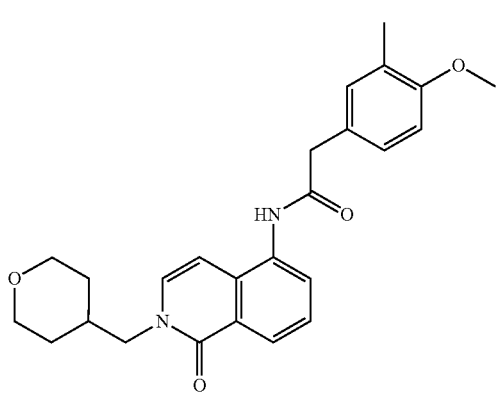 [SMILES: COc1ccc(CC(=O)Nc2cccc3c(=O)n(CC4CCOCC4)ccc23)cc1C] | | 1135 | 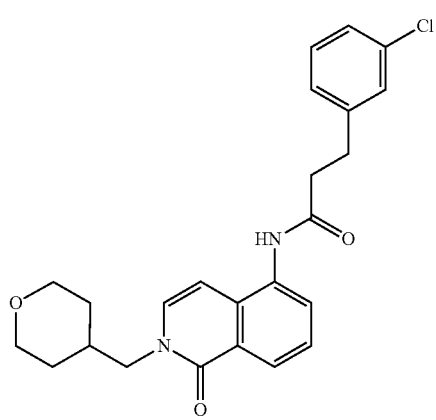 [SMILES: O=C(CCc1cccc(Cl)c1)Nc1cccc2c(=O)n(CC3CCOCC3)ccc12] |
| | | | 1148 | 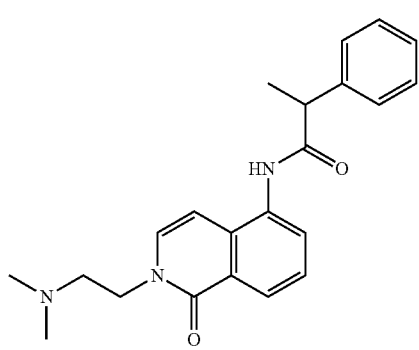 [SMILES: CC(C(=O)Nc1cccc2c(=O)n(CCN(C)C)ccc12)c1ccccc1] |

453
-continued
| ID | Structure |
|---|---|
| 1149 | 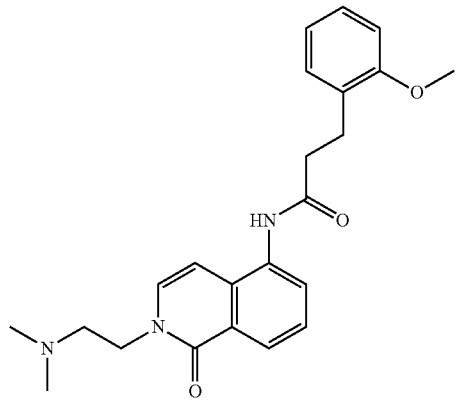 |
| 1150 | 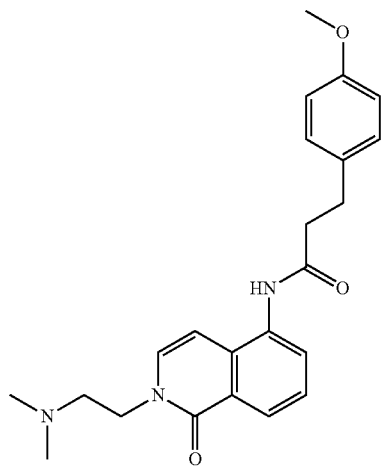 [SMILES: COc1ccc(CCC(=O)Nc2cccc3c(=O)n(CCN(C)C)ccc23)cc1] |
| 1152 | 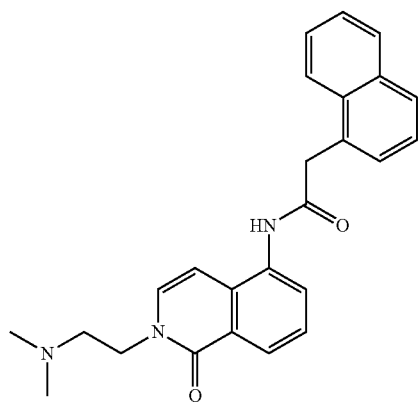 [SMILES: CN(C)CCn1ccc2c(NC(=O)Cc3cccc4ccccc34)cccc2c1=O] |
454
-continued
| ID | Structure |
|---|---|
| 1154 | 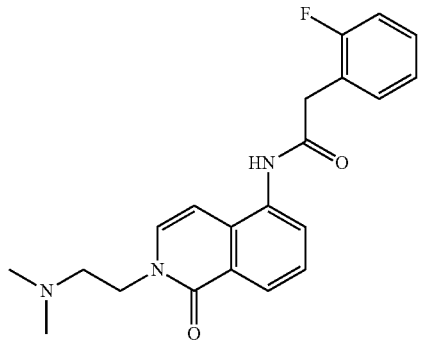 [SMILES: CN(C)CCn1ccc2c(NC(=O)Cc3ccccc3F)cccc2c1=O] |
| 1155 | 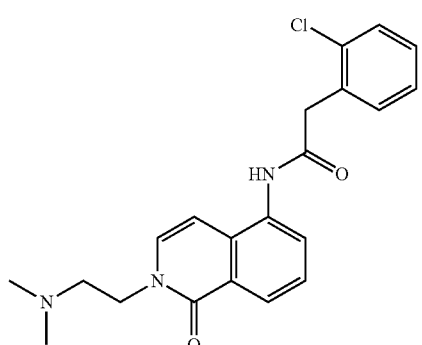 |
| 1156 | 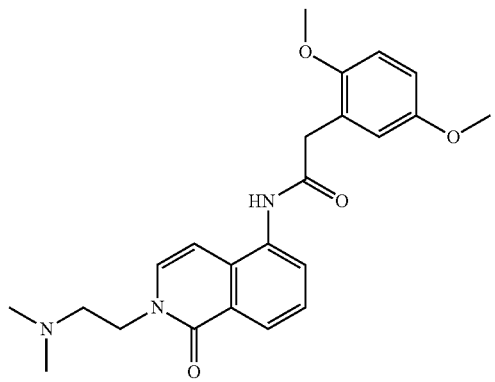 |
| 1157 | 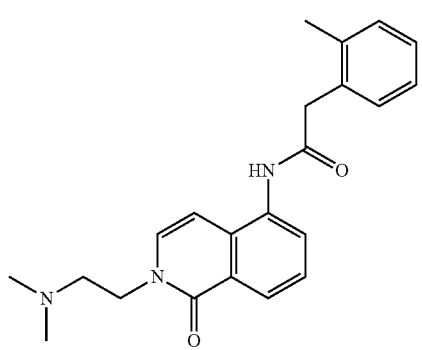 [SMILES: Cc1ccccc1CC(=O)Nc1cccc2c(=O)n(CCN(C)C)ccc12] |

| ID | Structure | | ID | Structure |
|---|---|---|---|---|
| 1158 | 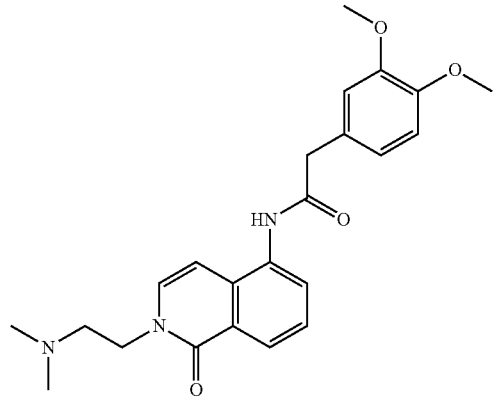 | | 1163 | 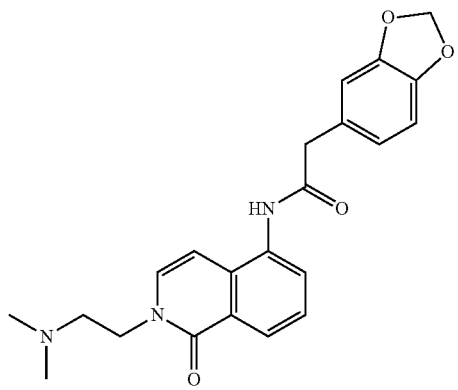 |
| 1159 | 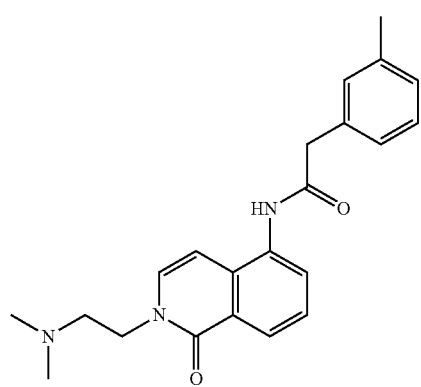 | | 1164 | 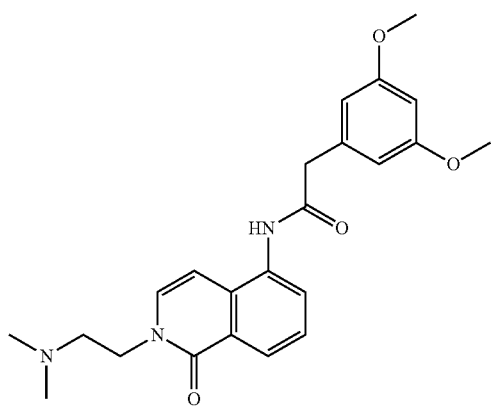 |
| 1160 | 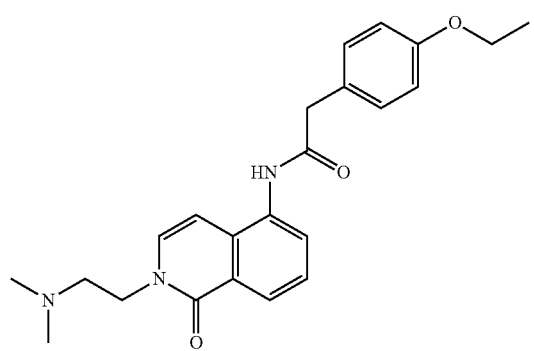 [SMILES: CCOc1ccc(CC(=O)Nc2cccc3c(=O)n(CCN(C)C)ccc23)cc1] | | 1171 | 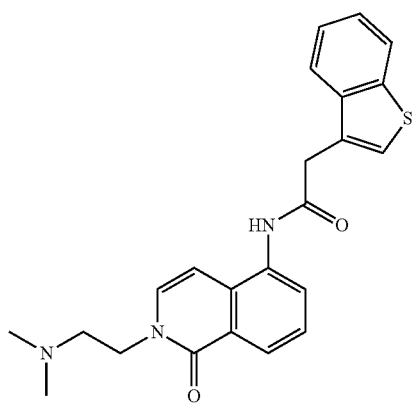 [SMILES: CN(C)CCn1ccc2c(NC(=O)Cc3csc4ccccc34)cccc2c1=O] |
| 1161 | 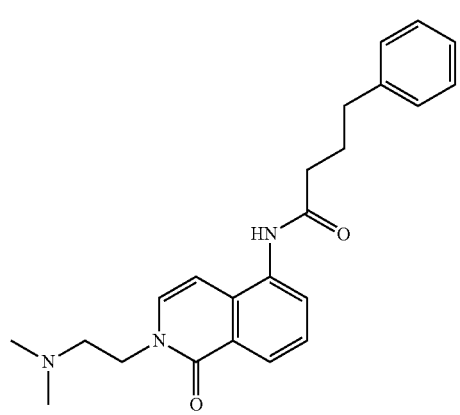 | | 1173 | 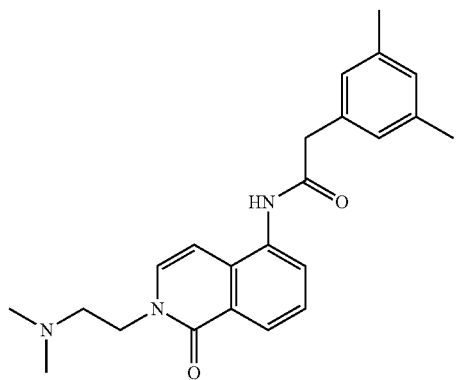 |

-continued
| ID | Structure |
|---|---|
| 1176 | 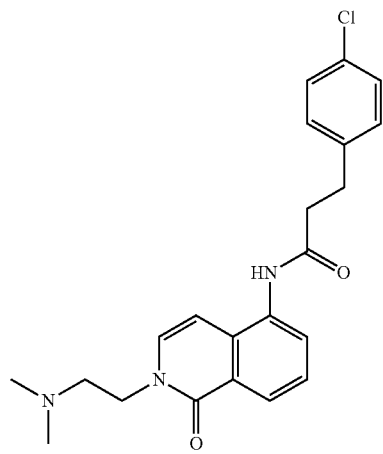 |
| 1177 | 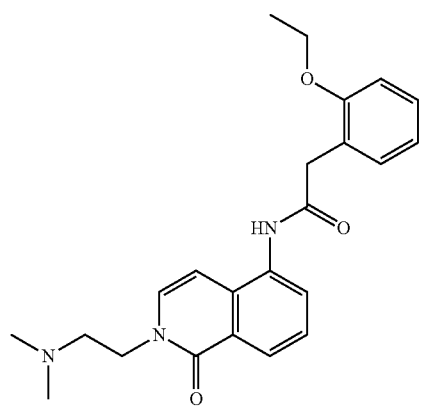 [SMILES: CCOc1ccccc1CC(=O)Nc1cccc2c(=O)n(CCN(C)C)ccc12] |
| 1178 | 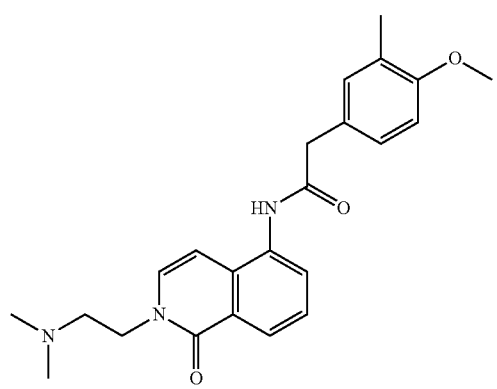 |
-continued
| ID | Structure |
|---|---|
| 1181 | 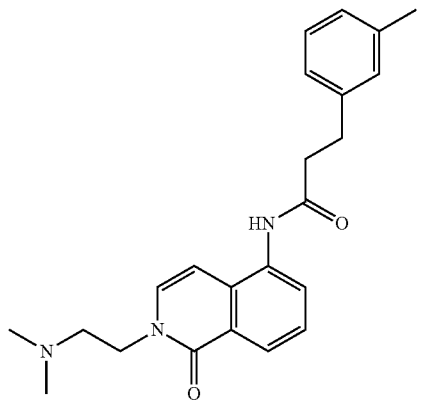 |
| 1185 | 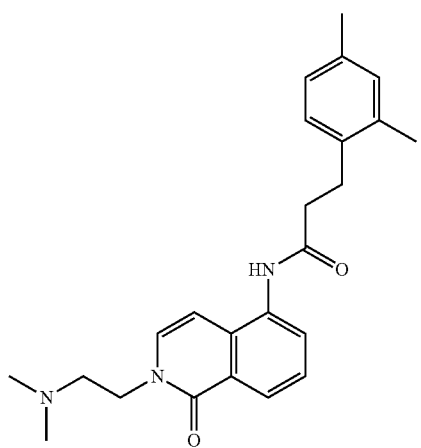 |
| 1186 | 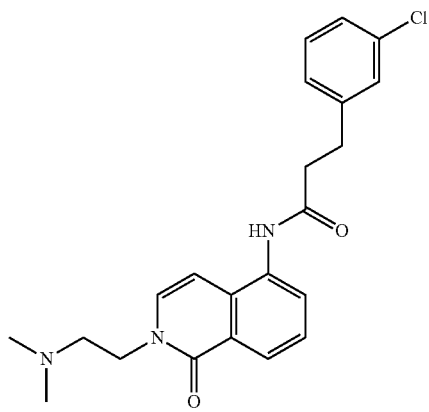 [SMILES: CN(C)CCn1ccc2c(NC(=O)CCc3cccc(Cl)c3)cccc2c1=O] |
| 1200 | 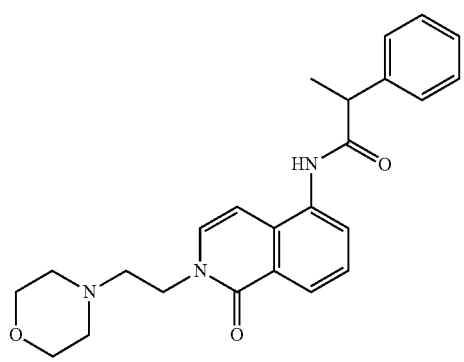 [SMILES: CC(C(=O)Nc1cccc2c(=O)n(CCN3CCOCC3)ccc12)c1ccccc1] |

| ID | Structure | | ID | Structure |
|---|---|---|---|---|
| 1201 | 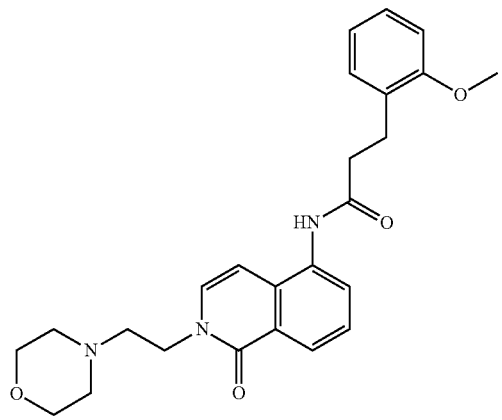 [SMILES: COc1ccccc1CCC(=O)Nc1cccc2c(=O)n(CCN3CCOCC3)ccc12] | | 1204 | 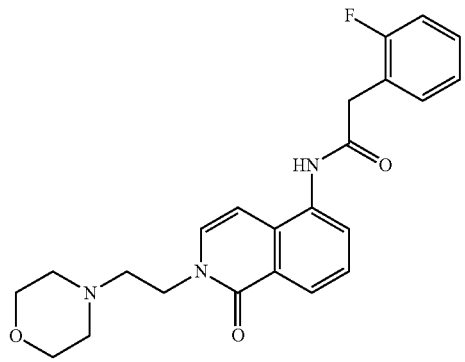 |
| 1202 | 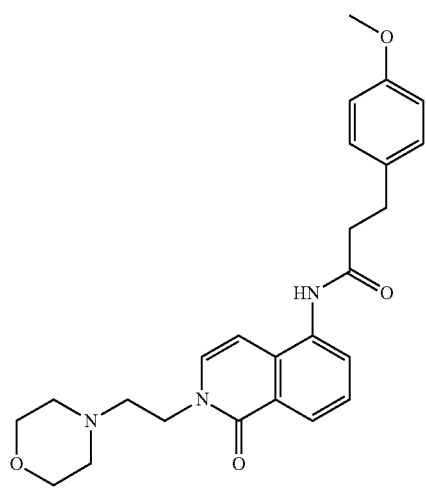 [SMILES: COc1ccc(CCC(=O)Nc2cccc3c(=O)n(CCN4CCOCC4)ccc23)cc1] | | 1205 | 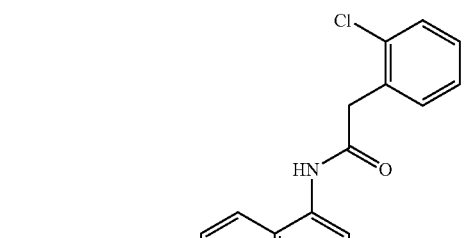 |
| | | | 1206 | 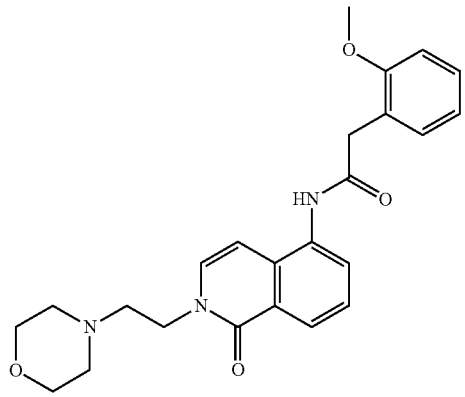 |
| 1203 | 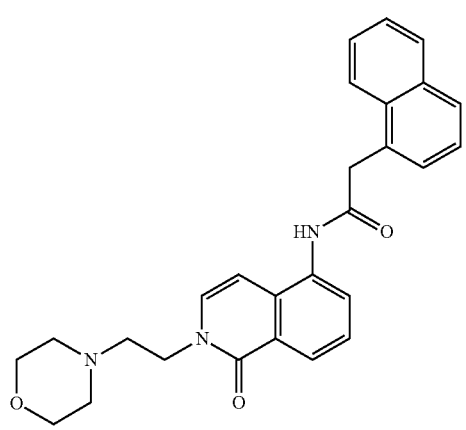 [SMILES: O=C(Cc1cccc2ccccc12)Nc1cccc2c(=O)n(CCN3CCOCC3)ccc12] | | 1207 | 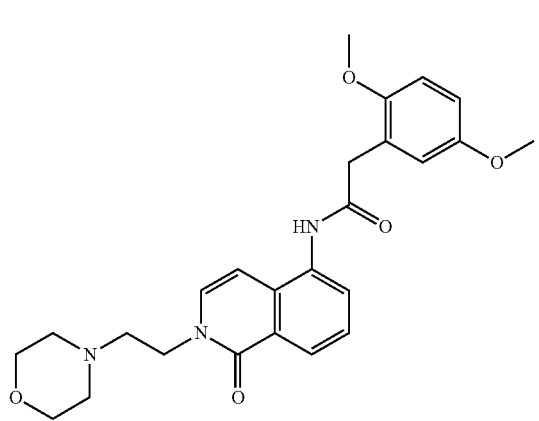 [SMILES: COc1ccc(OC)c(CC(=O)Nc2cccc3c(=O)n(CCN4CCOCC4)ccc23)c1] |

461
-continued
| ID | Structure |
|---|---|
| 1208 | 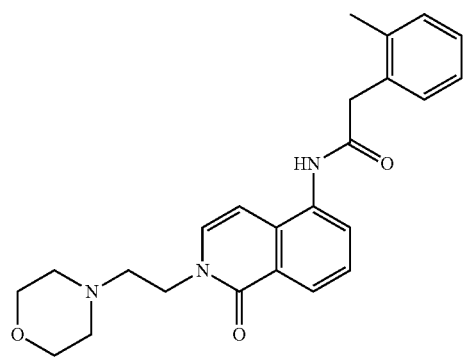 [SMILES: Cc1ccccc1CC(=O)Nc1cccc2c(=O)n(CCN3CCOCC3)ccc12] |
| 1209 | 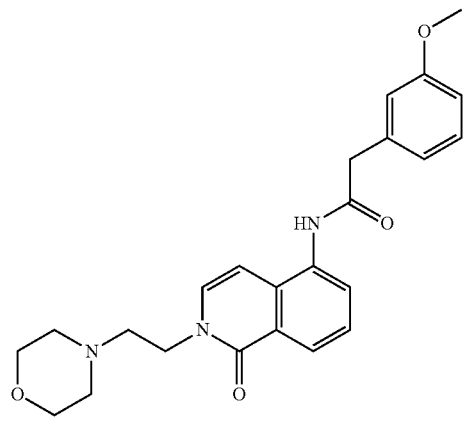 [SMILES: COc1cccc(CC(=O)Nc2cccc3c(=O)n(CCN4CCOCC4)ccc23)c1] |
| 1210 | 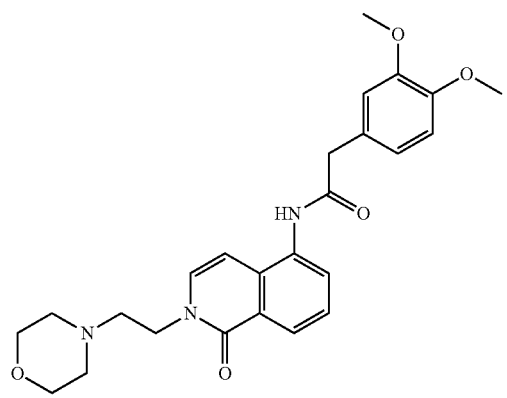 [SMILES: COc1ccc(CC(=O)Nc2cccc3c(=O)n(CCN4CCOCC4)ccc23)cc1OC] |
| 1211 | 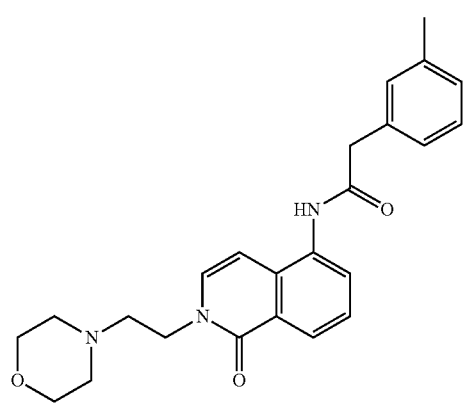 [SMILES: Cc1cccc(CC(=O)Nc2cccc3c(=O)n(CCN4CCOCC4)ccc23)c1] |
462
-continued
| ID | Structure |
|---|---|
| 1212 | 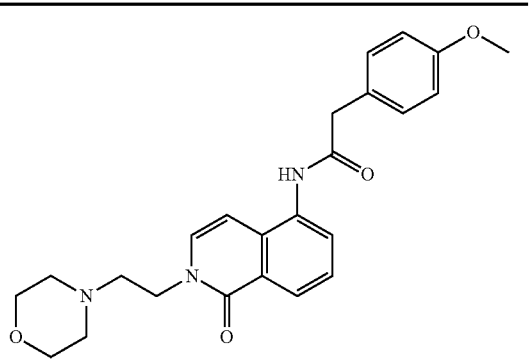 |
| 1213 | 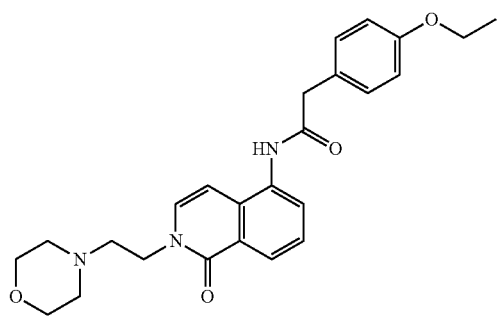 [SMILES: CCOc1ccc(CC(=O)Nc2cccc3c(=O)n(CCN4CCOCC4)ccc23)cc1] |
| 1214 | 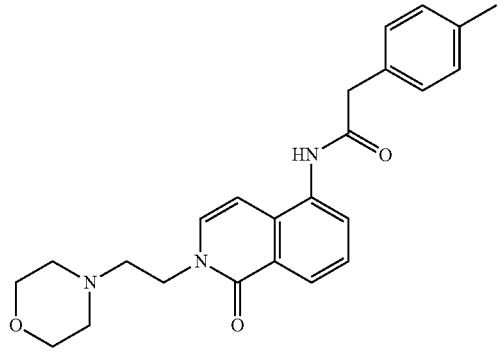 [SMILES: Cc1ccc(CC(=O)Nc2cccc3c(=O)n(CCN4CCOCC4)ccc23)cc1] |
| 1215 | 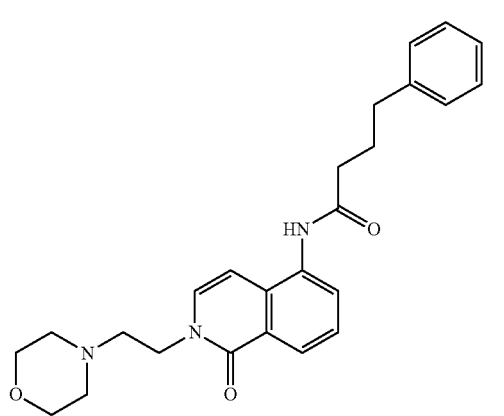 [SMILES: O=C(CCCc1ccccc1)Nc1cccc2c(=O)n(CCN3CCOCC3)ccc12] |

463
-continued
| ID | Structure |
|---|---|
| 1217 | 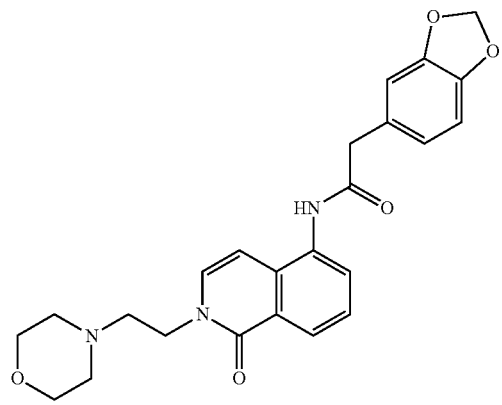 [SMILES: O=C(Cc1ccc2c(c1)OCO2)Nc1cccc2c(=O)n(CCN3CCOCC3)ccc12] |
| 1218 | 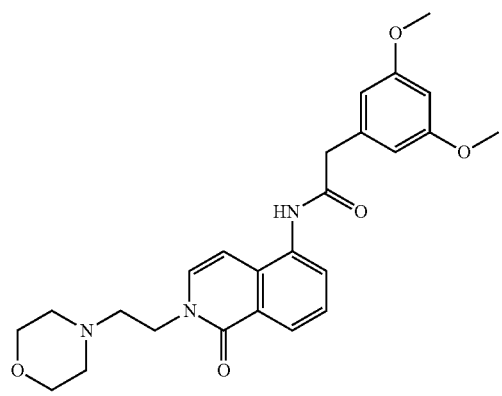 [SMILES: COc1cc(CC(=O)Nc2cccc3c(=O)n(CCN4CCOCC4)ccc23)cc(OC)c1] |
| 1226 | 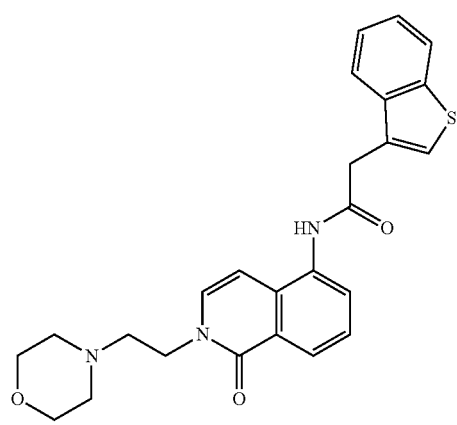 [SMILES: O=C(Cc1csc2ccccc12)Nc1cccc2c(=O)n(CCN3CCOCC3)ccc12] |
| 1228 | 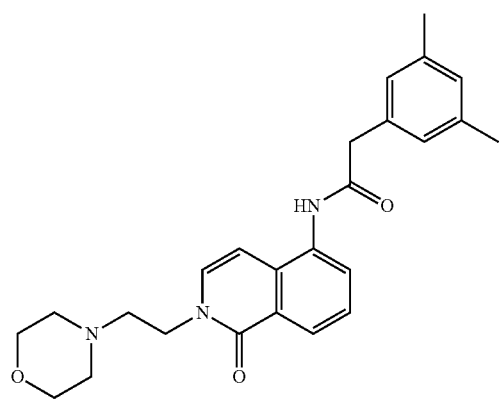 [SMILES: Cc1cc(C)cc(CC(=O)Nc2cccc3c(=O)n(CCN4CCOCC4)ccc23)c1] |
464
-continued
| ID | Structure |
|---|---|
| 1230 | 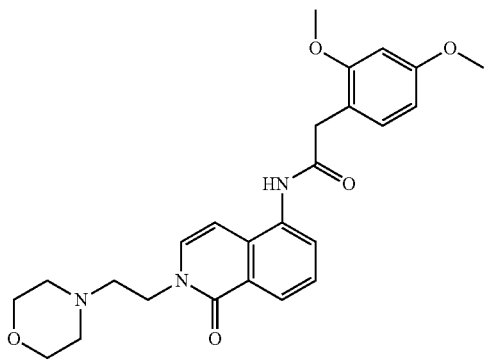 [SMILES: COc1ccc(CC(=O)Nc2cccc3c(=O)n(CCN4CCOCC4)ccc23)c(OC)c1] |
| 1232 | 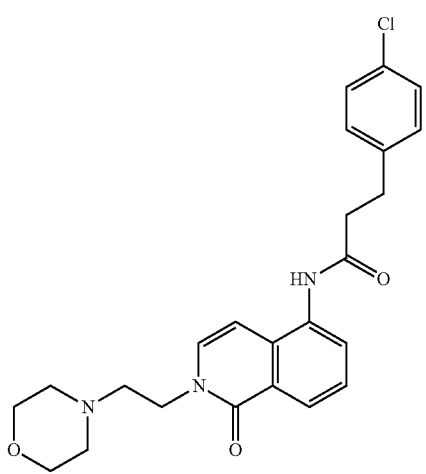 [SMILES: O=C(CCc1ccc(Cl)cc1)Nc1cccc2c(=O)n(CCN3CCOCC3)ccc12] |
| 1233 | 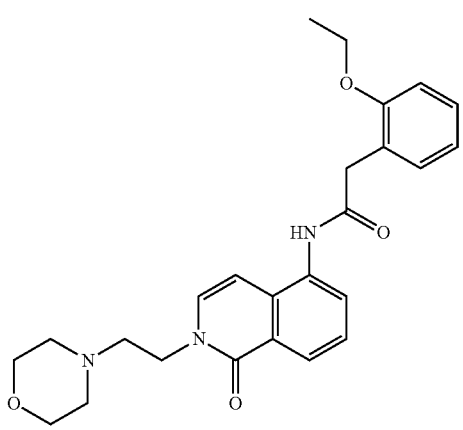 [SMILES: CCOc1ccccc1CC(=O)Nc1cccc2c(=O)n(CCN3CCOCC3)ccc12] |

465
-continued

| ID | Structure |
|---|---|
| 1234 | 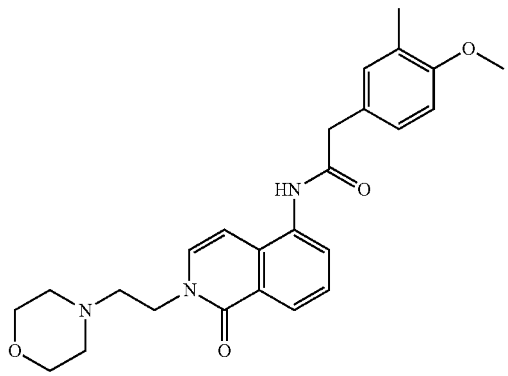 [SMILES: COc1ccc(CC(=O)Nc2cccc3c(=O)n(CCN4CCOCC4)ccc23)cc1C] |
| 1237 | 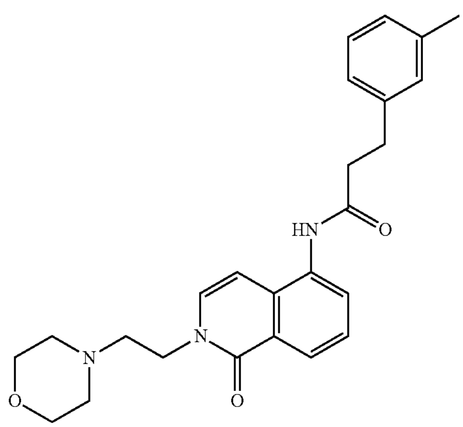 [SMILES: Cc1cccc(CCC(=O)Nc2cccc3c(=O)n(CCN4CCOCC4)ccc23)c1] |
| 1241 | 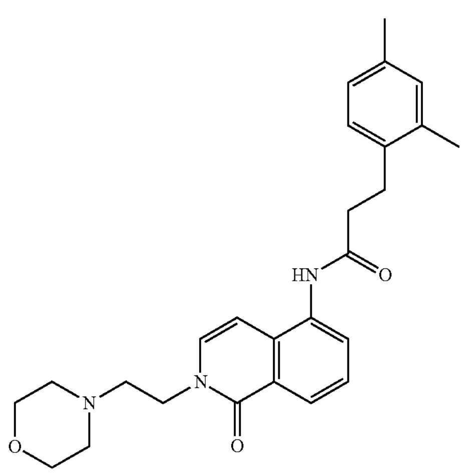 [SMILES: Cc1ccc(CCC(=O)Nc2cccc3c(=O)n(CCN4CCOCC4)ccc23)c(C)c1] |

466
-continued

| ID | Structure |
|---|---|
| 1242 | 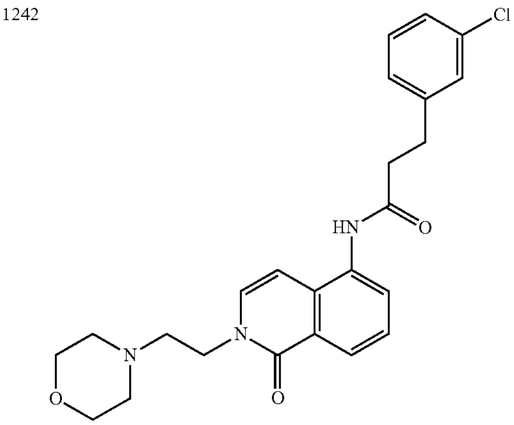 |
| 1247 | 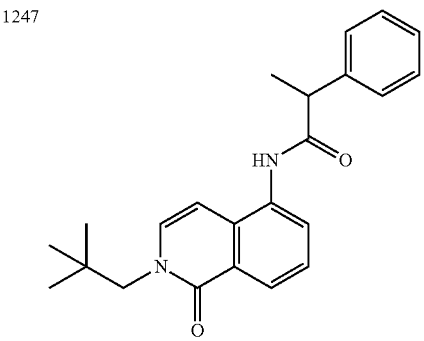 |
| 1248 | 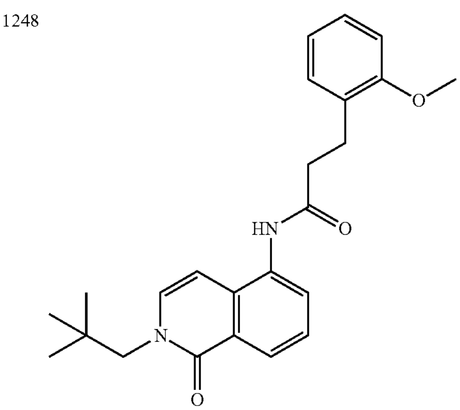 |
| 1250 | 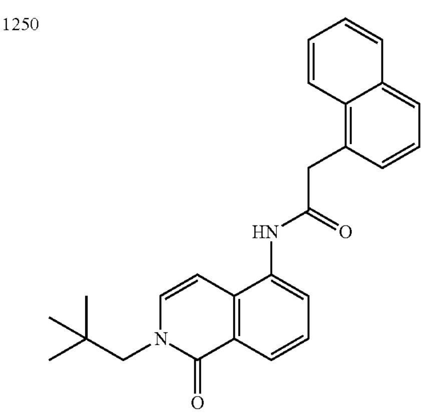 |

-continued
| ID | Structure |
|---|---|
| 1252 | 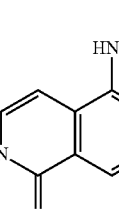 |
| 1253 | 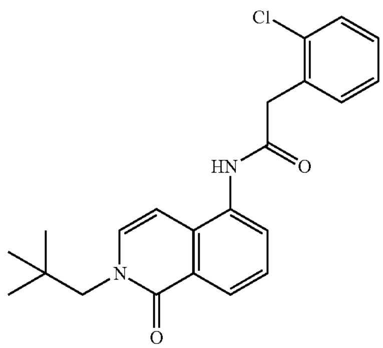 [SMILES: CC(C)(C)Cn1ccc2c(NC(=O)Cc3ccccc3Cl)cccc2c1=O] |
| 1254 | 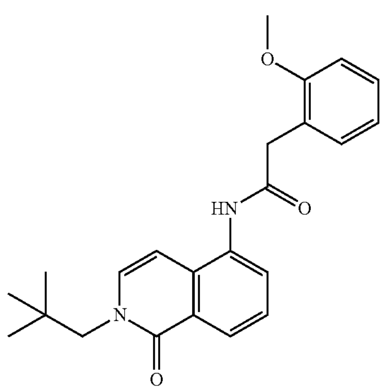 [SMILES: COc1ccccc1CC(=O)Nc1cccc2c(=O)n(CC(C)(C)C)ccc12] |
| 1255 | 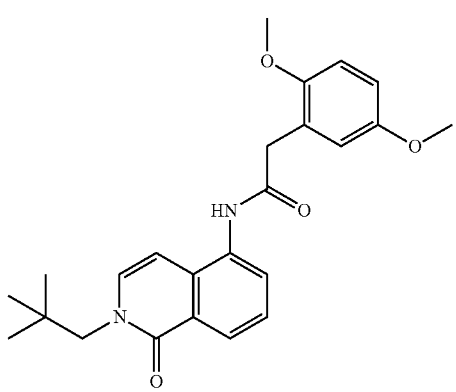 [SMILES: COc1ccc(OC)c(CC(=O)Nc2cccc3c(=O)n(CC(C)(C)C)ccc23)c1] |
-continued
| ID | Structure |
|---|---|
| 1256 | 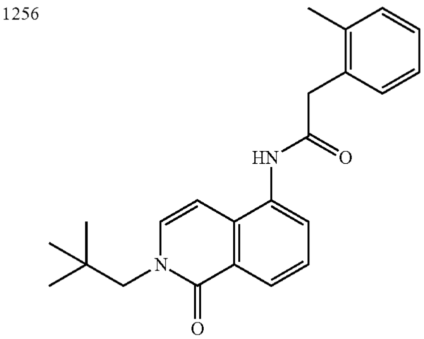 |
| 1257 | 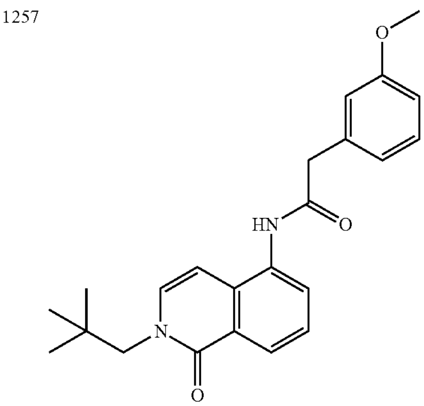 |
| 1258 | 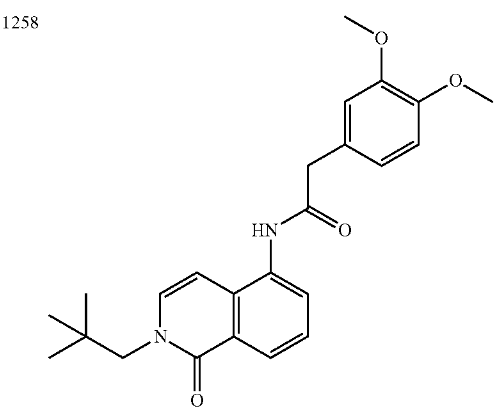 |
| 1259 | 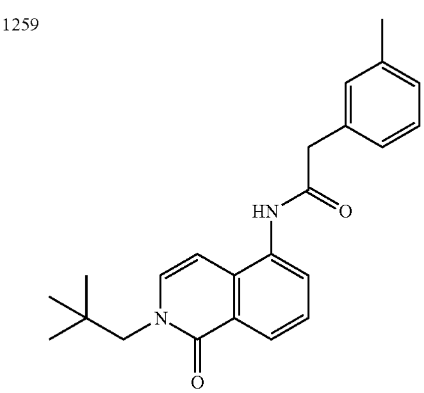 |

| ID | Structure |
|---|---|
| 1260 | 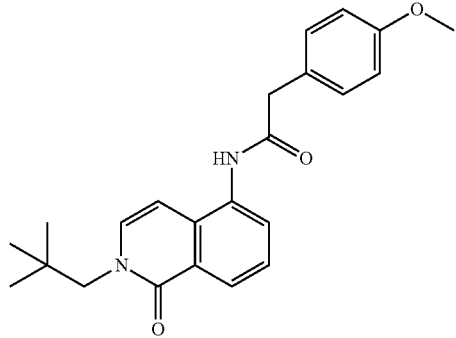 [SMILES: COc1ccc(CC(=O)Nc2cccc3c(=O)n(CC(C)(C)C)ccc23)cc1] |
| 1261 | 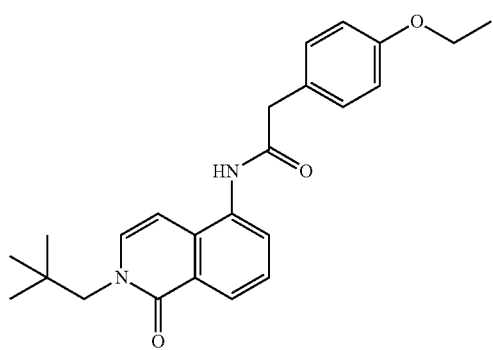 [SMILES: CCOc1ccc(CC(=O)Nc2cccc3c(=O)n(CC(C)(C)C)ccc23)cc1] |
| 1262 | 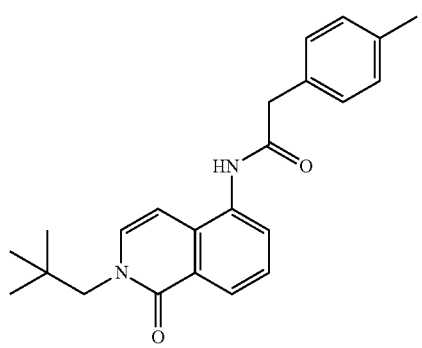 [SMILES: Cc1ccc(CC(=O)Nc2cccc3c(=O)n(CC(C)(C)C)ccc23)cc1] |
| 1263 | 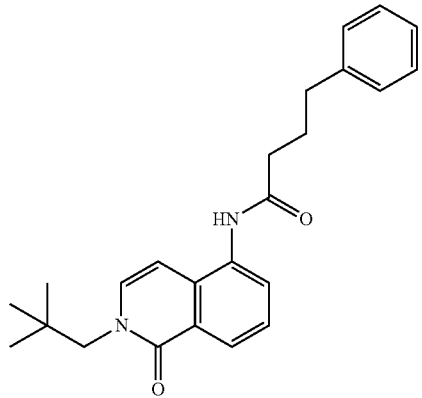 [SMILES: CC(C)(C)Cn1ccc2c(NC(=O)CCCc3ccccc3)cccc2c1=O] |
| ID | Structure |
|---|---|
| 1265 | 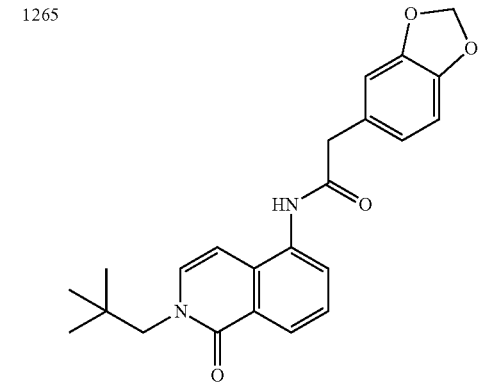 |
| 1266 | 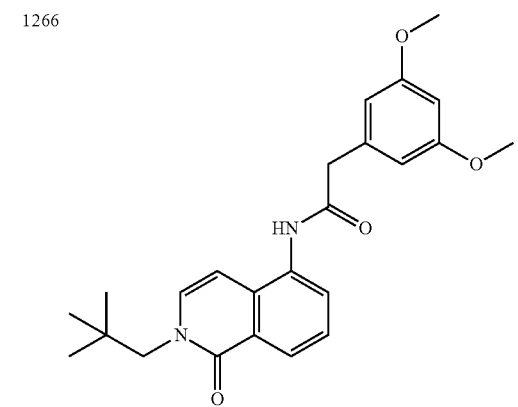 |
| 1274 | 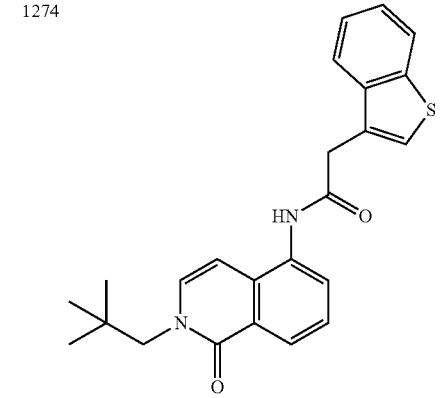 |
| 1276 | 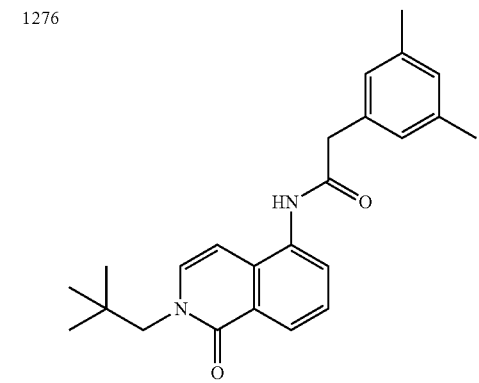 |

| ID | Structure | | ID | Structure |
|---|---|---|---|---|
| 1278 | 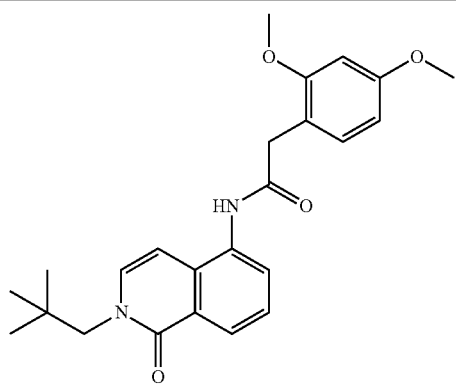 [SMILES: COc1ccc(CC(=O)Nc2cccc3c(=O)n(CC(C)(C)C)ccc23)c(OC)c1] | | 1286 | 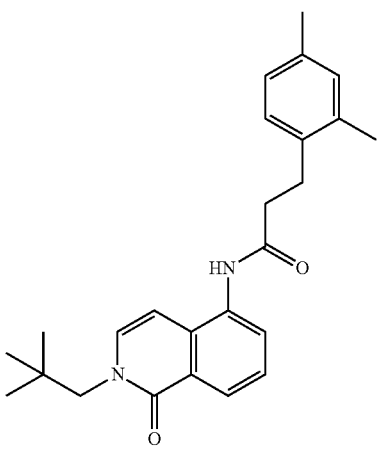 |
| 1280 | 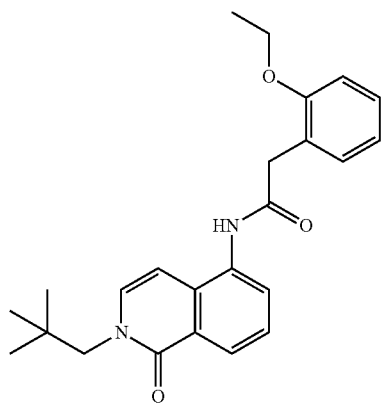 [SMILES: CCOc1ccccc1CC(=O)Nc1cccc2c(=O)n(CC(C)(C)C)ccc12] | | 1287 | 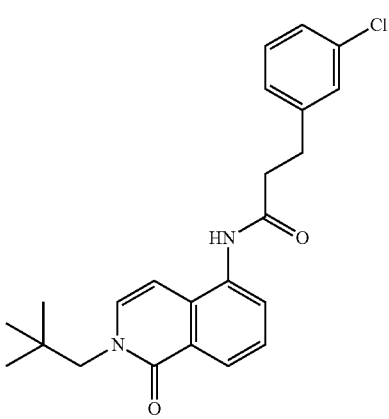 |
| 1281 | 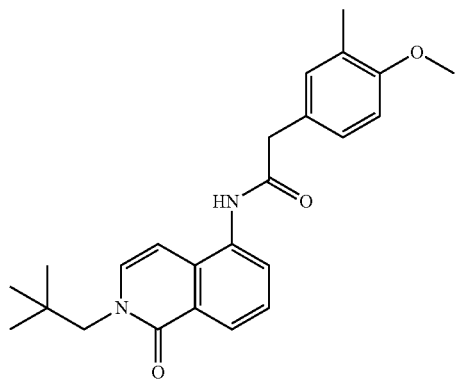 [SMILES: COc1ccc(CC(=O)Nc2cccc3c(=O)n(CC(C)(C)C)ccc23)cc1C] | | 1292 | 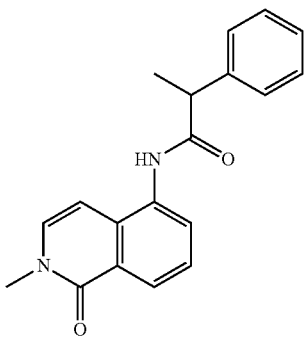 |
| 1284 | 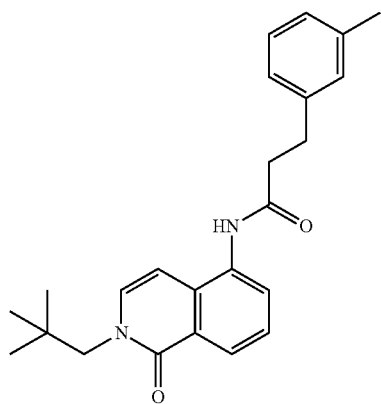 [SMILES: Cc1cccc(CCC(=O)Nc2cccc3c(=O)n(CC(C)(C)C)ccc23)c1] | | | |

| ID | Structure |
|----|-----------|
| 1293 | 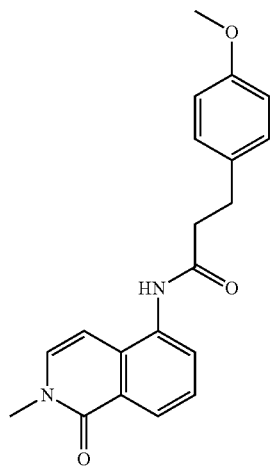 [SMILES: COc1ccc(CCC(=O)Nc2cccc3c(=O)n(C)ccc23)cc1] |
| 1294 | 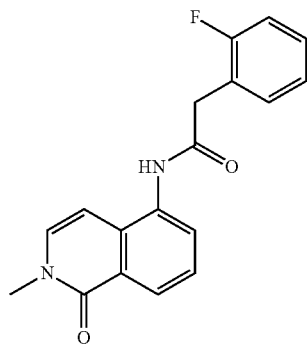 [SMILES: Cn1ccc2c(NC(=O)Cc3ccccc3F)cccc2c1=O] |
| 1295 | 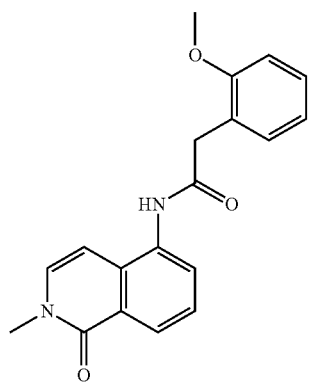 [SMILES: COc1ccccc1CC(=O)Nc1cccc2c(=O)n(C)ccc12] |
| 1296 | 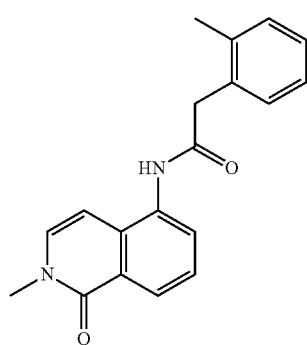 [SMILES: Cc1ccccc1CC(=O)Nc1cccc2c(=O)n(C)ccc12] |
| ID | Structure |
|----|-----------|
| 1297 | 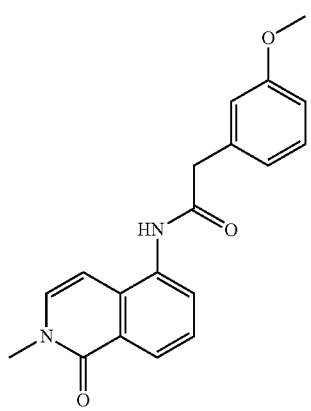 |
| 1298 | 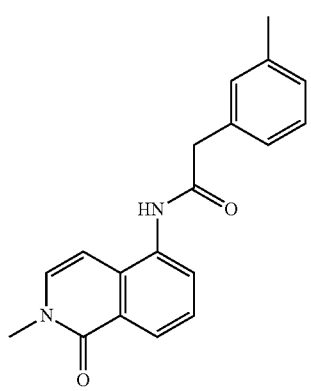 [SMILES: Cc1cccc(CC(=O)Nc2cccc3c(=O)n(C)ccc23)c1] |
| 1299 | 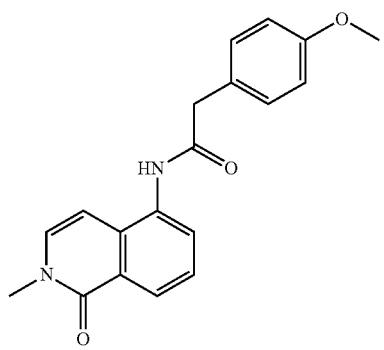 |
| 1301 | 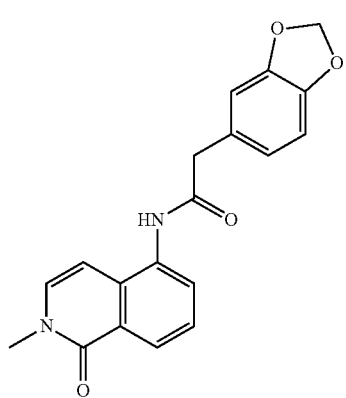 [SMILES: Cn1ccc2c(NC(=O)Cc3ccc4c(c3)OCO4)cccc2c1=O] |

475
-continued
| ID | Structure |
|---|---|
| 1307 | 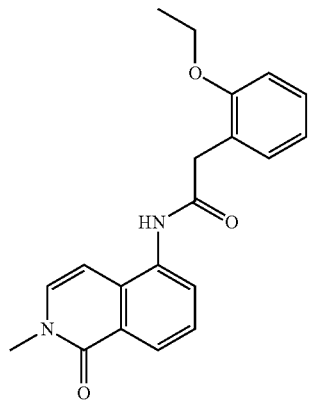 [SMILES: CCOc1ccccc1CC(=O)Nc1cccc2c(=O)n(C)ccc12] |
| 1309 | 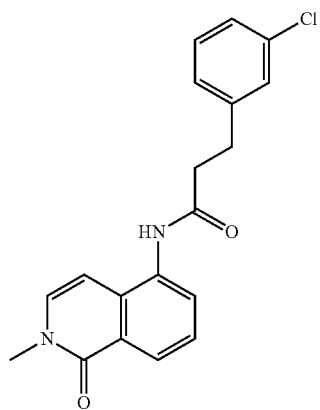 [SMILES: Cn1ccc2c(NC(=O)CCc3cccc(Cl)c3)cccc2c1=O] |
| 1311 | 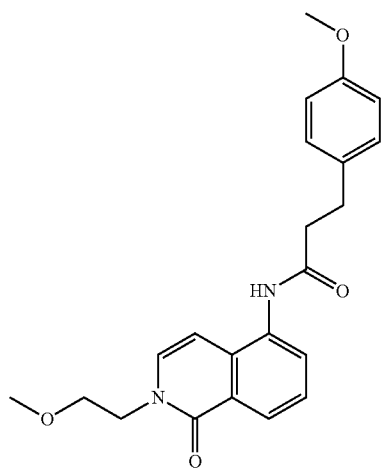 [SMILES: COCCn1ccc2c(NC(=O)CCc3ccc(OC)cc3)cccc2c1=O] |
476
-continued
| ID | Structure |
|---|---|
| 1313 | 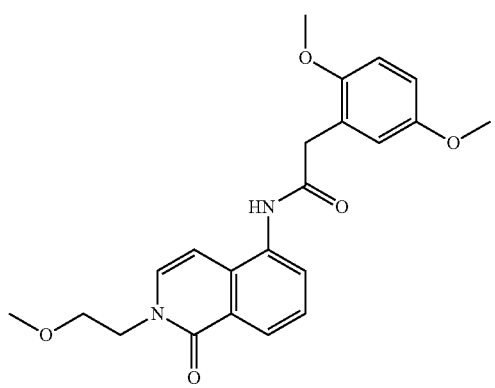 |
| 1314 | 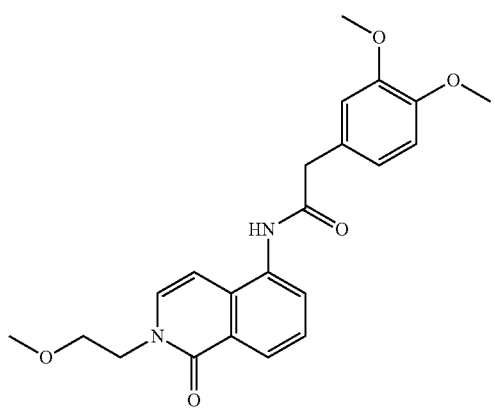 |
| 1315 | 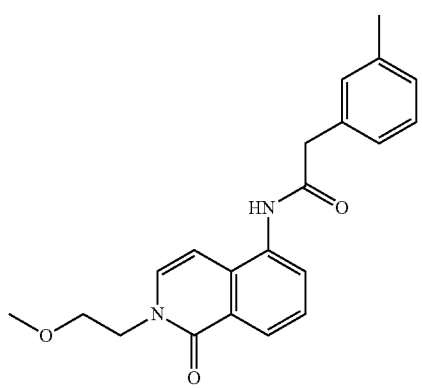 [SMILES: COCCn1ccc2c(NC(=O)Cc3cccc(C)c3)cccc2c1=O] |
| 1316 | 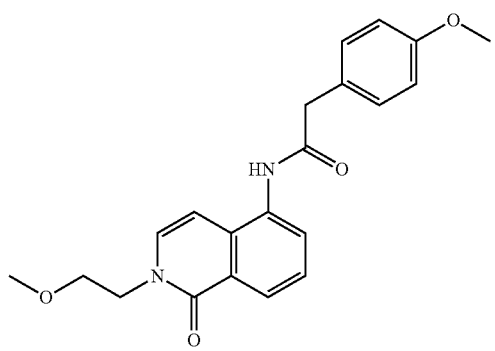 |

477
-continued
| ID | Structure |
|---|---|
| 1317 | 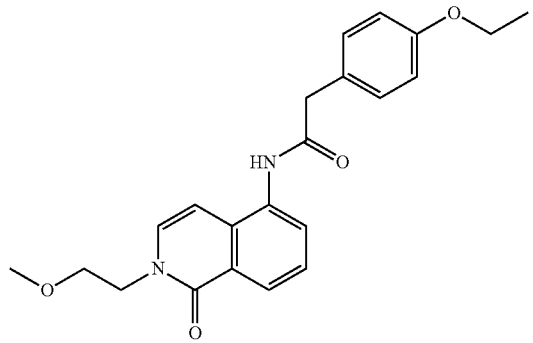 [SMILES: CCOc1ccc(CC(=O)Nc2cccc3c(=O)n(CCOC)ccc23)cc1] |
| 1318 | 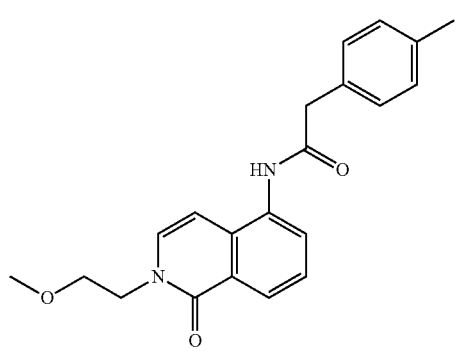 |
| 1319 | 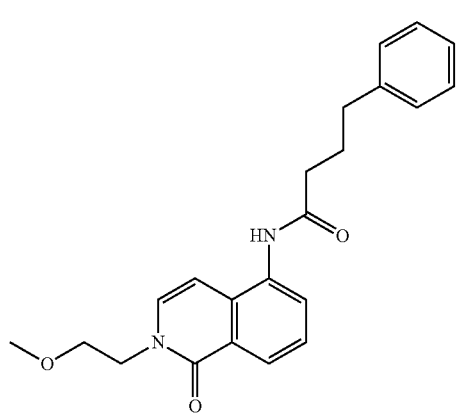 [SMILES: COCCn1ccc2c(NC(=O)CCCc3ccccc3)cccc2c1=O] |
| 1321 | 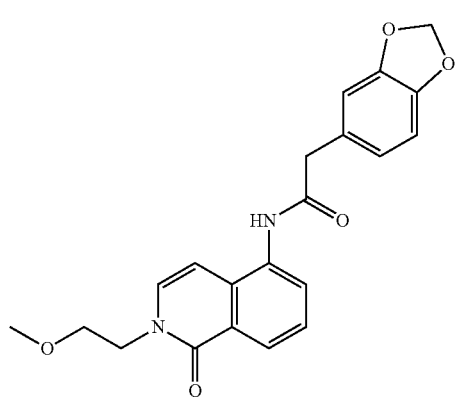 [SMILES: COCCn1ccc2c(NC(=O)Cc3ccc4c(c3)OCO4)cccc2c1=O] |
478
-continued
| ID | Structure |
|---|---|
| 1322 | 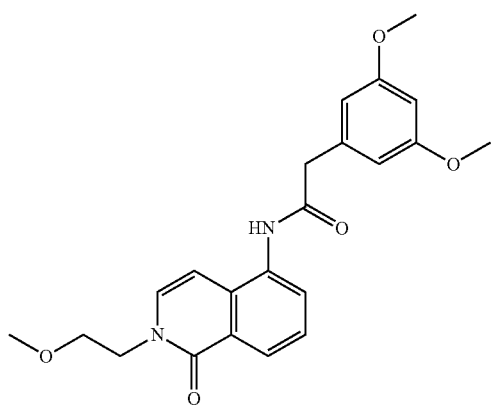 |
| 1329 | 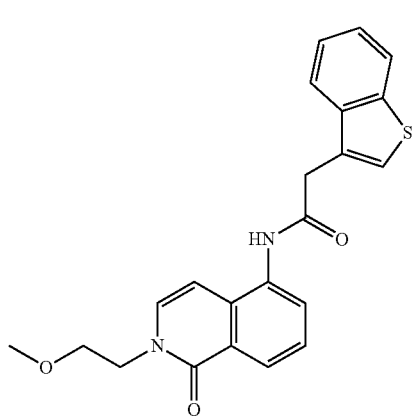 [SMILES: COCCn1ccc2c(NC(=O)Cc3csc4ccccc34)cccc2c1=O] |
| 1331 | 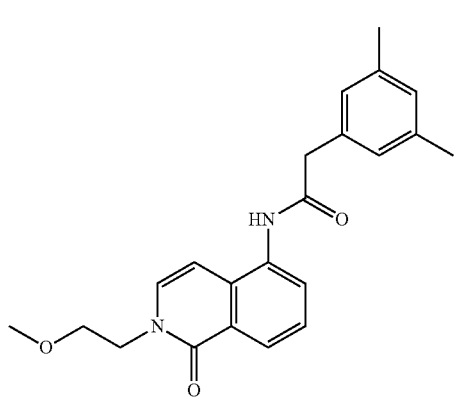 |
| 1333 | 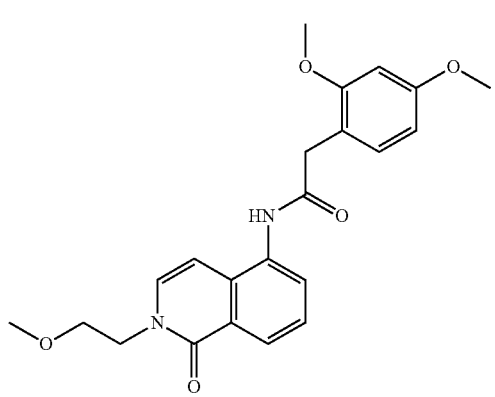 |

| ID | Structure |
|---|---|
| 1335 | 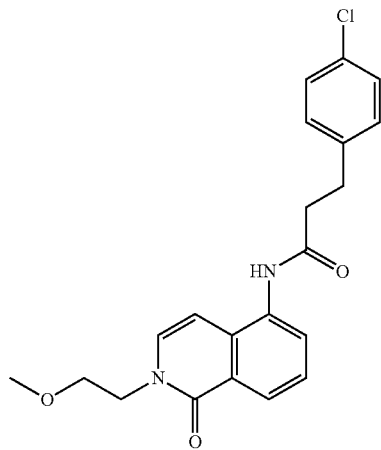 [SMILES: COCCn1ccc2c(NC(=O)CCc3ccc(Cl)cc3)cccc2c1=O] |
| 1336 | 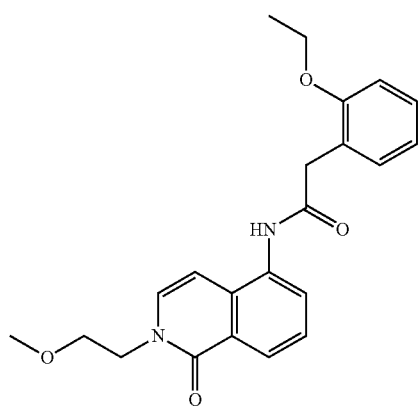 [SMILES: CCOc1ccccc1CC(=O)Nc1cccc2c(=O)n(CCOC)ccc12] |
| 1337 | 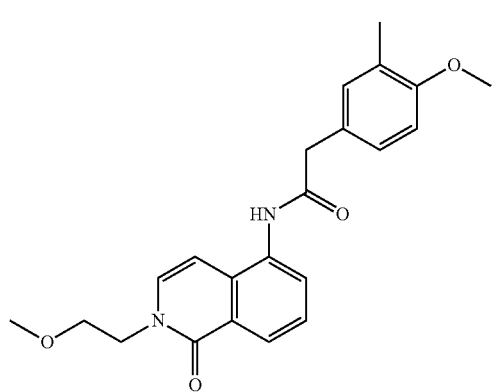 |
| ID | Structure |
|---|---|
| 1338 | 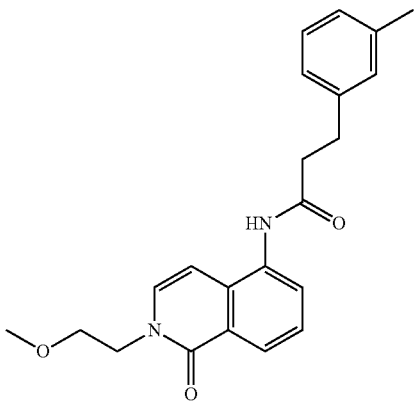 |
| 1341 | 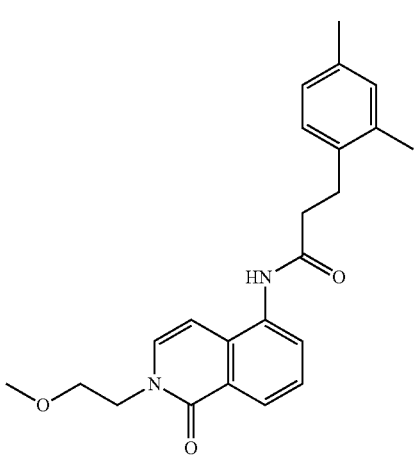 |
| 1342 | 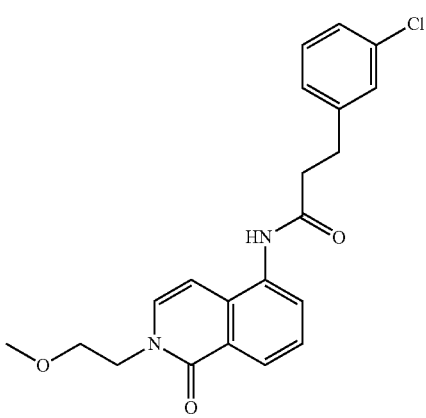 [SMILES: COCCn1ccc2c(NC(=O)CCc3cccc(Cl)c3)cccc2c1=O] |
| 1347 | 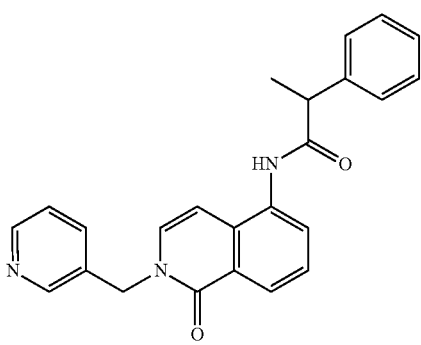 [SMILES: CC(C(=O)Nc1cccc2c(=O)n(Cc3cccnc3)ccc12)c1ccccc1] |

481
-continued
| ID | Structure |
|---|---|
| 1348 | 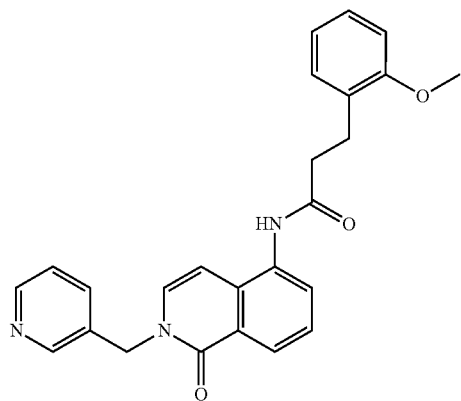 [SMILES: COc1ccccc1CCC(=O)Nc1cccc2c(=O)n(Cc3cccnc3)ccc12] |
| 1349 | 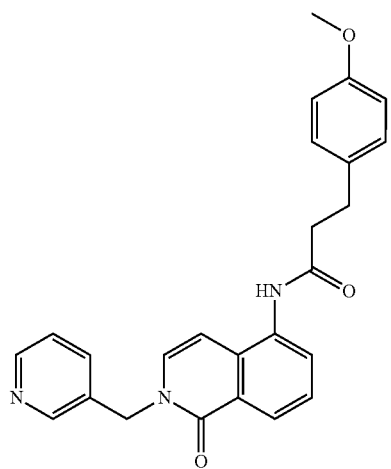 [SMILES: COc1ccc(CCC(=O)Nc2cccc3c(=O)n(Cc4cccnc4)ccc23)cc1] |
| 1350 | 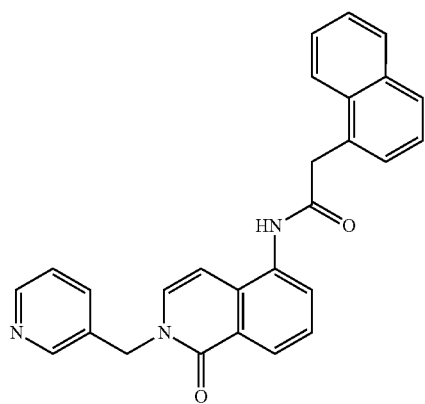 [SMILES: O=C(Cc1cccc2ccccc12)Nc1cccc2c(=O)n(Cc3cccnc3)ccc12] |
482
-continued
| ID | Structure |
|---|---|
| 1351 | 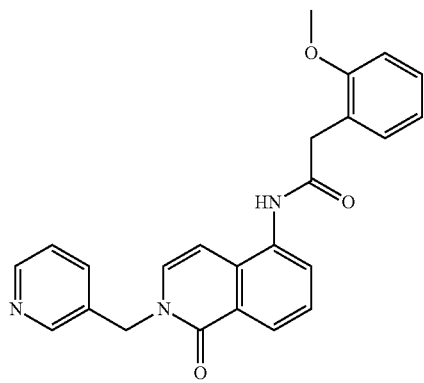 [SMILES: COc1ccccc1CC(=O)Nc1cccc2c(=O)n(Cc3cccnc3)ccc12] |
| 1352 | 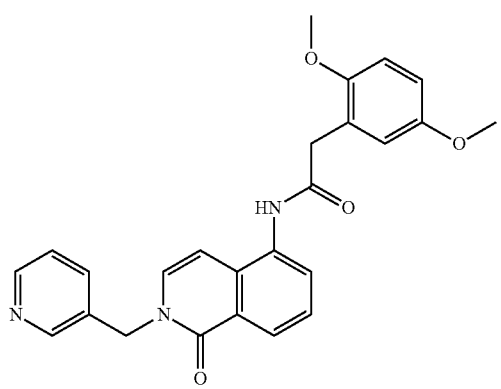 [SMILES: COc1ccc(OC)c(CC(=O)Nc2cccc3c(=O)n(Cc4cccnc4)ccc23)c1] |
| 1353 | 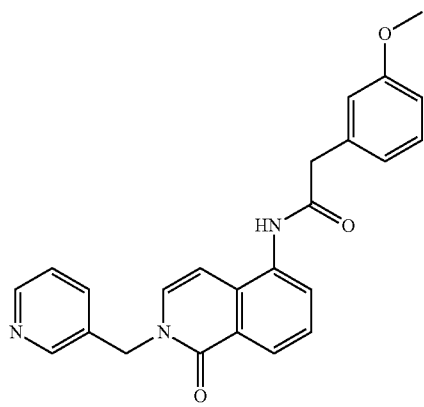 [SMILES: COc1cccc(CC(=O)Nc2cccc3c(=O)n(Cc4cccnc4)ccc23)c1] |
| 1354 | 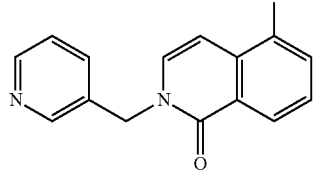 |

483
-continued
| ID | Structure |
|---|---|
| 1355 | 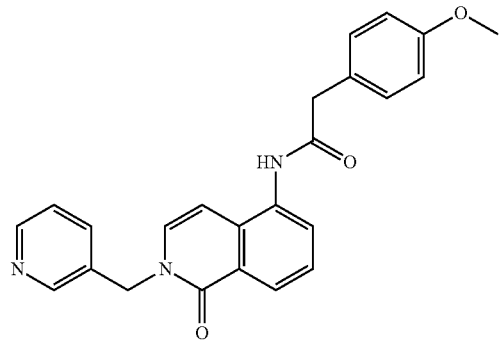 [SMILES: COc1ccc(CC(=O)Nc2cccc3c(=O)n(Cc4cccnc4)ccc23)cc1] |
| 1356 | 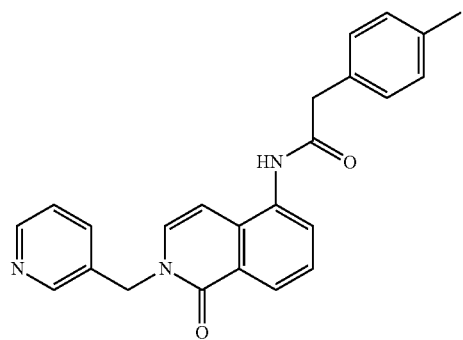 [SMILES: Cc1ccc(CC(=O)Nc2cccc3c(=O)n(Cc4cccnc4)ccc23)cc1] |
| 1357 | 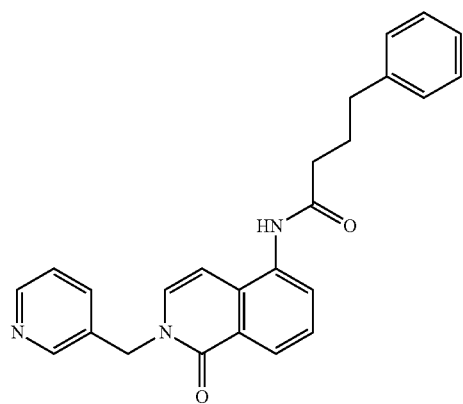 [SMILES: O=C(CCCc1ccccc1)Nc1cccc2c(=O)n(Cc3cccnc3)ccc12] |
| 1359 | 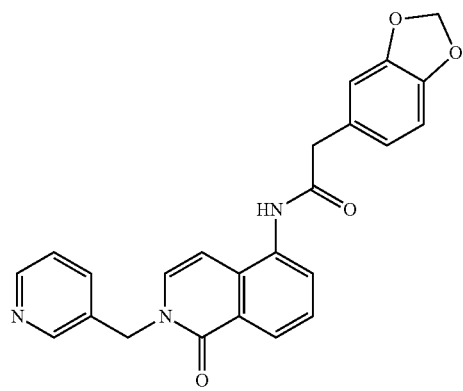 [SMILES: O=C(Cc1ccc2c(c1)OCO2)Nc1cccc2c(=O)n(Cc3cccnc3)ccc12] |
484
-continued
| ID | Structure |
|---|---|
| 1360 | 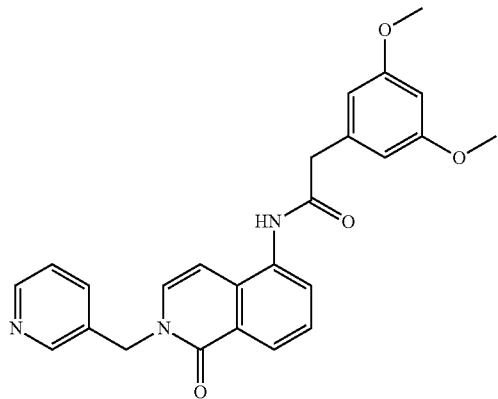 [SMILES: COc1cc(CC(=O)Nc2cccc3c(=O)n(Cc4cccnc4)ccc23)cc(OC)c1] |
| 1365 | 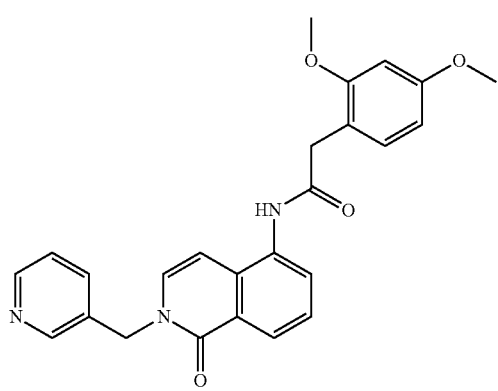 [SMILES: COc1ccc(CC(=O)Nc2cccc3c(=O)n(Cc4cccnc4)ccc23)c(OC)c1] |
| 1366 | 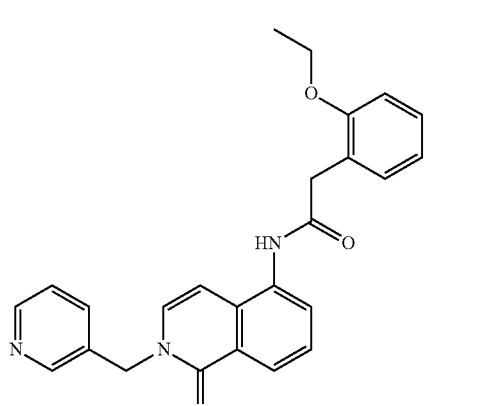 |
| 1367 | 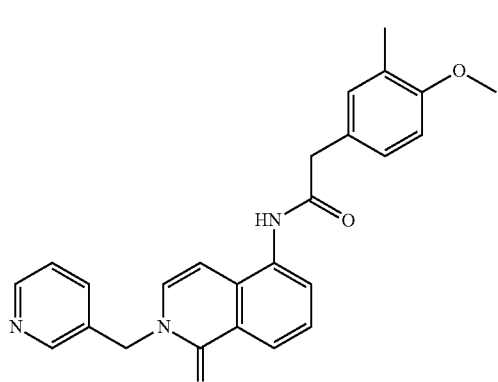 |

| ID | Structure |
|---|---|
| 1369 | 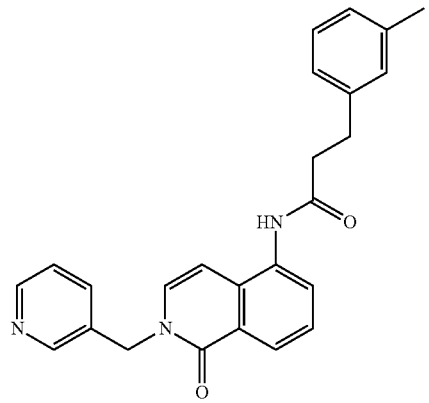 [SMILES: Cc1cccc(CCC(=O)Nc2cccc3c(=O)n(Cc4cccnc4)ccc23)c1] |
| 1374 | 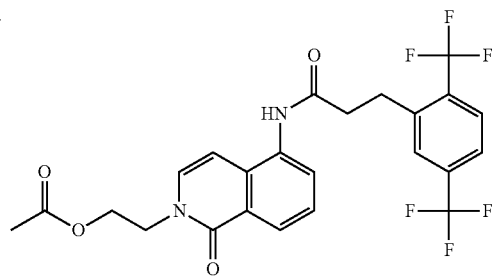 |
| 1376 | 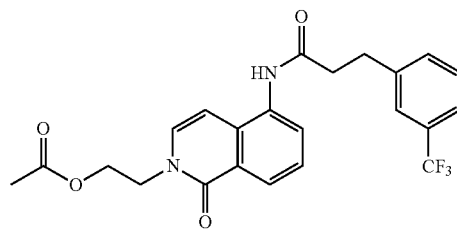 |
| 1377 | 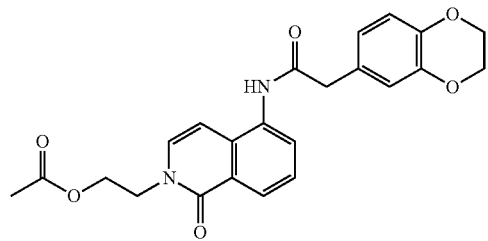 [SMILES: CC(=O)OCCn1ccc2c(NC(=O)Cc3ccc4c(c3)OCCO4)cccc2c1=O] |
| 1378 | 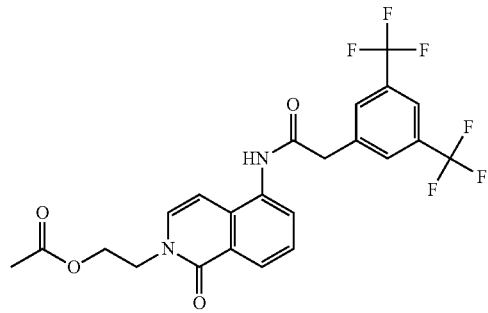 [SMILES: CC(=O)OCCn1ccc2c(NC(=O)Cc3cc(C(F)(F)F)cc(C(F)(F)F)c3)cccc2c1=O] |
| ID | Structure |
|---|---|
| 1380 | 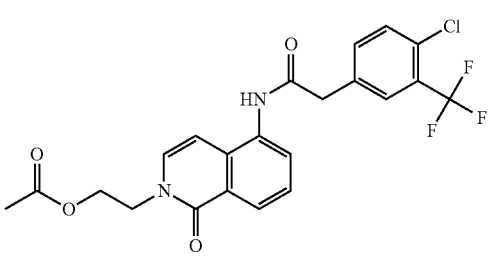 [SMILES: CC(=O)OCCn1ccc2c(NC(=O)Cc3ccc(Cl)c(C(F)(F)F)c3)cccc2c1=O] |
| 1381 | 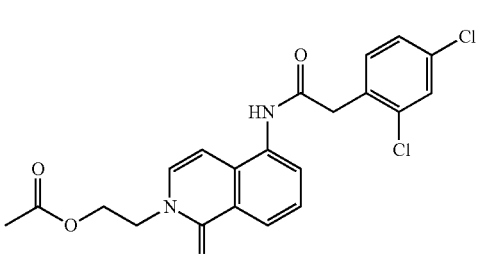 |
| 1382 | 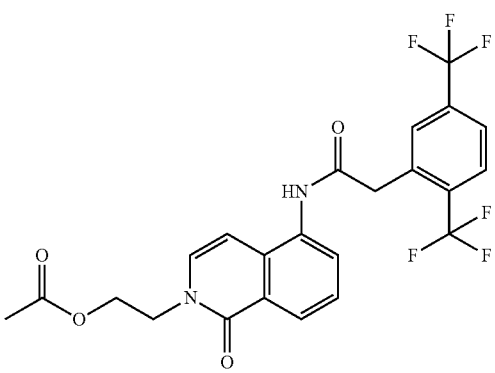 [SMILES: CC(=O)OCCn1ccc2c(NC(=O)Cc3cc(C(F)(F)F)ccc3C(F)(F)F)cccc2c1=O] |
| 1383 | 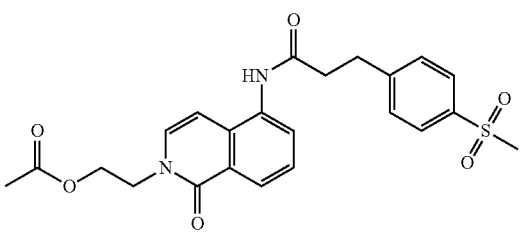 [SMILES: CC(=O)OCCn1ccc2c(NC(=O)CCc3ccc(S(C)(=O)=O)cc3)cccc2c1=O] |
| 1384 | 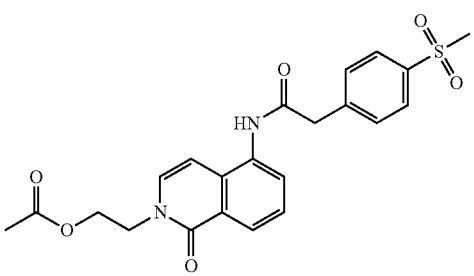 [SMILES: CC(=O)OCCn1ccc2c(NC(=O)Cc3ccc(S(C)(=O)=O)cc3)cccc2c1=O] |

| ID | Structure |
|---|---|
| 1385 | 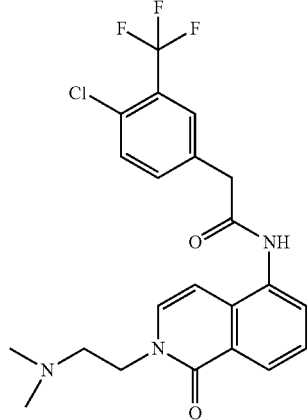 [SMILES: CN(C)CCn1ccc2c(NC(=O)Cc3ccc(Cl)c(C(F)(F)F)c3)cccc2c1=O] |
| 1386 | 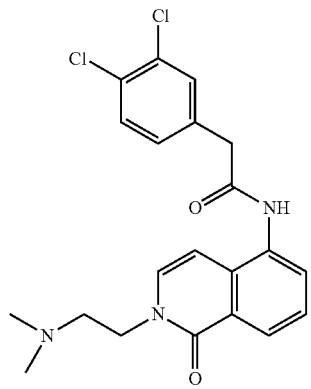 [SMILES: CN(C)CCn1ccc2c(NC(=O)Cc3ccc(Cl)c(Cl)c3)cccc2c1=O] |
| 1387 | 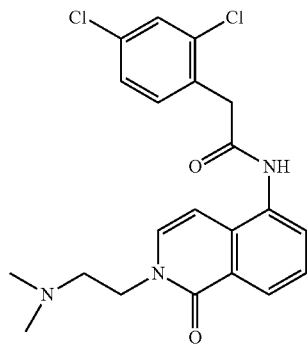 [SMILES: CN(C)CCn1ccc2c(NC(=O)Cc3ccc(Cl)cc3Cl)cccc2c1=O] |
| 1391 | 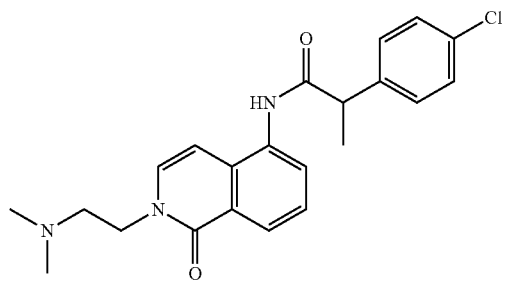 |
| ID | Structure |
|---|---|
| 1392 | 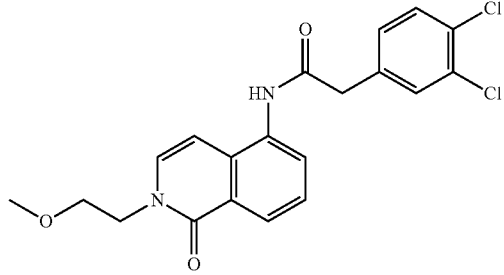 [SMILES: COCCn1ccc2c(NC(=O)Cc3ccc(Cl)c(Cl)c3)cccc2c1=O] |
| 1396 | 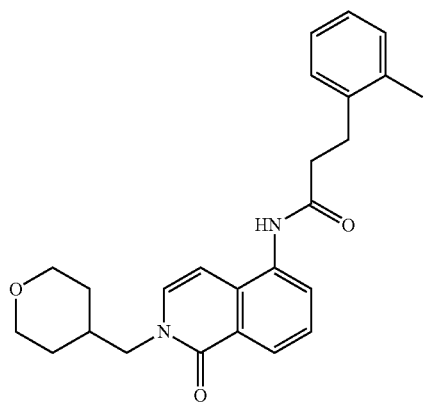 [SMILES: Cc1ccccc1CCC(=O)Nc1cccc2c(=O)n(CC3CCOCC3)ccc12] |
| 1399 | |
| 1400 | 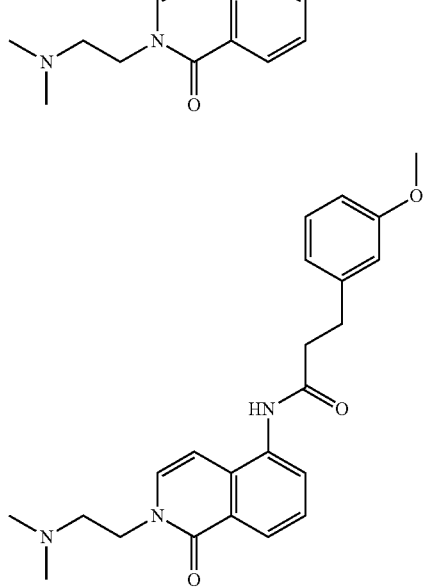 |

| ID | Structure | | ID | Structure |
|---|---|---|---|---|
| 1401 | 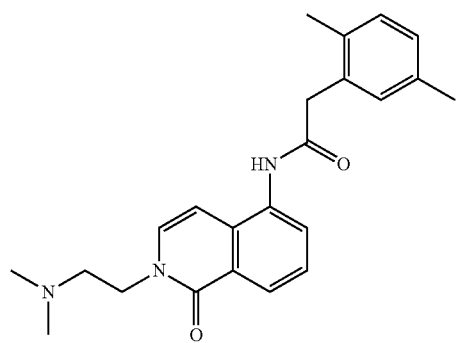 | | 1417 | 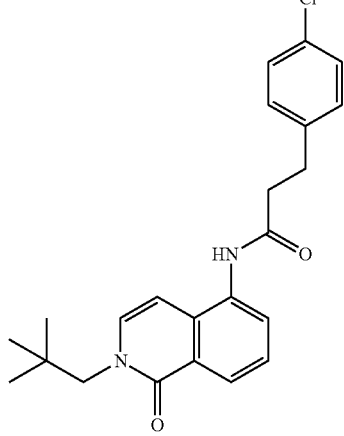 |
| 1404 | 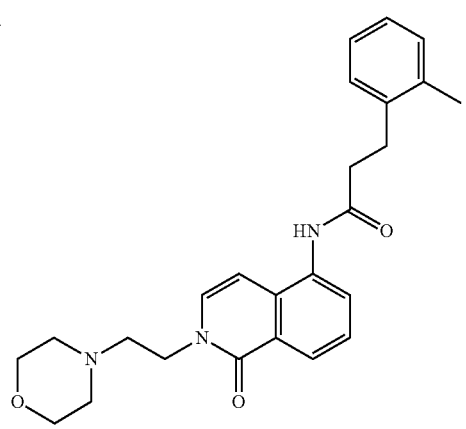 | | 1422 | 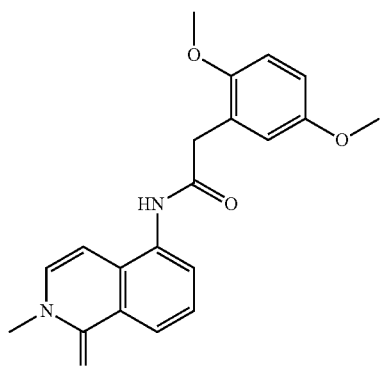 |
| 1406 | 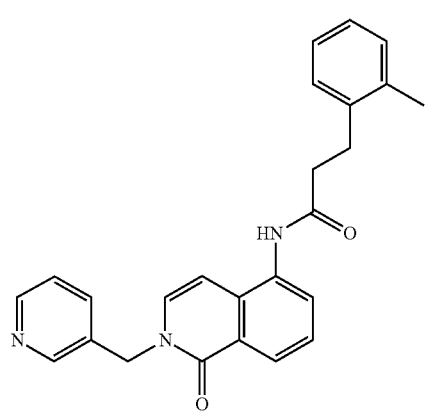 [SMILES: Cc1ccccc1CCC(=O)Nc1cccc2c(=O)n(Cc3cccnc3)ccc12] | | 1423 | 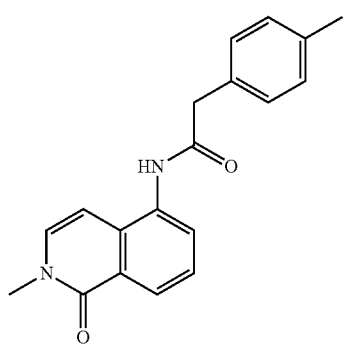 |
| 1409 | 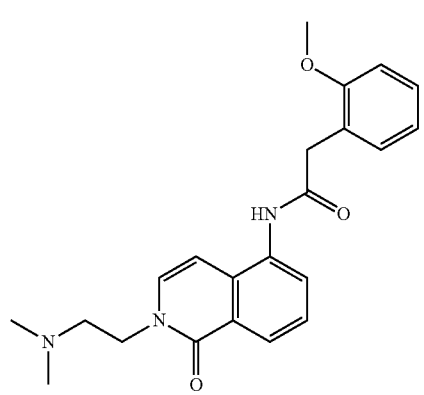 [SMILES: COc1ccccc1CC(=O)Nc1cccc2c(=O)n(CCN(C)C)ccc12] | | 1431 | 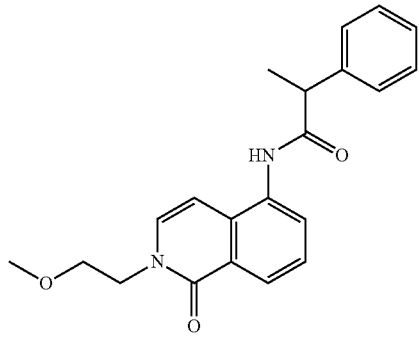 |

| ID | Structure | | ID | Structure |
|---|---|---|---|---|
| 1432 | 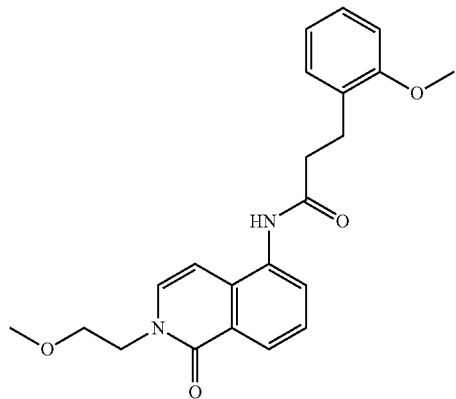 | | 1437 | 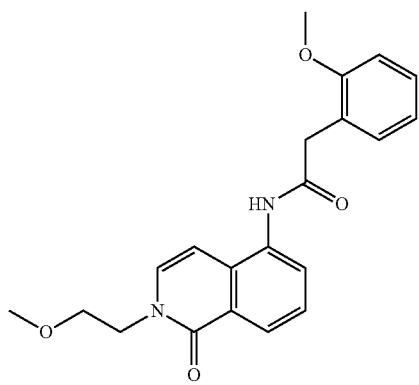 |
| 1433 | 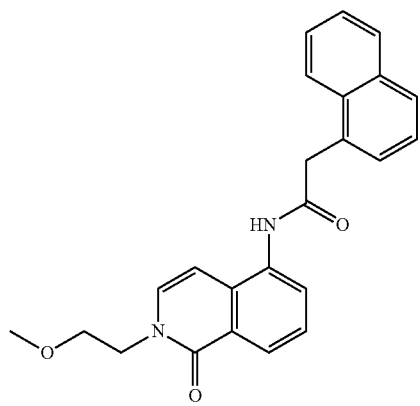 [SMILES: COCCn1ccc2c(NC(=O)Cc3cccc4ccccc34)cccc2c1=O] | | 1438 | 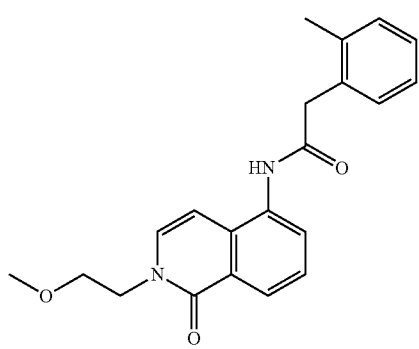 |
| 1435 | 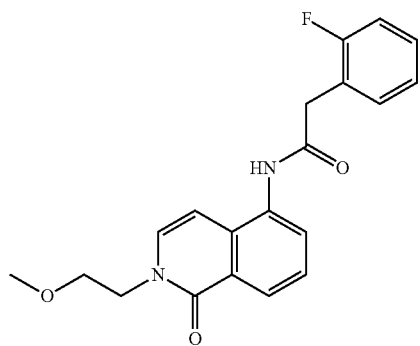 | | 1439 | 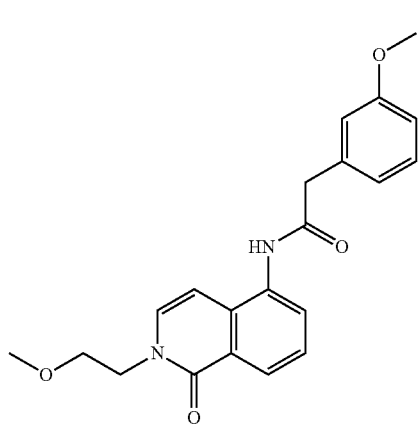 |
| 1436 | 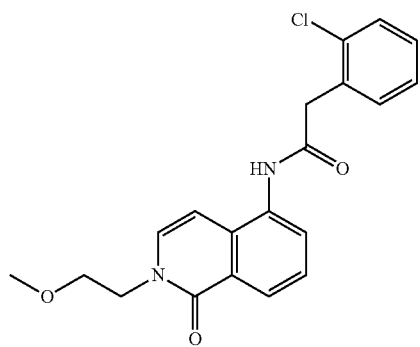 [SMILES: COCCn1ccc2c(NC(=O)Cc3ccccc3F)cccc2c1=O] | | 1449 | 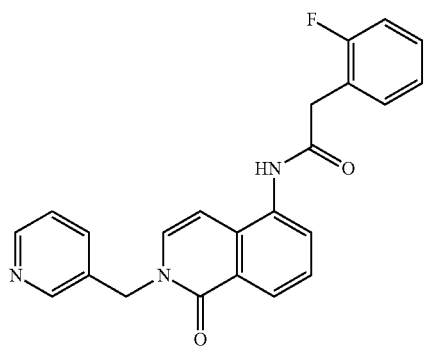 [SMILES: O=C(Cc1ccccc1F)Nc1cccc2c(=O)n(Cc3cccnc3)ccc12] |

| ID | Structure |
|---|---|
| 1468 | 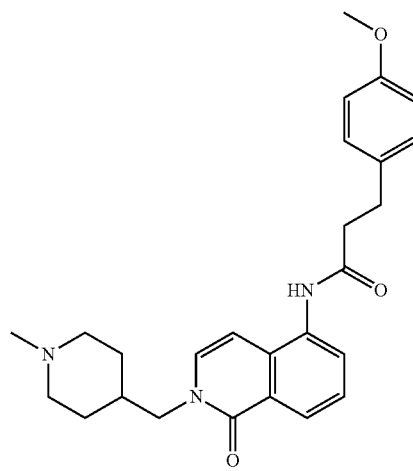 |
| 1470 | 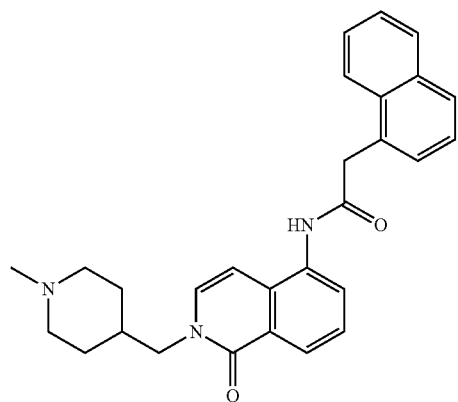 [SMILES: CN1CCC(Cn2ccc3c(NC(=O)Cc4cccc5ccccc45)cccc3c2=O)CC1] |
| 1472 | 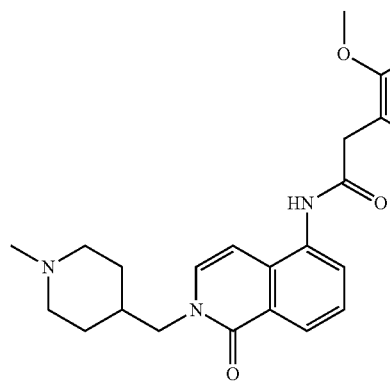 |
| ID | Structure |
|---|---|
| 1473 | 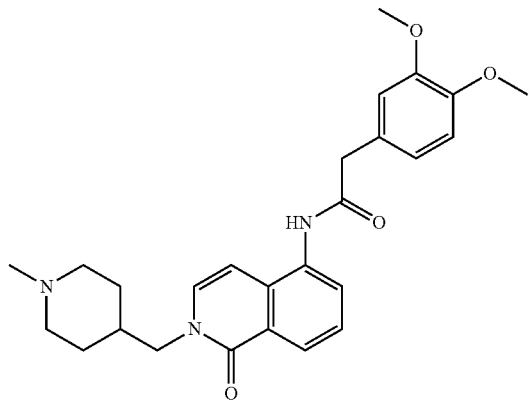 |
| 1474 | 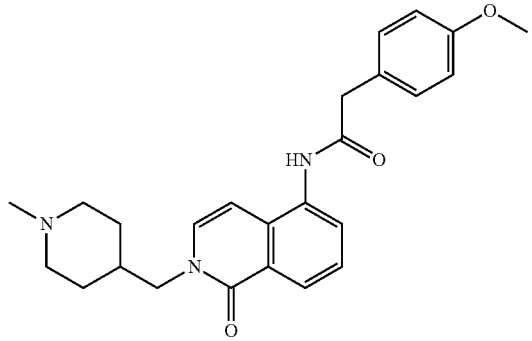 |
| 1475 | 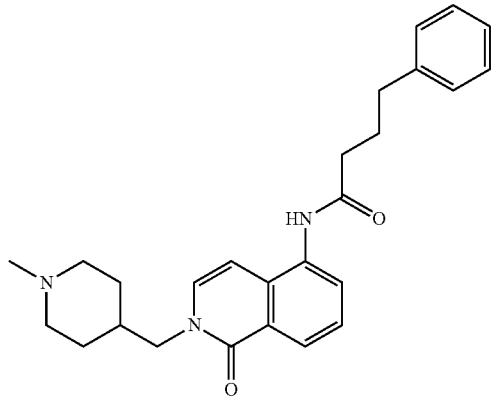 [SMILES: CN1CCC(Cn2ccc3c(NC(=O)CCCc4ccccc4)cccc3c2=O)CC1] |
| 1477 | 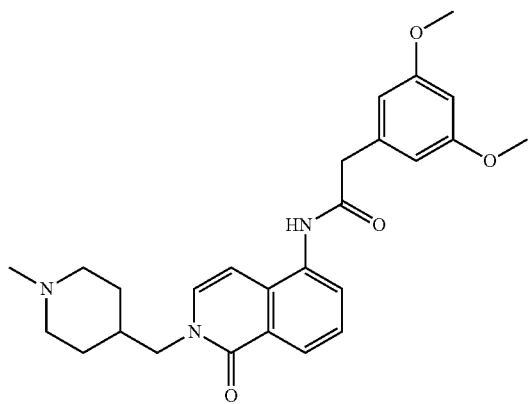 |

| ID | Structure |
|---|---|
| 1482 | 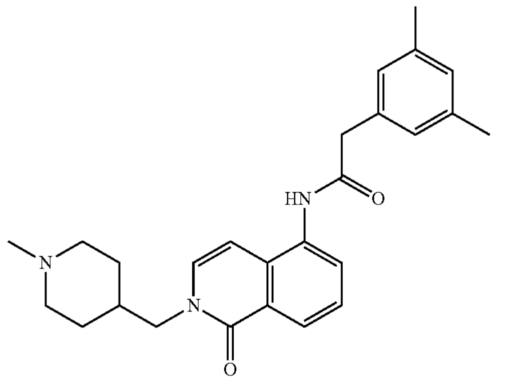 |
| 1484 | 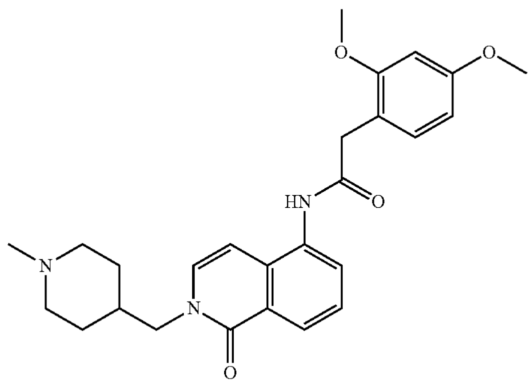 |
| 1485 | 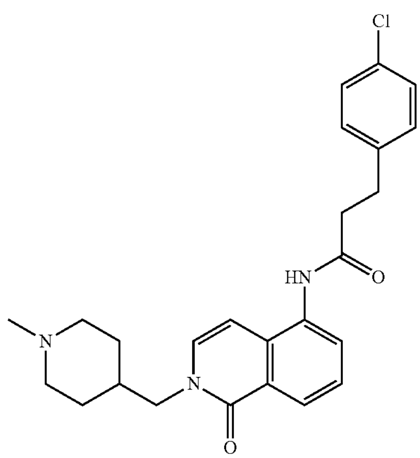 [SMILES: CN1CCC(Cn2ccc3c(NC(=O)CCc4ccc(Cl)cc4)cccc3c2=O)CC1] |
| 1488 | 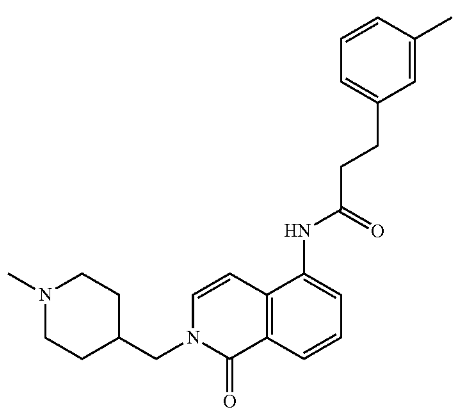 |

| ID | Structure |
|---|---|
| 1491 | 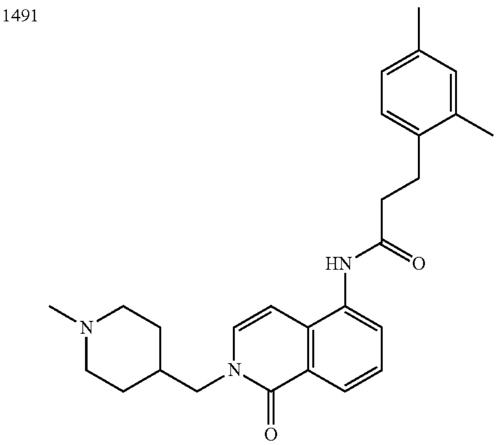 |
| 1492 | 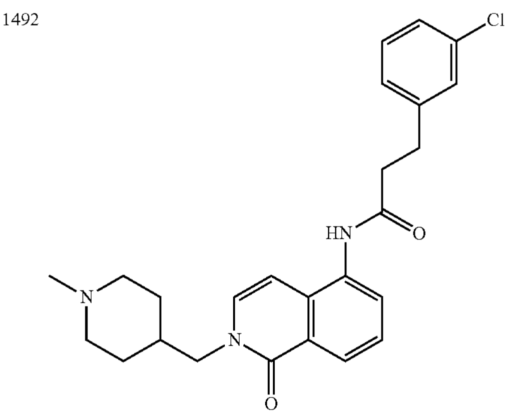 |
| 1495 | 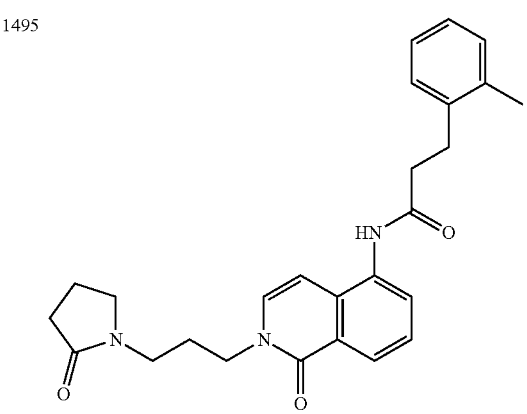 |

| 499 -continued | 500 -continued |
|---|---|
| ID Structure | ID Structure |
| 1497 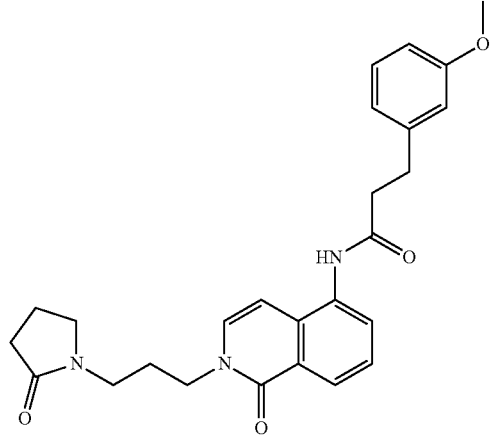 [SMILES: COc1cccc(CCC(=O)Nc2cccc3c(=O)n(CCCN4CCCC4=O)ccc23)c1] | 1502 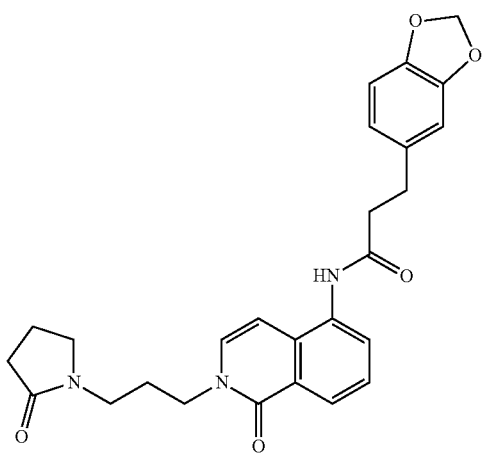 |
| 1498 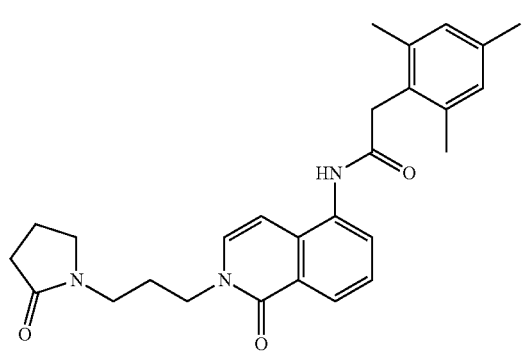 [SMILES: Cc1cc(C)c(CC(=O)Nc2cccc3c(=O)n(CCCN4CCCC4=O)ccc23)c(C)c1] | 1517 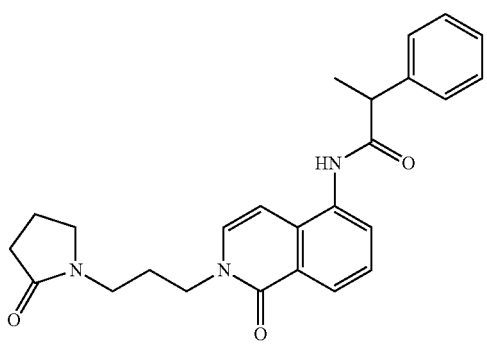 |
| 1499 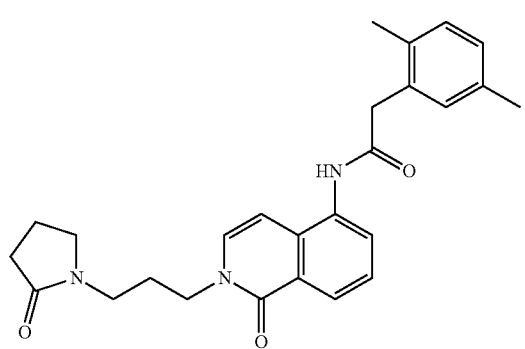 [SMILES: Cc1ccc(C)c(CC(=O)Nc2cccc3c(=O)n(CCCN4CCCC4=O)ccc23)c1] | 1518 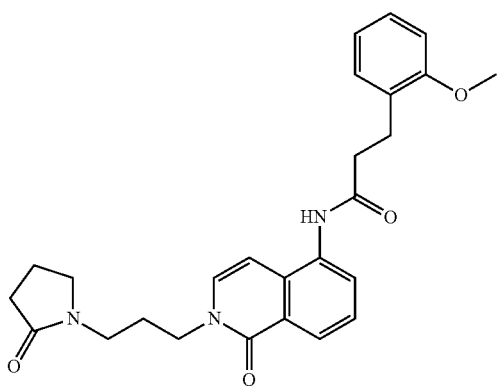 |
| 1501 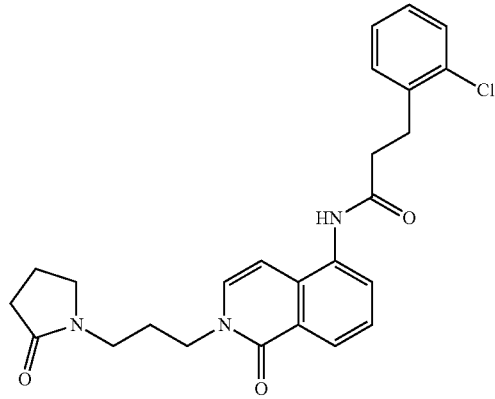 [SMILES: O=C(CCc1ccccc1Cl)Nc1cccc2c(=O)n(CCCN3CCCC3=O)ccc12] | 1519 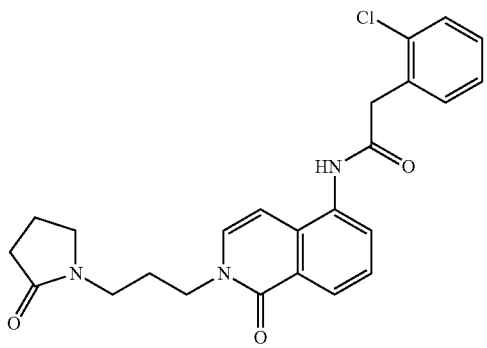 [SMILES: O=C(Cc1ccccc1Cl)Nc1cccc2c(=O)n(CCCN3CCCC3=O)ccc12] |

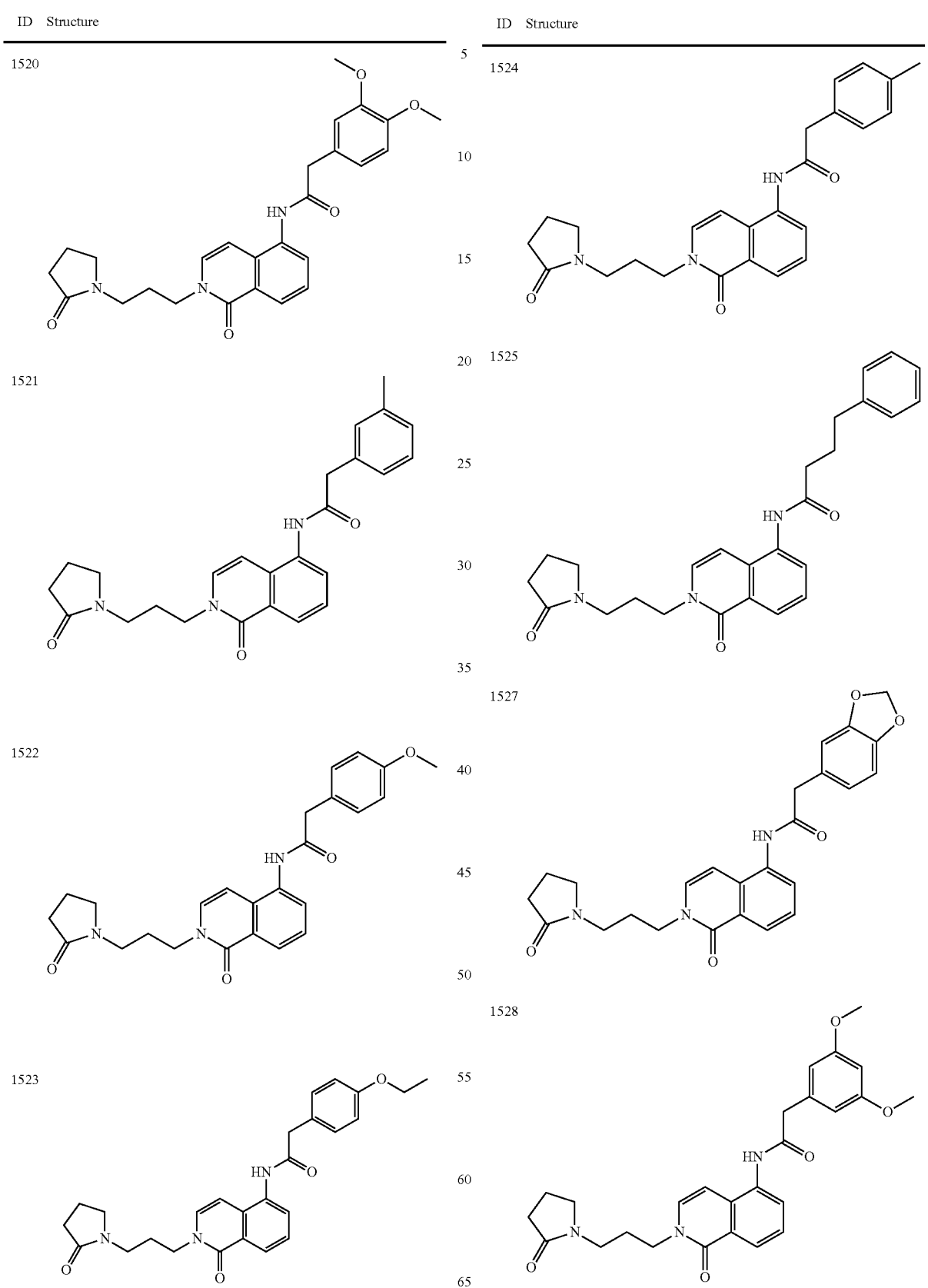

503
-continued
| ID | Structure |
|---|---|
| 1531 | 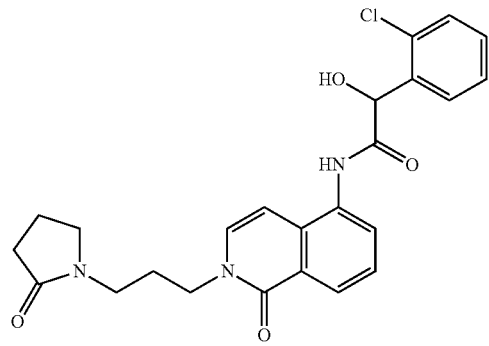 [SMILES: O=C(Nc1cccc2c(=O)n(CCCN3CCCC3=O)ccc12)C(O)c1ccccc1Cl] |
| 1535 | 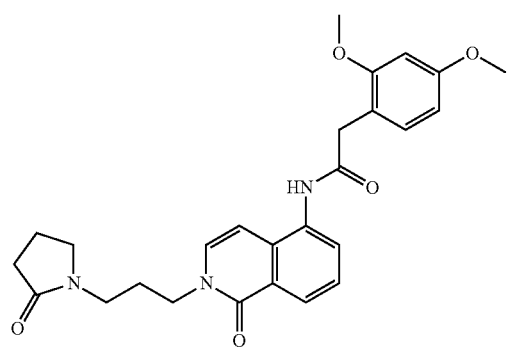 [SMILES: COc1ccc(CC(=O)Nc2cccc3c(=O)n(CCCN4CCCC4=O)ccc23)c(OC)c1] |
| 1537 | 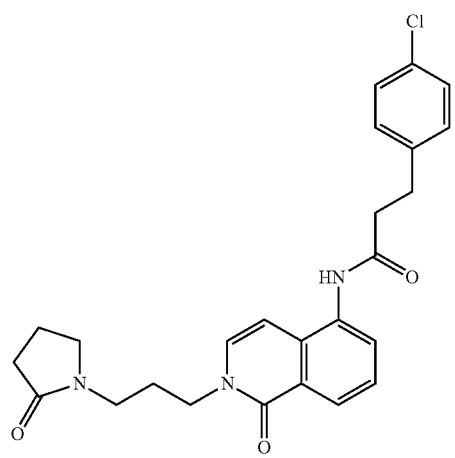 [SMILES: O=C(CCc1ccc(Cl)cc1)Nc1cccc2c(=O)n(CCCN3CCCC3=O)ccc12] |
| 1538 | 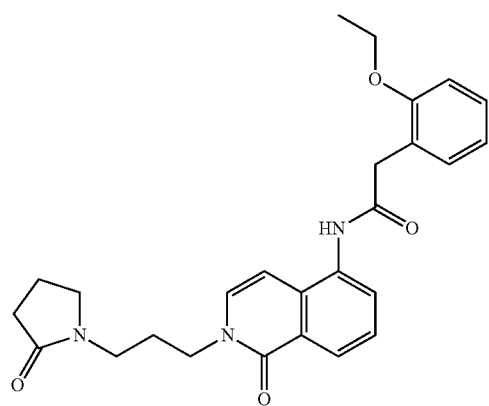 [SMILES: CCOc1ccccc1CC(=O)Nc1cccc2c(=O)n(CCCN3CCCC3=O)ccc12] |
504
-continued
| ID | Structure |
|---|---|
| 1539 | 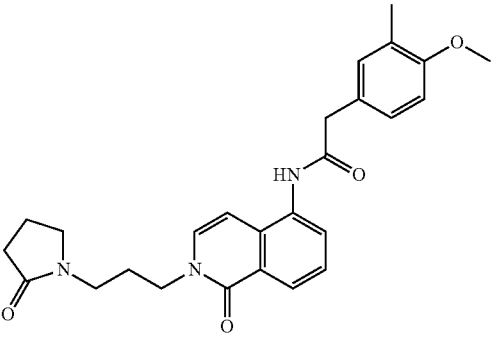 [SMILES: COc1ccc(CC(=O)Nc2cccc3c(=O)n(CCCN4CCCC4=O)ccc23)cc1C] |
| 1542 | 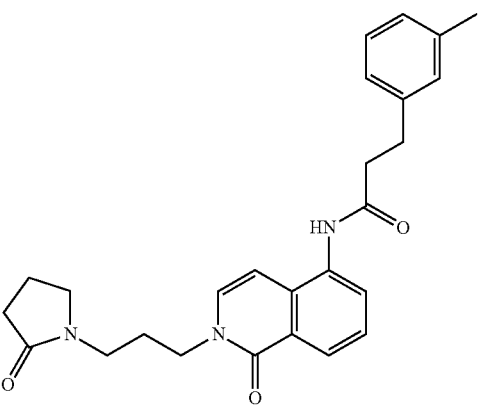 [SMILES: Cc1cccc(CCC(=O)Nc2cccc3c(=O)n(CCCN4CCCC4=O)ccc23)c1] |
| 1546 | 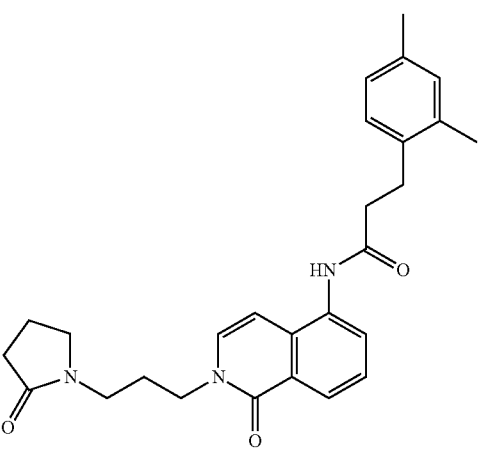 [SMILES: Cc1ccc(CCC(=O)Nc2cccc3c(=O)n(CCCN4CCCC4=O)ccc23)c(C)c1] |
| 1547 | 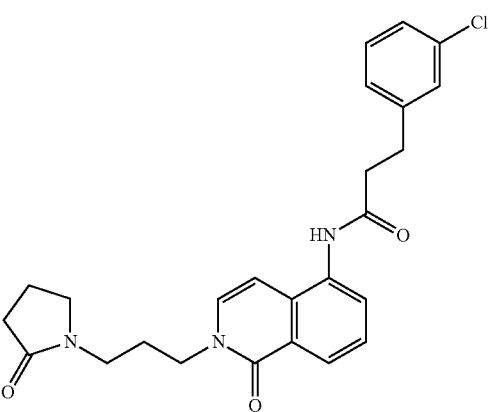 [SMILES: O=C(CCc1cccc(Cl)c1)Nc1cccc2c(=O)n(CCCN3CCCC3=O)ccc12] |

| 505 -continued | 506 -continued |
|---|---|
| ID Structure | ID Structure |
| 1550 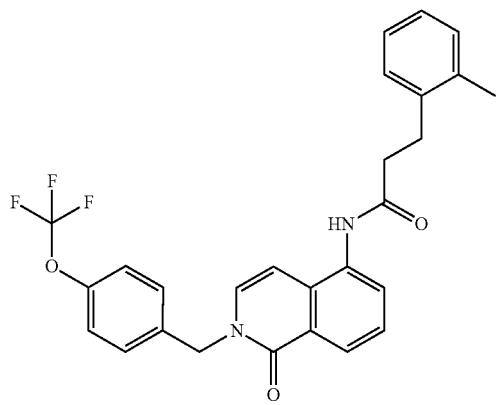 [SMILES: Cc1ccccc1CCC(=O)Nc1cccc2c(=O)n(Cc3ccc(OC(F)(F)F)cc3)ccc12] | 1557 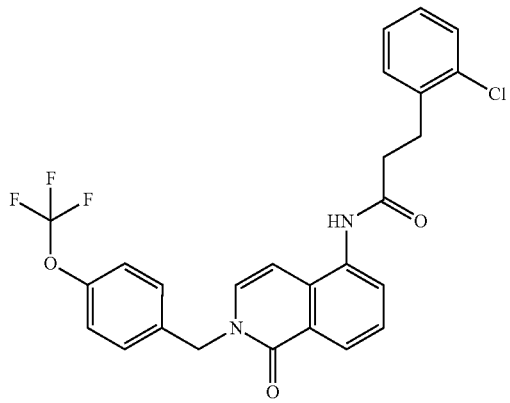 |
| 1552 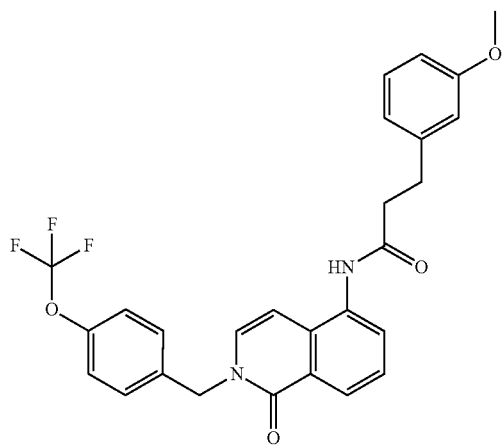 [SMILES: COc1cccc(CCC(=O)Nc2cccc3c(=O)n(Cc4ccc(OC(F)(F)F)cc4)ccc23)c1] | 1558 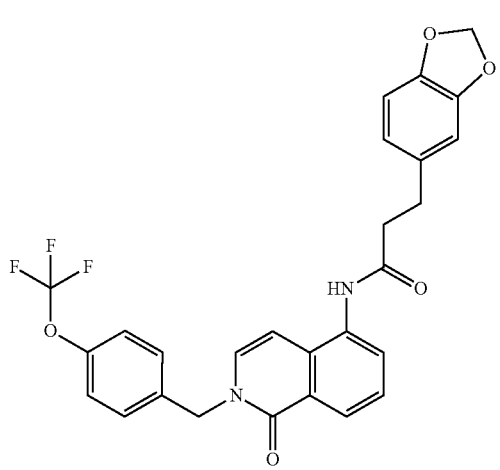 |
| 1553 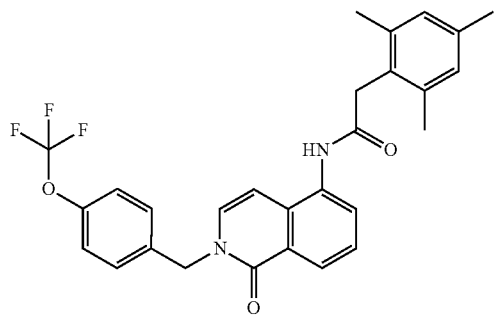 [SMILES: Cc1cc(C)c(CC(=O)Nc2cccc3c(=O)n(Cc4ccc(OC(F)(F)F)cc4)ccc23)c(C)c1] | 1570 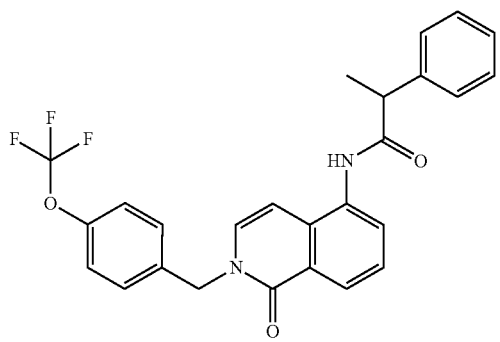 |
| 1554 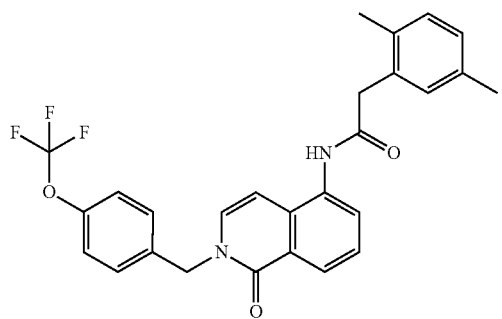 [SMILES: Cc1ccc(C)c(CC(=O)Nc2cccc3c(=O)n(Cc4ccc(OC(F)(F)F)cc4)ccc23)c1] | 1571 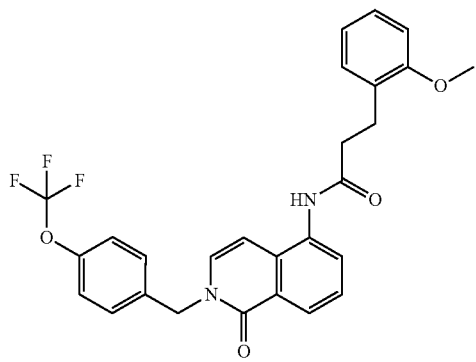 [SMILES: COc1ccccc1CCC(=O)Nc1cccc2c(=O)n(Cc3ccc(OC(F)(F)F)cc3)ccc12] |

507
-continued
| ID | Structure |
|---|---|
| 1572 | 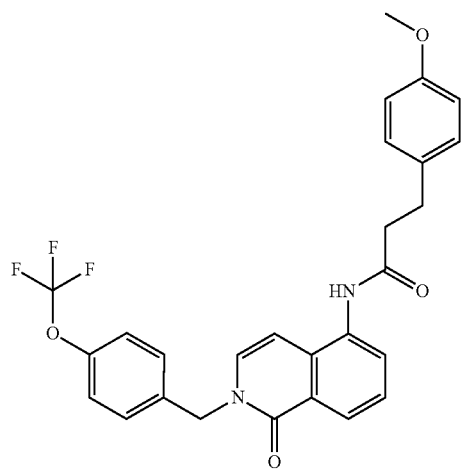 [SMILES: COc1ccc(CCC(=O)Nc2cccc3c(=O)n(Cc4ccc(OC(F)(F)F)cc4)ccc23)cc1] |
| 1573 | 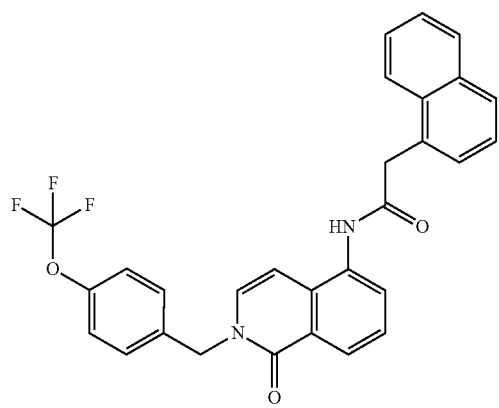 [SMILES: O=C(Cc1cccc2ccccc12)Nc1cccc2c(=O)n(Cc3ccc(OC(F)(F)F)cc3)ccc12] |
| 1575 | 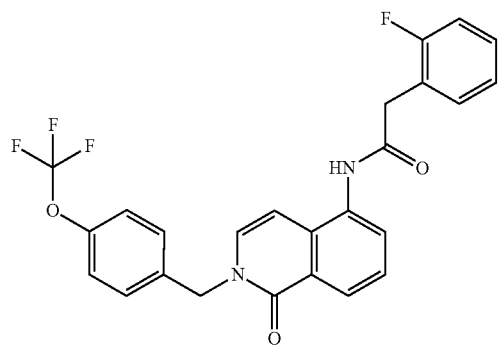 [SMILES: O=C(Cc1ccccc1F)Nc1cccc2c(=O)n(Cc3ccc(OC(F)(F)F)cc3)ccc12] |
| 1576 | 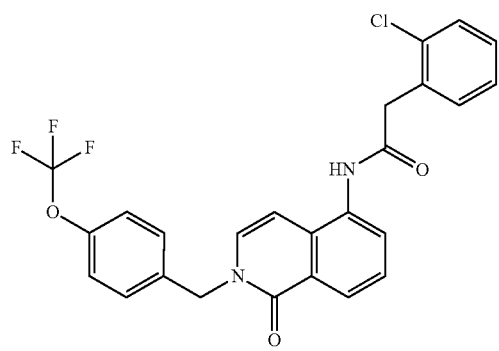 [SMILES: O=C(Cc1ccccc1Cl)Nc1cccc2c(=O)n(Cc3ccc(OC(F)(F)F)cc3)ccc12] |
508
-continued
| ID | Structure |
|---|---|
| 1577 | 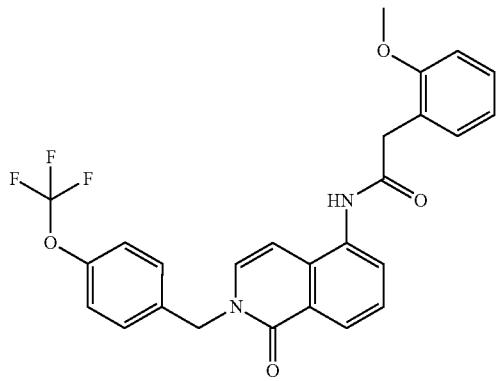 [SMILES: COc1ccccc1CC(=O)Nc1cccc2c(=O)n(Cc3ccc(OC(F)(F)F)cc3)ccc12] |
| 1578 | 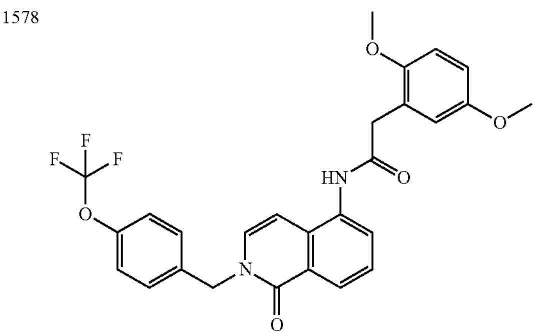 |
| 1579 | 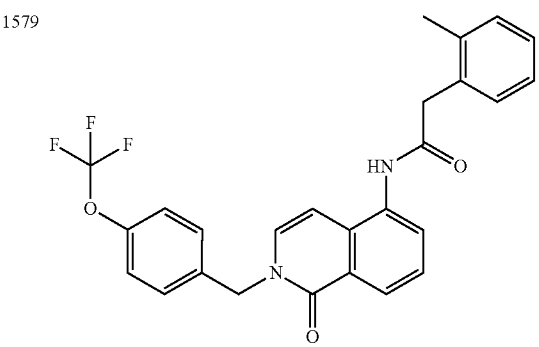 |
| 1580 | 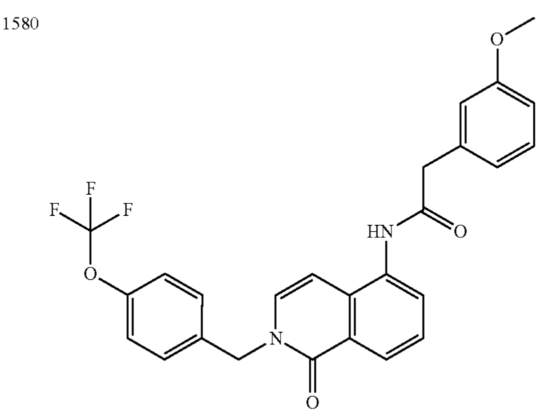 |

| ID | Structure |
|---|---|
| 1581 | 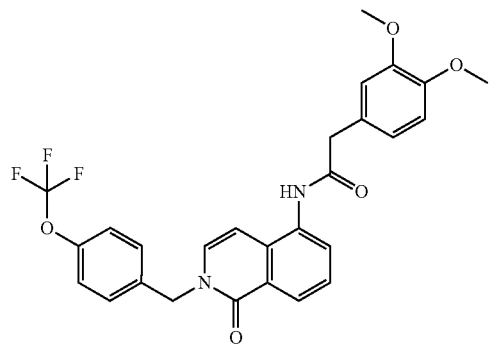 [SMILES: COc1ccc(CC(=O)Nc2cccc3c(=O)n(Cc4ccc(OC(F)(F)F)cc4)ccc23)cc1OC] |
| 1582 | 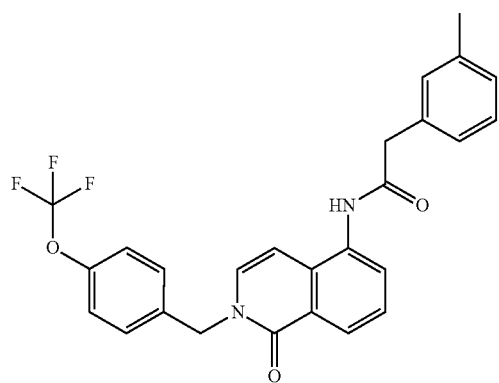 [SMILES: Cc1cccc(CC(=O)Nc2cccc3c(=O)n(Cc4ccc(OC(F)(F)F)cc4)ccc23)c1] |
| 1583 | 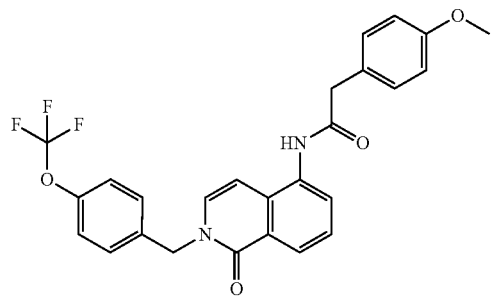 [SMILES: COc1ccc(CC(=O)Nc2cccc3c(=O)n(Cc4ccc(OC(F)(F)F)cc4)ccc23)cc1] |
| 1584 | 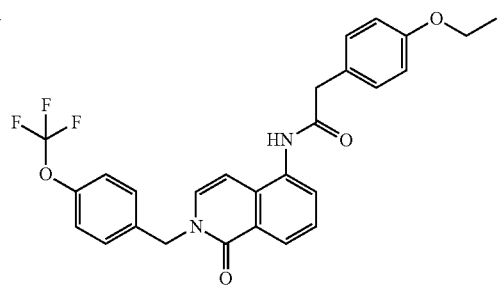 |
| ID | Structure |
|---|---|
| 1585 | 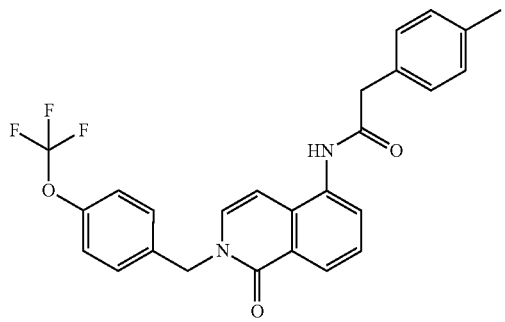 [SMILES: Cc1ccc(CC(=O)Nc2cccc3c(=O)n(Cc4ccc(OC(F)(F)F)cc4)ccc23)cc1] |
| 1586 | 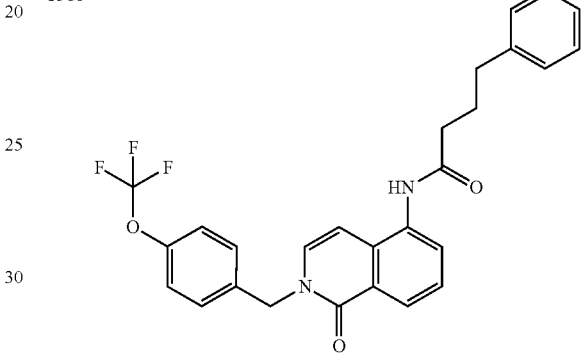 |
| 1588 | 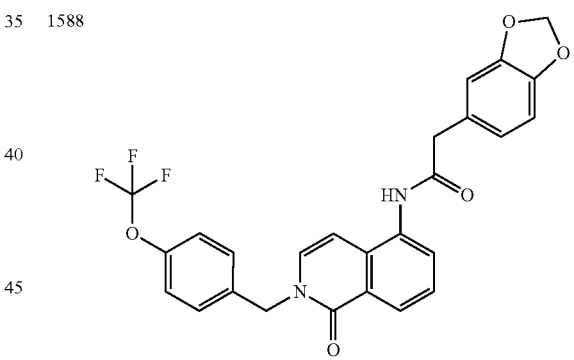 |
| 1589 | 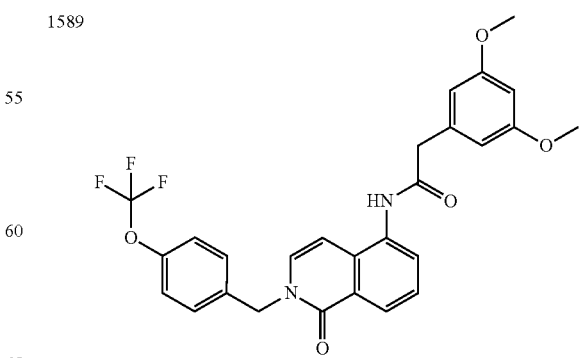 |

| 511 -continued | 512 -continued |
|---|---|
| ID Structure | ID Structure |
| 1597 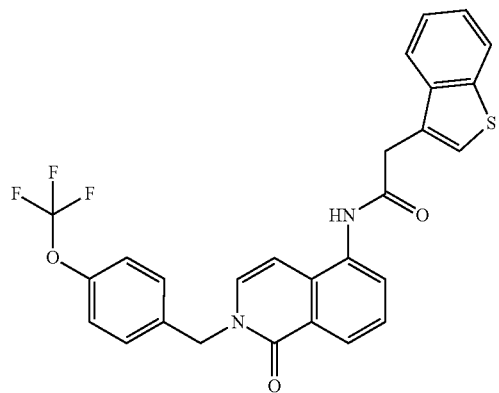 [SMILES: O=C(Cc1csc2ccccc12)Nc1cccc2c(=O)n(Cc3ccc(OC(F)(F)F)cc3)ccc12] | 1604 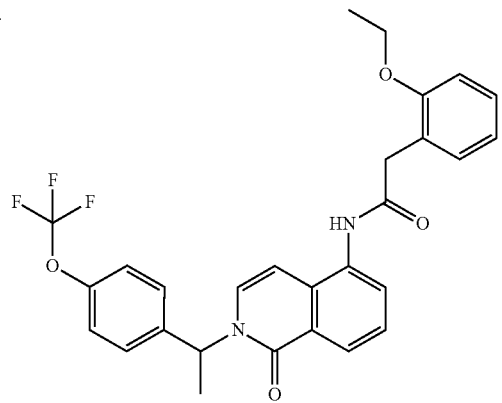 |
| 1599 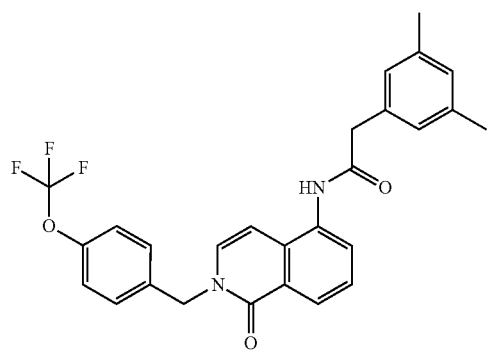 [SMILES: Cc1cc(C)cc(CC(=O)Nc2cccc3c(=O)n(Cc4ccc(OC(F)(F)F)cc4)ccc23)c1] | 1605 |
| 1601 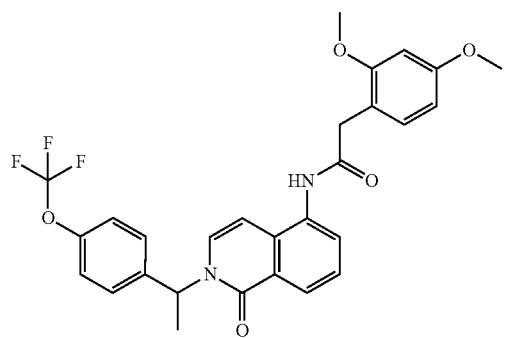 [SMILES: COc1ccc(CC(=O)Nc2cccc3c(=O)n(C(C)c4ccc(OC(F)(F)F)cc4)ccc23)c(OC)c1] | 1606 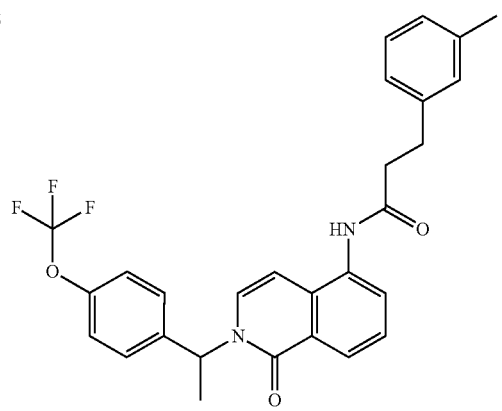 [SMILES: Cc1cccc(CCC(=O)Nc2cccc3c(=O)n(C(C)c4ccc(OC(F)(F)F)cc4)ccc23)c1] |
| 1603 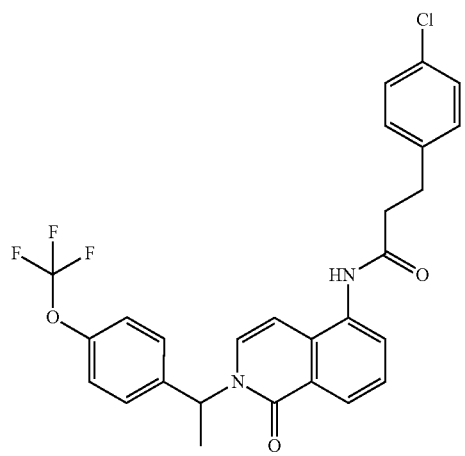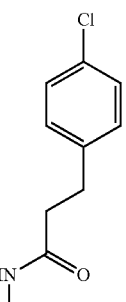 | 1609 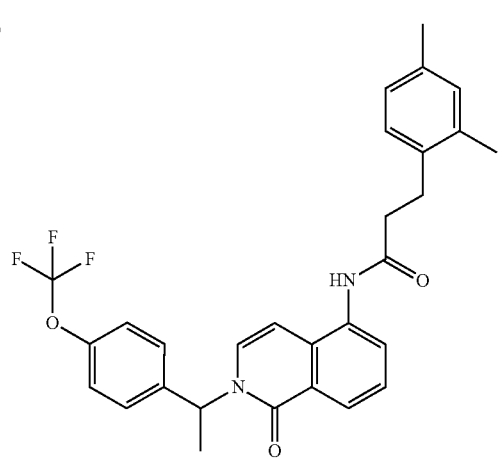 [SMILES: Cc1ccc(CCC(=O)Nc2cccc3c(=O)n(C(C)c4ccc(OC(F)(F)F)cc4)ccc23)c(C)c1] |

| ID | Structure |
|---|---|
| 1610 | 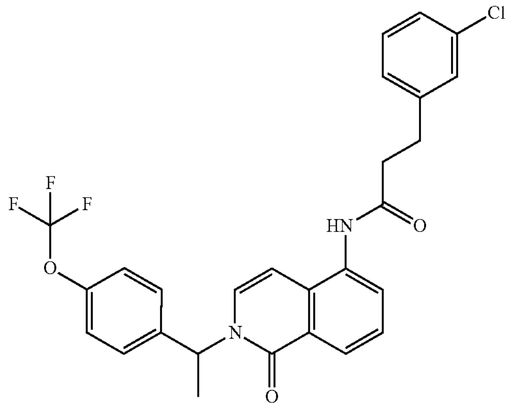 [SMILES: CC(c1ccc(OC(F)(F)F)cc1)n1ccc2c(NC(=O)CCc3cccc(Cl)c3)cccc2c1=O] |
| 1611 | 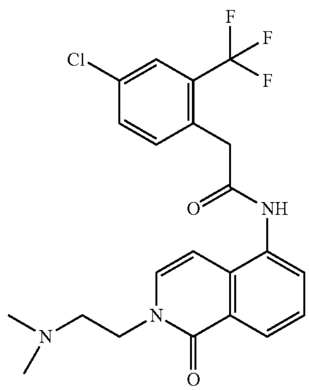 [SMILES: CN(C)CCn1ccc2c(NC(=O)Cc3ccc(Cl)cc3C(F)(F)F)cccc2c1=O] |
| 1612 | 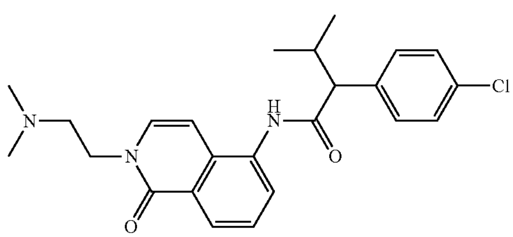 [SMILES: CC(C)C(C(=O)Nc1cccc2c(=O)n(CCN(C)C)ccc12)c1ccc(Cl)cc1] |
| 1613 | 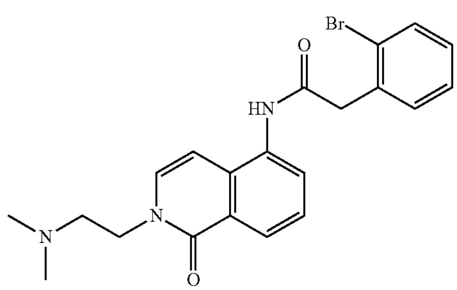 [SMILES: CN(C)CCn1ccc2c(NC(=O)Cc3ccccc3Br)cccc2c1=O] |
| 1614 | 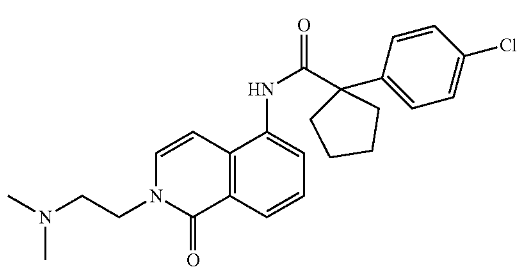 [SMILES: CN(C)CCn1ccc2c(NC(=O)C3(c4ccc(Cl)cc4)CCCC3)cccc2c1=O] |
| 1615 | (Chiral) |
| 1616 | (Chiral) |
| 1617 | |
| 1618 | |

US 8,546,579 B2
| 515 -continued | 516 -continued |
|---|---|
| ID Structure | ID Structure |
| 1620 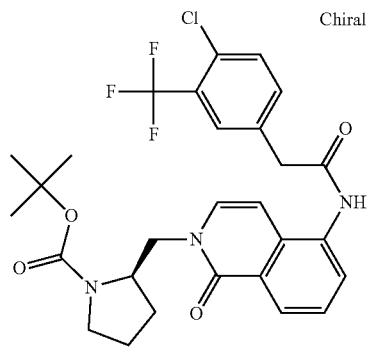 [SMILES: CC(C)(C)OC(=O)N1CCC[C@@H]1Cn1ccc2c(NC(=O)Cc3ccc(Cl)c(C(F)(F)F)c3)cccc2c1=O] | 1627 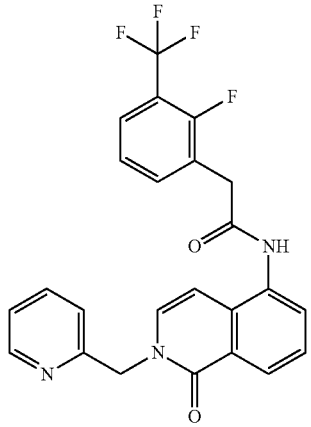 |
| 1621 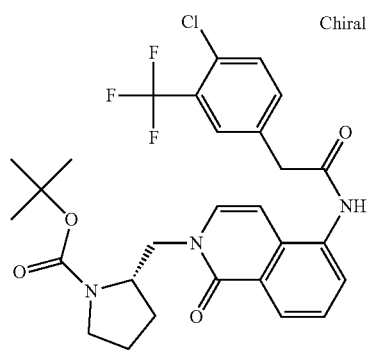 [SMILES: CC(C)(C)OC(=O)N1CCC[C@H]1Cn1ccc2c(NC(=O)Cc3ccc(Cl)c(C(F)(F)F)c3)cccc2c1=O] | 1628 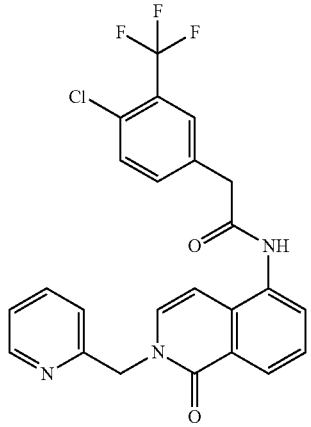 |
| 1623 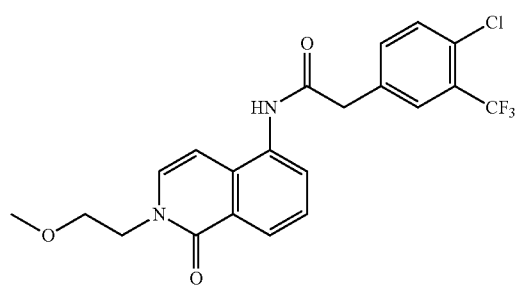 [SMILES: COCCn1ccc2c(NC(=O)Cc3ccc(Cl)c(C(F)(F)F)c3)cccc2c1=O] | |
| 1624 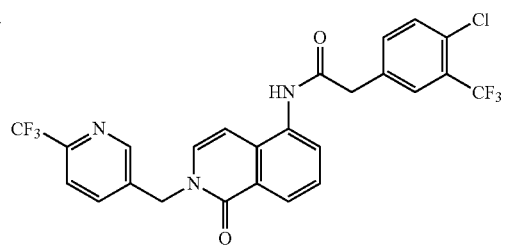 | 1630 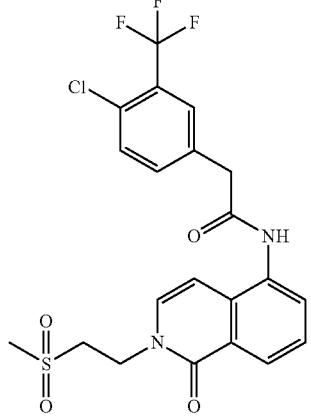 |
| 1626 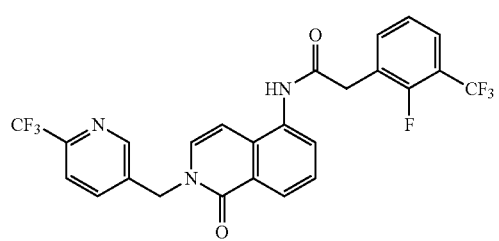 [SMILES: O=C(Cc1cccc(C(F)(F)F)c1F)Nc1cccc2c(=O)n(Cc3ccc(C(F)(F)F)nc3)ccc12] | |

| ID | Structure |
|---|---|
| 1631 | 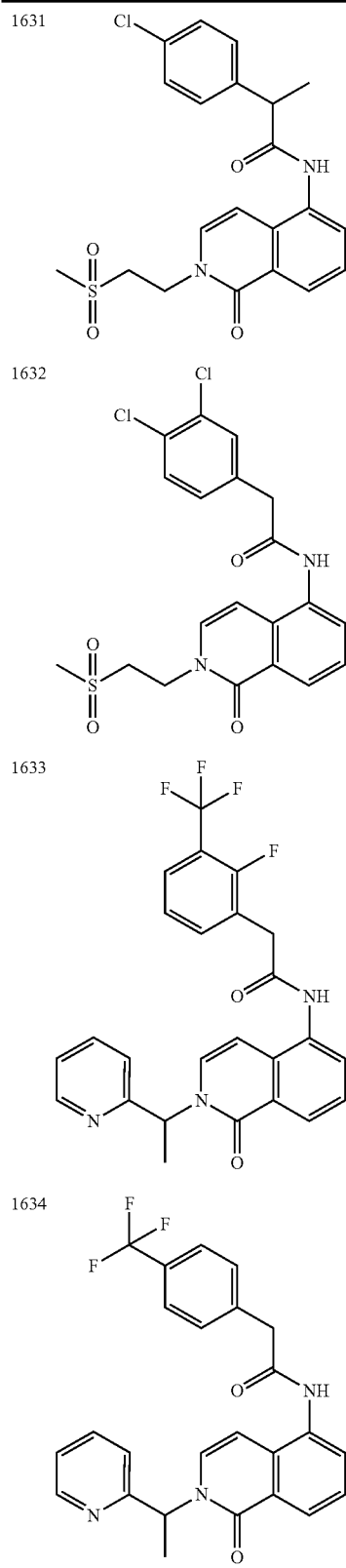 |
| 1632 | |
| 1633 | |
| 1634 | |
| ID | Structure |
|---|---|
| 1635 | 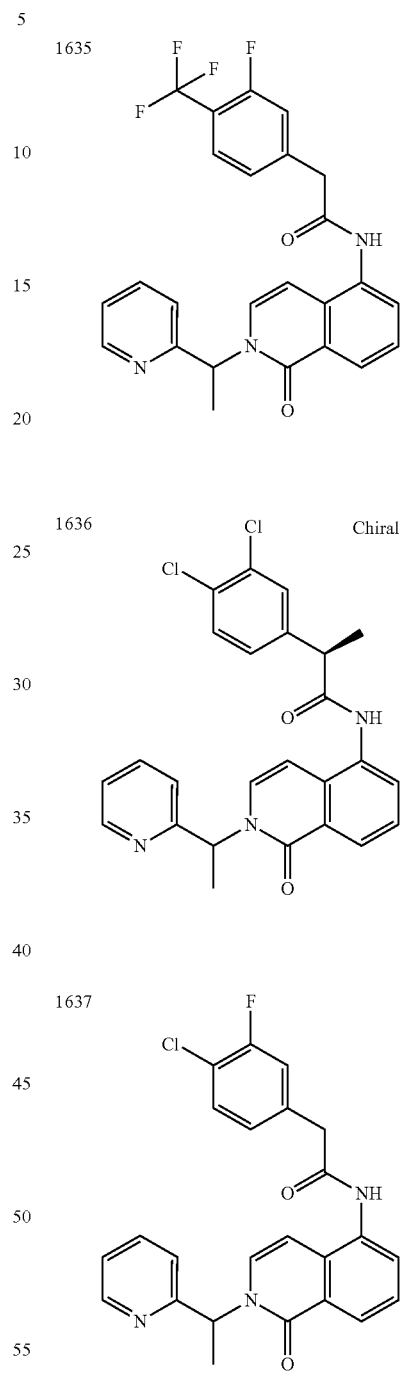 |
| 1636 | |
| 1637 | |
20. A pharmaceutical composition comprising a pharmaceutically acceptable carrier and a pharmaceutically effective amount of a compound of claim 1.
21. The pharmaceutical composition of claim 20, wherein the carrier is a parenteral, oral or topical carrier.
* * * * *